US012577299B2

(12) United States Patent
O'Neill et al.

(10) Patent No.: US 12,577,299 B2
(45) Date of Patent: Mar. 17, 2026

(54) ANTI-IL-27 ANTIBODIES AND USES THEREOF

(71) Applicant: Surface Oncology, LLC, Redwood City, CA (US)

(72) Inventors: Alison O'Neill, Cambridge, MA (US); Lauren Harshman, Cambridge, MA (US); Jonathan Hill, Cambridge, MA (US); Jou-Ku Chung, Cambridge, MA (US); Kerry White, Cambridge, MA (US); Robert Ross, Cambridge, MA (US); Benjamin Lee, Cambridge, MA (US)

(73) Assignee: SURFACE ONCOLOGY, LLC, Redwood City, CA (US)

( * ) Notice: Subject to any disclaimer, the term of this patent is extended or adjusted under 35 U.S.C. 154(b) by 708 days.

(21) Appl. No.: 17/738,927

(22) Filed: May 6, 2022

(65) Prior Publication Data

US 2022/0389089 A1 Dec. 8, 2022

Related U.S. Application Data

(60) Provisional application No. 63/277,035, filed on Nov. 8, 2021, provisional application No. 63/203,688, filed (Continued)

(51) Int. Cl.
C07K 16/24 (2006.01)
A61K 39/00 (2006.01)
A61P 35/00 (2006.01)

(52) U.S. Cl.
CPC ............ C07K 16/244 (2013.01); A61P 35/00 (2018.01); A61K 2039/505 (2013.01);

(Continued)

(58) Field of Classification Search
CPC .............. A61P 35/00; A61K 2039/505; A61K 2039/545; C07K 16/244; C07K 2317/565; C07K 2317/76; C07K 2317/92
See application file for complete search history.

(56) References Cited

U.S. PATENT DOCUMENTS 3,710,795 A 1/1973 Higuchi et al.
3,773,919 A 11/1973 Boswell et al.
(Continued)

FOREIGN PATENT DOCUMENTS

EP 0133988 A2 3/1985
EP 0088046 B1 12/1987
(Continued)

OTHER PUBLICATIONS

Janeway Jr et al., Immunology, 3rd Edition, Garland Publishing Inc., pp. 3:1-3:11) (Year: 1997).*

(Continued)

*Primary Examiner* — Zachariah Lucas
(74) *Attorney, Agent, or Firm* — ROTHWELL, FIGG, ERNST & MANBECK, P.C.

(57) ABSTRACT

The present disclosure relates to anti-IL-27 antibodies, and antigen-binding portions thereof. The disclosure also relates to methods for treating or ameliorating one or more symptoms of a disease, such as cancer, by administering the antibodies or antigen-binding portion thereof at a dose of at least about 0.003 mg/kg to at least about 20 mg/kg.

22 Claims, 44 Drawing Sheets

Specification includes a Sequence Listing.

Related U.S. Application Data on Jul. 28, 2021, provisional application No. 63/185,989, filed on May 7, 2021.

(52) U.S. Cl.
CPC .. *A61K 2039/545* (2013.01); *C07K 2317/565* (2013.01); *C07K 2317/76* (2013.01); *C07K 2317/92* (2013.01)

(56) References Cited

U.S. PATENT DOCUMENTS

| | | | |
|---|---|---|---|
| 4,676,980 A | 6/1987 | Segal et al. | |
| 4,863,457 A | 9/1989 | Lee | |
| 5,223,409 A | 6/1993 | Ladner et al. | |
| 5,403,484 A | 4/1995 | Ladner et al. | |
| 5,427,908 A | 6/1995 | Dower et al. | |
| 5,501,856 A | 3/1996 | Ohtori et al. | |
| 5,516,637 A | 5/1996 | Huang et al. | |
| 5,571,698 A | 11/1996 | Ladner et al. | |
| 5,580,717 A | 12/1996 | Dower et al. | |
| 5,624,821 A | 4/1997 | Winter et al. | |
| 5,648,260 A | 7/1997 | Winter et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,969,108 A | 10/1999 | McCafferty et al. | |
| 6,001,329 A | 12/1999 | Buchsbaum et al. | |
| 6,005,079 A | 12/1999 | Casterman et al. | |
| 6,194,551 B1 | 2/2001 | Idusogie et al. | |
| 6,933,368 B2 | 8/2005 | Co et al. | |
| 6,995,259 B1 | 2/2006 | Vargeese et al. | |
| 7,595,048 B2 | 9/2009 | Honjo et al. | |
| 7,943,743 B2 | 5/2011 | Korman et al. | |
| 8,008,449 B2 | 8/2011 | Korman et al. | |
| 8,354,509 B2 | 1/2013 | Carven et al. | |
| 8,728,474 B2 | 5/2014 | Honjo et al. | |
| 8,779,105 B2 | 7/2014 | Korman et al. | |
| 8,900,587 B2 | 12/2014 | Carven et al. | |
| 8,952,136 B2 | 2/2015 | Carven et al. | |
| 9,067,999 B1 | 6/2015 | Honjo et al. | |
| 9,073,994 B2 | 7/2015 | Honjo et al. | |
| 9,228,026 B2 * | 1/2016 | Smith | C07K 16/3069 |
| 2008/0241223 A1 | 10/2008 | Nivaggioli et al. | |
| 2012/0183548 A1 | 7/2012 | Wong et al. | |
| 2019/0031766 A1 | 1/2019 | Prinz et al. | |

FOREIGN PATENT DOCUMENTS

| | | | | |
|---|---|---|---|---|
| EP | 0143949 B1 | 10/1988 | | |
| EP | 0036676 B2 | 9/1990 | | |
| EP | 0488401 A1 | 6/1992 | | |
| EP | 0430539 B1 | 10/1994 | | |
| EP | 0058481 B2 | 5/2003 | | |
| EP | 1537878 B1 | 9/2010 | | |
| EP | 2170959 B1 | 10/2013 | | |
| EP | 2161336 B2 | 3/2017 | | |
| WO | WO-9002809 A1 | 3/1990 | | |
| WO | WO-9110737 A1 | 7/1991 | | |
| WO | WO-9201047 A1 | 1/1992 | | |
| WO | WO-9218619 A1 | 10/1992 | | |
| WO | WO-9311236 A1 | 6/1993 | | |
| WO | WO-9315722 A1 | 8/1993 | | |
| WO | WO-9404678 A1 | 3/1994 | | |
| WO | WO-9420069 A1 | 9/1994 | | |
| WO | WO-9425591 A1 | 11/1994 | | |
| WO | WO-9429351 A2 | 12/1994 | | |
| WO | WO-9515982 A2 | 6/1995 | | |
| WO | WO-9520401 A1 | 8/1995 | | |
| WO | WO-9627011 A1 | 9/1996 | | |
| WO | WO-9951642 A1 | 10/1999 | | |
| WO | WO-2007024715 A2 | 3/2007 | | |
| WO | WO-2008024188 A2 | 2/2008 | | |
| WO | WO-2010027827 A2 | 3/2010 | | |
| WO | WO-2010077634 A1 | 7/2010 | | |
| WO | WO-2011066342 A2 | 6/2011 | | |
| WO | WO-2013079174 A1 | 6/2013 | | |
| WO | WO-2013173223 A1 | 11/2013 | | |
| WO | WO-2015103072 A1 | 7/2015 | | |
| WO | WO-2016106159 A1 | 6/2016 | | |
| WO | WO-2019178269 A2 | 9/2019 | | |
| WO | WO-2019183499 A1 * | 9/2019 | ............ | A61K 38/20 |
| WO | WO-2021062244 A1 | 4/2021 | | |

OTHER PUBLICATIONS

Fabbi et al. (A Guide for Estimating the Maximum Safe Starting Dose and Conversion it between Animals and Humans. Mediators of Inflammation. p. 3958069) (Year: 2017).*

Briney et al. (Commonality despite exceptional diversity in the baseline human antibody repertoire. Nature. 566:393-399) (Year: 2019).*

Saadh et al. (A guide for estimating the maximum safe starting dose and conversion it between animals and humans. Systematic Reviews in Pharmacy. vol. 11(8), pp. 98-100) (Year: 2020).*

Wong et. al. (Ab-Ligity: identifying sequence-dissimilar antibodies that bind to the same epitope. mAbs. vol. 13(1), p. 1873478) (Year: 2021).*

Shimabukuro-Vornhagen et al., J ImmunoTherapy of Cancer, 6:56 (Year: 2018).*

Altschul, S.F., et al., "Basic Local Alignment Search Tool," Journal of Molecular Biology 215(3):403-410, Elsevier, Netherlands (Oct. 1990).

Altschul, S.F., et al., "Gapped Blast and PSI-Blast: A New Generation of Protein Database Search Programs," Nucleic Acids Research 25(17):3389-3402, Oxford University Press, United Kingdom (Sep. 1997).

Ames, R.S., et al., "Conversion of Murine Fabs Isolated From a Combinatorial Phage Display Library to Full Length Immunoglobulins," Journal of Immunological Methods 184(2):177-186, Elsevier, Netherlands (1995).

Baldridge, J.R. and Crane, R.T., "Monophosphoryl Lipid A (MPL) Formulations for the Next Generation of Vaccines," Methods, 19(1):103-107, Academic Press, United States (Sep. 1999).

Batzer, M.A., et al., "Enhanced evolutionary PCR using oligonucleotides with inosine at the 3'-terminus," Nucleic Acids Research 19(18):5081, Oxford University Press, United Kingdom (Sep. 1991).

Berge, S.M., et al., "Pharmaceutical Salts," Journal of Pharmaceutical Sciences 66(1):1-19, Elsevier, United States (Jan. 1977).

Bieg, S., et al., "Gad65 and Insulin B Chain Peptide (9-23) are Not Primary Autoantigens in the Type 1 Diabetes Syndrome of the Bb Rat," Autoimmunity 31(1):15-24, Taylor & Francis, United Kingdom (Jan. 1999).

Blank, C. and Mackensen, A., "Contribution of the PD-L1/PD-1 Pathway to T-cell Exhaustion: An Update on Implications for Chronic Infections and Tumor Evasion," Cancer Immunol Immunother 56(5):739-745, Springer Verlag, Germany (May 2007).

Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).

Bocci, G., et al., "Increased plasma vascular endothelial growth factor (VEGF) as a surrogate marker for optimal therapeutic dosing of VEGF receptor-2 monoclonal antibodies," Cancer Research 64(18):6616-6625, American Association for Cancer Research, United States (2004).

Boder, E,T. and Wittrup, K,D., "Yeast Surface Display for Directed Evolution of Protein Expression, Affinity, and Stability," Methods Enzymology, 328:430-444, Academic Press, United States (2000).

Brennan, M., et al., "Preparation of bispecific antibodies by chemical recombination of monoclonal immunoglobulin G1 fragments," Science 229:81-83, American Association for the Advancement of Science, United States (1985).

(56)　　　　　References Cited

OTHER PUBLICATIONS

Brinkmann, U., et al., "Phage Display of Disulfide-stabilized Fv Fragments," Journal of Immunological Methods 182(1):41-50, Elsevier, Netherlands (1995).
Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (Feb. 2003).
Burton, D.R., et al., "Human antibody effector function," Adv. Immunol. 51:1-18, Elsevier, Netherlands (1992).
Burton, D.R. and Barbas, C.F. 3rd, "Human Antibodies From Combinatorial Libraries," Advances in Immunology 57:191-280, Academic Press, United States (1994).
Canfield, S.M., et al., "The Binding Affinity of Human Igg for Its High Affinity Fc Receptor is Determined by Multiple Amino Acids in the Ch2 Domain and is Modulated by the Hinge Region," Journal of Experimental Medicine 173(6):1483-1491, Rockefeller University Press, United States (Jun. 1991).
Caron, P.C., et al., "Engineered Humanized Dimeric Forms of Igg are More Effective Antibodies," Journal of Experimental Medicine 176(4):1191-1195, Rockefeller University Press, United States (Oct. 1992).
Chasteen, L., et al., "Eliminating Helper Phage From Phage Display," Nucleic Acids Research, 34(21):e145, Oxford University Press, United Kingdom (2006).
Chen, D.S., and Mellman, I., "Oncology meets immunology: the cancer-immunity cycle," Immunity 39(1):1-10, Cell Press, United States (2013).
Cheung, R.C., et al., "Epitope-specific Antibody Response to the Surface Antigen of Duck Hepatitis B Virus in Infected Ducks," Virology 176(2):546-552, Academic Press, United States (1990).
ClinicalTrials.gov, "Study of SRF388 in Patients With Advanced Solid Tumors," Identifier NCT04374877, accessed at https://clinicaltrials.gov/ct2/show/NCT04374877, accessed on Feb. 10, 2023, 12 pages.
Co, M.S., et al., "Genetically engineered deglycosylation of the variable domain increases the affinity of an anti-CD33 monoclonal antibody," Mol. Immunol. 30:1361-1367, Elsevier, Netherlands (1993).
Cornelis, P., et al., "Expressing Genes in Different *Escherichia coli* Compartments," Current Opinion in Biotechnology 11(5):450-454, Elsevier, United Kingdom (Oct. 2000).
Deans, R.J., et al., "Expression of an Immunoglobulin Heavy Chain Gene Transfected Into Lymphocytes," Proceedings of the National Academy of Sciences of the United States of America, 81(5):1292-1296, National Academy of Sciences, United States (Mar. 1984).
Diakowski, D., et al., "Concentration of serum interleukin-27 increase in patients with lymph node metastatic gastroesophageal cancer," Adv. Clin. Exp. Med. 22(5):683-691, Wroclaw Medical University, Poland (2013).
Dietrich, C., et al., "A soluble form of IL-27Rα is a natural IL-27 antagonist," J. Immunol. 192:5382-5389, American Association of Immunologists, United States (2014).
Di Niro R., et al., "Characterizing Monoclonal Antibody Epitopes by Filtered Gene Fragment Phage Display," The American Journal of Pathology, 388(Pt 3):889-894, Elsevier, United States (Jun. 2005).
Dong, H. and Chen, L., "B7-H1 Pathway and its Role in the Evasion of Tumor Immunity," Journal of Molecular Medicine 81(5):281-287, Springer, Germany (May 2003).
Dong, H., et al., "Tumor-associated B7-H1 Promotes T-cell Apoptosis: A Potential Mechanism of Immune Evasion," Nature Medicine 8(8):793-800, Nature Publishing Company, United Kingdom (Aug. 2002).
Freeman, G.J., et al., "Protect the killer: CTLs need defenses against the tumor," Nat. Med. 8:787-789, Nature Publishing Group, United Kingdom (2002).
Duncan, A,R. and Winter, G., "The Binding Site for C1q on IgG," Nature, 332(6166):738-740, Nature Publishing Group, United Kingdom (Apr. 1988).

Engberg, J., et al., "Phage-Display Libraries of Murine and Human Antibody Fab Fragments," Methods in Molecular Biology, 51:355-376, Humana Press, United States (1995).
Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).
Etz, H., et al., "Bacterial Phage Receptors, Versatile Tools for Display of Polypeptides on the Cell Surface," Journal of Bacteriology 183(23):6924-6935, American Society for Microbiology, United States (Dec. 2001).
Fabbi, M., et al., "Dual Roles of IL-27 in Cancer Biology and Immunotherapy," Mediators Inflamm. 2017:3958069, Hindawi Publishers, United Arab Emirates (2017).
Fergusson, J.R., et al., "CD161 defines a transcriptional and functional phenotype across distinct human T cell lineages," Cell Reports 9(3):1075-1088, Cell Press, United States (2014).
Fursov, N., et al., "Development and Utilization of Activated STAT3 Detection Assays for Screening a Library of Secreted Proteins," 9(4):420-429, Mary Ann Liebert Inc., United States (2011).
Gao, Q., et al., "Overexpression of PD-L1 Significantly Associates with Tumor Aggressiveness and Postoperative Recurrence in Human Hepatocellular Carcinoma," Clinical Cancer Research 15(3): 971-979, The Association of Clinical Cancer Research, United States (Feb. 2009).
GenBank, "hPD-1 [*Homo sapiens*]," Accession No. AAC51773.1, accessed at https://www.ncbi.nlm.nih.gov/protein/AAC51773, accessed on Oct. 3, 2022, 2 pages.
GenBank, "Programmed Cell Death 1 Ligand 1," Accession No. Q9NZQ7, accessed at https://www.ncbi.nlm.nih.gov/protein/Q9NZQ7, accessed on Nov. 3, 2020, 5 pages.
GenBank, "stimulator of interferon genes protein isoform 2 [*Homo sapiens*]," Accession No. NP_001288667.1, accessed at https://www.ncbi.nlm.nih.gov/protein/NP_001288667.1/, accessed on Oct. 3, 2022, 3 pages.
GenBank, "Tigit_Human," Accession No. Q495A1, accessed at https://www.ncbi.nlm.nih.gov/protein/Q495A1, accessed on Feb. 10, 2023, 3 pages.
Ghebeh, H., et al., "The B7-H1 (PD-L1) T lymphocyte-Inhibitory Molecule is Expressed in Breast Cancer Patients With Infiltrating Ductal Carcinoma: Correlation With Important High-Risk Prognostic Factors," Neoplasia, 8(3):190-198, Neoplasia Press, United States (Mar. 2006).
Grabherr, R and Ernst, W., "The Baculovirus Expression System as a Tool for Generating Diversity by Viral Surface Display," Combinatorial Chemistry & High Throughput Screening, 4(2):185-192, Bentham Science Publishers, United Arab Emirates (Apr. 2001).
Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (Jun. 1994).
Gupta, R.K and Siber, G.R., "Adjuvants for Human Vaccines—current Status, Problems and Future Prospects," Vaccine, 13(14):1263-1276, Elsevier Science, Netherlands (Oct. 1995).
Hamanishi, J., et al., "Programmed Cell Death 1 Ligand 1 and Tumor-infiltrating CD8+ T Lymphocytes are Prognostic Factors of Human Ovarian Cancer," Proceedings of the National Academy of Sciences USA 104(9):3360-3365, National Academy of Sciences, United States (Feb. 2007).
Hanahan, D. and Weinberg, R.A., "Hallmarks of Cancer: The Next Generation," Cell 144(5):646-674, Cell Press, United States (2011).
Hanes, J., et al., "Picomolar Affinity Antibodies from a Fully Synthetic Naive Library Selected and Evolved by Ribosome Display," Nature Biotechnology 18(12):1287-1292, Nature America Publishing, United States (Dec. 2000).
Harding, F.A. and Lonberg, N., "Class Switching in Human Immunoglobulin Transgenic Mice," Annals of the New York Academy of Sciences 764:536-546, New York Academy of Sciences, United States (1995).
Hino, R., et al., "Tumor Cell Expression of Programmed Cell Death-1 Ligand 1 is a Prognostic Factor for Malignant Melanoma," Cancer 116(7):1757-1766, American Cancer Society by J. Wiley, United States (Apr. 2010).

(56) References Cited

OTHER PUBLICATIONS

Hisada, M., et al., "Potent Antitumor Activity of Interleukin-27," Cancer Research 64(3):1152-1156, Wiley, United States (Feb. 2004).

Holliger, P., et al., "Diabodies: Small Bivalent and Bispecific Antibody Fragments," Proceedings Proc Natl Acad Sci USA 90(14):6444-6448, National Academy of Sciences, United States (Jul. 1993).

Hoogenboom, H.R., et al., "Designing and Optimizing Library Selection Strategies for Generating High-affinity Antibodies," Trends in Biotechnology 15(2):62-70, Elsevier Science, United Kingdom (1997).

Hou, J. and Zhan, H., "Expression of Active Thrombopoietin and Identification of its Key Residues Responsible for Receptor Binding," Cytokine 10(5):319-330, Elsevier Science Ltd, United Kingdom (May 1998).

Houdebine, L.M., "Antibody Manufacture in Transgenic Animals and Comparisons With Other Systems," Current Opinion in Biotechnology 13(6):625-629, Elsevier, United Kingdom (Dec. 2002).

Hudson, P.J. and Kortt, A.A., "High Avidity scFv Multimers; Diabodies and Triabodies," Journal of Immunological Methods 231(1-2):177-189, Elsevier, Netherlands (Dec. 1999).

Inman, B.A., et al., "PD-L1 (B7-H1) Expression by Urothelial Carcinoma of the Bladder and BCG-induced Granulomata: Associations With Localized Stage Progression," Cancer 109(8):1499-1505, Wiley, United States (Apr. 2007).

Ishida, Y., et al., "Induced Expression of PD-1, a Novel Member of the Immunoglobulin Gene Superfamily, Upon Programmed Cell Death," The EMBO Journal (11):3887-3895, Oxford University Press, United Kingdom (Nov. 1992).

Isner, J.M and Asahara, T., "Angiogenesis and Vasculogenesis as Therapeutic Strategies for Postnatal Neovascularization," The Journal of Clinical Investigation 103(9):1231-1236, American Society for Clinical Investigation, United States (May 1999).

Iwai, Y., et al., "Involvement of PD-L1 on Tumor Cells in the Escape from Host Immune System and Tumor Immunotherapy by PD-L1 Blockade," Proc Natl Acad Sci USA 99(19):12293-12297, National Academy of Sciences, United States (Sep. 2002).

Jankowski, M., et al., "Interleukin-27: Biological Properties and Clinical Application," Archivum Immunologiae Et Therapiae Experimentalis 58(6):417-425, Birkhaüser, Switzerland (Dec. 2010).

Johnson, D.A., "3-O-Desacyl monophosphoryl lipid A Derivatives: Synthesis and Immunostimulant Activities," Journal of Medicinal Chemistry 42(22):4640-4649, American Chemical Society, United States (Nov. 1999).

Kaszubska, W., et al., "Expression, Purification, and Characterization of Human Recombinant Thrombopoietin in Chinese Hamster Ovary Cells," Protein Expression and Purification 18(2):213-220, Academic Press, United States (Mar. 2000).

Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).

Kieke, M.C., et al., "Isolation of Anti-T Cell Receptor ScFv Mutants by Yeast Surface Display," Protein Engineering, 10(11):1303-1310, Oxford University Press, United Kingdom (Nov. 1997).

Kim, S., et al., "Regulation of Angiogenesis in Vivo by Ligation of Integrin Alpha5beta1 With the Central Cell-binding Domain of Fibronectin," Am J Pathol, 156(4):1345-1362, Elsevier, United States (Apr. 2000).

Kim, S., et al., "Regulation of Integrin Alpha vbeta 3-Mediated Endothelial Cell Migration and Angiogenesis by Integrin Alpha5beta1 and Protein Kinase A," The Journal of Biological Chemistry, 275(43):33920-33928, American Society for Biochemistry and Molecular Biology, United States (Oct. 2000).

Kinstler, O., et al., "Mono-N-terminal Poly(Ethylene Glycol)-protein Conjugates," Advanced Drug Delivery Reviews 54(4):477-485, Elsevier Science Publishers, Netherlands (Jun. 2002).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).

Kitano, A., et al., "Tumour-infiltrating Lymphocytes are Correlated With Higher Expression Levels of Pd-1 and Pd-11 in Early Breast Cancer," ESMO Open, 2(2):e000150, Elsevier, London (May 2017).

Kleffel, S., et al., "Melanoma Cell-Intrinsic PD-1 Receptor Functions Promote Tumor Growth," Cell, 162(6):1242-1256, Cell Press, United States (Sep. 2015).

Klemm, P. and Schembri, M, A., "Fimbrial Surface Display Systems in Bacteria: From Vaccines to Random Libraries," Microbiology (Reading), 146(12):3025-3032, Microbiology Society, United Kingdom (Dec. 2000).

Konishi, J., et al., "B7-H1 Expression on Non-small Cell Lung Cancer Cells and its Relationship with Tumor-infiltrating Lymphocytes and their PD-1 Expression," Clinical Cancer Research 10(15):5094-5100, American Association for Cancer Research, United States (Aug. 2004).

Kostelny, S.A., et al., "Formation of a Bispecific Antibody by the Use of Leucine Zippers," The Journal of Immunology 148(5):1547-1553, American Association of Immunologists, United States (Mar. 1992).

Kumar, C.C., et al., "Targeting Integrins $\alpha v\beta 3$ and $\alpha v\beta 5$ for Bloking Tumor-Induced Angiogenesis," Angiogenesis, 476:169-180, Springer, Netherlands (2000).

Langer, R., et al., "Biocompatibility of Polymeric Delivery Systems for Macromolecules," J Biomed Mater Res, 15(2):267-277, Wiley, United States (Mar. 1981).

Langer, R., "Controlled release of macromolecules," Chem. Tech 12:98-105, American Chemical Society, United States (1982).

Larousserie, F., et al., "Analysis of Interleukin-27 (Ebi3/p28) Expression in Epstein-barr Virus- and Human T-cell Leukemia Virus Type 1-associated Lymphomas: Heterogeneous Expression of Ebi3 Subunit by Tumoral Cells," Am J Pathol, 166(4):1217-1228, Elsevier, United States (Apr. 2005).

Lee, L.S., et al., "Prolonged Circulating Lives of Single-chain Fv Proteins Conjugated With Polyethylene Glycol: a Comparison of Conjugation Chemistries and Compounds," Bioconjugate Chemistry, 10(6):973-981, American Chemical Society, United States (Nov.-Dec. 1999).

Liu, L., et al., "IL-27-Mediated Activation of Natural Killer Cells and Inflammation Produced Antitumor Effects for Human Oesophageal Carcinoma Cells," Scandinavian Journal of Immunology, 68(1):22-29, Blackwell Scientific Publications, United Kingdom (Jul. 2008).

Lodmell, D.L., et al., "DNA Vaccination of Mice Against Rabies Virus: Effects of the Rroute of Vaccination and The Adjuvant Monophosphoryl Lipid A (MPL)," Vaccine, 18(11-12):1059-1066, Elsevier Science, Netherlands (Jan. 2000).

Lonberg, N., et al., "Antigen-specific Human Antibodies from Mice Comprising Four Distinct Genetic Modifications," Nature 368(6474):856-859, Nature Publishing Group, United States (Apr. 1994).

Lonberg, N., "Chapter 3: Transgenic Approaches to Human Monoclonal Antibodies," The Pharmacology of Monoclonal Antibodies 113:49-101, part of the Handbook of Experimental Pharmacology book series, Springer, United States (1994).

Lonberg, N., "Human Antibodies from Transgenic Mice," Therapeutic Monoclonal Antibodies: From Bench to Clinic; Chapter 5; pp. 117-150 (2009).

Lonberg, N., "Human Antibodies From Transgenic Animals," Nature Biotechnology, 23(9):1117-1125, Nature America Publishing, United States (Sep. 2005).

Lusky, M. and Botchan, M., "Inhibition of Sv40 Replication in Simian Cells by Specific Pbr322 Dna Sequences," Nature, 293(5827):79-81, Nature Publishing Group, United Kingdom (Sep. 1981).

Merz, D.C., et al., "Generating a Phage Display Antibody Library Against an Identified Neuron," Journal of Neuroscience Methods, 62(1-2):213-219, Elsevier/North-Holland Biomedical Press, Netherlands (Nov. 1995).

Milstein, C. and Cuello, A.C., "Hybrid Hybridomas and their Use in Immunohistochemistry," Nature 305(5934):537-540, Nature Publishing Group, United Kingdom (Oct. 1983).

(56)          References Cited

OTHER PUBLICATIONS

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, United Kingdom (1990).

Morel, G.A., et al., "Monoclonal Antibodies to Bovine Serum Albumin: Affinity and Specificity Determinations," Molecular Immunology 25(1):7-15, Pergamon Press, United Kingdom (1988).

Motz, G, T. and Coukos, G., "Deciphering and Reversing Tumor Immune Suppression," Immunity, 39(1):61-73, Cell Press, United States (Jul. 2013).

Mueller, J.P., et al., "Humanized Porcine VCAM-specific Monoclonal Antibodies With Chimeric IgG2/G4 Constant Regions Block Human Leukocyte Binding to Porcine Endothelial Cells," Molecular Immunology 34(6):441-452, Pergamon Press, United Kingdom (Apr. 1997).

Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).

Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).

Myers, E.W. and Miller, W., "Optimal Alignments in Linear Space," Computer Applications in the Biosciences 4(1):11-17, Oxford University Press, United Kingdom (Mar. 1988).

Nakanishi, J., et al., "Overexpression of B7-h1 (Pd-l1) Significantly Associates With Tumor Grade and Postoperative Prognosis in Human Urothelial Cancers," Cancer Immunol Immunother Cancer Immunol Immunother, 56(8):1173-1182, Springer Verlag, Germany (Aug. 2007).

Needleman, S.B. and Wunsch, C.D., "A General Method Applicable to the Search for Similarities in the Amino Acid Sequence of Two Proteins," Journal of Molecular Biology 48(3):443-453, Elsevier, Netherlands (Mar. 1970).

Nuttall, S.D., et al., "Immunoglobulin VH Domains and Beyond: Design and Selection of Single-domain Binding and Targeting Reagents," Current Pharmaceutical Biotechnology 1(3):253-263, Bentham Science Publishers, Netherlands (2000).

Ohigashi, Y., et al., "Clinical significance of programmed death-1 ligand-1 and programmed death-1 ligand-2 expression in human esophageal cancer," Clinical Cancer Research, 11(8):2947-2953, The Association of Clinical Cancer Research, United States (Apr. 2005).

Ohtsuka, E., et al., "An Alternative Approach to Deoxyoligonucleotides as Hybridization Probes by Insertion of Deoxyinosine at Ambiguous Codon Positions," The Journal of Biological Chemistry 260(5):2605-2608, Elsevier Inc, United States (Mar. 1985).

Pavisic, R., et al., "Recombinant Human Granulocyte Colony Stimulating Factor Pre-screening and Screening of Stabilizing Carbohydrates and Polyols," International Journal of Pharmaceutics, 387(1-2):110-119, Amsterdam, Elsevier/North-Holland Biomedical Press, Netherlands (Mar. 2010).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Pereboev, A., et al., "Phage Display of Adenovirus Type 5 Fiber Knob as a Tool for Specific Ligand Selection and Validation," Journal of Virology, 75(15):7107-7113, American Society for Microbiology, United States (Aug. 2001).

Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).

Poljak, R.J., "Production and Structure of Diabodies," Structure 2(12):1121-1123, Cell Press, United States (1994).

Pollock, D. P., et al., "Transgenic milk as a method for the production of recombinant antibodies," Journal of Immunological Methods 231:147-157, Elsevier, Netherlands (1999).

Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).

Roberts, M.J., et al., "Chemistry for Peptide and Protein Pegylation," Advanced Drug Delivery Reviews, 54(4):459-476, Elsevier Science Publishers, B.V., Netherlands (Jun. 2002).

Rogers, B.E., et al., "Localization of Iodine-125-mip-des-met14-bombesin (7-13)nh2 in Ovarian Carcinoma Induced to Express the Gastrin Releasing Peptide Receptor by Adenoviral Vector-mediated Gene Transfer," The Journal of Nuclear Medicine, 38(8):1221-1229, Society of Nuclear Medicine, United States (Aug. 1997).

Rondon, I.J. and Marasco, W.A., "Intracellular Antibodies (Intrabodies) for Gene Therapy of Infectious Diseases," Annual Review of Microbiology, 51(1):257-283, Annual Reviews, United States (1997).

Rossolini, G.M., et al., "Use of Deoxyinosine-Containing Primers vs Degenerate Primers for Polymerase Chain Reaction Based on Ambiguous Sequence Information," Molecular and Cellular Probes 8(2):91-98, Academic Press, United Kingdom (Apr. 1994).

Sarver, N., et al., "Transformation and Replication in Mouse Cells of a Bovine Papillomavirus—pm12 Plasmid Vector That can be Rescued in Bacteria," Proceedings of the National Academy of Sciences of the United States of America, 79(23):7147-7151, National Academy of Sciences, United States (Dec. 1982).

Schaffitzel, C., et al., "Ribosome Display: An in Vitro Method for Selection and Evolution of Antibodies From Libraries," Journal of Immunological Methods 231(1-2):119-135, Elsevier, Netherlands (Dec. 1999).

Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1):217-225, The Rockefeller University Press, United States (Jan. 1992).

Shi, L., et al., "De Novo Selection of High-affinity Antibodies From Synthetic Fab Libraries Displayed on Phage as Pix Fusion Proteins," Journal of Molecular Biology, 397(2):385-396, Academic Press, United Kingdom (Mar. 2010).

Shimauchi, T., et al., "Augmented Expression of Programmed Death-1 in Both Neoplastic and Non-neoplastic Cd4+ T-cells in Adult T-cell Leukemia/lymphoma," International Journal of Cancer, 121(12):2585-2590, International Union Against Cancer, United States (Dec. 2007).

Shimizu, M., et al., "Antiangiogenic and Antitumor Activities of I1-27," Journal of Immunology, 176(12):7317-7324, American Association of Immunologists, United States (Jun. 2006).

Shiraishi, M., et al., "Short-step chemical synthesis of DNA by use of MMTrS group for protection of 5'-hydroxyl group," Nucleic Acids Symposium Series, 51:129-130, Oxford University Press, United Kingdom (2007).

Shopes, B., "A Genetically Engineered Human Igg Mutant With Enhanced Cytolytic Activity," Journal of Immunology 148(9):2918-2922, American Association of Immunologists, United States (May 1992).

Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).

Smith, T.F. and Waterman, M.S., "Comparison of Biosequences," Advances in Applied Mathematics 2(4):482-489, Academic Press, Inc., United States (Dec. 1981).

Songsivilai, S. and Lachmann, P.J., "Bispecific Antibody: A Tool for Diagnosis and Treatment of Disease," Clinical and Experimental Immunology 79(3):315-321, Blackwell Scientific Publications, United Kingdom (1990).

Southern, P.J. and Berg, P., "Transformation of Mammalian Cells to Antibiotic Resistance with a Bacterial Gene Under Control of the SV40 Early Region Promoter," Journal of Molecular and Applied Genetics 1(4):327-341, Raven Press, United States (1982).

(56)          References Cited

OTHER PUBLICATIONS

Stahli, C., et al., "Distinction of Epitopes by Monoclonal Antibodies," Methods in Enzymology 92:242-253, Academic Press, United States (1983).

Suresh, M.R., et al., "Bispecific Monoclonal Antibodies from Hybrid Hybridomas," Methods in Enzymology 121:210-228, Academic Press Inc., United States (1986).

Takahashi,T., et al., "Ischemia- and Cytokine-induced Mobilization of Bone Marrow-derived Endothelial Progenitor Cells for Neovascularization," Nature Medicine, 5(4):434-438, Nature Publishing Company, United States (Apr. 1999).

Thompson,R.H., et al., "Significance of B7-h1 Overexpression in Kidney Cancer," Clinical Genitourinary Cancer, 5(3):206-211, Cancer Information Group, United States (Dec. 2006).

Tochizawa, S., et al., "A Novel Modification of a Flow Cytometric Assay of Phosphorylated Stat1 in Whole Blood Lymphocytes for Rapid Detection of Interferon-alpha Signal in Vivo," Journal of Immunological Methods, 313(1-2):29-37, Elsevier, Netherlands (Jun. 2006).

Todorovska, A., et al., "Design and Application of Diabodies, Triabodies and Tetrabodies for Cancer Targeting," Journal of Immunological Methods 248(1-2):47-66, Elsevier, Netherlands (Feb. 2001).

Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).

Van Kuik-Romeijn, P., et al., "Expression of a Functional Mouse-human Chimeric Anti-cd19 Antibody in the Milk of Transgenic Mice," Transgenic Res, 9(2):155-159, Kluwer Academic Publishers, Netherlands (Apr. 2000).

Varner, J.A., et al., "Inhibition of Angiogenesis and Tumor Growth by Murine 7E3, the Parent Antibody of C7E3 Fab (Abciximab; Reopro)," Angiogenesis 3(1):53-60, Springer, Germany (1999).

Wigler, M., et al., "Transformation of mammalian cells with genes from procaryotes and eucaryotes," Cell 16(4):777-785, Cell Press, United States (Apr. 1979).

Wright, A., et al., "Antibody Variable Region Glycosylation: Position Effects on Antigen Binding and Carbohydrate Structure," The EMBO Journal 10(10):2717-2723, Wiley Blackwell, United Kingdom (1991).

Wu, C., et al., "Simultaneous Targeting of Multiple Disease Mediators by a Dual-variable-domain Immunoglobulin," Nature Biotechnology 25(11):1290-1297, Nature Publishing Co., United States (2007).

Yang, W., et al., "PD-L1: PD-1 Interaction Contributes to the Functional Suppression of T-Cell Responses to Human Uveal Melanoma Cells in Vitro," 49(6):2518-2525, Association for Research in Vision and Ophthalmology (Arvo), United States (Jun. 2008).

Yang, J.C., et al., "A Randomized Trial of Bevacizumab, an Anti-Vascular Endothelial Growth Factor Antibody, for Metastatic Renal Cancer," New England Journal of Medicine 349:427-434, Massachusetts Medical Society, United States (2003).

Yeung, Y.A., and Wittrup, D.K., "Quantitative Screening of Yeast Surface-displayed Polypeptide Libraries by Magnetic Bead Capture," Biotechnology Progress 18(2):212-220, American Institute of Chemical Engineers, United States (Mar.-Apr. 2002).

Yoshida, H., and Hunter, C.A., "The Immunobiology of Interleukin-27," Annual Review of Immunology 33:417-443, Annual Reviews Inc., United States (2015).

Zapata, G., et al., "Engineering Linear F(ab')2 Fragments for Efficient Production in *Escherichia coli* and Enhanced Antiproliferative Activity," Protein Engineering 8(10):1057-1062, Oxford University Press, United Kingdom (1995).

Zhan, M. M., et al., "From Monoclonal Antibodies to Small Molecules: the Development of Inhibitors Targeting the PD-1/PD-L1 Pathway," Drug Discovery Today 21(6): 1027-1036, Elsevier Science Ltd, United Kingdom (Jun. 2016).

International Search Report and Written Opinion PCT/US2022/028189, mailed Aug. 8, 2022, European Patent Office, Netherlands, 13 pages.

ClinicalTrials.gov, "History of Changes for Study: NCT04374877 Study of SRF388 in Patients with Advanced Solid Tumors," accessed at https://clinicaltrials.gov/ct2/history/NCT04374877?V_3=View, accessed on Feb. 13, 2023, 5 pages.

Kourko, O., et al., "IL-27, IL-30, and IL-35: A Cytokine Triumvirate in Cancer," Frontiers in Oncology 9:969, Frontiers Media, United States (2019).

Patnaik, A., et al., "Results of a phase 1 study of SRF388, a first-in-human, first-in-class, high- affinity anti-IL-27 antibody in advanced solid tumors," 2021 ASCO Annual Meeting Developmental Therapeutics-Immunotherapy 39:1-4, American Society of Clinical Oncology, United States (2021).

Brennan, F. R., et al., "Safety and immunotoxicity assessment of immunomodulatory monoclonal antibodies", mAbs, May 1, 2010, vol. 2, No. 3, pp. 233-255.

Frey, N. V. and Porter, D. L., "Cytokine release syndrome with novel therapeutics for acute lymphoblastic leukemia", Hematology American Society for Hematological Education Program, 2016, vol. 2016, No. 1, pp. 567-572.

Shimabukuro-Vornhagen, A., et al., "Cytokine release syndrome", Journal for ImmunoTherapy of Cancer, 2018, vol. 6, No. 56, 14 pages.

* cited by examiner

**\* No DLTs, additional slots per cohort to increase experience at this dose**

Note: DL1, 0.003 mg/kg was below level of quantification during cycle 1

FIG. 5B

Anti-pSTAT1 Y701
measured and
compared to pre-dose

FIG. 5A

T cells
77.6

T cells gated using an
anti-CD-3 antibody

Best Percent Change from Baseline in Sum of Target Lesions (n=27)

Best Percent Change from Baseline in Sum of Target Lesions (n=7)

| | | ◆ | Prior a-PD-(L)1 Therapy |
|---|---|---|---|
| 1 | ▨ | | DL1 (0.003 mg/kg) |
| 2 | ▨ | | DL2 (0.03 mg/kg) |
| 3 | ▨ | | DL3 (0.1 mg/kg) |
| 4 | | | DL4 (0.3 mg/kg) |
| 5 | ▨ | | DL5 (1.0 mg/kg) |
| 6 | ▨ | | DL6 (3.0 mg/kg) |
| 7 | ▨ | | DL7 (10.0 mg/kg) |
| 8 | ▨ | | DL8 (20.0 mg/kg) |

Target Lesion Change Over Time (n=7)

Note: 0.003 mg/kg Cycle 1 samples below the limit of quantitation

| | | | |
|---|---|---|---|
| 1 | —○— 0.03 mg/kg (n=1) | 5 | —○— 3.0 mg/kg (n=6) |
| 2 | —○— 0.1 mg/kg (n=1) | 6 | —○— 10.0 mg/kg (n=37) |
| 3 | 0.3 mg/kg (n=3) | 7 | —○— 20.0 mg/kg (n=6) |
| 4 | —○— 1.0 mg/kg (n=3) | ▲ | 10.0 mg/kg Q3W+Pembro (n=7) |

Best Percent Change from Baseline in Sum of Target Lesions (n=13)

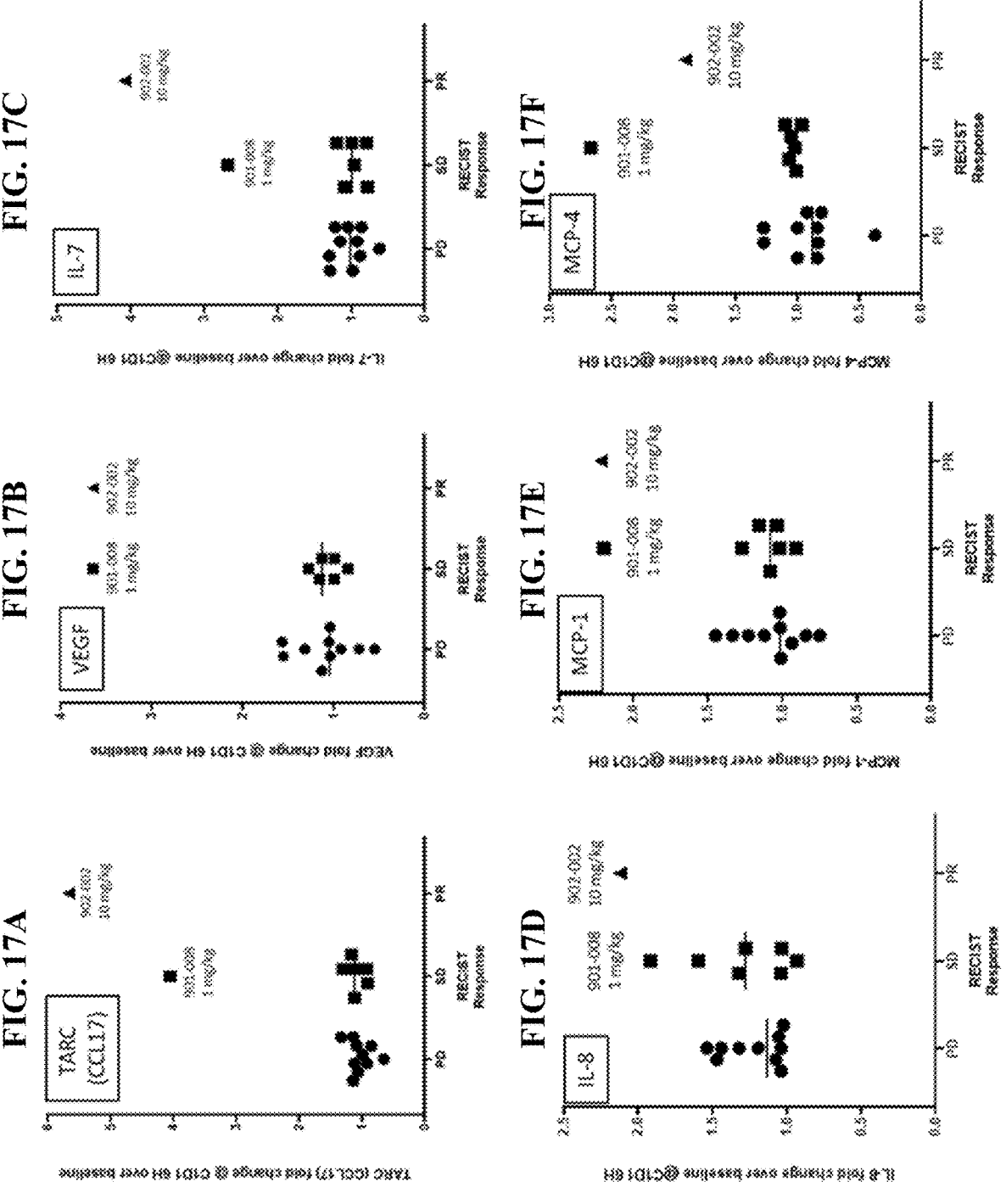

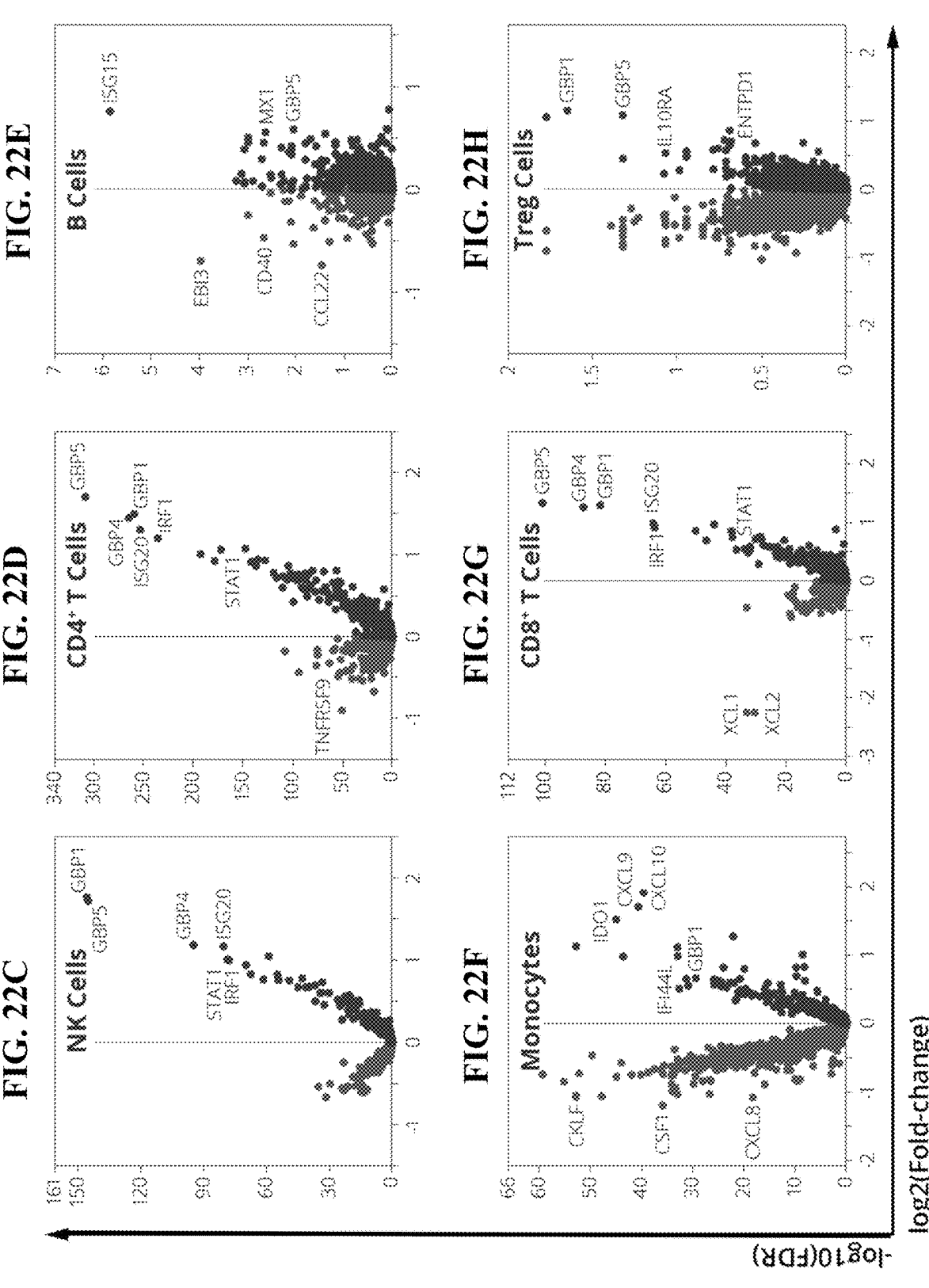

FIG. 24C          FIG. 24D
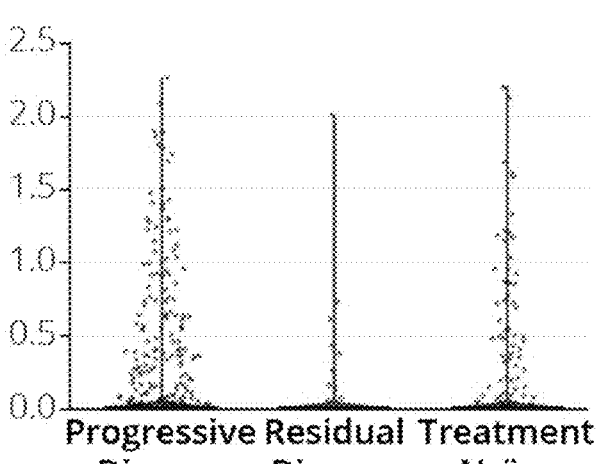 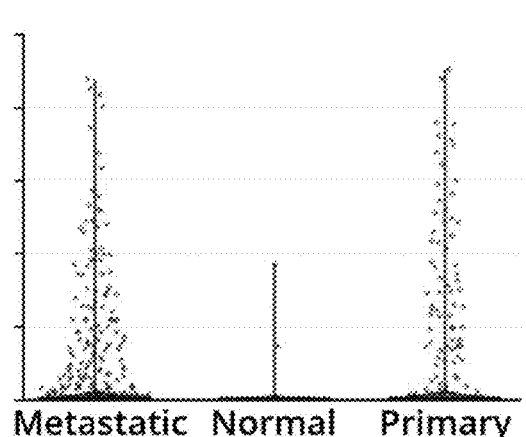
FIG. 24E
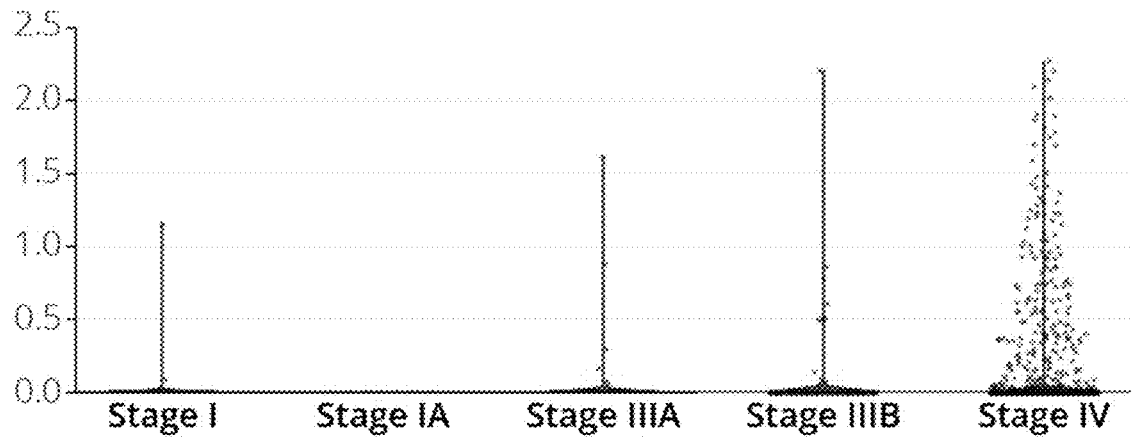

FIG. 24H

Lung SCC

FIG. 24G

Lung AdenoCa

ANTI-IL-27 ANTIBODIES AND USES THEREOF

CROSS-REFERENCE TO RELATED APPLICATION

This application claims priority to and benefit of U.S. Provisional Application Nos. U.S. 63/185,989, filed on May 7, 2021; U.S. 63/203,688, filed on Jul. 28, 2021; and U.S. 63/277,035, filed on Nov. 8, 2021; each of which is hereby incorporated by reference herein in its entirety.

REFERENCE TO SEQUENCE LISTING SUBMITTED ELECTRONICALLY VIA EFS-WEB

The content of the electronically submitted sequence listing (Name: 4416_0130004_Seqlisting_ST25.txt; Size: 156,680 bytes; and Date of Creation: May 6, 2022) is herein incorporated by reference in its entirety.

FIELD

The present disclosure relates generally to compositions and methods for modulating IL-27 signaling. More particularly, the present disclosure relates to immunogenic compositions (e.g., antibodies, antibody fragments, and the like) that bind to IL-27 and modulate IL-27 signaling.

BACKGROUND

In recent years, an increasing body of evidence suggests that the immune system operates as a significant barrier to tumor formation and progression. The principle that naturally occurring T cells with anti-tumor potential or activity exist in a patient with cancer has rationalized the development of immunotherapeutic approaches in oncology. Immune cells, such as T cells, macrophages, and natural killer cells, can exhibit anti-tumor activity and effectively control the occurrence and growth of malignant tumors. Tumor-specific or -associated antigens can induce immune cells to recognize and eliminate malignancies (Chen & Mellman, (2013) *Immunity* 39(1):1-10). In spite of the existence of tumor-specific immune responses, malignant tumors often evade or avoid immune attack through a variety of immunomodulatory mechanisms resulting in the failure to control tumor occurrence and progression (Motz & Coukos, (2013) *Immunity* 39(1):61-730). Indeed, an emerging hallmark of cancer is the exploitation of these immunomodulatory mechanisms and the disablement of anti-tumor immune responses, resulting in tumor evasion and escape from immunological killing (Hanahan and Weinberg (2011) *Cell* 144(5):646-674).

IL-27 is a heterodimeric cytokine, composed of two subunits (EBI3 and IL-27p28). IL-27 is structurally related to both the IL-12 and IL-6 cytokine families. IL-27 binds to and mediates signaling through a heterodimer receptor consisting of IL-27Rα (WSX1) and gp130 chains, which mediate signaling predominantly through STAT1 and STAT3. Initial reports characterized IL-27 as an immune-enhancing cytokine that supports CD4+ T cell proliferation, T helper (Th)1 cell differentiation, and IFN-γ production, often acting in concert with IL-12. Subsequent studies have shown that IL-27 displays complex immunomodulatory functions, resulting in either proinflammatory or anti-inflammatory effects depending on the biological context and experimental models being used. IL-27 may drive the expression of different immune-regulatory molecules in human cancer cells, which may support local derangement of the immune response in vivo (Fabbi et al., (2017) Mediators Inflamm 3958069. Published online 2017 Feb. 1. doi:10.1155/2017/3958069, and references contained therein).

Despite the significant advances being made in cancer treatment and management, there is still an ongoing need for new and effective therapies for treating and managing cancer.

SUMMARY OF THE DISCLOSURE

Some aspects of the present disclosure are directed to a method of stimulating an immune response in a subject, the method comprising administering to the subject an antibody that antagonizes human IL-27, or an antigen binding portion thereof, wherein the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii); wherein the antibody or antigen binding portion thereof is administered at a dose of at least about 0.003 mg/kg to at least about 20 mg/kg.

Some aspects of the present disclosure are directed to a method of treating a cancer in a subject in need thereof comprising administering to the subject an antibody that antagonizes human IL-27, or an antigen binding portion thereof, wherein the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii); wherein the antibody or antigen binding portion thereof is administered at a dose of at least about 0.003 mg/kg to at least about 20 mg/kg.

In some aspects, the antibody or antigen binding portion thereof is administered at a dose of at least about 0.003 mg/kg, at least about 0.006 mg/kg, at least about 0.009 mg/kg, at least about 0.03 mg/kg, at least about 0.06 mg/kg, at least about 0.09 mg/kg, at least about 0.3 mg/kg, at least about 0.6 mg/kg, at least about 0.9 mg/kg, at least about 1.0 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, or at least about 20 mg/kg.

In some aspects, the antibody or antigen binding portion thereof is administered once about every week, once about every two weeks, once about every three weeks, once about every four weeks, once about every 6 weeks, once about every 8 weeks, or once about every 12 weeks.

In some aspects, the antibody or antigen binding portion thereof is administered once about every four weeks. In some aspects, the antibody or antigen binding portion thereof is administered at a dose of about 0.3 mg/kg once about every four weeks. In some aspects, the antibody or antigen binding portion thereof is administered at a dose of about 1 mg/kg once about every four weeks. In some aspects, the antibody or antigen binding portion thereof is administered at a dose of about 3 mg/kg once about every four weeks. In some aspects, the antibody or antigen binding portion thereof is administered at a dose of about 6 mg/kg once about every four weeks. In some aspects, the antibody or antigen binding portion thereof is administered at a dose of about 10 mg/kg once about every four weeks. In some aspects, the antibody or antigen binding portion thereof is administered at a dose of about 13 mg/kg once about every four weeks. In some aspects, the antibody or antigen binding portion thereof is administered at a dose of about 16 mg/kg once about every four weeks. In some aspects, the antibody or antigen binding portion thereof is administered at a dose of about 20 mg/kg once about every four weeks.

In some aspects, the antibody or antigen binding portion thereof inhibits or reduces IL-27-dependent STAT1 and/or STAT3 phosphorylation in a cell in the subject. In some aspects, the antibody or antigen binding portion thereof inhibits or reduces inhibition of CD161 expression in a cell in the subject. In some aspects, the antibody or antigen binding portion thereof inhibits or reduces PD-L1 expression in a cell in the subject. In some aspects, the antibody or antigen binding portion thereof induces or enhances PD-1 mediated secretion of one or more cytokines from a cell in the subject. In some aspects, the anti-IL-27 antibody alters the expression of TIM-3 in a cell. In some aspects, the cell is a tumor cell or an immune cell.

In some aspects, the epitope comprises one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, or Glu164 of SEQ ID NO: 2 (IL-27p28). In some aspects, the epitope comprises Asp146, Arg149, and/or Phe153 of SEQ ID NO: 2 (IL-27p28). In some aspects, the epitope further comprises His150 and/or Leu156 of SEQ ID NO: 2 (IL-27p28). In some aspects, the epitope further comprises Gln37, Leu38, Glu42, Leu142, and/or Glu164 of SEQ ID NO: 2 (IL-27p28). In some aspects, the epitope further comprises Glu46, Val49, Ser50, and/or Leu162 of SEQ ID NO: 2 (IL-27p28). In some aspects, the epitope consists or consists essentially of Gln37, Leu38, Glu42, Glu46, Val49, Ser50, Leu142, Asp146, Arg149, His150, Phe153, Leu156, Leu162, and Glu164 of SEQ ID NO: 2 (IL-27p28). In some aspects, the epitope further comprises one or more amino acids of Leu53, Lys56, Asp143, Leu147, Arg152, Ala157, Gly159, Phe160, or Asn161 of SEQ ID NO: 2 (IL-27p28). In some aspects, the epitope further comprises one or more amino acids of Leu53, Lys56, Asp143, Arg145, Leu147, Arg152, Ala157, Gly159, Phe160, Asn161, or Pro163 of SEQ ID NO: 2 (IL-27p28). In some aspects, the epitope consists or consists essentially of Gln37, Leu38, Glu42, Glu46, Val49, Ser50, Leu53, Lys56, Leu142, Asp143, Asp146, Leu147, Arg149, His150, Arg152, Phe153, Leu156, Ala157, Gly159, Phe160, Asn161, Leu162, and Glu164 of SEQ ID NO: 2 (IL-27p28). In some aspects, the epitope consists or consists essentially of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164, of SEQ ID NO: 2 (IL-27p28).

In some aspects, the antibody or the antigen binding portion thereof comprise heavy chain CDR1, heavy chain CDR2, heavy chain CDR3, light chain CDR1, light chain CDR2, and light chain CDR3, wherein (i) light chain CDR1 consists of N-XXXXXXLFSSNXKXYXX-C, light chain CDR3 consists of N-XXXASAXXX-C, heavy chain CDR2 consists of N-XXSSSXSYXYXXXXXXX-C, and heavy chain CDR3 consists of N-XXXXGRTSYTATXHNXXXX-C, wherein X is any amino acids.

In some aspects, the antibody or the antigen binding portion thereof comprises a heavy chain CDR3 comprising the sequence set forth in SEQ ID NO: 121 or 124. In some aspects, the antibody or the antigen binding portion thereof comprises a heavy chain CDR2 comprising the sequence set forth in SEQ ID NO: 120 or 123. In some aspects, the antibody or the antigen binding portion thereof comprises a heavy chain CDR1 comprising the sequence set forth in SEQ ID NO: 119 or 122. In some aspects, the antibody or the antigen binding portion thereof comprises a light chain CDR3 comprising the sequence set forth in SEQ ID NO: 129 or 132. In some aspects, the antibody or the antigen binding portion thereof comprises a light chain CDR2 comprising the sequence set forth in SEQ ID NO: 128 or 131. In some aspects, the antibody or the antigen binding portion thereof comprises a light chain CDR1 comprising the sequence set forth in SEQ ID NO: 127 or 130.

In some aspects, the antibody or the antigen binding portion thereof comprises: (a) a heavy chain CDR1 comprising the amino acid sequence set forth in SEQ ID NO: 119, a heavy chain CDR2 comprising the amino acid sequence set forth in SEQ ID NO: 120, and a heavy chain CDR3 comprising the amino acid sequence set forth in SEQ ID NO: 121; or (b) a heavy chain CDR1 comprising the amino acid sequence set forth in SEQ ID NO: 122, a heavy chain CDR2 comprising the amino acid sequence set forth in SEQ ID NO: 123, and a heavy chain CDR3 comprising the amino acid sequence set forth in SEQ ID NO: 124.

In some aspects, the antibody or the antigen binding portion thereof comprises: (a) a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129; or (b) a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132.

In some aspects, the antibody or the antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129.

In some aspects, the antibody or the antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132.

In some aspects, the antibody or the antigen binding portion thereof comprises a heavy chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 125. In some aspects, the antibody or the antigen binding portion thereof comprises a heavy chain variable region comprising the amino acid sequence set forth in SEQ ID NO: 125. In some aspects, the antibody or the antigen binding portion thereof comprises a light chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 133. In some aspects, the antibody or the antigen binding portion thereof comprises a light chain variable region comprising the amino acid sequence set forth in SEQ ID NO: 133. In some aspects, the antibody or the antigen binding portion thereof comprises a heavy chain variable region comprising the amino acid sequence set forth in SEQ ID NO: 125 and a light chain variable region comprising the amino acid sequence set forth in SEQ ID NO: 133.

In some aspects, the antibody or the antigen binding portion thereof comprises a heavy chain comprising the amino acid sequence set forth in SEQ ID NO: 135. In some aspects, the antibody or the antigen binding portion thereof comprises a heavy chain comprising the amino acid sequence set forth in SEQ ID NO: 139. In some aspects, the antibody or the antigen binding portion thereof comprises a light chain comprising the amino acid sequence set forth in SEQ ID NO: 137. In some aspects, the antibody or the antigen binding portion thereof comprises a heavy chain comprising the amino acid sequence set forth in SEQ ID NO: 135 and a light chain comprising the amino acid sequence set forth in SEQ ID NO: 137. In some aspects, the antibody or the antigen binding portion thereof comprises a heavy chain comprising the amino acid sequence set forth in SEQ ID NO: 139 and a light chain comprising the amino acid sequence set forth in SEQ ID NO: 137.

In some aspects, the cancer is selected from lung cancer (e.g., non-small cell lung cancer), sarcoma, testicular cancer, ovarian cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma (HCC), gastric cancer, brain cancer, lymphoma (e.g., DL-BCL), leukemia (e.g., AML), renal cancer (e.g., renal cell carcinoma (RCC), e.g., clear cell RCC and/or non-clear cell RCC), and any combination thereof.

In some aspects, the method further comprises administering an additional therapeutic agent to the subject. In some aspects, the additional therapeutic agent is administered before the antibody or antigen-binding portion thereof, after the antibody or antigen-binding portion thereof, or concurrently with the antibody or antigen-binding portion thereof.

In some aspects, the additional therapeutic agent comprises a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, a cellular immunotherapy, a biologic agent, or a combination thereof. In some aspects, the additional therapeutic agent comprises a PD-1 antagonist, a PD-L1 inhibitor, a TIM-3 inhibitor, a LAG-3 inhibitor, a TIGIT inhibitor, a CD112R inhibitor, a TAM inhibitor, a STING agonist, a 4-1BB agonist, or a combination thereof.

In some aspects, the additional therapeutic agent comprises a PD-1 antagonist. In some aspects, the PD-1 antagonist is selected from the group consisting of: PDR001, nivolumab, pembrolizumab, pidilizumab, MEDI0680, REGN2810, TSR-042, PF-06801591, and AMP-224. In some aspects, the PD-L1 inhibitor is selected from the group consisting of: FAZ053, Atezolizumab, Avelumab, Durvalumab, and BMS-936559. In some aspects, the additional therapeutic agent is selected from the group consisting of Sunitinib)(SUTENT®, Cabozantinib (CABOMETYX®), Axitinib (INLYTA®), Lenvatinib (LENVIMA®), Everolimus (AFINITOR®), Bevacizumab (AVASTIN®), epacadostat, NKTR-214 (CD-122-biased agonist), Tivozanib (FOTIVDA®), abexinostat, Ipilimumab (YERVOY®), tremelimumab, Pazopanib (VOTRIENT®), Sorafenib (NEXAVAR®), Temsirolimus (TORISE®), Ramucirumab (CYRAMZA®), niraparib, savolitinib, vorolanib (X-82), Regorafenib (STIVARGO®), Donafenib (multikinase inhibitor), Camrelizumab (SHR-1210), pexastimogene devacirepvec (JX-594), Ramucirumab (CYRAMZA®), apatinib (YN968D1), encapsulated doxorubicin (THERMO-DOX®), Tivantinib (ARQ197), ADI-PEG 20, binimetinib, apatinib mesylate, nintedanib, lirilumab, Nivolumab) (OP-DIVO®), Pembrolizumab (KEYTRUDA®), Atezolizumab (TECENTRIQ®), Avelumab (BAVENCIO®), Durvalumab (IMFIMZI®), Cemiplimab-rwlc (LIB TAYO®), tislelizumab, and spartalizumab. In some aspects, the additional therapeutic agent is a TIM-3 inhibitor. In some aspects, the TIM-3 inhibitor is MGB453 or TSR-022. In some aspects, the additional therapeutic agent is a LAG-3 inhibitor. In some aspects, the LAG-3 inhibitor is selected from the group consisting of LAG525, BMS-986016, and TSR-033. In some aspects, the additional therapeutic agent is a TIGIT inhibitor. In some aspects, the additional therapeutic agent is a CD112R inhibitor. In some aspects, the additional therapeutic agent is a TAM (Axl, Mer, Tyro) inhibitor. In some aspects, the additional therapeutic agent is a 4-1BB agonist. In some aspects, the additional therapeutic agent is a Tyrosine Kinase Inhibitor (TKI).

In some aspects, following administration antibody or antigen binding portion thereof, the subject exhibits increased expression of one or more biomarkers selected from the group consisting of EBI3, IL-27, TNFα, MIP-1α (CCL3), IFNγ, IL-10, IL-6, and any combination thereof; wherein the increased expression of the one or more biomarkers is relative to the expression of the one or more biomarker prior to the administration. In some aspects, following administration antibody or antigen binding portion thereof, the subject exhibits increased expression of EBI3; wherein the increased expression EBI3 is relative to the expression EBI3 prior to the administration.

In some aspects, following administration antibody or antigen binding portion thereof, the subject exhibits increased expression of one or more biomarkers selected from the group consisting of Eotaxin-1 (CCL11), TARC (CCL17), VEGF-A, IL-7, IL-8, MCP-1, MCP-4, and any combination thereof; wherein the increased expression of the one or more biomarkers is relative to the expression of the one or more biomarker prior to the administration. In some aspects, following administration antibody or antigen binding portion thereof, the subject exhibits increased expression of Eotaxin-1 (CCL11), wherein the increased expression of Eotaxin-1 (CCL11) is relative to the expression of Eotaxin-1 (CCL11) prior to the administration.

In some aspects, following administration antibody or antigen binding portion thereof, the subject exhibits an increased circulating level of IFNγ, relative to the circulating level of IFNγ prior to the administration.

BRIEF DESCRIPTION OF THE DRAWINGS

Figures 5A, 5B:
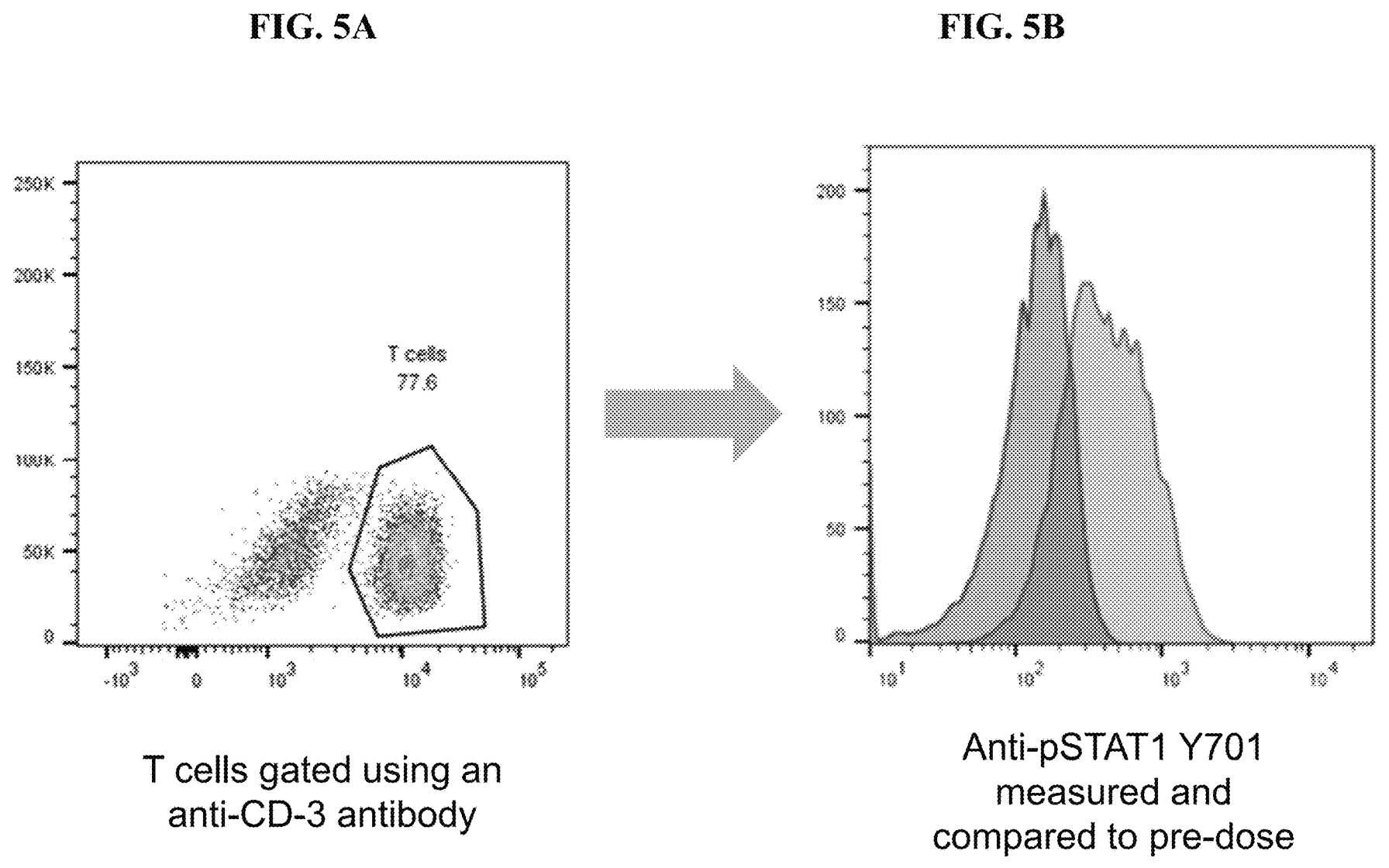

FIGS. 5A-5B are graphical representation of T cells gated using an anti-CD-3 antibody (FIG. 5A) and analyzed using an anti-pSTAT1 Y701 antibody, as compared to pre-dose (FIG. 5B).

FIGS. 6A and 6D are images at baseline, FIGS. 6B and 6E are images at week 8, and FIGS. 6C and 6F are images at week 12.

FIG. 8A is a waterfall plot depicting the best percentage change in target lesions from baseline (n=27). FIG. 8B is a spider plot depicting the target lesion change from baseline over time.

FIG. 9A is a waterfall plot depeciting the best percentage chaine in sum of target lesions. FIG. 9B is a spider plot depicting the lesion change over time.

FIG. 10A shows Cycle 1 anti-IL-27 Ab1 PK by dose regimen, irrespective of tumor type.

FIG. 10B shows the PK of anti-IL-27 Ab1 when given once every four weeks as monotherapy in the dose escalation phase of the study (mixed solid tumors) and in the HCC and ccRCC expansions.

FIG. 11A is a waterfall plot depeciting the best percentage chaine in sum of target lesions. FIG. 11B is a spider plot depicting the lesion change over time.

FIG. 12A is a waterfall plot depeciting the best percentage chaine in sum of target lesions. FIG. 12B is a spider plot depicting the lesion change over time.

FIGS. 17A-17F are graphical representations of fold-change expression relative to baseline of TARC (CCL17; FIG. 17A), VEGF-A (FIG. 17B), IL-7 (FIG. 17C), IL-8 (FIG. 17D), MCP-1 (FIG. 17E), and MCP-4 (FIG. 17F) in samples obtained from pateints administered anti-IL-27 Ab1.

FIG. 21A highlights (gray) enrichment of mRNA signatures associated with interferon signaling. FIG. 21B highlights (gray) hallmark IFNα signature genes.

FIG. 22A-22H are graphical representations of single cell RNA-sequencing analysis of PBMCs stimulated with anti-CD3 (0.25 µg/ml) in vitro in the presence or absence of rhIL-27 (100 ng/ml). FIG. 22A shows the clustering of the various types of immune cells. FIG. 22B is a volcano plot illustrating IL-27-mediated gene expression changes identified in the total PBMC population, which included many interferon-stimulated genes. FIGS. 22C-2211 are volcano plots illustrating the downregulation and upregulation of IL-27 signature genes in the immune cell subsets of NK cells (FIG. 22C), CD4⁺ T cells (FIG. 22D), B cells (FIG. 22E), monocytes (FIG. 22F), CD8⁺ T cells (FIG. 22G) and Treg cells (FIG. 2211).

FIGS. 23A-23B are bar graphs illustrating assessment of IL-17A (FIG. 23A) and IFN-γ (FIG. 23B) in cultured supernatants of pooled PBMCs activated in the presence of anti-CD3 (0.25 μg/ml) and anti-PD-1 (1 μg/ml) in the presence of various cytokines (100 ng/ml; x-axis) for 4 days.

FIGS. 24C-24E are graphical representations illustrating increased expression of IL27 in macrophages from patients with progressive disease (FIG. 24C); in macrophages from metastatic and primary tumors compared to normal tissue (FIG. 24F); and in macrophages from patients with Stage IV disease (FIG. 24E). FIGS. 24G-24H are images of immunohistochemistry for IL-27 on tissue microarrays showing positive expression in macrophages in the TME of lung adenocarcinoma (AdenoCa; FIG. 24G) and squamous cell carcinoma (SCC; FIG. 2411).

DETAILED DESCRIPTION

Figure 1A:
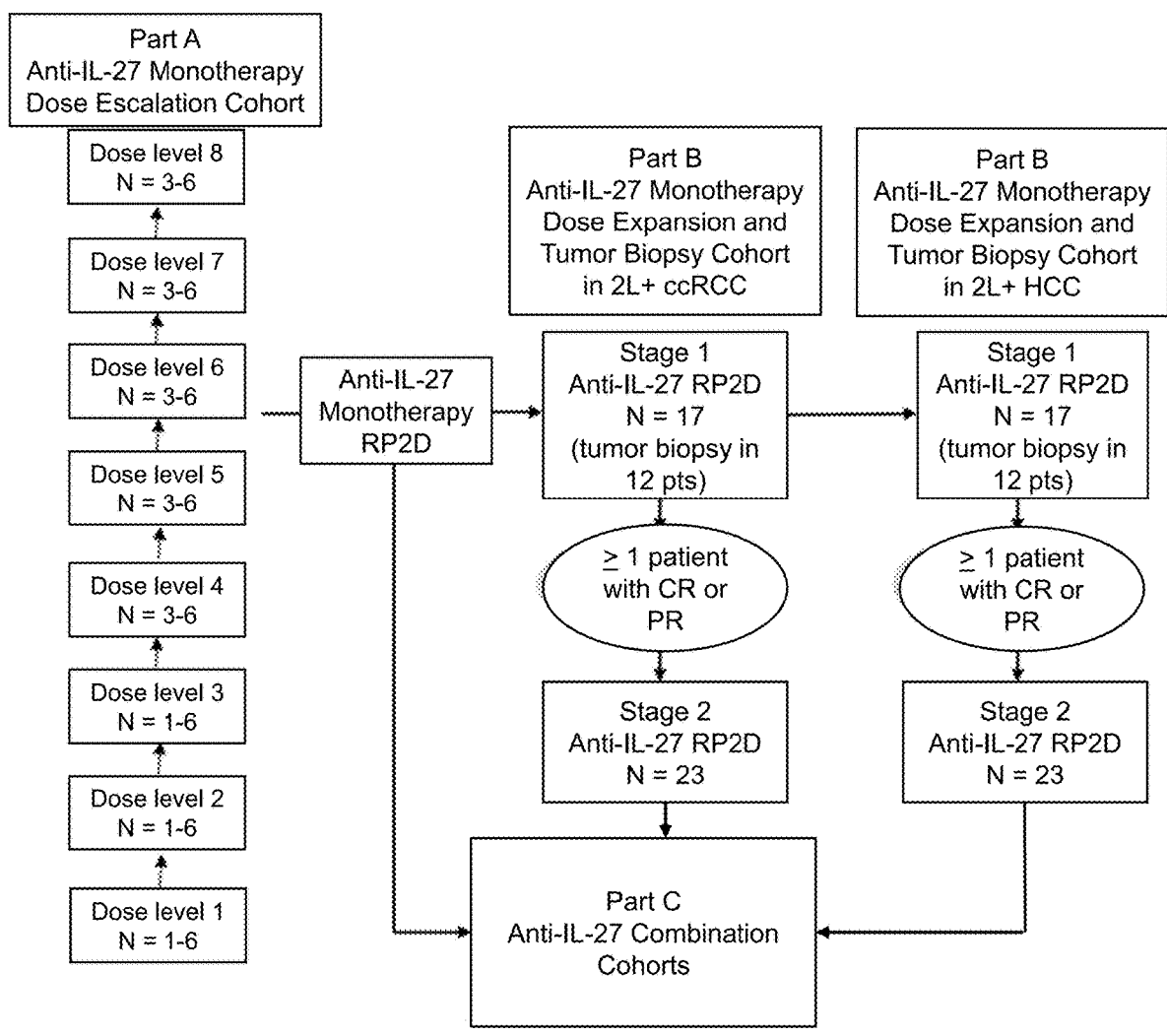
FIGS. 1A-1C are schematics of a phase 1 dose-escalation study for an anti-IL-27 antibody. ccRCC=clear cell renal cell carcinoma; CR=complete response; HCC=hepatocellular carcinoma; N=number; PR=partial response; pts=patients, RP2D=recommended Phase 2 dose; 2L=second line. Dose level 1=0.003 mg/kg; Dose level 2=0.03 mg/kg; Dose level 3=0.1 mg/kg; Dose level 4=0.3 mg/kg; Dose level 5=1.0 mg/kg; Dose level 6=3.0 mg/kg; Dose level 7=10.0 mg/kg; Dose level 8=20.0 mg/kg (FIG. 1A).

Some aspects of the present disclosure are directed to methods of stimulating an immune response in a subject, the method comprising administering to the subject an antibody or an antigen binding portion thereof that antagonizes human IL-27, or an antigen binding portion thereof. Some aspects of the present disclosure are directed to methods of treating a cancer in a subject in need thereof comprising administering to the subject an antibody that antagonizes human IL-27, or an antigen binding portion thereof. In some aspects, the antibody or an antigen binding portion thereof is administered at a dose of at least about 0.003 mg/kg to at least about 20 mg/kg. In some aspects, the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii).

I. Definitions

Terms used in the claims and specification are defined as set forth below unless otherwise specified.

It must be noted that, as used in the specification and the appended claims, the singular forms "a," "an" and "the" include plural references unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "agonist" refers to any molecule that partially or fully promotes, induces, increases, and/or activates a biological activity of a native polypeptide disclosed herein. Suitable agonist molecules specifically include agonist antibodies or antibody fragments, fragments or amino acid sequence variants of native polypeptides, peptides or proteins. In some aspects, activation in the presence of the agonist is observed in a dose-dependent manner. In some aspects, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), FORTE BIO® systems, and radioimmunoassay (RIA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

As used herein, the term "alanine scanning" refers to a technique used to determine the contribution of a specific wild-type residue to the stability or function(s) (e.g., binding affinity) of given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "amount" or "level" is used in the broadest sense and refers to a quantity, concentration or abundance of a substance (e.g., a metabolite, a small molecule, a protein, an mRNA, a marker). When referring to a metabolite or small molecule (e.g. a drug), the terms "amount", "level" and "concentration" are generally used interchangeably and generally refer to a detectable amount in a biological sample. "Elevated levels" or "increased levels" refers to an increase in the quantity, concentration or abundance of a substance within a sample relative to a control sample, such as from an individual or individuals who are not suffering from the disease or disorder (e.g., cancer) or an internal control. In some aspects, the elevated level of a substance (e.g., a drug) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., HPLC). "Reduced levels" refers to a decrease in the quantity, concentration or abundance of a substance (e.g., a drug) in an individual relative to a control, such as from an individual or individuals who are not suffering from the disease or disorder (e.g., cancer) or an internal control. In some aspects, a reduced level is little or no detectable quantity, concentration or abundance. In some aspects, the reduced level of a substance (e.g., a drug) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, HPLC).

When referring to a protein, mRNA or a marker, such as those described herein, the terms "level of expression" or "expression level" in general are used interchangeably and generally refer to a detectable amount of a protein, mRNA, or marker in a biological sample. In some aspects, a detectable amount or detectable level of a protein, mRNA or a marker is associated with a likelihood of a response to an agent, such as those described herein. "Expression" generally refers to the process by which information contained within a gene is converted into the structures (e.g., a protein marker, such as PD-L1) present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). "Elevated expression," "elevated expression levels," or "elevated levels" refers to an increased expression or increased levels of a substance within a sample relative to a control sample, such as an individual or individuals who are not suffering from the disease or disorder (e.g., cancer) or an internal control. In some aspects, the elevated expression of a substance (e.g., a protein marker, such as PD-L1) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., FACS). "Reduced expression," "reduced expression levels," or "reduced levels" refers to a decrease expression or decreased levels of a substance (e.g., a protein marker) in an individual relative to a control, such as an individual or individuals who are not suffering from the disease or disorder (e.g., cancer) or an internal control. In some aspects, reduced expression is little or no expression. In some aspects, the reduced expression of a substance (e.g., a protein marker) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, FACS).

As used herein, the term "angiogenesis" or "neovascularization" refers to the process by which new blood vessels develop from pre-existing vessels (Varner et al., (1999) *Angiogen.* 3:53-60; Mousa et al., (2000) *Angiogen. Stim Inhib.* 35:42-44; Kim et al., (2000) *Amer. J. Path.* 156:1345-1362.; Kim et al., (2000) *J. Biol. Chem.* 275:33920-33928; Kumar et al. (2000) *Angiogenesis: Front Molecular to Integrative Pharm.* 169-180), Endothelial cells from preexisting blood vessels or from circulating endothelial stem cells (Takahashi et al., (1995) *Nat. Med.* 5:434-438; Isner et al., (1999) *J. Clin. Invest.* 103:1231-1236) become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

The term "antagonist," as used herein, refers to an inhibitor of a target molecule and may be used synonymously herein with the term "inhibitor." As used herein, the term "antagonist" refers to any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides or proteins. In some aspects, inhibition in the presence of the antagonist is observed in a dose-dependent manner. In some aspects, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), ForteBio®systems, radioimmunoassay (RIA), Meso Scale Discovery assay (e.g., Meso Scale Discovery Electrochemiluminescence (MSD-ECL), and bead-based Luminex® assay. These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the phrase "antibody that antagonizes human IL-27, or an antigen binding portion thereof" refers to an antibody that antagonizes at least one art-recognized activity of human IL-27 (e.g., IL-27 biological activity and/or downstream pathway(s) mediated by IL-27 signaling or other IL-27-mediated function), for example, relating to a decrease (or reduction) in human IL-27 activity that is at least 5%, 10%, 20%, 30%, 40%, 50%, 60%, 70%, 80%, 90%, or more. Additional examples of IL-27 biological activities and/or downstream pathway(s) mediated by IL-27 signaling or other IL-27-mediated function are described in additional detail below and elsewhere herein.

As used herein, the term "anti-IL-27 antagonist antibody" (interchangeably termed "anti-IL-27 antibody") refers to an antibody that specifically binds to IL-27 and inhibits IL-27 biological activity and/or downstream pathway(s) mediated by IL-27 signaling or other IL-27-mediated function. An anti-IL-27 antagonist antibody encompasses antibodies that block, antagonize, suppress, inhibit or reduce an IL-27 biological activity (e.g., ligand binding, enzymatic activity), including downstream pathways mediated by IL-27 signaling or function, such as receptor binding and/or elicitation of a cellular response to IL-27 or its metabolites. In some aspects, an anti-IL-27 antagonist antibody provided by the disclosure binds to human IL-27 and prevents, blocks, or inhibits binding of human IL-27 to its cognate or normal receptor (e.g., IL-27 receptor), or one or more receptor subunits (e.g., gp130 and/or IL-27Rα (also known as WSX1/TCCR)). In some aspects, the anti-IL-27 antagonist antibody prevents, blocks, or inhibits the binding of human IL-27 to the gp130. In some aspects, the anti-IL-27 antagonist antibody prevents, blocks, or inhibits the binding of human IL-27 to the IL-27Ra. In some aspects, the anti-IL-27 antagonist antibody prevents, blocks, or inhibits the dimerization of IL-27 monomers. In some aspects, the anti-IL-27 antibody does not specifically bind to the EBI3 monomer. In some aspects, the anti-IL-27 antibody specifically binds to the IL-27p28 monomer. In some aspects, the anti-IL-27 antibody specifically binds to a non-contiguous epitope comprising P28, but does not bind to the EBI3 monomer. In some aspects, the anti-IL-27 antibody inhibits or reduces STAT1 and/or STAT3 phosphorylation in a cell. In some aspects, the anti-IL-27 antibody inhibits or reduces inhibition of CD161 expression in a cell (e.g., ameliorates or relieves IL-27 mediated inhibition of CD161 expression in a cell). In some aspects, the anti-IL-27 antibody inhibits or reduces PD-L1 expression in a cell. In some aspects, the anti-IL-27 induces or enhances PD-1-mediated secretion of one or more cytokines from a cell. In some aspects, the anti-IL-27 antibody alters the expression of TIM-3 in a cell. In some aspects, an anti-IL-27 antagonist antibody binds to human IL-27 and stimulates or enhances an anti-tumor response. In some aspects, the anti-IL-27 antagonist antibody binds to human IL-27 with an affinity of 15 nM or less. In some aspects, the anti-IL-27 antagonist antibody binds to human IL-27 and comprises a wild type or mutant IgG1 heavy chain constant region or a wild type or mutant IgG4 heavy chain constant region. Examples of anti-IL-27 antagonist antibodies are provided herein.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody. As used herein, the term "antibody fragment," "antigen-binding fragment," or similar terms refer to a fragment of an antibody that retains the ability to bind to a target antigen (e.g., IL-27) and inhibit the activity of the target antigen. Such fragments include, e.g., a single chain antibody, a single chain Fv fragment (scFv), an Fd fragment, an Fab fragment, an Fab' fragment, or an F(ab')2 fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) *J. Immunol.* Methods 248(1): 47-66; Hudson and Kortt, (1999) 1 *Immunol.* Methods 231(1):177-189; Poljak, (1994) *Structure* 2(12): 1121-1123; Rondon and Marasco, (1997) *Annu. Rev. Microbiol.* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) *Trends Biochem. Sci.* 26:230-235; Nuttall et al., (2000) *Curr. Pharm. Biotech.* 1:253-263; Reichmann et al., (1999) *J. Immunol. Meth.* 231:25-38; PCT application publication nos. WO 94/04678 and WO 94/25591; and U.S. Pat. No. 6,005,079, all of which are incorporated herein by reference in their entireties. In some aspects, the disclosure provides single domain antibodies comprising two VH domains with modifications such that single domain antibodies are formed.

In some aspects, an antigen-binding fragment includes the variable region of a heavy chain polypeptide and the variable region of a light chain polypeptide. In some aspects, an antigen-binding fragment described herein comprises the CDRs of the light chain and heavy chain polypeptide of an antibody.

The term "antigen presenting cell" or "APC" is a cell that displays foreign antigen complexed with MHC on its surface. T cells recognize this complex using T cell receptor (TCR). Examples of APCs include, but are not limited to, B cells, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or WW-II conjugate.

As used herein, the term "apoptosis" refers to the process of programmed cell death that occurs in multicellular organisms (e.g. humans). The highly regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

As used herein, the term "B cell" (alternatively "B lymphocyte") refers to a type of white blood cell of the lymphocyte subtype. B cells function in the humoral immunity component of the adaptive immune system by secreting antibodies. B cells also present antigen and secrete cytokines. B cells, unlike the other two classes of lymphocytes, T cells and natural killer cells, express B cell receptors (BCRs) on their cell membrane. BCRs allow the B cell to bind to a specific antigen, against which it will initiate an antibody response.

As used herein, the term "binds to immobilized IL-27," refers to the ability of an antibody of the disclosure to bind to IL-27, for example, expressed on the surface of a cell or which is attached to a solid support.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992)*J. Immunol.* 148:1547-1553.

Traditionally, the recombinant production of bispecific antibodies is based on the co-expression of two immunoglobulin heavy-chain/light-chain pairs, where the two heavy chain/light chain pairs have different specificities (Milstein and Cuello, (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) *Methods Enzymol.* 121:210; PCT Publication No. WO 96/27011; Brennan et al., (1985) *Science* 229:81; Shalaby et al., *J. Exp. Med.* (1992) 175:217-225; Kostelny et al., (1992) 1 *Immunol.* 148(5): 1547-1553; Hollinger et al., (1993) *Proc. Natl. Acad. Sci. USA* 90:6444-6448; Gruber et al., (1994) *J. Immunol.* 152: 5368; and Tutt et al., (1991) *J. Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

Antibodies with more than two valencies (e.g., trispecific antibodies) are contemplated and described in, e.g., Tutt et al. (1991) *J Immunol* 147:60.

The disclosure also embraces variant forms of multi-specific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some aspects, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

As used herein, "cancer antigen" or "tumor antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "cancer-specific immune response" refers to the immune response induced by the presence of tumors, cancer cells, or cancer antigens. In certain aspects, the response includes the proliferation of cancer antigen specific lymphocytes. In certain aspects, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain aspects, the cancer-specific immune response is a T cell response.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-IL-27 antibodies described herein can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "CD112R" refers to a member of poliovirus receptor—like proteins and is a co-inhibitory receptor for human T cells. CD112R is an inhibitory receptor primarily expressed by T cells and NK cells and competes for CD112 binding with the activating receptor CD226. The interaction of CD112 with CD112R is of higher affinity than with CD226 and thereby effectively regulates CD226 mediated cell activation. Anti-CD112R antagonists that block the interaction with CD112 limit inhibitory signaling directly downstream of CD112R while simultaneously promoting greater immune cell activation by increasing CD226 interactions with CD112. As used herein the term "CD112R inhibitor" refers to an agent that disrupts, blocks or inhibits the biological function or activity of CD112R.

As used herein, the term "CD137" (alternatively "4-1BB") refers to a member of the tumor necrosis factor (TNF) receptor superfamily. 4-1BB is a co-stimulatory immune checkpoint molecule, primarily for activated T cells. Crosslinking of CD137 enhances T cell proliferation, IL-2 secretion, survival and cytolytic activity. As used herein, the term "4-1BB agonist" refers to an agent that stimulates, induces or increases one or more function of 4-1BB. An exemplary 4-1BB agonist is Utomilumab (PF-05082566), a fully human IgG2 monoclonal antibody that targets this 4-1BB to stimulate T cells.

As used herein, the term "CD161" (alternatively known as Killer cell lectin-like receptor subfamily B, member 1 (KLRB1); NK1.1, or NKR-P1A) refers to a member of the C-type lectin superfamily. CD161 is a marker of T cells and CD161 expression has been associated with T cell infiltration into the tumor microenvironment for a number of different cancer types. CD161 is further described in Fergusson et al., (2014) Cell Reports 9(3):1075-1088, which is incorporated herein by reference it its entirety.

As used herein, the term "IL-27" or "interleukin 27" refers to the IL-27 cytokine. IL-27 is related to the IL-6/IL-12 cytokine families, and is a heterodimeric cytokine that comprises a first subunit known as Epstein-Barr Virus Induced Gene 3 (EBI3; also known as IL-27 subunit β and IL-27B) and a second subunit known as IL-27p28 (also known as IL30, IL-27 subunit α and IL-27A). IL-27 is predominantly synthesized by activated antigen-presenting cells including monocytes, endothelial cells and dendritic cells (Jankowski et al. (2010) Arch Immunol. Ther. Exp. 58:417-425, Diakowski et al. (2013) Adv. Clin. Exp. Med. (2013) 22(5): 683-691). Although IL-27 can have proinflammatory effects, many studies suggest an important role of IL-27 as an immunosuppressive agent (Shimizu et al. (2006) J. Immunol. 176:7317-7324, Hisada et al. (2004) Cancer Res. 64:1152-1156, Diakowski (2013) supra). Although it was initially described as a factor promoting the initiation of Th1 responses, IL-27 was later found to play a major T-cell suppressive function by limiting Th1 responses, inhibiting Th2 and Th17 cell differentiation, and regulating the development of Tr1 and other T regulatory cell populations (Dietrich et al. (2014) J. Immunol. 192:5382-5389). In addition to its role as an immunoregulator, IL-27 also regulates angiogenesis, hematopoiesis, and osteocalstogenesis (Id.).

IL-27 signals through a heterodimeric type I cytokine receptor (the IL-27 receptor or IL-27R) that comprises a first subunit known as WSX1 (also known as IL-27 receptor subunit α, IL-27RA, T-Cell Cytokine Receptor Type 1 (TCCR), and Cytokine Receptor-Like 1 (CRL1)) and a second subunit known as gp130 (also known as Interleukin-6 Signal Transducer (IL6ST), Interleukin-6 Receptor Subunit β (IL-6RB), and Oncostatin M Receptor). gp130 is also a receptor subunit for the IL-6 family cytokines (Liu et al. (2008) Scan. J. Immunol. 68:22-299, Diakowski (2013) supra). IL-27 signaling through IL-27R activates multiple signaling cascades, including the JAK-STAT and p38 MAPK pathways.

EBI3 is also believed to have biological functions independent of p28 or the IL-27 heterodimer. For example, EBI3 also interacts with p35 to form the heterodimeric cytokine IL-35 (Yoshida et al. (2015) Annu. Rev Immunol. 33:417-

43) and has been shown to be selectively overexpressed in certain cell types without a corresponding increase in p28 or IL-27 (Larousserie et al. (2005) Am. J. Pathol. 166(4):1217-28).

An amino acid sequence of an exemplary human EBI3 protein is provided in SEQ ID NO: 1
(NCBI Reference Sequence: NP_005746.2;
N-mtpqlllalvlwascppcsgrkgppaaltlprvqcrasrypiavdcs wtlppapnstspvsfiatyrlgmaarghswpclqqtptstsctitdvql fsmapyvlnvtavhpwgssssfvpfitehiikpdppegvrlsplaerql qvqweppgswpfpeifslkywirykrqgaarfhrvgpieatsfilravr praryyvqvaaqdltdygelsdwslpatatmslgk-C).

An amino acid sequence of an exemplary human p28 protein is provided in SEQ ID NO: 2
(NCBI Reference Sequence: NP_663634.2;
N-mgqtagdlgwrlslllllplllvqagvwgfprppgrpqlslqelrref tvslhlarkllsevrgqahrfaeshlpgvnlyllplgeqlpdvsltfqa wrrlsdperlcfisttlqpfhallgglgtqgrwtnmermqlwamrldlr dlqrhlrfqvlaagfnlpeeeeeeeeeeeeerkgllpgalgsalqgpaq vswpqllstyrllhslelvlsravrellllskaghsvwplgfptlspq p-C).

An amino acid sequence of an exemplary human WSX1 protein is provided in SEQ ID NO: 3
(NCBI Reference Sequence: NP_004834.1;
N-mrggrgapfwlwplpklallpllwvlfqrtrpqgsagplqcygvgpl gdlncsweplgdlgapselhlqsqkyrsnktqtvavaagrswvaipreq ltmsdkllvwgtkagqplwppvfvnletqmkpnaprlgpdvdfseddpl eatvhwapptwpshkvlicqfhyrrcqeaawtllepelktipltpveiq dlelatgykvygrcrmekeedlwgewspilsfqtppsapkdvwvsgnlc gtpggeeplllwkapgpcvqvsykvwfwvggrelspegitcccslipsg aewarvsavnatswepltnlslvcldsasaprsvavssiagstellvtw qpgpgeplehvvdwardgdpleklnwvrlppgnlsallpgnftvgvpyr itvtavsasglasassvwgfreelaplvgptlwrlqdappgtpaiawge vprhqlrghlthytlcaqsgtspsvcmnvsgntqsvtlpdlpwgpcelw vtastiagqgppgpilrlhlpdntlrwkvlpgilflwglfllgcglsla tsgrcyhlrhkvlprwvwekvpdpansssgqphmeqvpeaqplgdlpil eveemepppvmessqpaqatapldsgyekhflptpeelgllgpprpqvl a-C).

An amino acid sequence of an exemplary human gp130 protein is provided in SEQ ID NO: 4
(NCBI Reference Sequence: NP_002175.2;
N-mltlqtwlvqalfiflttestgelldpcgyispespvvqlhsnftav cvlkekcmdyfhvnanyivwktnhftipkeqytiinrtassvtftdias lniqltcniltfgqleqnvygitiisglppekpknlscivnegkkmrce wdggrethletnftlksewathkfadckakrdtptsctvdystvyfvni evwveaenalgkvtsdhinfdpvykvkpnpphnlsvinseelssilklt wtnpsiksviilkyniqyrtkdastwsqippedtastrssftvqdlkpf teyvfrircmkedgkgywsdwseeasgityedrpskapsfwykidpsht -continued qgyrtvqlvwktlppfeangkildyevtltrwkshlqnytvnatkltvn ltndrylatltvrnlvgksdaavltipacdfqathpvmdlkafpkdnml wvewttpresvkkyilewcvlsdkapcitdwqqedgtvhrtylrgnlae skcylitvtpvyadgpgspesikaylkqappskgptvrtkkvgkneavl ewdqlpvdvqngfirnytifyrtiignetavnvdsshteytlssltsdt lymvrmaaytdeggkdgpeftfttpkfaqgeieaivvpvclaflltll gvlfcfnkrdlikkhiwpnvpdpskshiaqwsphtpprhnfnskdqmys dgnftdvsvveieandkkpfpedlksldlfkkekinteghssgiggssc msssrpsisssdenessqntsstvqystvvhsgyrhqvpsvqvfsrses tqplldseerpedlqlvdhvdggdgilprqqyfkqncsqhesspdishf erskqvssvneedfvrlkqqisdhisqscgsgqmkmfqevsaadafgpg tegqverfetvgmeaatdegmpksylpqtvrqggympq-C).

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody) to a common antigen (e.g., IL-27 or a fragment thereof).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain aspects, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain aspects, the antibodies of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, and the like.

It will also be understood by one of ordinary skill in the art that the antibodies suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antibodies suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain aspects, a string of amino acids can be replaced with a structurally similar string that differs in order and/or composition of side chain family members. Alternatively, in certain aspects, mutations may be introduced randomly along all or part of a coding sequence, such as by saturation mutagenesis, and the resultant mutants can be incorporated into binding polypeptides of the disclosure and screened for their ability to bind to the desired target.

As used herein, the term antigen "cross-presentation" refers to presentation of exogenous protein antigens to T cells via MEW class I and class II molecules on APCs.

As used herein, the term "cross-reacts" refers to the ability of an antibody of the disclosure to bind to IL-27 from a different species. For example, an antibody of the present disclosure which binds human IL-27 may also bind another species of IL-27. As used herein, cross-reactivity is measured by detecting a specific reactivity with purified antigen in binding assays (e.g., SPR, ELISA) or binding to, or otherwise functionally interacting with, cells physiologically expressing IL-27. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

As used herein, the term "cytotoxic T lymphocyte (CTL) response" refers to an immune response induced by cytotoxic T cells. CTL responses are mediated primarily by CD8+ T cells.

As used herein, the term "dendritic cell" or "DC" refers to type of antigen-presenting cells that are bone marrow (BM)-derived leukocytes and are the most potent type of antigen-presenting cells. DCs are capture and process antigens, converting proteins to peptides that are presented on major histocompatibility complex (MEW) molecules recognized by T cells. DCs are heterogeneous, e.g. myeloid and plasmacytoid DCs; although all DCs are capable of antigen uptake, processing and presentation to naive T cells, the DC subtypes have distinct markers and differ in location, migratory pathways, detailed immunological function and dependence on infections or inflammatory stimuli for their generation. During the development of an adaptive immune response, the phenotype and function of DCs play a role in initiating tolerance, memory, and polarized T-helper 1 (Th1), Th2 and Th17 differentiation.

As used herein, the term "dendritic cell activation" refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli. Mature human dendritic cells are cells that are positive for the expression of CD40, CD80, CD86, and HLA-class II (e.g., HLA-DR). An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive. Discrimination of mature dendritic cells is routinely performed by those skilled in the art, and the respective markers described above and methods for measuring their expression are also well known to those skilled in the art.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a site on an antigen to which an immunoglobulin or antibody specifically binds. The term "epitope mapping" refers to a process or method of identifying the binding site, or epitope, of an antibody, or antigen binding fragment thereof, on its target protein antigen. Epitope mapping methods and techniques are provided herein. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from IL-27 are tested for reactivity with the given anti-IL-27 antibody. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Also encompassed by the present disclosure are antibodies that bind to an epitope on IL-27 which comprises all or a portion of an epitope recognized by the particular antibodies described herein (e.g., the same or an overlapping region or a region between or spanning the region).

Also encompassed by the present disclosure are antibodies that bind the same epitope and/or antibodies that compete for binding to human IL-27 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as IL-27. Numerous types of competitive binding assays are known, for example: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label MA using I-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen:antibody complexes which provides atomic resolution of the epitope and mass spectrometry combined with hydrogen/deuterium (H/D) exchange which studies the conformation and dynamics of antigen:antibody interactions. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fcγ receptor. In some aspects, the tumor antigen-targeting antibody has effector function, e.g., ADCC activity. In some aspects, a tumor antigen-targeting antibody described herein comprises a variant constant region having increased effector function (e.g. increased ability to mediate ADCC) relative to the unmodified form of the constant region.

As used herein, the term "Fc receptor" refers to a polypeptide found on the surface of immune effector cells, which is bound by the Fc region of an antibody. In some aspects, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fc receptors FcγRI, FcγRIIA and FcγRIIIA FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some aspects, the agonistic and/or therapeutic activity of the antibodies described herein is dependent on binding of the Fc region to the Fc receptor (e.g., FcγR). In some aspects, the agonistic and/or therapeutic activity of the antibodies described herein is enhanced by binding of the Fc region to the Fc receptor (e.g., FcγR).

A list of certain Fc receptor sequences employed in the instant disclosure is set forth as Table 1B below.

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The terms "inducing an immune response" and "enhancing an immune response" are used interchangeably and refer to the stimulation of an immune response (i.e., either passive or adaptive) to a particular antigen. The terms "induce" as used with respect to inducing CDC or ADCC refer to the stimulation of particular direct cell killing mechanisms.

As used herein, the term "immunogenic cell death" (alternatively known as "immunogenic apoptosis" refers to a cell death modality associated with the activation of one or more signaling pathways that induces the pre-mortem expression and emission of damaged-associated molecular pattern (DAMPs) molecules (e.g., adenosine triphosphate, ATP) from the tumor cell, resulting in the increase of immunogenicity of the tumor cell and the death of the tumor cell in an immunogenic manner (e.g., by phagocytosis). As used herein, the term "immunogenic cell death-inducing agent" refers to a chemical, biological, or pharmacological agent that induces an immunogenic cell death process, pathway, or modality.

As used herein, the terms "inhibits", "reduces" or "blocks" (e.g., referring to inhibition or reduction of human IL-27-mediated phosphorylation of STAT1 and/or STAT3 in a cell) are used interchangeably and encompass both partial and complete inhibition/blocking. The inhibition/blocking of IL-27 reduces or alters the normal level or type of activity that occurs without inhibition or blocking. Inhibition and blocking are also intended to include any measurable decrease in the binding affinity of IL-27 when in contact with an anti-IL-27 antibody as compared to IL-27 not in contact with an anti-IL-27 antibody, e.g., inhibits binding of IL-27 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%.

As used herein, the terms "inhibits angiogenesis," "diminishes angiogenesis," and "reduces angiogenesis" refer to reducing the level of angiogenesis in a tissue to a quantity which is at least 10%, 15%, 20%, 25%, 30%, 35%, 40%, 45%. 50% 55%, 60%, 65%, 70%, 75%, 80%, 85%, 90%, 95%, 99% or less than the quantity in a corresponding control tissue, and most preferably is at the same level which is observed in a control tissue.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-IL-27 antibody).

The term "in vivo" refers to processes that occur in a living organism.

As used herein, the term "isolated antibody" is intended to refer to an antibody which is substantially free of other antibodies having different antigenic specificities (e.g., an isolated antibody that specifically binds to human IL-27 is substantially free of antibodies that specifically bind antigens other than IL-27). An isolated antibody that specifically binds to an epitope may, however, have cross-reactivity to other IL-27 proteins from different species. However, the antibody continues to display specific binding to human IL-27 in a specific binding assay as described herein. In addition, an isolated antibody is typically substantially free of other cellular material and/or chemicals. In some aspects, a combination of "isolated" antibodies having different IL-27 specificities is combined in a well-defined composition.

As used herein, the term "isolated nucleic acid molecule" refers to nucleic acids encoding antibodies or antibody portions (e.g., VH, VL, CDR3) that bind to IL-27, is intended to refer to a nucleic acid molecule in which the nucleotide sequences encoding the antibody or antibody portion are free of other nucleotide sequences encoding antibodies or antibody portions that bind antigens other than IL-27, which other sequences may naturally flank the nucleic acid in human genomic DNA. For example, a sequence selected from a sequence set forth in Table 1A corresponds to the nucleotide sequences comprising the heavy chain (VH) and light chain (VL) variable regions of anti-IL-27 antibody monoclonal antibodies described herein.

As used herein, "isotype" refers to the antibody class (e.g., IgM or IgG1) that is encoded by heavy chain constant region genes. In some aspects, a human monoclonal antibody of the disclosure is of the IgG1 isotype. In some aspects, a human monoclonal antibody of the disclosure is of the IgG2 isotype. In some aspects, a human monoclonal antibody of the disclosure is of the IgG3 isotype. In some aspects, a human monoclonal antibody of the disclosure is of the IgG4 isotype. As is apparent to a skilled artisan, identification of antibody isotypes (e.g., IgG1, IgG2, IgG3, IgG4, IgM, IgA1 IgA2, IgD, and IgE) is routine in the art and commonly involves a combination of sequence alignments with known antibodies, published Fc variant sequences and conserved sequences.

As used herein, the term "isotype switching" refers to the phenomenon by which the class, or isotype, of an antibody changes from one Ig class to one of the other Ig classes.

As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of an antibody from an antibody/antigen complex. The value of $k_d$ is a numeric representation of the fraction of complexes that decay or dissociate per second, and is expressed in units $sec^{-1}$.

As used herein, the term "ka" or "$k_a$" (alternatively "kon" or "$k_{on}$") is intended to refer to the on-rate constant for the association of an antibody with an antigen. The value of ka is a numeric representation of the number of antibody/ antigen complexes formed per second in a 1 molar (1M) solution of antibody and antigen, and is expressed in units $M^{-1}sec^{-1}$.

As used herein, the term "leukocyte" refers to a type of white blood cell involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes).

As used herein, the term "lymphocytes" refers to a type of leukocyte or white blood cell that is involved in the immune defenses of the body. There are two main types of lymphocytes: B-cells and T-cells.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some aspects, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "monocyte" refers to a type of leukocyte and can differentiate into macrophages and dendritic cells to effect an immune response.

As used herein, the term "natural killer (NK) cell" refers to a type of cytotoxic lymphocyte. These are large, usually granular, non-T, non-B lymphocytes, which kill certain tumor cells and play an important role in innate immunity to viruses and other intracellular pathogens, as well as in antibody-dependent cell-mediated cytotoxicity (ADCC).

As used herein, the term "naturally occurring" as applied to an object refers to the fact that an object can be found in nature. For example, a polypeptide or polynucleotide sequence that is present in an organism (including viruses)

that can be isolated from a source in nature and which has not been intentionally modified by man in the laboratory is naturally occurring.

As used herein, the term "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$, and human $\Sigma_\mu$ ($\delta$-associated deletion). Alternative non-classical switching mechanisms, such as intertransgene and/or interchromosomal recombination, among others, may occur and effectuate isotype switching.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

As used herein, the term "PD-1 antagonist" refers to any chemical compound or biological molecule that inhibits the PD-1 signaling pathway or that otherwise inhibits PD-1 function in a cell (e.g. an immune cell). In some aspects, a PD-1 antagonist blocks binding of PD-L1 to PD-1 and/or PD-L2 to PD-1. In some aspects, the PD-1 antagonist specifically binds PD-1. In some aspects, the PD-1 antagonist specifically binds PD-L1.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "Programmed Cell Death Protein 1" or "PD-1" refers to the Programmed Cell Death Protein 1 polypeptide, an immune-inhibitory receptor belonging to the CD28 family and is encoded by the PDCD1 gene in humans. Alternative names or synonyms for PD-1 include: PDCD1, PD1, CD279 and SLEB2. PD-1 is expressed predominantly on previously activated T cells, B cells, and myeloid cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773.

As used herein, the term "Programmed Death Ligand-1" or "PD-L1" is one of two cell surface glycoprotein ligands for PD-1 (the other being PD-L2) that downregulates T cell activation and cytokine secretion upon binding to PD-1. Alternative names and synonyms for PD-L1 include: PDCD1L1, PDL1, B7H1, B7-4, CD274 and B7-H. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

PD-1 is known as an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745). The interaction between PD-1 and PD-L1 can act as an immune checkpoint, which can lead to a decrease in T-cell receptor mediated proliferation (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

For several cancers, tumor survival and proliferation is sustained by tumor-mediated immune checkpoint modulation. This modulation can result in the disruption of anticancer immune system functions. For example, recent studies have indicated that the expression of immune checkpoint receptors ligands, such as PD-L1 or PD-L2, by tumor cells can downregulate immune system activity in the tumor microenvironment and promote cancer immune evasion. particularly by suppressing T cells. PD-L1 is abundantly expressed by a variety of human cancers (Dong et al., (2002) Nat Med 8:787-789). The receptor for PD-L1, PD-1, is expressed on lymphocytes (e.g., activated T cells) and is normally involved in down-regulating the immune system and promoting self-tolerance, particularly by suppressing T cells. However, when PD-1 receptors expressed on T cells bind to cognate PD-L1 ligands on tumor cells, the resulting T cell suppression contributes to an impaired immune response against the tumor (e.g., a decrease in tumor infiltrating lymphocytes or the establishment of immune evasion by cancer cells).

In large sample sets of e.g. ovarian, renal, colorectal, pancreatic, liver cancers and melanoma, it was shown that PD-L1 expression correlated with poor prognosis and reduced overall survival irrespective of subsequent treatment (see e.g., Dong et al., (2002) Nat Med 8(8):793-800; Yang et al., (2008) Invest Ophthalmol Vis Sci 49(6):2518-2525; Ghebeh et al., (2006) Neoplasia 8:190-198; Hamanishi et al., (2007) Proc Nat Acad Sci USA 104:3360-3365; Thompson et al., (2006) Clin Genitourin Cancer 5:206-211; Nomi et al., (2005) Clin Cancer Res 11:2947-2953; Inman et al., (2007) Cancer 109:1499-1505; Shimauchi et al., (2007) Int J Cancer 121:2585-2590; Gao et al., (2009) Clin Cancer Res 15:971-979; Nakanishi et al., (2007) Cancer Immunol Immunother 56:1173-1182; Hino et al., (2010) Cancer 116(7):1757-1766). Similarly, PD-1 expression on tumor lymphocytes was found to mark dysfunctional T cells in breast cancer (Kitano et al., (2017) ESMO Open 2(2): e000150) and melanoma (Kleffel et al., (2015) Cell 162(6): 1242-1256). PD-1 antagonists, such as those that affect the function of the PD-1/PD-L1/PD-L2 signaling axis and/or disrupt the interaction between PD-1 and PD-L1 and/or PD-L2, for example, have been developed and represent a novel class of anti-tumor inhibitors that function via modulation of immune cell-tumor cell interaction.

As used herein, the term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on IL-27 and is used to establish a relationship between itself and one or more distinct antibodies, wherein the relationship is the binding of the reference antibody and the one or more distinct antibodies to the same epitope on IL-27. As used herein, the term connotes an anti-IL-27 antibody that is useful in a test or assay, such as those described herein, (e.g., a competitive binding assay), as a competitor, wherein the assay is useful for the discovery, identification or development, of one or more distinct antibodies that bind to the same epitope.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-6}$ M, such as approximately less than $10^{-7}$, $10^{-8}$ M, $10^{-9}$ M or $10^{-10}$ M or even lower when determined by surface plasmon resonance (SPR) technology in a BIACORE 2000 instrument using recombinant human IL-27 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. In certain aspects, an antibody that specifically binds to IL-27 binds with an equilibrium dissociation constant ($K_D$) of approximately less than 100 nM ($10^{-7}$ M), optionally approximately less than 50 nM ($5 \times 10^{-8}$ M), optionally approximately less than 15 nM ($1.5 \times 10^{-8}$ M), optionally approximately less than 10 nM ($10^{-8}$ M), optionally approximately less than 5 nM ($5 \times 10^{-9}$M), optionally approximately less than 1 nM ($10^{-9}$M), optionally approximately less than 0.1 nM ($10^{-10}$ M), optionally approximately less than 0.01 nM ($10^{-7}$ M), or even lower, when determined by surface plasmon resonance (SPR) technology in a BIA-CORE 2000 instrument using recombinant human IL-27 as the analyte and the antibody as the ligand, where binding to the predetermined antigen occurs with an affinity that is at least two-fold greater than the antibody's affinity for binding to a non-specific antigen (e.g., BSA, casein) other than the predetermined antigen or a closely-related antigen The phrases "an antibody recognizing an antigen" and "an antibody specific for an antigen" are used interchangeably herein with the term "an antibody which binds specifically to an antigen."

As used herein, the term "STAT1 phosphorylation" refers to the phosphorylation of the Signal Transducer and Activator of Transcription 1 (STAT1) polypeptide, a transcription factor encoded by the STAT1 gene in humans. STAT molecules are phosphorylated by receptor associated kinases, that cause activation and dimerization by forming homo- or heterodimers which translocate to the nucleus to work as transcription factors. STAT1 can be activated (i.e., phosphorylated) in response to signaling via several ligands, including IL-27. IL-27 signaling through the IL-27R results in phosphorylation of STAT1 (pSTAT1). STAT1 has a key role in gene expression involved in survival of the cell, viability or pathogen response. Methods to determine STAT1 phosphorylation as a result of IL-27 signaling include, but are not limited to, flow cytometric analysis of cells labeled with antibodies that specifically recognize phosphorylated STAT1 (see e.g., Tochizawa et al., (2006) J Immunol Methods 313(1-2):29-37).

As used herein, the term "STAT3 phosphorylation" refers to the phosphorylation of the Signal Transducer and Activator of Transcription 3 (STAT3) polypeptide, a transcription factor encoded by the STAT3 gene in humans. STAT3 mediates the expression of a variety of genes in response to cell stimuli, and thus plays a key role in many cellular processes such as cell growth and apoptosis. Methods to determine STAT3 phosphorylation as a result of IL-27 signaling include, but are not limited to, analysis of cells or cell extracts labeled with antibodies that specifically recognize phosphorylated STAT3 (see e.g., Fursov et al., (2011) Assay Drug Dev Technol 9(4):420-429).

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, the term "subject" includes any human or non-human animal. For example, the methods and compositions of the present disclosure can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgap-dna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48): 444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the disclosure. BLAST protein searches can be performed with the XBLAST program, score=50, wordlength=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25 (17): 3389-3402. When utilizing BLAST and Gapped BLAST programs, the default parameters of the respective programs (e.g., XBLAST and NBLAST) can be used. See ncbi.nlm-.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "STING" (alternatively TMEM173) refers to the Stimulator of Interferon Genes, a protein that functions both as a direct cytosolic DNA sensor and as an adaptor protein. In humans, STING is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection by binding to the same cell that secretes it and nearby cells. An exemplary amino acid sequence for STING is provided by the NCBI Genbank database under the accession number NP_001288667.

The term "T cell" refers to a type of white blood cell that can be distinguised from other white blood cells by the presence of a T cell receptor on the cell surface. There are several subsets of T cells, including, but not limited to, T helper cells (a.k.a. $T_H$ cells or CD4$^+$ T cells) and subtypes, including $T_H1$, $T_H2$, $T_H3$, $T_H17$, $T_H9$, and TFH cells, cytotoxic T cells (a.k.a $T_C$ cells, CD8$^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4$^+$ FOXP3$^+$ $T_{reg}$ cells, CD4$^+$FOXP3$^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells ($\gamma\delta$ T cells), including V$\gamma$9/V$\delta$2 T cells. Any one or more of the aforementioned or unmentioned T cells may be the target cell type for a method of use of the disclosure.

As used herein, the term "T cell-mediated response" refers to any response mediated by T cells, including, but not limited to, effector T cells (e.g., CD8$^+$ cells) and helper T cells (e.g., CD4$^+$ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., an anti-IL-27 antibody or an antigen-binding fragment thereof) that will elicit the desired biological or medical response (e.g., an improvement in one or more symptoms of a cancer).

As used herein, the term "TAM receptor" refers to the TAM receptor protein tyrosine kinases (TYRO3, AXL and MER). TAM receptors are involved in the regulation of immune system homeostasis. In a cancer setting, TAM receptors have a dual regulatory role, controlling the initiation and progression of tumor development and, at the same time, the associated anti-tumor responses of diverse immune cells. Further description of TAM receptors is found in Paolino and Penninger (2016) Cancers 8(97): doi:10.3390/cancers8100097). As used herein, the term "TAM receptor inhibitor" or "TAM inhibitor" refers to an agent that inhibits, blocks or reduces the function or activity of a TAM receptor.

As used herein, the term "TIGIT" or "T-cell immunoreceptor with Ig and ITIM domains" refers to any native TIGIT from any vertebrate source, including mammals such as primates (e.g., humans) and rodents (e.g., mice and rats), unless otherwise indicated. TIGIT is also known in the art as DKFZp667A205, FLJ39873, V-set and immunoglobulin domain-containing protein 9, V-set and transmembrane domain-containing protein 3, VSIG9, VSTM3, and WUCAM. The term also encompasses naturally occurring variants of TIGIT, e.g., splice variants or allelic variants. The amino acid sequence of an exemplary human TIGIT may be found under UniProt Accession Number Q495A1.

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

As used herein, the term "unrearranged" or "germline configuration" refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

II. Methods of the Disclosure

Some aspects of the present disclosure are directed to methods of stimulating an immune response in a subject, the method comprising administering to the subject an antibody or an antigen binding portion thereof that antagonizes human IL-27, or an antigen binding portion thereof. Some aspects of the present disclosure are directed to methods of treating a cancer in a subject in need thereof comprising administering to the subject an antibody that antagonizes human IL-27, or an antigen binding portion thereof. Some aspects of the present disclosure are directed to methods of inhibiting or reducing STAT1 and/or STAT3 phosphorylation in a cell, the method comprising contacting the cell with an isolated antibody, or antigen binding fragment, provided by the disclosure, wherein the antibody, or antigen binding portion thereof, inhibits or reduces STAT1 and/or STAT3 phosphorylation in a cell. Some aspects of the present disclosure are directed to methods of inhibiting or reducing inhibition of CD161 expression in a cell, the method comprising contacting the cell with an isolated antibody, or antigen binding fragment, provided by the disclosure, wherein the antibody, or antigen binding portion thereof, inhibits or reduces inhibition of CD161 expression in a cell. Some aspects of the present disclosure are directed to methods of inhibiting or reducing PD-L1 expression in a cell, the method comprising contacting the cell with an isolated antibody, or antigen binding fragment, provided by the disclosure, wherein the antibody, or antigen binding portion thereof, inhibits or reduces PD-L1 expression in a cell. Some aspects of the present disclosure are directed to methods of altering TIM-3 expression in a cell, the method comprising contacting the cell with an isolated antibody, or antigen binding fragment, provided by the disclosure, wherein the antibody, or antigen binding portion thereof, alters TIM-3 expression. Some aspects of the present disclosure are directed to methods of inducing or enhancing secretion of one or more cytokines from a cell, the method comprising contacting the cell with the isolated antibody, or antigen binding fragment, provided by the disclosure, wherein the antibody, or antigen binding portion thereof, induces or enhances PD-1 mediated secretion of one or more cytokines from a cell.

In some aspects, the antibody or an antigen binding portion thereof is administered at a dose of at least about 0.003 mg/kg to at least about 20 mg/kg. In some aspects, the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii). In some aspects, the antibody or an antigen binding portion thereof is administered at a dose that is sufficient to maintain IC90 of pSTAT1 inhibition level, i.e., above about 0.7 ug/mL for the duration of the treatment, e.g., 28 days, 56 days, or 84 days.

In some aspects, the antibody or antigen binding portion thereof is administered at a dose of at least about 0.006 mg/kg to at least about 20 mg/kg, at least about 0.009 mg/kg to at least about 20 mg/kg, at least about 0.01 mg/kg to at least about 20 mg/kg, at least about 0.03 mg/kg to at least about 20 mg/kg, at least about 0.06 mg/kg to at least about 20 mg/kg, at least about 0.09 mg/kg to at least about 20 mg/kg, at least about 0.1 mg/kg to at least about 20 mg/kg, at least about 0.3 mg/kg to at least about 20 mg/kg, at least about 0.6 mg/kg to at least about 20 mg/kg, at least about 0.9 mg/kg to at least about 20 mg/kg, at least about 1 mg/kg to at least about 20 mg/kg, at least about 1 mg/kg to at least about 20 mg/kg, at least about 3 mg/kg to at least about 20 mg/kg, at least about 6 mg/kg to at least about 20 mg/kg, at least about 10 mg/kg to at least about 20 mg/kg, at least about 13 mg/kg to at least about 20 mg/kg, at least about 13 mg/kg to at least about 18 mg/kg, at least about 13 mg/kg to at least about 16 mg/kg, at least about 16 mg/kg to at least about 20 mg/kg, at least about 16 mg/kg to at least about 18 mg/kg, at least about 3 mg/kg to at least about 18 mg/kg, at least about 6 mg/kg to at least about 15 mg/kg, at least about 13 mg/kg to at least about 18 mg/kg, or at least about 10 mg/kg to at least about 15 mg/kg. In some aspects, the antibody or antigen binding portion thereof is administered at a dose of at least about 0.006 mg/kg to at least about 10 mg/kg, at least about 0.009 mg/kg to at least about 10 mg/kg, at least about 0.01 mg/kg to at least about 10 mg/kg, at least about 0.03 mg/kg to at least about 10 mg/kg, at least about 0.06 mg/kg to at least about 10 mg/kg, at least about 0.09 mg/kg to at least about 10 mg/kg, at least about 0.1 mg/kg to at least about 10 mg/kg, at least about 0.3 mg/kg to at least about 10 mg/kg, at least about 0.6 mg/kg to at least about 10 mg/kg, at least about 0.9 mg/kg to at least about 10 mg/kg, at least about 1 mg/kg to at least about 10 mg/kg, at least about 1 mg/kg to at least about 9 mg/kg, at least about 3 mg/kg to at least about 9 mg/kg, at least about 1 mg/kg to at least about 6 mg/kg, at least about 3 mg/kg to at least about 6 mg/kg, or at least about 1 mg/kg to at least about 3 mg/kg.

In some aspects, the antibody or antigen binding portion thereof is administered at a dose of at least about 0.003 mg/kg, at least about 0.006 mg/kg, at least about 0.009 mg/kg, at least about 0.01 mg/kg, at least about 0.03 mg/kg, at least about 0.06 mg/kg, at least about 0.09 mg/kg, at least about 0.1 mg/kg, at least about 0.3 mg/kg, at least about 0.6 mg/kg, at least about 0.9 mg/kg, at least about 1.0 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9, or at least about 10 mg/kg. In some aspects, the antibody or antigen binding portion thereof is administered at a dose of at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19, or at least about 20 mg/kg. In some aspects, the antibody or antigen binding portion thereof is administered at a dose of at least about 0.003 mg/kg. In some aspects, the antibody or antigen binding portion thereof is administered at a dose of at least about 0.006 mg/kg. In some aspects, the antibody or antigen binding portion thereof is administered at a dose of at least about 0.009 mg/kg. In some aspects, the antibody or antigen binding portion thereof is administered at a dose of at least about 0.01 mg/kg. In some aspects, the antibody or antigen binding portion thereof is administered at a dose of at least about 0.03 mg/kg. In some aspects, the antibody or antigen binding portion thereof is administered at a dose of at least about 0.06 mg/kg. In some aspects, the antibody or antigen binding portion thereof is administered at a dose of at least about 0.09 mg/kg. In some aspects, the antibody or antigen binding portion thereof is administered at a dose of at least about 0.1 mg/kg. In some aspects, the antibody or antigen binding portion thereof is administered at a dose of at least about 0.3 mg/kg. In some aspects, the antibody or antigen binding portion thereof is administered at a dose of at least about 0.6 mg/kg. In some aspects, the antibody or antigen binding portion thereof is administered at a dose of at least about 0.9 mg/kg. In some aspects, the antibody or antigen binding portion thereof is administered at a dose of at least about 1.0 mg/kg. In some aspects, the antibody or antigen binding portion thereof is administered at a dose of at least about 2 mg/kg. In some aspects, the antibody or antigen binding portion thereof is administered at a dose of at least about 3 mg/kg. In some aspects, the antibody or antigen binding portion thereof is administered at a dose of at least about 4 mg/kg. In some aspects, the antibody or antigen binding portion thereof is administered at a dose of at least about 5 mg/kg. In some aspects, the antibody or antigen binding portion thereof is administered at a dose of at least about 6 mg/kg. In some aspects, the antibody or antigen binding portion thereof is administered at a dose of at least about 7 mg/kg. In some aspects, the antibody or antigen binding portion thereof is administered at a dose of at least about 8 mg/kg. In some aspects, the antibody or antigen binding portion thereof is administered at a dose of at least about 9. In some aspects, the antibody or antigen binding portion thereof is administered at a dose of at least about 10 mg/kg. In some aspects, the antibody or antigen binding portion thereof is administered at a dose of at least about 11 mg/kg. In some aspects, the antibody or antigen binding portion thereof is administered at a dose of at least about 12 mg/kg. In some aspects, the antibody or antigen binding portion thereof is administered at a dose of at least about 13 mg/kg. In some aspects, the antibody or antigen binding portion thereof is administered at a dose of at least about 14 mg/kg. In some aspects, the antibody or antigen binding portion thereof is administered at a dose of at least about 15 mg/kg. In some aspects, the antibody or antigen binding portion thereof is administered at a dose of at least about 16 mg/kg. In some aspects, the antibody or antigen binding portion thereof is administered at a dose of at least about 17 mg/kg. In some aspects, the antibody or antigen binding portion thereof is administered at a dose of at least about 18 mg/kg. In some aspects, the antibody or antigen binding portion thereof is administered at a dose of at least about 19 mg/kg. In some aspects, the antibody or antigen binding portion thereof is administered at a dose of at least about 20 mg/kg.

In some aspects, the antibody or antigen binding portion thereof is administered once about every week, once about every two weeks, once about every three weeks, once about every four weeks, once about every 6 weeks, once about every 8 weeks, or once about every 12 weeks. In some aspects, the antibody or antigen binding portion thereof is administered once about every four weeks.

In some aspects, the antibody or antigen binding portion thereof is administered at a dose of about 0.3 mg/kg once about every week. In some aspects, the antibody or antigen binding portion thereof is administered at a dose of about 1 mg/kg once about every week. In some aspects, the antibody or antigen binding portion thereof is administered at a dose of about 2 mg/kg once about every week. In some aspects, the antibody or antigen binding portion thereof is administered at a dose of about 3 mg/kg once about every week. In some aspects, the antibody or antigen binding portion thereof is administered at a dose of about 4 mg/kg once about every week. In some aspects, the antibody or antigen binding portion thereof is administered at a dose of about 5 mg/kg once about every week. In some aspects, the antibody or antigen binding portion thereof is administered at a dose of about 6 mg/kg once about every week. In some aspects, the antibody or antigen binding portion thereof is administered at a dose of about 7 mg/kg once about every week. In some aspects, the antibody or antigen binding portion thereof is administered at a dose of about 8 mg/kg once about every week. In some aspects, the antibody or antigen binding portion thereof is administered at a dose of about 9 mg/kg once about every week. In some aspects, the antibody or antigen binding portion thereof is administered at a dose of about 10 mg/kg once about every week. In some aspects, the antibody or antigen binding portion thereof is administered at a dose of about 11 mg/kg once about every week. In some aspects, the antibody or antigen binding portion thereof is administered at a dose of about 12 mg/kg once about every week. In some aspects, the antibody or antigen binding portion thereof is administered at a dose of about 13 mg/kg once about every week. In some aspects, the antibody or antigen binding portion thereof is administered at a dose of about 14 mg/kg once about every week. In some aspects, the antibody or antigen binding portion thereof is administered at a dose of about 15 mg/kg once about every week. In some aspects, the antibody or antigen binding portion thereof is administered at a dose of about 16 mg/kg once about every week. In some aspects, the antibody or antigen binding portion thereof is administered at a dose of about 17 mg/kg once about every week. In some aspects, the antibody or antigen binding portion thereof is administered at a dose of about 18 mg/kg once about every week. In some aspects, the antibody or antigen binding portion thereof is administered at a dose of about 19 mg/kg once about every week. In some aspects, the antibody or antigen binding portion thereof is administered at a dose of about 20 mg/kg once about every week.

In some aspects, the antibody or antigen binding portion thereof is administered at a dose of about 0.3 mg/kg once about every two weeks. In some aspects, the antibody or antigen binding portion thereof is administered at a dose of about 1 mg/kg once about every two weeks. In some aspects, the antibody or antigen binding portion thereof is administered at a dose of about 2 mg/kg once about every two weeks. In some aspects, the antibody or antigen binding portion thereof is administered at a dose of about 3 mg/kg once about every two weeks. In some aspects, the antibody or antigen binding portion thereof is administered at a dose of about 4 mg/kg once about every two weeks. In some aspects, the antibody or antigen binding portion thereof is administered at a dose of about 5 mg/kg once about every two weeks. In some aspects, the antibody or antigen binding portion thereof is administered at a dose of about 6 mg/kg once about every two weeks. In some aspects, the antibody or antigen binding portion thereof is administered at a dose of about 7 mg/kg once about every two weeks. In some aspects, the antibody or antigen binding portion thereof is administered at a dose of about 8 mg/kg once about every two weeks. In some aspects, the antibody or antigen binding portion thereof is administered at a dose of about 9 mg/kg once about every two weeks. In some aspects, the antibody or antigen binding portion thereof is administered at a dose of about 10 mg/kg once about every two weeks. In some aspects, the antibody or antigen binding portion thereof is administered at a dose of about 11 mg/kg once about every two weeks. In some aspects, the antibody or antigen binding portion thereof is administered at a dose of about 12 mg/kg once about every two weeks. In some aspects, the antibody or antigen binding portion thereof is administered at a dose of about 13 mg/kg once about every two weeks. In some aspects, the antibody or antigen binding portion thereof is administered at a dose of about 14 mg/kg once about every two weeks. In some aspects, the antibody or antigen binding portion thereof is administered at a dose of about 15 mg/kg once about every two weeks. In some aspects, the antibody or antigen binding portion thereof is administered at a dose of about 16 mg/kg once about every two weeks. In some aspects, the antibody or antigen binding portion thereof is administered at a dose of about 17 mg/kg once about every two weeks. In some aspects, the antibody or antigen binding portion thereof is administered at a dose of about 18 mg/kg once about every two weeks. In some aspects, the antibody or antigen binding portion thereof is administered at a dose of about 19 mg/kg once about every two weeks. In some aspects, the antibody or antigen binding portion thereof is administered at a dose of about 20 mg/kg once about every two weeks.

In some aspects, the antibody or antigen binding portion thereof is administered at a dose of about 0.3 mg/kg once about every three weeks. In some aspects, the antibody or antigen binding portion thereof is administered at a dose of about 1 mg/kg once about every three weeks. In some aspects, the antibody or antigen binding portion thereof is administered at a dose of about 2 mg/kg once about every three weeks. In some aspects, the antibody or antigen binding portion thereof is administered at a dose of about 3 mg/kg once about every three weeks. In some aspects, the antibody or antigen binding portion thereof is administered at a dose of about 4 mg/kg once about every three weeks. In some aspects, the antibody or antigen binding portion thereof is administered at a dose of about 5 mg/kg once about every three weeks. In some aspects, the antibody or antigen binding portion thereof is administered at a dose of about 6 mg/kg once about every three weeks. In some aspects, the antibody or antigen binding portion thereof is administered at a dose of about 7 mg/kg once about every three weeks. In some aspects, the antibody or antigen binding portion thereof is administered at a dose of about 8 mg/kg once about every three weeks. In some aspects, the antibody or antigen binding portion thereof is administered at a dose of about 9 mg/kg once about every three weeks. In some aspects, the antibody or antigen binding portion thereof is administered at a dose of about 10 mg/kg once about every three weeks. In some aspects, the antibody or antigen binding portion thereof is administered at a dose of about 11 mg/kg once about every three weeks. In some aspects, the antibody or antigen binding portion thereof is administered at a dose of about 12 mg/kg once about every three weeks. In some aspects, the antibody or antigen binding portion thereof is administered at a dose of about 13 mg/kg once about every three weeks. In some aspects, the antibody or antigen binding portion thereof is administered at a dose of about 14 mg/kg once about every three weeks. In some aspects, the antibody or antigen binding portion thereof is administered at a dose of about 15 mg/kg once about every three weeks. In some aspects, the antibody or antigen binding portion thereof is administered at a dose of about 16 mg/kg once about every three weeks. In some aspects, the antibody or antigen binding portion thereof is administered at a dose of about 17 mg/kg once about every three weeks. In some aspects, the antibody or antigen binding portion thereof is administered at a dose of about 18 mg/kg once about every three weeks. In some aspects, the antibody or antigen binding portion thereof is administered at a dose of about 19 mg/kg once about every three weeks. In some aspects, the antibody or antigen binding portion thereof is administered at a dose of about 20 mg/kg once about every three weeks.

In some aspects, the antibody or antigen binding portion thereof is administered at a dose of about 0.3 mg/kg once about every four weeks. In some aspects, the antibody or antigen binding portion thereof is administered at a dose of about 1 mg/kg once about every four weeks. In some aspects, the antibody or antigen binding portion thereof is administered at a dose of about 2 mg/kg once about every four weeks. In some aspects, the antibody or antigen binding portion thereof is administered at a dose of about 3 mg/kg once about every four weeks. In some aspects, the antibody or antigen binding portion thereof is administered at a dose of about 4 mg/kg once about every four weeks. In some aspects, the antibody or antigen binding portion thereof is administered at a dose of about 5 mg/kg once about every four weeks. In some aspects, the antibody or antigen binding portion thereof is administered at a dose of about 6 mg/kg once about every four weeks. In some aspects, the antibody or antigen binding portion thereof is administered at a dose of about 7 mg/kg once about every four weeks. In some aspects, the antibody or antigen binding portion thereof is administered at a dose of about 8 mg/kg once about every four weeks. In some aspects, the antibody or antigen binding portion thereof is administered at a dose of about 9 mg/kg once about every four weeks. In some aspects, the antibody or antigen binding portion thereof is administered at a dose of about 10 mg/kg once about every four weeks. In some aspects, the antibody or antigen binding portion thereof is administered at a dose of about 11 mg/kg once about every four weeks. In some aspects, the antibody or antigen binding portion thereof is administered at a dose of about 12 mg/kg once about every four weeks. In some aspects, the antibody or antigen binding portion thereof is administered at a dose of about 13 mg/kg once about every four weeks. In some aspects, the antibody or antigen binding portion thereof is administered at a dose of about 14 mg/kg once about every four weeks. In some aspects, the antibody or antigen binding portion thereof is administered at a dose of about 15 mg/kg once about every four weeks. In some aspects, the antibody or antigen binding portion thereof is administered at a dose of about 16 mg/kg once about every four weeks. In some aspects, the antibody or antigen binding portion thereof is administered at a dose of about 17 mg/kg once about every four weeks. In some aspects, the antibody or antigen binding portion thereof is administered at a dose of about 18 mg/kg once about every four weeks. In some aspects, the antibody or antigen binding portion thereof is administered at a dose of about 19 mg/kg once about every four weeks. In some aspects, the antibody or antigen binding portion thereof is administered at a dose of about 20 mg/kg once about every four weeks.

Certain aspects of the present disclosure are directed to methods of treating a cancer in a subject in need thereof. In some aspects, the cancer is selected from Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (RCC), hepatocellular carcinoma (HCC), hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, retinoblastoma, rhabdomyosarcoma, rectal cancer; cancer of the respiratory system, sarcoma, skin cancer, stomach cancer, testicular cancer, thyroid cancer, uterine cancer, cancer of the urinary system, and any combination thereof. In some aspects, the cancer is chosen from lung cancer (e.g., non-small cell lung cancer), sarcoma, testicular cancer, ovarian cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma (e.g., DL-BCL), leukemia (e.g., AML) or renal cancer (e.g., renal cell carcinoma, e.g., clear cell RCC and/or non-clear cell RCC). In some aspects, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

In some aspects, the compositions disclosed herein are administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as silastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some aspects, an anti-IL-27 antibody or antigen-binding fragment thereof is therapeutically delivered to a subject by way of local administration.

In certain aspects, the route of administration is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain aspects, the compositions can be administered by bolus injection or continuously by infusion, or by implantation device. In certain aspects, individual elements of the combination therapy may be administered by different routes.

In certain aspects, the composition can be administered locally via implantation of a membrane, sponge or another appropriate material onto which the desired molecule has been absorbed or encapsulated. In certain aspects, where an implantation device is used, the device can be implanted into any suitable tissue or organ, and delivery of the desired molecule can be via diffusion, timed-release bolus, or continuous administration. In certain aspects, it can be desirable to use a pharmaceutical composition comprising an anti-IL-27 antibody in an ex vivo manner. In such instances, cells, tissues and/or organs that have been removed from the patient are exposed to a pharmaceutical composition comprising an anti-IL-27 antibody after which the cells, tissues and/or organs are subsequently implanted back into the patient.

In certain aspects, an anti-IL-27 antibody can be delivered by implanting certain cells that have been genetically engineered, using methods such as those described herein, to express and secrete the polypeptides. In certain aspects, such cells can be animal or human cells, and can be autologous, heterologous, or xenogeneic. In certain aspects, the cells can be immortalized. In certain aspects, in order to decrease the chance of an immunological response, the cells can be encapsulated to avoid infiltration of surrounding tissues. In certain aspects, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In some aspects, following administration antibody or antigen binding portion thereof, the subject exhibits increased expression of one or more biomarkers selected from the group consisting of Eotaxin-1 (CCL11), TARC (CCL17), VEGF-A, IL-7, IL-8, MCP-1, MCP-4, and any combination thereof; wherein the increased expression of the one or more biomarkers is relative to the expression of the one or more biomarker prior to the administration. In some aspects, following administration antibody or antigen binding portion thereof, the subject exhibits increased expression of Eotaxin-1 (CCL11), wherein the increased expression of Eotaxin-1 (CCL11) is relative to the expression of Eotaxin-1 (CCL11) prior to the administration.

In some aspects, following administration antibody or antigen binding portion thereof, the subject exhibits increased expression of TARC (CCL17), wherein the increased expression of TARC (CCL17) is relative to the expression of TARC (CCL17) prior to the administration.

In some aspects, following administration antibody or antigen binding portion thereof, the subject exhibits increased expression of VEGF-A, wherein the increased expression of VEGF-A is relative to the expression of VEGF-A prior to the administration.

In some aspects, following administration antibody or antigen binding portion thereof, the subject exhibits increased expression of IL-7, wherein the increased expression of IL-7 is relative to the expression of IL-7 prior to the administration.

In some aspects, following administration antibody or antigen binding portion thereof, the subject exhibits increased expression of IL-8, wherein the increased expression of IL-8 is relative to the expression of IL-8 prior to the administration.

In some aspects, following administration antibody or antigen binding portion thereof, the subject exhibits increased expression of MCP-1, wherein the increased expression of MCP-1 is relative to the expression of MCP-1 prior to the administration.

In some aspects, following administration antibody or antigen binding portion thereof, the subject exhibits increased expression of MCP-4, wherein the increased expression of MCP-4 is relative to the expression of MCP-4 prior to the administration.

A. Anti-IL-27 Antibodies and Antigen-Binding Portions Thereof

Certain aspects of the present disclosure are directed to methods of administering antibodies, and antigen binding portions thereof, that specifically bind to IL-27p28 and antagonize IL-27, in particular human IL-27.

In some aspects, the antibody or antigen binding portion thereof inhibits or reduces STAT1 and/or STAT3 phosphorylation in a cell in the subject. In some aspects, the antibody or antigen binding portion thereof inhibits or reduces pSTAT1 signaling (e.g., IL-27 mediated pSTAT1 signaling). In some aspects, the antibody or antigen binding portion thereof inhibits or reduces pSTAT1 signaling (e.g., IL-27 mediated pSTAT1 signaling) by at least about 25%, at least about 50%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, relative to pSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 90% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 91% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 92% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 93% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 94% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 95% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 96% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 97% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 98% relative to PSTAT1 signaling (e.g., IL-27 mediated pSTAT1 signaling) prior to administration of the antibody or antigen binding portion thereof (e.g., an anti-IL-27 antibody disclosed herein). In some aspects, the antibody or antigen binding portion thereof inhibits or reduces PSTAT1 signaling (e.g., IL-27 mediated pSTAT1 signaling) by at least about 99% relative to PSTAT1 signaling (e.g., IL-27 mediated pSTAT1 signaling) prior to administration of the antibody or antigen binding portion thereof (e.g., an anti-IL-27 antibody disclosed herein).

In some aspects, the antibody or antigen binding portion thereof inhibits or reduces inhibition of CD161 expression in a cell in the subject. In some aspects, the antibody or antigen binding portion thereof inhibits or reduces PD-L1 expression in a cell in the subject. In some aspects, the antibody or antigen binding portion thereof induces or enhances PD-1 mediated secretion of one or more cytokines from a cell in the subject. In some aspects, the antibody or antigen binding portion thereof alters TIM-3 expression in a cell in the subject. In some aspects, the cell is a tumor cell or an immune cell.

Accordingly, in one aspect, the disclosure provides an isolated antibody that specifically binds to and antagonizes human IL-27, or an antigen binding portion thereof, wherein the antibody or antigen binding portion thereof specifically binds to the epitopes disclosed herein and exhibits at least one or more of the following properties: (i) binds to human IL-27 with an equilibrium dissociation constant ($K_D$) of 15 nM or less; (ii) blocks binding of IL-27 to IL-27 receptor; (iii) inhibits or reduces STAT1 and/or STAT3 phosphorylation in a cell; (iv) inhibits or reduces IL-27 mediated inhibition of CD161 expression in a cell; (v) inhibits or reduces IL-27 mediated PD-L1 expression in a cell; (vi) induces or enhances PD-1 mediated secretion of one or more cytokines from a cell; (vii) alters TIM-3 expression in a cell; and (viii) a combination of (i)-(vii).

In some aspects, the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii). In some aspects, an isolated antibody of the disclosure that antagonizes human IL-27, or an antigen binding portion thereof, specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, or Glu164 of SEQ ID NO: 2 (IL-27p28).

Some aspects of the present disclosure are directed to a method of treating a cancer in a subject in need thereof comprising administering to the subject an antibody that antagonizes human IL-27, or an antigen binding portion thereof, wherein the antibody or antigen binding portion thereof specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii); wherein the antibody or antigen binding portion thereof is administered at a dose of at least about 0.003 mg/kg to at least about 10 mg/kg; wherein the antibody or the antigen binding portion thereof comprises a heavy chain CDR3 comprising the sequence set forth in SEQ ID NO: 121 or 124. In some aspects, the antibody or the antigen binding portion thereof comprises a heavy chain CDR3 comprising the sequence set forth in SEQ ID NO: 121. In some aspects, the antibody or the antigen binding portion thereof comprises a heavy chain CDR3 comprising the sequence set forth in SEQ ID NO: 124. In some aspects, the antibody or the antigen binding portion thereof comprises a heavy chain CDR2 comprising the sequence set forth in SEQ ID NO: 120 or 123. In some aspects, the antibody or the antigen binding portion thereof comprises a heavy chain CDR2 comprising the sequence set forth in SEQ ID NO: 120. In some aspects, the antibody or the antigen binding portion thereof comprises a heavy chain CDR2 comprising the sequence set forth in SEQ ID NO: 123. In some aspects, the antibody or the antigen binding portion thereof comprises a heavy chain CDR1 comprising the sequence set forth in SEQ ID NO: 119 or 122. In some aspects, the antibody or the antigen binding portion thereof comprises a heavy chain CDR1 comprising the sequence set forth in SEQ ID NO: 119. In some aspects, the antibody or the antigen binding portion thereof comprises a heavy chain CDR1 comprising the sequence set forth in SEQ ID NO: 122. In some aspects, the antibody or the antigen binding portion thereof comprises a light chain CDR3 comprising the sequence set forth in SEQ ID NO: 129 or 132. In some aspects, the antibody or the antigen binding portion thereof comprises a light chain CDR3 comprising the sequence set forth in SEQ ID NO: 129. In some aspects, the antibody or the antigen binding portion thereof comprises a light chain CDR3 comprising the sequence set forth in SEQ ID NO: 132. In some aspects, the antibody or the antigen binding portion thereof comprises a light chain CDR2 comprising the sequence set forth in SEQ ID NO: 128 or 131. In some aspects, the antibody or the antigen binding portion thereof comprises a light chain CDR2 comprising the sequence set forth in SEQ ID NO: 128. In some aspects, the antibody or the antigen binding portion thereof comprises a light chain CDR2 comprising the sequence set forth in SEQ ID NO: 131. In some aspects, the antibody or the antigen binding portion thereof comprises a light chain CDR1 comprising the sequence set forth in SEQ ID NO: 127 or 130. In some aspects, the antibody or the antigen binding portion thereof comprises a light chain CDR1 comprising the sequence set forth in SEQ ID NO: 127. In some aspects, the antibody or the antigen binding portion thereof comprises a light chain CDR1 comprising the sequence set forth in SEQ ID NO: 130.

In some aspects, the antibody or the antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, and a heavy chain CDR3 comprising the amino acid sequence set forth in SEQ ID NO: 121. In some aspects, the antibody or the antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, and a heavy chain CDR3 comprising the amino acid sequence set forth in SEQ ID NO: 124.

In some aspects, the antibody or the antigen binding portion thereof comprises: a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the antibody or the antigen binding portion thereof comprises: a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132.

In some aspects, the antibody or the antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 1 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 3 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 6 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 10 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129. In some aspects, the method comprises administering a dose of at least about 20 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129.

In some aspects, the antibody or the antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 1 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 3 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 6 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 10 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132. In some aspects, the method comprises administering a dose of at least about 20 mg/kg of an antibody that antagonizes human IL-27, or an antigen binding portion thereof, wherein the antibody or antigen binding portion thereof comprises: a heavy chain CDR1 comprising the amino acid sequence set forth in SEQ ID NO: 122, a heavy chain CDR2 comprising the amino acid sequence set forth in SEQ ID NO: 123, a heavy chain CDR3 comprising the amino acid sequence set forth in SEQ ID NO: 124 a light chain CDR1 comprising the amino acid sequence set forth in SEQ ID NO: 130, a light chain CDR2 comprising the amino acid sequence set forth in SEQ ID NO: 131, and a light chain CDR3 comprising the amino acid sequence set forth in SEQ ID NO: 132.

In some aspects, the antibody or the antigen binding portion thereof comprises a heavy chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 125. In some aspects, the antibody or the antigen binding portion thereof comprises a heavy chain variable region comprising the amino acid sequence set forth in SEQ ID NO: 125.

In some aspects, the antibody or the antigen binding portion thereof comprises a light chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 133. In some aspects, the antibody or the antigen binding portion thereof comprises a light chain variable region comprising the amino acid sequence set forth in SEQ ID NO: 133.

In some aspects, the antibody or the antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 1 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 3 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 6 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 10 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133. In some aspects, the method comprises administering a dose of at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 125 and a light chain variable region comprising the amino acid sequence set forth in SEQ ID NO: 133.

In some aspects, the antibody or the antigen binding portion thereof comprises a heavy chain comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 135. In some aspects, the antibody or the antigen binding portion thereof comprises a heavy chain comprising the amino acid sequence set forth in SEQ ID NO: 135.

In some aspects, the antibody or the antigen binding portion thereof comprises a heavy chain comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 139. In some aspects, the antibody or the antigen binding portion thereof comprises a heavy chain comprising the amino acid sequence set forth in SEQ ID NO: 139.

In some aspects, the antibody or the antigen binding portion thereof comprises a light chain comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 137. In some aspects, the antibody or the antigen binding portion thereof comprises a light chain comprising the amino acid sequence set forth in SEQ ID NO: 137.

In some aspects, the antibody or the antigen binding portion thereof comprises a heavy chain comprising the amino acid sequence set forth in SEQ ID NO: 135 and a light chain comprising the amino acid sequence set forth in SEQ ID NO: 137. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137. In some aspects, the method comprises administering a dose of at least about 1 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137. In some aspects, the method comprises administering a dose of at least about 3 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137. In some aspects, the method comprises administering a dose of at least about 6 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137. In some aspects, the method comprises administering a dose of at least about 10 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137. In some aspects, the method comprises administering a dose of at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 135 and a light chain variable region comprising the amino acid sequence set forth in SEQ ID NO: 137.

In some aspects, the antibody or the antigen binding portion thereof comprises a heavy chain comprising the amino acid sequence set forth in SEQ ID NO: 139 and a light chain comprising the amino acid sequence set forth in SEQ ID NO: 137. In some aspects, the method comprises administering a dose of at least about 0.003 mg/kg to at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137. In some aspects, the method comprises administering a dose of at least about 1 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137. In some aspects, the method comprises administering a dose of at least about 3 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137. In some aspects, the method comprises administering a dose of at least about 6 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137. In some aspects, the method comprises administering a dose of at least about 10 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137. In some aspects, the method comprises administering a dose of at least about 20 mg/kg of an antibody that antagonizes human IL-27, or an antigen binding portion thereof, wherein the antibody or antigen binding portion thereof comprises a heavy chain variable region comprising the amino acid sequence set forth in SEQ ID NO: 139 and a light chain variable region comprising the amino acid sequence set forth in SEQ ID NO: 137.

In some aspects, the antibody or antigen-binding portion thereof comprises an amino acid sequence set forth in Table 1A.

TABLE 1A

| SEQ ID NO | Description | Sequence |
|---|---|---|
| | Anti-IL-27 Antibodies | |
| | | anti-IL-27 Ab2-A |
| 9 | HCDR1 (IMGT) | GFTFSSYS |
| 10 | HCDR2 (IMGT) | ISSSSSYI |
| 11 | HCDR3 (IMGT) | ARDGGRTSYTATAHNWFDP |
| 12 | HCDR1 (NT) | FTFSSYSMN |
| 13 | HCDR2 (NT) | SISSSSSYIYYADSVKG |
| 14 | HCDR3 (NT) | ARDGGRTSYTATAHNWFDP |

TABLE 1A-continued

Anti-IL-27 Antibodies

| SEQ ID NO | Description | Sequence |
|---|---|---|
| 15 | VH | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 16 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGCTATAGCATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 17 | LCDR1 (IMGT) | QSVLFSSNNKNY |
| 18 | LCDR2 (IMGT) | WAS |
| 19 | LCDR3 (IMGT) | QQHASAPPT |
| 20 | LCDR1 (NT) | KSSQSVLFSSNNKNYLA |
| 21 | LCDR2 (NT) | WASTRES |
| 22 | LCDR3 (NT) | QQHASAPPT |
| 23 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 24 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 25 | Heavy Chain | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 26 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGCTATAGCATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC |

TABLE 1A-continued

Anti-IL-27 Antibodies

| SEQ ID NO | Description | Sequence |
|---|---|---|
| | | ATAACGCGAAAACCAAACCGCGCGAAGAACAGTATAACAGCACC |
| | | TATCGCGTGGTGAGCGTGCTGACCGTGCTGCATCAGGATTGGCT |
| | | GAACGGCAAAGAATATAAATGCAAAGTGAGCAACAAAGCGCTGC |
| | | CGGCGCCGATTGAAAAAACCATTAGCAAAGCGAAAGGCCAGCCG |
| | | CGCGAACCGCAGGTGTATACCCTGCCGCCGAGCCGCGATGAACT |
| | | GACCAAAAACCAGGTGAGCCTGACCTGCCTGGTGAAAGGCTTTT |
| | | ATCCGAGCGATATTGCGGTGGAATGGGAAAGCAACGGCCAGCCG |
| | | GAAAACAACTATAAAACCACCCCGCCGGTGCTGGATAGCGATGG |
| | | CAGCTTTTTTCTGTATAGCAAACTGACCGTGGATAAAAGCCGCT |
| | | GGCAGCAGGGCAACGTGTTTAGCTGCAGCGTGATGCATGAAGCG |
| | | CTGCATAACCATTATACCCAGAAAAGCCTGAGCCTGAGCCCGGG |
| | | CAAA |
| 27 | Light Chain | DIVMTQSPDSLAVSLGERATINCKSSQSVLFSSNNKNYLAWYQQ |
| | | KPGQPPKLLIYWASTRESGVPDRFSGSGSGTDFTLTISSLQAED |
| | | VAVYYCQQHASAPPTFGGGTKVEIKRTVAAPSVFIFPPSDEQLK |
| | | SGTASVVCLLNNFYPREAKVQWKVDNALQSGNSQESVTEQDSKD |
| | | STYSLSSTLTLSKADYEKHKVYACEVTHQGLSSPVTKSFNRGEC |
| 28 | DNA Light Chain | GACATCGTGATGACCCAGTCTCCAGACTCCCTGGCTGTGTCTCT |
| | | GGGCGAGAGGGCCACCATCAACTGCAAGTCCAGCCAGAGTGTTT |
| | | TATTCAGCTCCAACAATAAGAACTACTTAGCTTGGTACCAGCAG |
| | | AAACCAGGACAGCCTCCTAAGCTGCTCATTTACTGGGCATCTAC |
| | | CCGGGAATCCGGGGTCCCTGACCGATTCAGTGGCAGCGGGTCTG |
| | | GGACAGATTTCACTCTCACCATCAGCAGCCTGCAGGCTGAAGAT |
| | | GTGGCAGTTTATTACTGTCAGCAGCACGCCAGTGCCCCTCCTAC |
| | | TTTTGGCGGAGGGACCAAGGTTGAGATCAAACGTACGGTGGCCG |
| | | CTCCCTCCGTGTTCATCTTCCCACCCTCCGACGAGCAGCTGAAG |
| | | TCCGGCACCGCCTCCGTCGTGTGCCTGCTGAACAACTTCTACCC |
| | | TCGCGAGGCCAAAGTGCAGTGGAAAGTGGACAACGCCCTGCAGT |
| | | CCGGCAACTCCCAGGAATCCGTCACCGAGCAGGACTCCAAGGAC |
| | | AGCACCTACTCCCTGTCCTCCACCCTGACCCTGTCCAAGGCCGA |
| | | CTACGAGAAGCACAAAGTGTACGCCTGCGAAGTGACCCACCAGG |
| | | GCCTGTCCAGCCCCGTGACCAAGTCCTTCAACCGGGGCGAGTGC | anti-IL-27 Ab2-B

| SEQ ID NO | Description | Sequence |
|---|---|---|
| 29 | Heavy Chain | EVQLVESGGGLVKPGGSLRLSCAASGFTFSSYSMNWVRQAPGKG |
| | | LEWVSSISSSSSYIYYADSVKGRFTISRDNAKNSLYLQMNSLRA |
| | | EDTAVYYCARDGGRTSYTATAHNWFDPWGQGTLVTVSSASTKGP |
| | | SVFPLAPCSRSTSESTAALGCLVKDYFPEPVTVSWNSGALTSGV |
| | | HTFPAVLQSSGLYSLSSVVTVPSSSLGTKTYTCNVDHKPSNTKV |
| | | DKRVESKYGPPCPSCPAPEFLGGPSVFLFPPKPKDTLMISRTPE |
| | | VTCVVVDVSQEDPEVQFNWYVDGVEVHNAKTKPREEQFNSTYRV |
| | | VSVLTVLHQDWLNGKEYKCKVSNKGLPSSIEKTISKAKGQPREP |
| | | QVYTLPPSQEEMTKNQVSLTCLVKGFYPSDIAVEWESNGQPENN |
| | | YKTTPPVLDSDGSFFLYSRLTVDKSRWQEGNVFSCSVMHEALHN |
| | | HYTQKSLSLSLG |
| 30 | DNA Heavy Chain | GAGGTGCAGCTGGTGGAGTCTGGGGGAGGCCTGGTCAAGCCTGG |
| | | GGGGTCCCTGAGACTCTCCTGTGCAGCCTCTGGATTCACCTTCA |
| | | GTAGCTATAGCATGAACTGGGTCCGCCAGGCTCCAGGGAAGGGG |
| | | CTGGAGTGGGTCTCATCCATTAGTAGTAGTAGTAGTTACATATA |
| | | CTACGCAGACTCAGTGAAGGGCCGATTCACCATCTCCAGAGACA |
| | | ACGCCAAGAACTCACTGTATCTGCAAATGAACAGCCTGAGAGCC |
| | | GAGGACACGGCGGTGTACTACTGCGCCAGAGATGGTGGAAGAAC |
| | | GTCCTACACCGCCACAGCCCACAATTGGTTCGACCCCTGGGGAC |
| | | AGGGTACATTGGTCACCGTCTCCTCAGCTTCCACCAAGGGCCCC |
| | | TCCGTGTTCCCTCTGGCCCCTTGCTCCCGGTCCACCTCCGAGTC |
| | | TACCGCCGCTCTGGGCTGCCTCGTGAAGGACTACTTCCCCGAGC |
| | | CCGTGACCGTGTCCTGGAACTCTGGCGCCCTGACCTCCGGCGTG |
| | | CACACCTTCCCTGCCGTGCTGCAGTCCTCCGGCCTGTACTCCCT |
| | | GTCCAGCGTCGTGACCGTGCCCTCCTCCAGCCTGGGCACCAAGA |
| | | CCTACACCTGTAACGTGGACCACAAGCCCTCCAACACCAAAGTG |
| | | GACAAGCGGGTGGAATCTAAGTACGGCCCTCCCTGCCCTTCCTG |
| | | CCCTGCCCCTGAGTTCCTGGGCGGACCTTCCGTGTTCCTGTTCC |
| | | CTCCAAAGCCCAAGGACACCCTGATGATCTCCCGGACCCCTGAA |
| | | GTGACCTGCGTGGTGGTGGACGTGTCCCAGGAAGATCCCGAAGT |
| | | CCAGTTCAATTGGTACGTGGACGGCGTGGAAGTGCACAACGCCA |
| | | AGACCAAGCCCAGAGAGGAACAGTTCAACTCCACCTACCGGGTG |
| | | GTGTCCGTGCTGACCGTGCTGCACCAGGACTGGCTGAACGGCAA |
| | | AGAGTACAAGTGCAAAGTGTCCAACAAGGGCCTGCCCTCCAGCA |
| | | TCGAAAAGACCATCTCCAAGGCCAAGGGCCAGCCCCGCGAGCCC |
| | | CAAGTGTACACCCTGCCTCCCAGCCAGGAAGAGATGACCAAGAA |
| | | TCAAGTGTCCCTGACTTGTCTGGTCAAGGGCTTCTACCCCTCCG |

TABLE 1A-continued

| | | Anti-IL-27 Antibodies | | |
|---|---|---|---|---|

| SEQ ID NO | Description | Sequence |
|---|---|---|
| | | ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |

| | | anti-IL-27 Ab3-A | |
|---|---|---|

| SEQ ID NO | Description | Sequence |
|---|---|---|
| 31 | HCDR1 (IMGT) | GFTFRSYG |
| 32 | HCDR2 (IMGT) | ISSSSSYI |
| 33 | HCDR3 (IMGT) | ARDGGRTSYTATAHNWFDP |
| 34 | HCDR1 (NT) | FTFRSYGMN |
| 35 | HCDR2 (NT) | SISSSSYIYYADSVKG |
| 36 | HCDR3 (NT) | ARDGGRTSYTATAHNWFDP |
| 37 | VH | EVQLVESGGGLVKPGGSLRLSCAASGFTFRSYGMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 38 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCC GGAGCTATGGGATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 39 | LCDR1 (IMGT) | QSVLFSSNNKNY |
| 40 | LCDR2 (IMGT) | WAS |
| 41 | LCDR3 (IMGT) | QQHASAPPT |
| 42 | LCDR1 (NT) | KSSQSVLFSSNNKNYLA |
| 43 | LCDR2 (NT) | WASTRES |
| 44 | LCDR3 (NT) | QQHASAPPT |
| 45 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 46 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 47 | Heavy Chain | EVQLVESGGGLVKPGGSLRLSCAASGFTFRSYGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST |

TABLE 1A-continued

Anti-IL-27 Antibodies

| SEQ ID NO | Description | Sequence |
|---|---|---|
| | | YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 48 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCC GGAGCTATGGGATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 49 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 50 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC | anti-IL-27 Ab3-B

| 51 | Heavy Chain | EVQLVESGGGLVKPGGSLRLSCAASGFTFRSYGMNWVRQAPGKG LEWVSSISSSSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |

TABLE 1A-continued

Anti-IL-27 Antibodies

| SEQ ID NO | Description | Sequence |
|---|---|---|
| 52 | DNA Heavy Chain | GAGGTGCAGCTGGTGGAGTCTGGGGGAGGCCTGGTCAAGCCTGG<br>GGGGTCCCTGAGACTCTCCTGTGCAGCCTCTGGATTCACCTTCC<br>GGAGCTATGGGATGAACTGGGTCCGCCAGGCTCCAGGGAAGGGG<br>CTGGAGTGGGTCTCATCCATTAGTAGTAGTAGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCAGCTTCCACCAAGGGCCCC<br>TCCGTGTTCCCTCTGGCCCCTTGCTCCCGGTCCACCTCCGAGTC<br>TACCGCCGCTCTGGGCTGCCTCGTGAAGGACTACTTCCCCGAGC<br>CCGTGACCGTGTCCTGGAACTCTGGCGCCCTGACCTCCGGCGTG<br>CACACCTTCCCTGCCGTGCTGCAGTCCTCCGGCCTGTACTCCCT<br>GTCCAGCGTCGTGACCGTGCCCTCCTCCAGCCTGGGCACCAAGA<br>CCTACACCTGTAACGTGGACCACAAGCCCTCCAACACCAAAGTG<br>GACAAGCGGGTGGAATCTAAGTACGGCCCTCCCTGCCCTTCCTG<br>CCCTGCCCCTGAGTTCCTGGGCGGACCTTCCGTGTTCCTGTTCC<br>CTCCAAAGCCCAAGGACACCCTGATGATCTCCCGGACCCCTGAA<br>GTGACCTGCGTGGTGGTGGACGTGTCCCAGGAAGATCCCGAAGT<br>CCAGTTCAATTGGTACGTGGACGGCGTGGAAGTGCACAACGCCA<br>AGACCAAGCCCAGAGAGGAACAGTTCAACTCCACCTACCGGGTG<br>GTGTCCGTGCTGACCGTGCTGCACCAGGACTGGCTGAACGGCAA<br>AGAGTACAAGTGCAAAGTGTCCAACAAGGGCCTGCCCTCCAGCA<br>TCGAAAAGACCATCTCCAAGGCCAAGGGCCAGCCCCGCGAGCCC<br>CAAGTGTACACCCTGCCTCCCAGCCAGGAAGAGATGACCAAGAA<br>TCAAGTGTCCCTGACTTGTCTGGTCAAGGGCTTCTACCCCTCCG<br>ATATCGCCGTGGAGTGGGAGTCCAACGGCCAGCCCGAGAACAAC<br>TACAAGACCACCCCTCCCGTGCTGGACTCCGACGGCTCCTTCTT<br>CCTGTACTCTCGGCTGACCGTGGACAAGTCCCGGTGGCAGGAAG<br>GCAACGTCTTCTCCTGCTCCGTGATGCACGAGGCCCTGCACAAC<br>CACTACACCCAGAAGTCCCTGTCCCTGTCTCTGGGC | anti-IL-27 Ab4-A

| SEQ ID NO | Description | Sequence |
|---|---|---|
| 53 | HCDR1 (IMGT) | GFTFSRTG |
| 54 | HCDR2 (IMGT) | ISSSSSYI |
| 55 | HCDR3 (IMGT) | ARDGGRTSYTATAHNWFDP |
| 56 | HCDR1 (NT) | FTFSRTGMN |
| 57 | HCDR2 (NT) | SISSSSSYIYYADSVKG |
| 58 | HCDR3 (NT) | ARDGGRTSYTATAHNWFDP |
| 59 | VH | EVQLVESGGGLVKPGGSLRLSCAASGFTFSRTGMNWVRQAPGKG<br>LEWVSSISSSSSYIYYADSVKGRFTISRDNAKNSLYLQMNSLRA<br>EDTAVYYCARDGGRTSYTATAHNWFDPWGQGTLVTVSS |
| 60 | DNA VH | GAGGTGCAGCTGGTGGAGTCTGGGGGAGGCCTGGTCAAGCCTGG<br>GGGGTCCCTGAGACTCTCCTGTGCAGCCTCTGGATTCACCTTCA<br>GTAGGACTGGGATGAACTGGGTCCGCCAGGCTCCAGGGAAGGGG<br>CTGGAATGGGTCTCATCCATTAGTAGTAGTAGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCA |
| 61 | LCDR1 (IMGT) | QSVLFSSNNKNY |
| 62 | LCDR2 (IMGT) | WAS |
| 63 | LCDR3 (IMGT) | QQHASAPPT |
| 64 | LCDR1 (NT) | KSSQSVLFSSNNKNYLA |
| 65 | LCDR2 (NT) | WASTRES |

TABLE 1A-continued

Anti-IL-27 Antibodies

| SEQ ID NO | Description | Sequence |
| --- | --- | --- |
| 66 | LCDR3 (NT) | QQHASAPPT |
| 67 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 68 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 69 | Heavy Chain | EVQLVESGGGLVKPGGSLRLSCAASGFTFSRTGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 70 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGACTGGGATGAACTGGGTCCGCCAGGCTCCAGGGAAGGGG CTGGAATGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 71 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 72 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG |

TABLE 1A-continued

Anti-IL-27 Antibodies

| SEQ ID NO | Description | Sequence |
|---|---|---|
| | | CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC | anti-IL-27 Ab4-B

| 73 | Heavy Chain | EVQLVESGGGLVKPGGSLRLSCAASGFTFSRTGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 74 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGACTGGGATGAACTGGGTCCGCCAGGCTCCAGGGAAGGGG CTGGAATGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC | anti-IL-27 Ab5-A

| 75 | HCDR1 (IMGT) | GFTFSRYG |
| 76 | HCDR2 (IMGT) | ISSSSAYI |
| 77 | HCDR3 (IMGT) | ARDGGRTSYTATAHNWFDP |
| 78 | HCDR1 (NT) | FTFSRYGMN |
| 79 | HCDR2 (NT) | SISSSSAYILYADSVKG |
| 80 | HCDR3 (NT) | ARDGGRTSYTATAHNWFDP |
| 81 | VH | EVQLVESGGGLVKPGGSLRLSCAASGFTFSRYGMNWVRQAPGKG LEWVSSISSSSAYILYADSVKGRFTISRDNAKNSLYLQMNSLRA EDTAVYYCARDGGRTSYTATAHNWFDPWGQGTLVTVSS |

TABLE 1A-continued

<div align="center">Anti-IL-27 Antibodies</div>

| SEQ ID NO | Description | Sequence |
|---|---|---|
| 82 | DNA VH | GAGGTGCAGCTGGTGGAGTCTGGGGGAGGCCTGGTCAAGCCTGG<br>GGGGTCCCTGAGACTCTCCTGTGCAGCCTCTGGATTCACCTTCA<br>GTAGGTATGGGATGAACTGGGTCCGCCAGGCTCCAGGGAAGGGG<br>CTGGAGTGGGTCTCATCCATTAGTAGTAGTAGTGCTTACATACT<br>GTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCA |
| 83 | LCDR1<br>(IMGT) | QSVLFSSNNKNY |
| 84 | LCDR2<br>(IMGT) | WAS |
| 85 | LCDR3<br>(IMGT) | QQHASAPPT |
| 86 | LCDR1 (NT) | KSSQSVLFSSNNKNYLA |
| 87 | LCDR2 (NT) | WASTRES |
| 88 | LCDR3 (NT) | QQHASAPPT |
| 89 | VL | DIVMTQSPDSLAVSLGERATINCKSSQSVLFSSNNKNYLAWYQQ<br>KPGQPPKLLIYWASTRESGVPDRFSGSGSGTDFTLTISSLQAED<br>VAVYYCQQHASAPPTFGGGTKVEIK |
| 90 | DNA VL | GACATCGTGATGACCCAGTCTCCAGACTCCCTGGCTGTGTCTCT<br>GGGCGAGAGGGCCACCATCAACTGCAAGTCCAGCCAGAGTGTTT<br>TATTCAGCTCCAACAATAAGAACTACTTAGCTTGGTACCAGCAG<br>AAACCAGGACAGCCTCCTAAGCTGCTCATTTACTGGGCATCTAC<br>CCGGGAATCCGGGGTCCCTGACCGATTCAGTGGCAGCGGGTCTG<br>GGACAGATTTCACTCTCACCATCAGCAGCCTGCAGGCTGAAGAT<br>GTGGCAGTTTATTACTGTCAGCAGCACGCCAGTGCCCCTCCTAC<br>TTTTGGCGGAGGGACCAAGGTTGAGATCAAA |
| 91 | Heavy Chain | EVQLVESGGGLVKPGGSLRLSCAASGFTFSRYGMNWVRQAPGKG<br>LEWVSSISSSSAYILYADSVKGRFTISRDNAKNSLYLQMNSLRA<br>EDTAVYYCARDGGRTSYTATAHNWFDPWGQGTLVTVSSASTKGP<br>SVFPLAPSSKSTSGGTAALGCLVKDYFPEPVTVSWNSGALTSGV<br>HTFPAVLQSSGLYSLSSVVTVPSSSLGTQTYICNVNHKPSNTKV<br>DKKVEPKSCDKTHTCPPCPAPELLGGPSVFLFPPKPKDTLMISR<br>TPEVTCVVVDVSHEDPEVKFNWYVDGVEVHNAKTKPREEQYNST<br>YRVVSVLTVLHQDWLNGKEYKCKVSNKALPAPIEKTISKAKGQP<br>REPQVYTLPPSRDELTKNQVSLTCLVKGFYPSDIAVEWESNGQP<br>ENNYKTTPPVLDSDGSFFLYSKLTVDKSRWQQGNVFSCSVMHEA<br>LHNHYTQKSLSLSPGK |
| 92 | DNA Heavy<br>Chain | GAGGTGCAGCTGGTGGAGTCTGGGGGAGGCCTGGTCAAGCCTGG<br>GGGGTCCCTGAGACTCTCCTGTGCAGCCTCTGGATTCACCTTCA<br>GTAGGTATGGGATGAACTGGGTCCGCCAGGCTCCAGGGAAGGGG<br>CTGGAGTGGGTCTCATCCATTAGTAGTAGTAGTGCTTACATACT<br>GTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCAGCGAGCACCAAAGGCCCG<br>AGCGTGTTTCCGCTGGCGCCGAGCAGCAAAAGCACCAGCGGCGG<br>CACCGCGGCGCTGGGCTGCCTGGTGAAAGATTATTTTCCGGAAC<br>CGGTGACCGTGAGCTGGAACAGCGGCGCGCTGACCAGCGGCGTG<br>CATACCTTTCCGGCGGTGCTGCAGAGCAGCGGCCTGTATAGCCT<br>GAGCAGCGTGGTGACCGTGCCGAGCAGCAGCCTGGGCACCCAGA<br>CCTATATTTGCAACGTGAACCATAAACCGAGCAACACCAAAGTG<br>GATAAAAAAGTGGAACCGAAAAGCTGCGATAAAACCCATACCTG<br>CCCGCCGTGCCCGGCGCCGGAACTGCTGGGCGGCCCGAGCGTGT<br>TTCTGTTTCCGCCGAAACCGAAAGATACCCTGATGATTAGCCGC<br>ACCCCGGAAGTGACCTGCGTGGTGGTGGATGTGAGCCATGAAGA<br>TCCGGAAGTGAAATTTAACTGGTATGTGGATGGCGTGGAAGTGC<br>ATAACGCGAAAACCAAACCGCGCGAAGAACAGTATAACAGCACC<br>TATCGCGTGGTGAGCGTGCTGACCGTGCTGCATCAGGATTGGCT<br>GAACGGCAAAGAATATAAATGCAAAGTGAGCAACAAAGCGCTGC<br>CGGCGCCGATTGAAAAAACCATTAGCAAAGCGAAAGGCCAGCCG<br>CGCGAACCGCAGGTGTATACCCTGCCGCCGAGCCGCGATGAACT |

TABLE 1A-continued

Anti-IL-27 Antibodies

| SEQ ID NO | Description | Sequence |
|---|---|---|
| | | GACCAAAAACCAGGTGAGCCTGACCTGCCTGGTGAAAGGCTTTT |
| | | ATCCGAGCGATATTGCGGTGGAATGGGAAAGCAACGGCCAGCCG |
| | | GAAAACAACTATAAAACCACCCCGCCGGTGCTGGATAGCGATGG |
| | | CAGCTTTTTTCTGTATAGCAAACTGACCGTGGATAAAAGCCGCT |
| | | GGCAGCAGGGCAACGTGTTTAGCTGCAGCGTGATGCATGAAGCG |
| | | CTGCATAACCATTATACCCAGAAAAGCCTGAGCCTGAGCCCGGG |
| | | CAAA |
| 93 | Light Chain | DIVMTQSPDSLAVSLGERATINCKSSQSVLFSSNNKNYLAWYQQ |
| | | KPGQPPKLLIYWASTRESGVPDRFSGSGSGTDFTLTISSLQAED |
| | | VAVYYCQQHASAPPTFGGGTKVEIKRTVAAPSVFIFPPSDEQLK |
| | | SGTASVVCLLNNFYPREAKVQWKVDNALQSGNSQESVTEQDSKD |
| | | STYSLSSTLTLSKADYEKHKVYACEVTHQGLSSPVTKSFNRGEC |
| 94 | DNA Light Chain | GACATCGTGATGACCCAGTCTCCAGACTCCCTGGCTGTGTCTCT |
| | | GGGCGAGAGGGCCACCATCAACTGCAAGTCCAGCCAGAGTGTTT |
| | | TATTCAGCTCCAACAATAAGAACTACTTAGCTTGGTACCAGCAG |
| | | AAACCAGGACAGCCTCCTAAGCTGCTCATTTACTGGGCATCTAC |
| | | CCGGGAATCCGGGGTCCCTGACCGATTCAGTGGCAGCGGGTCTG |
| | | GGACAGATTTCACTCTCACCATCAGCAGCCTGCAGGCTGAAGAT |
| | | GTGGCAGTTTATTACTGTCAGCAGCACGCCAGTGCCCCTCCTAC |
| | | TTTTGGCGGAGGGACCAAGGTTGAGATCAAACGTACGGTGGCCG |
| | | CTCCCTCCGTGTTCATCTTCCCACCCTCCGACGAGCAGCTGAAG |
| | | TCCGGCACCGCCTCCGTCGTGTGCCTGCTGAACAACTTCTACCC |
| | | TCGCGAGGCCAAAGTGCAGTGGAAAGTGGACAACGCCCTGCAGT |
| | | CCGGCAACTCCCAGGAATCCGTCACCGAGCAGGACTCCAAGGAC |
| | | AGCACCTACTCCCTGTCCTCCACCCTGACCCTGTCCAAGGCCGA |
| | | CTACGAGAAGCACAAAGTGTACGCCTGCGAAGTGACCCACCAGG |
| | | GCCTGTCCAGCCCCGTGACCAAGTCCTTCAACCGGGGCGAGTGC | anti-IL-27 Ab5-B

| 95 | Heavy Chain | EVQLVESGGGLVKPGGSLRLSCAASGFTFSRYGMNWVRQAPGKG |
| | | LEWVSSISSSSAYILYADSVKGRFTISRDNAKNSLYLQMNSLRA |
| | | EDTAVYYCARDGGRTSYTATAHNWFDPWGQGTLVTVSSASTKGP |
| | | SVFPLAPCSRSTSESTAALGCLVKDYFPEPVTVSWNSGALTSGV |
| | | HTFPAVLQSSGLYSLSSVVTVPSSSLGTKTYTCNVDHKPSNTKV |
| | | DKRVESKYGPPCPSCPAPEFLGGPSVFLFPPKPKDTLMISRTPE |
| | | VTCVVVDVSQEDPEVQFNWYVDGVEVHNAKTKPREEQFNSTYRV |
| | | VSVLTVLHQDWLNGKEYKCKVSNKGLPSSIEKTISKAKGQPREP |
| | | QVYTLPPSQEEMTKNQVSLTCLVKGFYPSDIAVEWESNGQPENN |
| | | YKTTPPVLDSDGSFFLYSRLTVDKSRWQEGNVFSCSVMHEALHN |
| | | HYTQKSLSLSLG |
| 96 | DNA Heavy Chain | GAGGTGCAGCTGGTGGAGTCTGGGGGAGGCCTGGTCAAGCCTGG |
| | | GGGGTCCCTGAGACTCTCCTGTGCAGCCTCTGGATTCACCTTCA |
| | | GTAGGTATGGGATGAACTGGGTCCGCCAGGCTCCAGGGAAGGGG |
| | | CTGGAGTGGGTCTCATCCATTAGTAGTAGTAGTGCTTACATACT |
| | | GTACGCAGACTCAGTGAAGGGCCGATTCACCATCTCCAGAGACA |
| | | ACGCCAAGAACTCACTGTATCTGCAAATGAACAGCCTGAGAGCC |
| | | GAGGACACGGCGGTGTACTACTGCGCCAGAGATGGTGGAAGAAC |
| | | GTCCTACACCGCCACAGCCCACAATTGGTTCGACCCCTGGGGAC |
| | | AGGGTACATTGGTCACCGTCTCCTCAGCTTCCACCAAGGGCCCC |
| | | TCCGTGTTCCCTCTGGCCCCTTGCTCCCGGTCCACCTCCGAGTC |
| | | TACCGCCGCTCTGGGCTGCCTCGTGAAGGACTACTTCCCCGAGC |
| | | CCGTGACCGTGTCCTGGAACTCTGGCGCCCTGACCTCCGGCGTG |
| | | CACACCTTCCCTGCCGTGCTGCAGTCCTCCGGCCTGTACTCCCT |
| | | GTCCAGCGTCGTGACCGTGCCCTCCTCCAGCCTGGGCACCAAGA |
| | | CCTACACCTGTAACGTGGACCACAAGCCCTCCAACACCAAAGTG |
| | | GACAAGCGGGTGGAATCTAAGTACGGCCCTCCCTGCCCTTCCTG |
| | | CCCTGCCCCTGAGTTCCTGGGCGGACCTTCCGTGTTCCTGTTCC |
| | | CTCCAAAGCCCAAGGACACCCTGATGATCTCCCGGACCCCTGAA |
| | | GTGACCTGCGTGGTGGTGGACGTGTCCCAGGAAGATCCCGAAGT |
| | | CCAGTTCAATTGGTACGTGGACGGCGTGGAAGTGCACAACGCCA |
| | | AGACCAAGCCCAGAGAGGAACAGTTCAACTCCACCTACCGGGTG |
| | | GTGTCCGTGCTGACCGTGCTGCACCAGGACTGGCTGAACGGCAA |
| | | AGAGTACAAGTGCAAAGTGTCCAACAAGGGCCTGCCCTCCAGCA |
| | | TCGAAAAGACCATCTCCAAGGCCAAGGGCCAGCCCCGCGAGCCC |
| | | CAAGTGTACACCCTGCCTCCCAGCCAGGAAGAGATGACCAAGAA |
| | | TCAAGTGTCCCTGACTTGTCTGGTCAAGGGCTTCTACCCCTCCG |
| | | ATATCGCCGTGGAGTGGGAGTCCAACGGCCAGCCCGAGAACAAC |

TABLE 1A-continued

Anti-IL-27 Antibodies

| SEQ ID NO | Description | Sequence |
|---|---|---|
| | | TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC | anti-IL-27 Ab6-A

| SEQ ID NO | Description | Sequence |
|---|---|---|
| 97 | HCDR1 (IMGT) | GFTFASYG |
| 98 | HCDR2 (IMGT) | ISSSSSYI |
| 99 | HCDR3 (IMGT) | ARDGGRTSYTATAHNWFDP |
| 100 | HCDR1 (NT) | FTFASYGMN |
| 101 | HCDR2 (NT) | SISSSSSYIYYADSVKG |
| 102 | HCDR3 (NT) | ARDGGRTSYTATAHNWFDP |
| 103 | VH | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 104 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCCGGTGTACTACTGCGCGCAGAGATGGTGGAAGAAC GTCCTACACCGCCACAGCCCACAATTGGTTCGACCCCTGGGGAC AGGGTACATTGGTCACCGTCTCCTCA |
| 105 | LCDR1 (IMGT) | QSVLFSSNNKNY |
| 106 | LCDR2 (IMGT) | WAS |
| 107 | LCDR3 (IMGT) | QQHASAPPT |
| 108 | LCDR1 (NT) | KSSQSVLFSSNNKNYLA |
| 109 | LCDR2 (NT) | WASTRES |
| 110 | LCDR3 (NT) | QQHASAPPT |
| 111 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 112 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCGCCAGTGCCCCTCCTAC TTTTGGCGGAGGGACCAAGGTTGAGATCAAA |
| 113 | Heavy Chain | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |

TABLE 1A-continued

Anti-IL-27 Antibodies

| SEQ ID NO | Description | Sequence |
|---|---|---|
| 114 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 115 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 116 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC | anti-IL-27 Ab6-B

| 117 | Heavy Chain | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 118 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA CTACGCAGACTCAGTGAAGGGCCGATTCACCATCTCCAGAGACA |

TABLE 1A-continued

Anti-IL-27 Antibodies

| SEQ ID NO | Description | Sequence |
|---|---|---|
| | | ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCAGCTTCCACCAAGGGCCCC<br>TCCGTGTTCCCTCTGGCCCCTTGCTCCCGGTCCACCTCCGAGTC<br>TACCGCCGCTCTGGGCTGCCTCGTGAAGGACTACTTCCCCGAGC<br>CCGTGACCGTGTCCTGGAACTCTGGCGCCCTGACCTCCGGCGTG<br>CACACCTTCCCTGCCGTGCTGCAGTCCTCCGGCCTGTACTCCCT<br>GTCCAGCGTCGTGACCGTGCCCTCCTCCAGCCTGGGCACCAAGA<br>CCTACACCTGTAACGTGGACCACAAGCCCTCCAACACCAAAGTG<br>GACAAGCGGGTGGAATCTAAGTACGGCCCTCCCTGCCCTTCCTG<br>CCCTGCCCCTGAGTTCCTGGGCGGACCTTCCGTGTTCCTGTTCC<br>CTCCAAAGCCCAAGGACACCCTGATGATCTCCCGGACCCCTGAA<br>GTGACCTGCGTGGTGGTGGACGTGTCCCAGGAAGATCCCGAAGT<br>CCAGTTCAATTGGTACGTGGACGGCGTGGAAGTGCACAACGCCA<br>AGACCAAGCCCAGAGAGGAACAGTTCAACTCCACCTACCGGGTG<br>GTGTCCGTGCTGACCGTGCTGCACCAGGACTGGCTGAACGGCAA<br>AGAGTACAAGTGCAAAGTGTCCAACAAGGGCCTGCCCTCCAGCA<br>TCGAAAAGACCATCTCCAAGGCCAAGGGCCAGCCCCGCGAGCCC<br>CAAGTGTACACCCTGCCTCCCAGCCAGGAAGAGATGACCAAGAA<br>TCAAGTGTCCCTGACTTGTCTGGTCAAGGGCTTCTACCCCTCCG<br>ATATCGCCGTGGAGTGGGAGTCCAACGGCCAGCCCGAGAACAAC<br>TACAAGACCACCCCTCCCGTGCTGGACTCCGACGGCTCCTTCTT<br>CCTGTACTCTCGGCTGACCGTGGACAAGTCCCGGTGGCAGGAG<br>GCAACGTCTTCTCCTGCTCCGTGATGCACGAGGCCCTGCACAAC<br>CACTACACCCAGAAGTCCCTGTCCCTGTCTCTGGGC |
| | | anti-IL-27 Ab1-A |
| 119 | HCDR1<br>(IMGT) | GFTFRSYG |
| 120 | HCDR2<br>(IMGT) | ISSSGSYI |
| 121 | HCDR3<br>(IMGT) | ARDGGRTSYTATAHNWFDP |
| 122 | HCDR1 (NT) | FTFRSYGMN |
| 123 | HCDR2 (NT) | GISSSGSYIYYADSVKG |
| 124 | HCDR3 (NT) | ARDGGRTSYTATAHNWFDP |
| 125 | VH | EVQLVESGGGLVKPGGSLRLSCAASGFTFRSYGMNWVRQAPGKG<br>LEWVSGISSSGSYIYYADSVKGRFTISRDNAKNSLYLQMNSLRA<br>EDTAVYYCARDGGRTSYTATAHNWFDPWGQGTLVTVSS |
| 126 | DNA VH | GAGGTGCAGCTGGTGGAGTCTGGGGGAGGCCTGGTCAAGCCTGG<br>GGGGTCCCTGAGACTCTCCTGTGCAGCCTCTGGATTCACCTTCC<br>GTAGCTATGGGATGAACTGGGTCCGCCAGGCTCCAGGGAAGGGG<br>CTGGAGTGGGTCTCAGGTATTAGTAGTAGTGGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCA |
| 127 | LCDR1<br>(IMGT) | QSVLFSSNNKNY |
| 128 | LCDR2<br>(IMGT) | WAS |
| 129 | LCDR3<br>(IMGT) | QQHASAPPT |
| 130 | LCDR1 (NT) | KSSQSVLFSSNNKNYLA |
| 131 | LCDR2 (NT) | WASTRES |
| 132 | LCDR3 (NT) | QQHASAPPT |

TABLE 1A-continued

Anti-IL-27 Antibodies

| SEQ ID NO | Description | Sequence |
|---|---|---|
| 133 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 134 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 135 | Heavy Chain | EVQLVESGGGLVKPGGSLRLSCAASGFTFRSYGMNWVRQAPGKG LEWVSGISSSGSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 136 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCC GTAGCTATGGGATGAACTGGGTCCGCCAGGCTCCAGGGAAGGGG CTGGAGTGGGTCTCAGGTATTAGTAGTAGTGGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 137 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 138 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT |

TABLE 1A-continued

Anti-IL-27 Antibodies

| SEQ ID NO | Description | Sequence |
|---|---|---|
| | | CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC |
| | anti-IL-27 Ab1-B | |
| 139 | Heavy Chain | EVQLVESGGGLVKPGGSLRLSCAASGFTFRSYGMNWVRQAPGKG LEWVSGISSSGSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 140 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCC GTAGCTATGGGATGAACTGGGTCCGCCAGGCTCCAGGGAAGGGG CTGGAGTGGGTCTCAGGTATTAGTAGTAGTGGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |
| 141 | FLAG | DYKDDDDK |
| 142 | 6-HIS | HHHHHH |
| 143 | HA | YPYDVPDYA |

In some aspects, the antibody, or antigen binding portion thereof, comprises an Fc sequence set forth in Table 1B. In some aspects, the antibody, or antigen binding portion thereof, comprises a heavy chain, wherein the heavy chain comprises an Fc region having an amino acid at least about 70%, at least about 75%, at least about 80%, at least about 85%, at least about 90%, at least about 95%, at least about 96%, at least about 97%, at least about 98%, at least about 99%, or about 100% sequence identity to the sequence set forth in SEQ ID NO: 5, 6, 7, or 8. In some aspects, the antibody, or antigen binding portion thereof, comprises a heavy chain, wherein the heavy chain comprises an Fc region comprising the amino acid sequence set forth in SEQ ID NO: 5. In some aspects, the antibody, or antigen binding portion thereof, comprises a heavy chain, wherein the heavy chain comprises an Fc region comprising the amino acid sequence set forth in SEQ ID NO: 6. In some aspects, the antibody, or antigen binding portion thereof, comprises a heavy chain, wherein the heavy chain comprises an Fc region comprising the amino acid sequence set forth in SEQ ID NO: 7. In some aspects, the antibody, or antigen binding portion thereof, comprises a heavy chain, wherein the heavy chain comprises an Fc region comprising the amino acid sequence set forth in SEQ ID NO: 8.

TABLE 1B

| Name | Alias | Amino Acid Sequence |
|------|-------|---------------------|
| Human IgG1 | 1.0 | EPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SRDELTKNQVSLTCLVKGFYPSDIAVEWESNGQPENNYKTTPPVLD SDGSFFLYSKLTVDKSRWQQGNVFSCSVMHEALHNHYTQKSLSLSP GK (SEQ ID NO: 5) |
| Human IgG4 | 4.0 | ESKYGPPCPSCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 6) |
| Human IgG4 (S228P) | 4.1 | ESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 7) |
| Human IgG4 (S228P/ L235E) | 4.2 | ESKYGPPCPPCPAPEFEGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 8) |

In some aspects, an antibody, or antigen binding portion thereof, of the present disclosure specifically binds to an epitope comprising Asp146 and Arg149 of SEQ ID NO: 2 (IL-27p28). In some aspects, an antibody, or antigen binding portion thereof, of the present disclosure specifically binds to an epitope comprising Asp146 and Phe153 of SEQ ID NO: 2 (IL-27p28). In some aspects, an antibody, or antigen binding portion thereof, of the present disclosure specifically binds to an epitope comprising Arg149 and Phe153 of SEQ ID NO: 2 (IL-27p28). In some aspects, an antibody, or antigen binding portion thereof, of the present disclosure specifically binds to an epitope comprising Asp146, Arg149, and/or Phe153 of SEQ ID NO: 2 (IL-27p28). In some aspects, an antibody, or antigen binding portion thereof, of the present disclosure specifically binds to an epitope comprising Asp146, Arg149, and Phe153 of SEQ ID NO: 2 (IL-27p28). In some aspects, the epitope comprises Asp146, Arg149, His150, and Phe153 of SEQ ID NO: 2 (IL-27p28). In some aspects, the epitope comprises Asp146, Arg149, Phe153, and Leu156 of SEQ ID NO: 2 (IL-27p28). In some aspects, the epitope comprises Asp146, Arg149, His150, Phe153, and Leu156 of SEQ ID NO: 2 (IL-27p28).

In some aspects, an antibody, or antigen binding portion thereof, of the present disclosure specifically binds to an epitope comprising at least one, at least two, at least three, at least four, at least five, or at least six amino acids of IL-27p28 selected from Leu142, Asp146, Arg149, His150, Phe153, Leu156, and Glu164 of SEQ ID NO: 2 (IL-27p28). In some aspects, an antibody, or antigen binding portion thereof, of the present disclosure specifically binds to an epitope comprising Leu142, Asp146, Arg149, His150, Phe153, Leu156, and Glu164 of SEQ ID NO: 2 (IL-27p28). In some aspects, the epitope comprises Gln37, Leu38, Glu42, Asp146, Arg149, His150, Phe153, and Leu156 of SEQ ID NO: 2 (IL-27p28). In some aspects, an antibody, or antigen binding portion thereof, of the present disclosure specifically binds to an epitope comprising Gln37, Leu38, Glu42, Leu142, Asp146, Arg149, His150, Phe153, Leu156, and Glu164 of SEQ ID NO: 2 (IL-27p28).

In some aspects, an antibody, or antigen binding portion thereof, of the present disclosure specifically binds to an epitope comprising Leu142, Asp146, Arg149, His150, Phe153, Leu156, Leu162, and Glu164 of SEQ ID NO: 2 (IL-27p28). In some aspects, an antibody, or antigen binding portion thereof, of the present disclosure specifically binds to an epitope comprising at least one, at least two, at least three, at least four, at least five, or at least six, at least seven, at least eight, or at least nine amino acids of IL-27p28 selected from Glu46, Val49, Ser50, Leu142, Asp146, Arg149, His150, Phe153, Leu156, and Glu164 of SEQ ID NO: 2 (IL-27p28). In some aspects, an antibody, or antigen binding portion thereof, of the present disclosure specifically binds to an epitope comprising Glu46, Val49, Ser50, Leu142, Asp146, Arg149, His150, Phe153, Leu156, and Glu164 of SEQ ID NO: 2 (IL-27p28). In some aspects, an antibody, or antigen binding portion thereof, of the present disclosure specifically binds to an epitope comprising at least one, at least two, at least three, at least four, at least five, or at least six, at least seven, at least eight, or at least nine amino acids of IL-27p28 selected from Gln37, Leu38, Glu42, Glu46, Val49, Ser50, Leu142, Asp146, Arg149, His150, Phe153, Leu156, Leu162, and Glu164 of SEQ ID NO: 2 (IL-27p28). In some aspects, an antibody, or antigen binding portion thereof, of the present disclosure specifically binds to an epitope comprising Gln37, Leu38, Glu42, Glu46, Val49, Ser50, Leu142, Asp146, Arg149, His150, Phe153, Leu156, Leu162, and Glu164 of SEQ ID NO: 2 (IL-27p28).

In some aspects, an antibody, or antigen binding portion thereof, of the present disclosure specifically binds to an epitope consisting of or consisting essentially of Gln37, Leu38, Glu42, Glu46, Val49, Ser50, Leu142, Asp146, Arg149, His150, Phe153, Leu156, Leu162, and Glu164 of SEQ ID NO: 2 (IL-27p28).

In some aspects, an antibody, or antigen binding portion thereof, of the present disclosure specifically binds to an epitope comprising Gln37, Leu38, Glu42, Glu46, Val49, Ser50, Leu142, Asp146, Arg149, His150, Phe153, Leu156, Leu162, and Glu164 of SEQ ID NO: 2 (IL-27p28) and at least one residues selected from the group consisting of: Leu53, Lys56, Asp143, Leu147, Arg152, Ala157, Gly159, Phe160, or Asn161 of SEQ ID NO: 2 (IL-27p28).

In some aspects, an antibody, or antigen binding portion thereof, of the present disclosure specifically binds to an epitope comprising Gln37, Leu38, Glu42, Glu46, Val49, Ser50, Leu142, Asp146, Arg149, His150, Phe153, Leu156, Leu162, and Glu164 of SEQ ID NO: 2 (IL-27p28) and at least one residues selected from the group consisting of: Leu53, Lys56, Asp143, Arg145, Leu147, Arg152, Ala157, Gly159, Phe160, Asn161, or Pro163 of SEQ ID NO: 2 (IL-27p28).

In some aspects, an antibody, or antigen binding portion thereof, of the present disclosure specifically binds to an epitope consisting or consisting essentially of Gln37, Leu38, Glu42, Glu46, Val49, Ser50, Leu53, Lys56, Leu142, Asp143, Asp146, Leu147, Arg149, His150, Arg152, Phe153, Leu156, Ala157, Gly159, Phe160, Asn161, Leu162, and Glu164 of SEQ ID NO: 2 (IL-27p28).

In some aspects, an antibody, or antigen binding portion thereof, of the present disclosure specifically binds to an epitope consisting or consisting essentially of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28).

In some aspects, the disclosure provides an isolated antibody that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28) and antagonizes human IL-27, or an antigen binding portion thereof, wherein the antibody or antigen binding portion thereof exhibits at least one or more of the following properties: (i) binds to human IL-27 with an equilibrium dissociation constant ($K_D$) of 15 nM or less; (ii) blocks binding of IL-27 to IL-27 receptor; (iii) inhibits or reduces STAT1 and/or STAT3 phosphorylation in a cell; (iv) inhibits or reduces inhibition of CD161 expression in a cell; (v) inhibits or reduces PD-L1 expression in a cell; (vi) induces or enhances PD-1 mediated secretion of one or more cytokines from a cell; (vii) alters TIM-3 expression in a cell; and (viii) a combination of (i)-(vii).

In some aspects, the isolated antibody, or antigen binding portion thereof, binds to an epitope of one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (human IL-27p28) with an equilibrium dissociation constant ($K_D$) of 15 nM or less.

In some aspects, the isolated antibody, or antigen binding portion thereof, binds to recombinant human IL-27p28. In some aspects, the isolated antibody, or antigen binding portion thereof, binds to murine IL-27p28.

In some aspects, the isolated antibody, or antigen binding portion thereof, inhibits or reduces STAT1 phosphorylation in a cell. In some aspects, the isolated antibody, or antigen binding portion thereof, inhibits or reduces STAT3 phosphorylation in a cell. In some aspects, the isolated antibody, or antigen binding portion thereof, inhibits or reduces STAT1 and STAT3 phosphorylation in a cell. In some aspects, the isolated antibody, or antigen binding portion thereof, inhibits or reduces STAT1 phosphorylation in a cell by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 50%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 60%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 70%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 75%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 80%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 85%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 90%, relative to the STAT1 phosphorylation in the cell prior to contacting the cell with the antibody, or antigen binding portion thereof. In some aspects, the isolated antibody, or antigen binding portion thereof, inhibits or reduces STAT1 phosphorylation in a cell by at least about 95%, relative to the STAT1 phosphorylation in the cell prior to contacting the cell with the antibody, or antigen binding portion thereof. In some aspects, the isolated antibody, or antigen binding portion thereof, eliminates STAT1 phosphorylation in the cell.

In some aspects, the isolated antibody, or antigen binding portion thereof, inhibits or reduces STAT3 phosphorylation in a cell by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 50%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 60%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 70%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 75%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 80%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 85%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 90%, relative to the STAT3 phosphorylation in the cell prior to contacting the cell with the antibody, or antigen binding portion thereof. In some aspects, the isolated antibody, or antigen binding portion thereof, inhibits or reduces STAT3 phosphorylation in a cell by at least about 95%, relative to the STAT3 phosphorylation in the cell prior to contacting the cell with the antibody, or antigen binding portion thereof. In some aspects, the isolated antibody, or antigen binding portion thereof, eliminates STAT3 phosphorylation in the cell.

In some aspects, the cell is an immune cell. In some aspects, the cell is a cancer cell.

In some aspects, the isolated antibody, or antigen binding portion thereof, inhibits or reduces inhibition of CD161 expression in a cell (e.g. ameliorates or relieves the inhibition of CD161 expression in a cell). In some aspects, the cell is an immune cell.

In some aspects, the isolated antibody, or antigen binding portion thereof, inhibits or reduces PD-L1 expression in a cell. In some aspects, PD-L1 expression is inhibited or reduced. In some aspects, TIM-3 expression is altered. In some aspects, both PD-L1 expression and TIM-3 expression is altered. In some aspects, the cell is an immune cell. In some aspects, the antibodies are monoclonal antibodies.

In some aspects, the isolated antibody, or antigen binding portion thereof, induces or enhances the PD-1-mediated secretion of one or more cytokines from a cell. In some aspects, the one or more cytokines is TNFα. In some aspects, the one or more cytokine is IL-6. In some aspects, the one or more cytokine is TNFα and IL-6. In some aspects, the cell is an immune cell.

In some aspects, the isolated antibody, or antigen binding portion thereof, is selected from the group consisting of an IgG1, an IgG2, an IgG3, an IgG4, an IgM, an IgA1 an IgA2, an IgD, and an IgE antibody. In some aspects, the antibody is an IgG1 antibody or an IgG4 antibody. In some aspects, the antibody comprises a wild type IgG1 heavy chain constant region. In some aspects, the antibody comprises a wild type IgG4 heavy chain constant region. In some aspects, the antibody comprises an Fc domain comprising at least one mutation. In some aspects, the antibody comprises a mutant IgG1 heavy chain constant region. In some aspects, the antibody comprises a mutant IgG4 heavy chain constant region. In some aspects, the mutant IgG4 heavy chain constant region comprises any one of the substitutions S228P, L235E, L235A, or a combination thereof, according to EU numbering.

In some aspects, the disclosure provides an isolated antibody, or antigen binding portion thereof, that binds to substantially the same epitope on IL-27 as the antibody, or antigen binding portion thereof, according to any one of the aforementioned aspects.

In some aspects, the disclosure provides an isolated antibody, or antigen binding portion thereof, that binds to at least one of the amino acid residues selected from the group consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28) bound by the antibody, or antigen binding portion thereof, according to any one of the aforementioned aspects.

In some aspects, the disclosure provides an isolated antibody, or antigen binding portion thereof, wherein a mutation of the epitope (Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28)) bound by the antibody or antigen binding portion thereof inhibits, reduces, or blocks binding to both the antibody or antigen binding portion thereof and to the antibody or antigen binding portion thereof according to any one of the aforementioned aspects.

In some aspects, the antibody, or antigen binding portion thereof, comprises heavy chain CDR1, heavy chain CDR2, heavy chain CDR3, light chain CDR1, light chain CDR2, and light chain CDR3, wherein light chain CDR1 consists of N-XXXXXXLFSSNXKXYXX-C. In some aspects, the antibody, or antigen binding portion thereof, comprises heavy chain CDR1, heavy chain CDR2, heavy chain CDR3, light chain CDR1, light chain CDR2, and light chain CDR3, wherein light chain CDR3 consists of N-XXXASAXXX-C. In some aspects, the antibody, or antigen binding portion thereof, comprises heavy chain CDR1, heavy chain CDR2, heavy chain CDR3, light chain CDR1, light chain CDR2, and light chain CDR3, wherein heavy chain CDR2 consists of N-XXSSSXSYXYXXXXXXX-C. In some aspects, the antibody, or antigen binding portion thereof, comprises heavy chain CDR1, heavy chain CDR2, heavy chain CDR3, light chain CDR1, light chain CDR2, and light chain CDR3, wherein heavy chain CDR3 consists of N-XXXXGRT-SYTATXHNXXXX-C, wherein X is any amino acids.

In some aspects, the antibody, or antigen binding portion thereof, comprises heavy chain CDR1, heavy chain CDR2, heavy chain CDR3, light chain CDR1, light chain CDR2, and light chain CDR3, wherein light chain CDR1 consists of N-XXXXXXLFSSNXKXYXX-C and light chain CDR3 consists of N-XXXASAXXX-C. In some aspects, the antibody, or antigen binding portion thereof, comprises heavy chain CDR1, heavy chain CDR2, heavy chain CDR3, light chain CDR1, light chain CDR2, and light chain CDR3, wherein heavy chain CDR2 consists of N-XXSSSXSYXYXXXXXXX-C and heavy chain CDR3 consists of N-XXXXGRTSYTATXHNXXXX-C, wherein X is any amino acids.

In some aspects, the antibody, or antigen binding portion thereof, comprises heavy chain CDR1, heavy chain CDR2, heavy chain CDR3, light chain CDR1, light chain CDR2, and light chain CDR3, wherein light chain CDR1 consists of N-XXXXXXLFSSNXKXYXX-C, light chain CDR3 consists of N-XXXASAXXX-C, heavy chain CDR2 consists of N-XXSSSXSYXYXXXXXXX-C, and heavy chain CDR3 consists of N-XXXXGRTSYTATXHNXXXX-C, wherein X is any amino acids.

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 9, 10 and 11, respectively, and light chain CDR1, CDR2 and CDR3 sequences set forth in SEQ ID NOs: 17, 18 and 19, respectively;

(ii) heavy chain CDR1, CDR2 and CDR3 sequences set forth in SEQ ID NOs: 31, 32 and 33, respectively, and light chain CDR1, CDR2 and CDR3 sequences set forth in SEQ ID NOs: 39, 40 and 41, respectively;

(iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 61, 62 and 63, respectively;

(iv) heavy chain CDR1, CDR2 and CDR3 sequences set forth in SEQ ID NOs: 75, 76 and 77, respectively, and light chain CDR1, CDR2 and CDR3 sequences set forth in SEQ ID NOs: 83, 84 and 85, respectively;

(v) heavy chain CDR1, CDR2 and CDR3 sequences set forth in SEQ ID NOs: 97, 98 and 99, respectively, and light chain CDR1, CDR2 and CDR3 sequences set forth in SEQ ID NOs: 105, 106 and 107, respectively; or (vi) heavy chain CDR1, CDR2 and CDR3 sequences set forth in SEQ ID NOs: 119, 120 and 121, respectively, and light chain CDR1, CDR2 and CDR3 sequences set forth in SEQ ID NOs: 127, 128 and 129, respectively.

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 9, 10 and 11, respectively, and light chain CDR1, CDR2 and CDR3 sequences set forth in SEQ ID NOs: 17, 18 and 19, respectively;

(ii) heavy chain CDR1, CDR2 and CDR3 sequences set forth in SEQ ID NOs: 31, 32 and 33, respectively, and light chain CDR1, CDR2 and CDR3 sequences set forth in SEQ ID NOs: 39, 40 and 41, respectively;

(iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 61, 62 and 63, respectively;

(iv) heavy chain CDR1, CDR2 and CDR3 sequences set forth in SEQ ID NOs: 75, 76 and 77, respectively, and light chain CDR1, CDR2 and CDR3 sequences set forth in SEQ ID NOs: 83, 84 and 85, respectively;

(v) heavy chain CDR1, CDR2 and CDR3 sequences set forth in SEQ ID NOs: 97, 98 and 99, respectively, and light chain CDR1, CDR2 and CDR3 sequences set forth in SEQ ID NOs: 105, 106 and 107, respectively; or (vi) heavy chain CDR1, CDR2 and CDR3 sequences set forth in SEQ ID NOs: 119, 120 and 121, respectively, and light chain CDR1, CDR2 and CDR3 sequences set forth in SEQ ID NOs: 127, 128 and 129, respectively.

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 9, 10 and 11, respectively, and light chain CDR1, CDR2 and CDR3 sequences set forth in SEQ ID NOs: 17, 18 and 19, respectively;

(ii) heavy chain CDR1, CDR2 and CDR3 sequences set forth in SEQ ID NOs: 31, 32 and 33, respectively, and light chain CDR1, CDR2 and CDR3 sequences set forth in SEQ ID NOs: 39, 40 and 41, respectively;

(iii) heavy chain CDR1, CDR2 and CDR3 sequences set forth in SEQ ID NOs: 53, 54 and 55, respectively, and light chain CDR1, CDR2 and CDR3 sequences set forth in SEQ ID NOs: 61, 62 and 63, respectively;

(iv) heavy chain CDR1, CDR2 and CDR3 sequences set forth in SEQ ID NOs: 75, 76 and 77, respectively, and light chain CDR1, CDR2 and CDR3 sequences set forth in SEQ ID NOs: 83, 84 and 85, respectively;

(v) heavy chain CDR1, CDR2 and CDR3 sequences set forth in SEQ ID NOs: 97, 98 and 99, respectively, and light chain CDR1, CDR2 and CDR3 sequences set forth in SEQ ID NOs: 105, 106 and 107, respectively; or (vi) heavy chain CDR1, CDR2 and CDR3 sequences set forth in SEQ ID NOs: 119, 120 and 121, respectively, and light chain CDR1, CDR2 and CDR3 sequences set forth in SEQ ID NOs: 127, 128 and 129, respectively.

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 12, 13 and 14, respectively, and light chain CDR1, CDR2 and CDR3 sequences set forth in SEQ ID NOs: 20, 21 and 22, respectively;

(ii) heavy chain CDR1, CDR2 and CDR3 sequences set forth in SEQ ID NOs: 34, 35 and 36, respectively, and light chain CDR1, CDR2 and CDR3 sequences set forth in SEQ ID NOs: 42, 43 and 44, respectively;

(iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 64, 65 and 66, respectively;

(iv) heavy chain CDR1, CDR2 and CDR3 sequences set forth in SEQ ID NOs: 78, 79 and 80, respectively, and light chain CDR1, CDR2 and CDR3 sequences set forth in SEQ ID NOs: 86, 88 and 89, respectively;

(v) heavy chain CDR1, CDR2 and CDR3 sequences set forth in SEQ ID NOs: 100, 101 and 102, respectively, and light chain CDR1, CDR2 and CDR3 sequences set forth in SEQ ID NOs: 108, 109 and 110, respectively; or (vi) heavy chain CDR1, CDR2 and CDR3 sequences set forth in SEQ ID NOs: 122, 123 and 124, respectively, and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 12, 13 and 14, respectively, and light chain CDR1, CDR2 and CDR3 sequences set forth in SEQ ID NOs: 20, 21 and 22, respectively;

(ii) heavy chain CDR1, CDR2 and CDR3 sequences set forth in SEQ ID NOs: 34, 35 and 36, respectively, and light chain CDR1, CDR2 and CDR3 sequences set forth in SEQ ID NOs: 42, 43 and 44, respectively;

(iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 64, 65 and 66, respectively;

(iv) heavy chain CDR1, CDR2 and CDR3 sequences set forth in SEQ ID NOs: 78, 79 and 80, respectively, and light chain CDR1, CDR2 and CDR3 sequences set forth in SEQ ID NOs: 86, 88 and 89, respectively;

(v) heavy chain CDR1, CDR2 and CDR3 sequences set forth in SEQ ID NOs: 100, 101 and 102, respectively, and light chain CDR1, CDR2 and CDR3 sequences set forth in SEQ ID NOs: 108, 109 and 110, respectively; or (vi) heavy chain CDR1, CDR2 and CDR3 sequences set forth in SEQ ID NOs: 122, 123 and 124, respectively, and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise heavy and light chain CDRs selected from the group consisting of:

(i) heavy chain CDR1, CDR2 and CDR3 sequences set forth in SEQ ID NOs: 12, 13 and 14, respectively, and light chain CDR1, CDR2 and CDR3 sequences set forth in SEQ ID NOs: 20, 21 and 22, respectively;

(ii) heavy chain CDR1, CDR2 and CDR3 sequences set forth in SEQ ID NOs: 34, 35 and 36, respectively, and light chain CDR1, CDR2 and CDR3 sequences set forth in SEQ ID NOs: 42, 43 and 44, respectively;

---

(iii) heavy chain CDR1, CDR2 and CDR3 sequences set forth in SEQ ID NOs: 56, 57 and 58, respectively, and light chain CDR1, CDR2 and CDR3 sequences set forth in SEQ ID NOs: 64, 65 and 66, respectively;

(iv) heavy chain CDR1, CDR2 and CDR3 sequences set forth in SEQ ID NOs: 78, 79 and 80, respectively, and light chain CDR1, CDR2 and CDR3 sequences set forth in SEQ ID NOs: 86, 88 and 89, respectively;

(v) heavy chain CDR1, CDR2 and CDR3 sequences set forth in SEQ ID NOs: 100, 101 and 102, respectively, and light chain CDR1, CDR2 and CDR3 sequences set forth in SEQ ID NOs: 108, 109 and 110, respectively; or (vi) heavy chain CDR1, CDR2 and CDR3 sequences set forth in SEQ ID NOs: 122, 123 and 124, respectively, and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not consist of N-GFTF[S/A/R][S/R][T/Y][G/S]-C (SEQ ID NO: 144) and/or the heavy chain CDR2 does not consist of N-ISSS[S/G][S/A]YI-C (SEQ ID NO: 146).

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not consist of N-GFTF[S/A/R][S/R][T/Y][G/S]-C (SEQ ID NO: 144) and/or the heavy chain CDR2 does not consist of N-ISSS[S/G][S/A]YI-C (SEQ ID NO: 146).

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not consist of N-GFTF[S/A/R][S/R][T/Y][G/S]-C (SEQ ID NO: 144) and/or the heavy chain CDR2 does not consist of N-ISSS[S/G][S/A]YI-C (SEQ ID NO: 146).

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2

(IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not comprise N-FTF[S/A/R][S/R][T/Y] [G/S]MN-C (SEQ ID NO: 148) and/or the heavy chain CDR2 does not comprise N-[G/S]ISSS[S/G][S/A]YI[L/Y] YADSVKG-C (SEQ ID NO: 149).

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not comprise N-FTF[S/A/R][S/R][T/Y][G/S]MN-C (SEQ ID NO: 148) and/or the heavy chain CDR2 does not comprise N-[G/S] ISSS[S/G][S/A]YI[L/Y]YADSVKG-C (SEQ ID NO: 149).

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain CDR1, a heavy chain CDR2, a heavy chain CDR3, a light chain CDR1, a light chain CDR2, and a light chain CDR3 and wherein the heavy chain CDR1 does not comprise N-FTF[S/A/R][S/R][T/Y] [G/S]MN-C (SEQ ID NO: 148) and/or the heavy chain CDR2 does not comprise N-[G/S]ISSS[S/G][S/A]YI[L/Y] YADSVKG-C (SEQ ID NO: 149).

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise:

(i) heavy chain CDR1 consisting of N-GFTFXXXX-C (SEQ ID NO: 145), heavy chain CDR2 consisting of N-ISSSXXYI-C (SEQ ID NO: 147), and heavy chain CDR3 sequence set forth in SEQ ID NO: 121; and light chain CDR1, CDR2 and CDR3 sequences set forth in SEQ ID NOs: 127, 128 and 129, respectively; or (ii) heavy chain CDR1 consisting of N-FTFXXXXMN-C (SEQ ID NO: 150), heavy chain CDR2 consisting of N-XISSSXXYIXYADSVKG-C (SEQ ID NO: 151), and heavy chain CDR3 sequence set forth in SEQ ID NO: 124; and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof does not comprise:

(i) heavy chain CDR1 consisting of N-GFTFXXXX-C (SEQ ID NO: 145), heavy chain CDR2 consisting of N-ISSSXXYI-C (SEQ ID NO: 147), and heavy chain CDR3 sequence set forth in SEQ ID NO: 121; and light chain CDR1, CDR2 and CDR3 sequences set forth in SEQ ID NOs: 127, 128 and 129, respectively; or (ii) heavy chain CDR1 consisting of N-FTFXXXXMN-C (SEQ ID NO: 150), heavy chain CDR2 consisting of N-XISSSXXYIXYADSVKG-C (SEQ ID NO: 151), and heavy chain CDR3 sequence set forth in SEQ ID NO: 124; and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise:

(i) heavy chain CDR1 consisting of N-GFTFXXXX-C (SEQ ID NO: 145), heavy chain CDR2 consisting of N-ISSSXXYI-C (SEQ ID NO: 147), and heavy chain CDR3 sequence set forth in SEQ ID NO: 121; and light chain CDR1, CDR2 and CDR3 sequences set forth in SEQ ID NOs: 127, 128 and 129, respectively; or (ii) heavy chain CDR1 consisting of N-FTFXXXXMN-C (SEQ ID NO: 150), heavy chain CDR2 consisting of N-XISSSXXYIXYADSVKG-C (SEQ ID NO: 151), and heavy chain CDR3 sequence set forth in SEQ ID NO: 124; and light chain CDR1, CDR2 and CDR3 sequences set forth in SEQ ID NOs: 130, 131 and 132, respectively.

In some aspects, the present disclosure provides an isolated antibody or antigen binding portion thereof that specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise:heavy chain CDR1 consisting of N-GFTFXXXX-C (SEQ ID NO: 145), heavy chain CDR2 consisting of N-IXXXXXXX-C (SEQ ID NO: 152), and heavy chain CDR3 sequence consisting of N-AR[X]$_{n=6-15}$DX-C (SEQ ID NO: 153); and light chain CDR1 consisting of N-QS[X]$_{n=1-3}$SS[X]$_{n=0-4}$Y-C (SEQ ID NO: 154), light chain CDR2 consisting of N-XXS-C (SEQ ID NO: 155), and light chain CDR3 sequence consisting of N-QQXXXXP[X]$_{n=0-1}$T-C(SEQ ID NO: 156), respectively.

In some aspects, the present disclosure provides an isolated antibody or antigen binding portion thereof that specifically binds to an epitope comprising or consisting of Gln37, Leu38, Glu42, Glu46, Val49, Ser50, Leu142, Asp146, Arg149, His150, Phe153, Leu156, Leu162, and Glu164 of SEQ ID NO: 2 (IL-27p28), wherein the antibody or antigen binding portion thereof does not comprise:heavy chain CDR1 consisting of N-GFTFXXXX-C (SEQ ID NO: 145), heavy chain CDR2 consisting of N-IXXXXXXX-C (SEQ ID NO: 152), and heavy chain CDR3 sequence consisting of N-AR[X]$_{n=6-15}$DX-C (SEQ ID NO: 153); and light chain CDR1 consisting of N-QS[X]$_{n=1-3}$SS[X]$_{n=0-4}$Y-C (SEQ ID NO: 154), light chain CDR2 consisting of N-XXS-C(SEQ ID NO: 155), and light chain CDR3 sequence consisting of N-QQXXXXP[X]$_{n=0-1}$T-C (SEQ ID NO: 156), respectively.

In some aspects, the present disclosure provides an isolated antibody or antigen binding portion thereof that specifically binds to an epitope comprising or consisting of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof does not comprise:heavy chain CDR1 consisting of N-GFTFXXXX-C (SEQ ID NO: 145), heavy chain CDR2 consisting of N-IXXXXXXX-C (SEQ ID NO: 152), and heavy chain CDR3 sequence consisting of N-AR[X]$_{n=6-15}$DX-C (SEQ ID NO: 153); and light chain CDR1 consisting of N-QS[X]$_{n=1-3}$SS[X]$_{n=0-4}$Y-C (SEQ ID NO: 154), light chain CDR2 consisting of N-XXS-C(SEQ ID NO: 155), and light chain CDR3 sequence consisting of N-QQXXXXP[X]$_{n=0-}$T-C (SEQ ID NO: 156), respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises heavy and light chain variable regions, wherein the heavy chain variable region does not comprise an amino acid sequence selected from the group consisting of SEQ ID NOs: 15, 37, 59, 81, 103, and 125; and wherein the light chain variable region does not comprise an amino acid sequence selected from the group consisting of SEQ ID NOs: 23, 45, 67, 89, 111, and 133.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises heavy and light chain variable regions, wherein the heavy chain variable region and the light chain variable region are not amino acid sequences selected from the group consisting of:

(i) SEQ ID NO: 15 and 65, respectively;
(ii) SEQ ID NO: 37 and 45, respectively;
(iii) SEQ ID NO: 59 and 67, respectively;
(iv) SEQ ID NO: 81 and 89, respectively;
(v) SEQ ID NO: 103 and 111, respectively; and
(vi) SEQ ID NO: 125 and 133, respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises heavy and light chain variable regions, wherein the heavy chain variable region does not comprise an amino acid sequence which is at least 90% identical to the amino acid sequence selected from the group consisting of SEQ ID NOs: 15, 37, 59, 81, 103, and 125; and wherein the light chain variable region does not comprise an amino acid sequence which is at least 90% identical to the amino acid sequence selected from the group consisting of SEQ ID NOs: 23, 45, 67, 89, 111, and 133.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises heavy and light chain variable regions, wherein the heavy chain variable region and the light chain variable region do not comprise amino acid sequences at least 90% identical to the amino acid sequences selected from the group consisting of:

(i) SEQ ID NO: 15 and 65, respectively;
(ii) SEQ ID NO: 37 and 45, respectively;
(iii) SEQ ID NO: 59 and 67, respectively;
(iv) SEQ ID NO: 81 and 89, respectively;
(v) SEQ ID NO: 103 and 111, respectively; and
(vi) SEQ ID NO: 125 and 133, respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain and a light chain, wherein the heavy chain does not comprise an amino acid sequence selected from the group consisting of SEQ ID NOs: 25, 47, 69, 91, 113, and 135; and wherein the light chain does not comprise an amino acid sequence selected from the group consisting of SEQ ID NOs: 20, 42, 71, 93, and 1115.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy and a light chain, wherein the heavy chain does not comprise an amino acid sequence which is at least 90% identical to the amino acid sequence selected from the group consisting of SEQ ID NOs: 25, 47, 69, 91, 113, and 135; and wherein the light chain does not comprise an amino acid sequence which is at least 90% identical to the amino acid sequence selected from the group consisting of SEQ ID NOs: 20, 42, 71, 93, and 115.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain and a light chain, wherein the heavy chain does not comprise an amino acid sequence selected from the group consisting of SEQ ID NOs: 29, 51, 73, 95, 117, and 139; and wherein the light chain does not comprise an amino acid sequence selected from the group consisting of SEQ ID NOs: 71, 49, 71, 93, 115, and 137.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy and a light chain, wherein the heavy chain does not comprise an amino acid sequence which is at least 90% identical to the amino acid sequence selected from the group consisting of SEQ ID NOs: 29, 51, 73, 95, 117, and 139; and wherein the light chain does not comprise an amino acid sequence which is at least 90% identical to the amino acid sequence selected from the group consisting of SEQ ID NOs: 71, 49, 71, 93, 115, and 137.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain and a light chain, and wherein the heavy chain and the light chain do not comprise amino acid sequences selected from the group consisting of:

(i) SEQ ID NO: 25 and 27, respectively;
(ii) SEQ ID NO: 47 and 49, respectively;
(iii) SEQ ID NO: 69 and 71, respectively;
(iv) SEQ ID NO: 91 and 93, respectively;
(v) SEQ ID NO: 113 and 115, respectively; and
(vi) SEQ ID NO: 135 and 137, respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy chain and a light chain and wherein the heavy chain and the light chain do not comprise amino acid sequences at least 90% identical to the amino acid sequences selected from the group consisting of:

(i) SEQ ID NO: 25 and 27, respectively;
(ii) SEQ ID NO: 47 and 49, respectively;
(iii) SEQ ID NO: 69 and 71, respectively;
(iv) SEQ ID NO: 91 and 93, respectively;
(v) SEQ ID NO: 113 and 115, respectively; and
(vi) SEQ ID NO: 135 and 137, respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28), wherein the antibody or antigen binding portion thereof comprises a heavy and a light chain and wherein the heavy chain and the light chain do not comprise amino acid sequences selected from the group consisting of:

(i) SEQ ID NO: 29 and 27, respectively;
(ii) SEQ ID NO: 51 and 49, respectively;
(iii) SEQ ID NO: 73 and 72, respectively;
(iv) SEQ ID NO: 95 and 93, respectively;
(v) SEQ ID NO: 117 and 115, respectively; and
(vi) SEQ ID NO: 139 and 137, respectively.

In some aspects, the present disclosure provides an isolated antibody or antigen binding portion thereof that antagonizes IL-27 and specifically binds to an epitope comprising one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL27-p28), wherein the antibody or antigen binding portion thereof comprises a heavy and a light chain and wherein the heavy chain and the light chain do not comprise amino acid sequences at least 90% identical to the amino acid sequences selected from the group consisting of: (i) SEQ ID NO: 29 and 27, respectively; (ii) SEQ ID NO: 51 and 49, respectively; (iii) SEQ ID NO: 73 and 72, respectively; (iv) SEQ ID NO: 95 and 93, respectively; (v) SEQ ID NO: 117 and 115, respectively; and (vi) SEQ ID NO: 139 and 137, respectively.

B. Pharmaceutical Compositions and Formulations

In some aspects, the antibody, or antigen-binding portion thereof, useful in the methods and compositions disclosed herein is present in a pharmaceutical composition. As such, some aspects of the present disclosure are directed to a pharmaceutical composition comprising an anti-IL-27 antibody with a pharmaceutically acceptable diluent, carrier, solubilizer, emulsifier, preservative and/or adjuvant.

In certain aspects, acceptable formulation materials preferably are nontoxic to recipients at the dosages and concentrations employed. In certain aspects, the formulation material(s) are for s.c. and/or I.V. administration. In certain aspects, the pharmaceutical composition comprises formulation materials for modifying, maintaining or preserving, for example, the pH, osmolality, viscosity, clarity, color, isotonicity, odor, sterility, stability, rate of dissolution or release, adsorption or penetration of the composition. In certain aspects, suitable formulation materials include, but are not limited to, amino acids (such as glycine, glutamine, asparagine, arginine or lysine); antimicrobials; antioxidants (such as ascorbic acid, sodium sulfite or sodium hydrogensulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain aspects, the formulation comprises PBS; 20 mM NaOAC, pH 5.2, 50 mM NaCl; and/or 10 mM NAOAC, pH 5.2, 9% Sucrose. In certain aspects, the optimal pharmaceutical composition will be determined by one skilled in the art depending upon, for example, the intended route of administration, delivery format and desired dosage. See, for example, Remington's Pharmaceutical Sciences, supra. In certain aspects, such compositions influence the physical state, stability, rate of in vivo release and/or rate of in vivo clearance of the anti-IL-27 antibody.

In certain aspects, the primary vehicle or carrier in a pharmaceutical composition is either aqueous or non-aqueous in nature. For example, in certain aspects, a suitable vehicle or carrier is water for injection, physiological saline solution or artificial cerebrospinal fluid, possibly supplemented with other materials common in compositions for parenteral administration. In certain aspects, the saline comprises isotonic phosphate-buffered saline. In certain aspects, neutral buffered saline or saline mixed with serum albumin are further exemplary vehicles. In certain aspects, pharmaceutical compositions comprise Tris buffer of about pH 7.0-8.5, or acetate buffer of about pH 4.0-5.5. In some aspects, the pharmaceutical compositon further comprises sorbitol or a suitable substitute therefore. In certain aspects, a composition comprising an anti-IL-27 antibody is prepared for storage by mixing the selected composition having the desired degree of purity with optional formulation agents (Remington's Pharmaceutical Sciences, supra) in the form of a lyophilized cake or an aqueous solution. Further, in certain aspects, a composition comprising an anti-IL-27 antibody is formulated as a lyophilizate using appropriate excipients such as sucrose.

In certain aspects, the pharmaceutical composition is selected for parenteral delivery. In certain aspects, the compositions is selected for inhalation or for delivery through the digestive tract, such as orally. The preparation of such pharmaceutically acceptable compositions is within the ability of one skilled in the art.

In certain aspects, the formulation components are present in concentrations that are acceptable to the site of administration. In certain aspects, buffers are used to maintain the composition at physiological pH or at a slightly lower pH, typically within a pH range of from about 5 to about 8.

In certain aspects, when parenteral administration is contemplated, a therapeutic composition is in the form of a pyrogen-free, parenterally acceptable aqueous solution comprising an anti-IL-27 antibody, in a pharmaceutically acceptable vehicle. In certain aspects, a vehicle for parenteral injection is sterile distilled water in which an anti-IL-27 antibody is formulated as a sterile, isotonic solution, and properly preserved. In certain aspects, the preparation involves the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain aspects, hyaluronic acid is also used. Hyaluronic acid, when present, can have the effect of promoting sustained duration in the circulation. In certain aspects, implantable drug delivery devices are used to introduce the desired molecule.

In certain aspects, a pharmaceutical composition is formulated for inhalation. In certain aspects, an anti-IL-27 antibody is formulated as a dry powder for inhalation. In certain aspects, an inhalation solution comprising an anti-IL-27 antibody is formulated with a propellant for aerosol delivery. In certain aspects, solutions are nebulized. Pulmonary administration is further described in PCT application No. PCT/US94/001875, which describes pulmonary delivery of chemically modified proteins.

In certain aspects, the pharmaceutical composition disclosed herein is formulated for oral administration. In some aspects, the pharmaceutical composition is administered orally. In certain aspects, an anti-IL-27 antibody that is administered in this fashion is formulated with or without those carriers customarily used in the compounding of solid dosage forms such as tablets and capsules. In certain aspects, a capsule is designed to release the active portion of the formulation at the point in the gastrointestinal tract when bioavailability is maximized and pre-systemic degradation is minimized. In certain aspects, at least one additional agent is included to facilitate absorption of an anti-IL-27 antibody. In certain aspects, diluents, flavorings, low melting point waxes, vegetable oils, lubricants, suspending agents, tablet disintegrating agents, and binders are also employed.

In certain aspects, a pharmaceutical composition involves an effective quantity of an anti-IL-27 antibody in a mixture with non-toxic excipients which are suitable for the manufacture of tablets. In certain aspects, by dissolving the tablets in sterile water, or another appropriate vehicle, solutions are prepared in unit-dose form. In certain aspects, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-IL-27 antibody in sustained- or controlled-delivery formulations. In certain aspects, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain aspects, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(-)-3-hydroxybutyric acid (EP 133,988). In certain aspects, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain aspects, this is accomplished by filtration through sterile filtration membranes. In certain aspects, where the composition is lyophilized, sterilization using this method is conducted either prior to or following lyophilization and reconstitution. In certain aspects, the composition for parenteral administration is stored in lyophilized form or in a solution. In certain aspects, parenteral compositions generally are placed into a container having a sterile access port, for example, an intravenous solution bag or vial having a stopper pierceable by a hypodermic injection needle.

In certain aspects, once the pharmaceutical composition has been formulated, it is stored in sterile vials as a solution, suspension, gel, emulsion, solid, or as a dehydrated or lyophilized powder. In certain aspects, such formulations are stored either in a ready-to-use form or in a form (e.g., lyophilized) that is reconstituted prior to administration.

In certain aspects, kits are provided for producing a single-dose administration unit. In certain aspects, the kit comprises both a first container having a dried protein and a second container having an aqueous formulation. In certain aspects, kits comprising single and multi-chambered pre-filled syringes (e.g., liquid syringes and lyosyringes) are included.

C. Combination Therapy

In some aspects, an anti-IL-27 antibody, or antigen binding portion thereof, provided by the disclosure, can be combined with one or more additional therapeutics or treatments, e.g., another therapeutic or treatment for a cancer. For example, the anti-IL-27 antibody, or antigen binding portion thereof, can be administered to a subject (e.g., a human patient) in combination with one or more additional therapeutics, wherein the combination provides a therapeutic benefit to a subject who has, or is at risk of developing, cancer.

In some aspects, an anti-IL-27 antibody, or antigen binding portion thereof, and the one or more additional therapeutics are administered at the same time (e.g., simultaneously). In other aspects, the anti-IL-27 antibody, or antigen binding portion thereof, is administered first in time and the one or more additional therapeutics are administered second in time (e.g., sequentially). In some aspects, the one or more additional therapeutics are administered first in time and the anti-IL-27 antibody is administered second in time.

An anti-IL-27 antibody or an antigen-binding fragment thereof described herein can replace or augment a previously or currently administered therapy. For example, upon treating with an anti-IL-27 antibody or antigen-binding fragment thereof, administration of the one or more additional therapeutics can cease or diminish, e.g., be administered at lower levels. In some aspects, administration of the previous therapy can be maintained. In some aspects, a previous therapy will be maintained until the level of the anti-IL-27 antibody reaches a level sufficient to provide a therapeutic effect.

In some aspects, the disclosure provides a method of treating cancer in a subject, the method comprising administering to the subject an effective amount of an isolated antibody, or antigen binding portion thereof, that specifically binds to and antagonizes IL-27, provided by the disclosure, in combination with one or more additional therapeutic agents or procedure, wherein the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, a biologic agent, or a combination thereof.

In some aspects, the one or more additional therapeutic agents is a PD-1 antagonist, a TIM-3 inhibitor, a LAG-3 inhibitor, a TIGIT inhibitor, a CD112R inhibitor, a TAM inhibitor, a STING agonist, a 4-1BB agonist, or a combination thereof. In some aspects, the one or more additional therapeutic agents is a CD39 antagonist, a CD73 antagonist, a CCR8 antagonist, or a combination thereof. In some aspects, the anti-CD73 is any anti-CD73 antibody disclosed in, e.g., U.S. Publication No. 2019/0031766 A1, which is incorporated by reference herein in its entirety. In some aspects, the anti-CD39 is any anti-CD39 antibody disclosed in, e.g., Int'l Publication No. WO 2019/178269 A2, which is incorporated by reference herein in its entirety.

In some aspects, the one or more additional therapeutic agents is a PD-1 antagonist. In some aspects, the PD-1 antagonist is selected from the group consisting of: PDR001, nivolumab, pembrolizumab, pidilizumab, tislelizumab, zimberelimuab, MEDI0680, REGN2810, TSR-042, PF-06801591, and AMP-224. In certain aspects, the one or more additional therapeutic agents is a PD-L1 inhibitor. In some aspects, the PD-L1 inhibitor is selected from the group consisting of: FAZ053, Atezolizumab, Avelumab, Durvalumab, and BMS-936559. In some aspects, the disclosure provides a method of enhancing one or more activities of an anti-PD-1 antibody (e.g., enhances PD-1-mediated cytokine secretion; enhances anti-PD-1 mediated TNFα secretion; enhances anti-PD-1 mediated IL-6 secretion from a cell exposed to anti-PD-1 antibodies), the method comprising exposing a cell to an antibody, or antigen binding portion thereof, provided by the disclosure, concurrently with or sequentially to an anti-PD-1 antibody, thereby to enhance one or more activities of the anti-PD1 antibody.

In some aspects, the one or more additional therapeutic agents is Sunitinib (Sutent®), Cabozantinib (CABOMETYX®), Axitinib (INLYTA®), Lenvatinib (LENVIMA®), Everolimus (AFINITOR®), Bevacizumab (AVASTIN®), epacadostat, NKTR-214 (CD-122-biased agonist), tivozanib)(FOTIVDA®, abexinostat, Ipilimumab (YERVOY®), tremelimumab, Pazopanib (VOTRIENT®), Sorafenib (NEXAVAR®), Temsirolimus (TORISE®), Ramucirumab (CYRAMZA®), niraparib, savolitinib, vorolanib (X-82), Regorafenib (STIVARGO®), Donafenib (multikinase inhibitor), Camrelizumab (SHR-1210), pexastimogene devacirepvec (JX-594), Ramucirumab (CYRAMZA®), apatinib (YN968D1), encapsulated doxorubicin (THERMODOX®), Tivantinib (ARQ197), ADI-PEG 20, binimetinib, apatinib mesylate, nintedanib, lirilumab, Nivolumab (OPDIVO®), Pembrolizumab (KEYTRUDA®), Atezolizumab (TECENTRIQ®), Avelumab (BAVENCIO®), Durvalumab (IMFIMZI®), Cemiplimab-rwlc) (LIBTAYO®), tislelizumab, and/or spartalizumab.

In some aspects, the one or more additional therapeutic agents is a TIM-3 inhibitor, optionally wherein the TIM-3 inhibitor is MGB453 or TSR-022.

In some aspects, the one or more additional therapeutic agents is a LAG-3 inhibitor, optionally wherein the LAG-3 inhibitor is selected from the group consisting of LAG525, BMS-986016, and TSR-033.

In some aspects, the one or more additional therapeutic agents is a TIGIT inhibitor. In some aspects, the one or more additional therapeutic agents is a CD112R inhibitor. In some aspects, the one or more additional therapeutic agents is a TAM (Axl, Mer, Tyro) inhibitor. In some aspects, the one or more additional therapeutic agents is a STING agonist. In some aspects, the one or more additional therapeutic agents is a 4-1BB agonist.

In some aspects, the one or more additional therapeutic agents is a tyrosine kinase inhibitor, an agent targeting the adenosine axis (for example a CD39 antagonist, a CD73 antagonist or a A2AR, A2BR or dual A2AR/A2BR antagonist), a CCR8 antagonist, a CTLA4 antagonist, a VEG-F inhibitor or a combination thereof.

1. Combination with Chemotherapeutic Agents

In some aspects, the methods disclosed herein comprise administering an antibody or an antigen-binding portion thereof that specifically binds to to IL-27 and a chemotherapeutic agent. Chemotherapeutic agents suitable for combination and/or co-administration with compositions of the present disclosure include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g., mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g., daunorubicin (formerly daunomycin) and doxorubicin), antibiotics (e.g., dactinomcin (formerly actinomycin), bleomycin, mithramycin, and anthramycin (AMC)), and antimitotic agents (e.g., vincristine and vinblastine) and temozolomide.

2. Combination with PD-1/PD-L1 Antagonists

In some aspects, the methods disclosed herein comprise administering an antibody or an antigen-binding portion thereof that specifically binds to to IL-27 and one or more PD-1 antagonist. In some aspects, the one or more PD-1 antagonist specifically binds to human PD-1 or PD-L1 and inhibits PD-1/PD-L1 biological activity and/or downstream pathway(s) and/or cellular processed mediated by human PD-1/PD-L1 signaling or other human PD-1/PD-L1-mediated functions.

Accordingly, provided herein are PD-1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1 antagonists that reduce the quantity or amount of human PD-1 or PD-L1 produced by a cell or subject.

In some aspects, the disclosure provides a PD-1 antagonist that binds human PD-1 and prevents, inhibits or reduces PD-L1 binding to PD-1. In some aspects, the PD-1 antagonist binds to the mRNA encoding PD-1 or PD-L1 and prevents translation. In some aspects, the PD-1 antagonist binds to the mRNA encoding PD-1 or PD-L1 and causes degradation and/or turnover.

In some aspects, the PD-1 antagonist inhibits PD-1 signaling or function. In some aspects, the PD-1 antagonist blocks binding of PD-1 to PD-L1, PD-L2, or to both PD-L1 and PD-L2. In some aspects, the PD-1 antagonist blocks binding of PD-1 to PD-L1. In some aspects, the PD-1 antagonist blocks binding of PD-1 to PD-L2. In some aspects, the PD-1 antagonist blocks the binding of PD-1 to PD-L1 and PD-L2. In some aspects, the PD-1 antagonist specifically binds PD-1. In some aspects, the PD-1 antagonist specifically binds PD-L1. In some aspects, the PD-1 antagonist specifically binds PD-L2.

In some aspects, the PD-1 antagonist inhibits the binding of PD-1 to its cognate ligand. In some aspects, the PD-1 antagonist inhibits the binding of PD-1 to PD-L1, PD-1 to PD-L2, or PD-1 to both PD-L1 and PD-L2. In some aspects, the PD-1 antagonist does not inhibit the binding of PD-1 to its cognate ligand.

In some aspects, the PD-1 antagonist is an isolated antibody (mAb), or antigen binding fragment thereof, which specifically binds to PD-1 or PD-L1. In some aspects, the PD-1 antagonist is an antibody or antigen binding fragment thereof that specifically binds to human PD-1. In some aspects, the PD-1 antagonist is an antibody or antigen binding fragment thereof that specifically binds to human PD-L1. In some aspects, the PD-1 antagonist is an antibody or antigen binding fragment that binds to human PD-L1 and inhibits the binding of PD-L1 to PD-1. In some aspects, the PD-1 antagonist is an antibody or antigen binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 antibodies, or antigen binding fragments thereof, that may comprise the PD-1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595, 048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some aspects the PD-1 antagonist is pembrolizumab. In some aspects, the PD-1 antagonist is nivolumab. In some aspects, the methods disclosed herein comprise administering an antibody or an antigen-binding portion thereof that specifically binds to to IL-27 and pembrolizumab. In some aspects, the methods disclosed herein comprise administering an antibody or an antigen-binding portion thereof that specifically binds to to IL-27 and nivolumab.

Examples of anti-human PD-L1 antibodies, or antigen binding fragments thereof, that may comprise the PD-1 antagonist in any of the compositions, methods, and uses provided by the disclosure include, but are not limited to: BAVENCIO® (avelumab, MSB0010718C, see WO2013/ 79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/ 173223, both of which are incorporated herein by reference in their entirety; Medarex/BMS), and FAZ053 (Novartis). Accordingly, in some aspects the PD-1 antagonist is avelumab. In some aspects, the PD-1 antagonist is durvalumab. In some aspects, the PD-1 antagonist is atezolizumab.

In some aspects, the PD-1 antagonist is an immunoadhesin that specifically bind to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342, both of which are incorporated herein by reference in their entirety. In some aspects, the PD-1 antagonist is AMP-224 (also known as B7-DCIg), which is a PD-L2-FC fusion protein that specifically binds to human PD-1.

It will be understood by one of ordinary skill that any PD-1 antagonist which binds to PD-1 or PD-L1 and disrupts the PD-1/PD-L1 signaling pathway, is suitable for compositions, methods, and uses disclosed herein.

In some aspects, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) Drug Discov Today 21(6):1027-1036.

3. Combinations with TIM-3 Inhibitors

In some aspects, the methods disclosed herein comprise administering an antibody or an antigen-binding portion thereof that specifically binds to to IL-27 and a TIM-3 inhibitor. The TIM-3 inhibitor may be an antibody, an antigen binding fragment thereof, an immunoadhesin, a fusion protein, or an oligopeptide. In some aspects, the TIM-3 inhibitor is chosen from MGB453 (Novartis), TSR-022 (Tesaro), or LY3321367 (Eli Lilly). In some aspects, the anti-IL-27 antibody, or antigen binding portion thereof, is administered in combination with MGB453. In some aspects, the anti-IL-27 antibody, or antigen binding portion thereof, is administered in combination with TSR-022.

4. Combinations with LAG-3 Inhibitors

In some aspects, the methods disclosed herein comprise administering an antibody or an antigen-binding portion thereof that specifically binds to to IL-27 and a LAG-3 inhibitor. In some aspects, the LAG-3 inhibitor is an antibody, an antigen binding fragment thereof, an immunoadhesin, a fusion protein, an oligopeptide, or any combination thereof. In some aspects, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

5. Other Combinations

In some aspects, the methods disclosed herein comprise administering an antibody or an antigen-binding portion thereof that specifically binds to to IL-27 and a TIGIT inhibitor. In some aspects, the methods disclosed herein comprise administering an antibody or an antigen-binding portion thereof that specifically binds to to IL-27 and a kinase inhibitor (e.g., a tyrosine kinase inhibitor (TKI)). In some aspects, the methods disclosed herein comprise administering an antibody or an antigen-binding portion thereof that specifically binds to to IL-27 and a CD112R inhibitor. In some aspects, the methods disclosed herein comprise administering an antibody or an antigen-binding portion thereof that specifically binds to to IL-27 and a TAM receptor inhibitor. In some aspects, the methods disclosed herein comprise administering an antibody or an antigen-binding portion thereof that specifically binds to to IL-27 and a STING agonist and/or a 4-1BB agonist. In some aspects, an anti-IL-27 antibody, or antigen binding portion thereof, provided by the disclosure is combined (e.g., administered in combination) with a tyrosine kinase inhibitor, an agent targeting the adenosine axis (for example a CD39 antagonist, a CD73 antagonist or a A2AR, A2BR or dual A2AR/A2BR antagonist), a CCR8 antagonist, a CTLA4 antagonist, a VEG-F inhibitor or a combination thereof.

In some aspects, the methods disclosed herein comprise administering an antibody or an antigen-binding portion thereof that specifically binds to to IL-27 and a cell therapy. In some aspects, the cell therapy comprises a modified immune cell therapy. In some aspects, the cell therapy comprises a chimeric antigen receptor (CAR) modified immune cell therapy, e.g., CAR T therapy. In some aspects, the cell therapy comprises an engineered T cell receptor (TCR) immune cell therapy. In some aspects, the cell therapy comprises an allogeneic tumor infiltrating lymphocyte (TIL) therapy.

III. Methods for Producing Anti-IL-27 Antibodies and Antigen-binding Fragments Thereof The disclosure also features methods for producing any of the anti-IL-27 antibodies or antigen-binding fragments thereof described herein. In some aspects, methods for preparing an antibody described herein can include immunizing a subject (e.g., a non-human mammal) with an appropriate immunogen. Suitable immunogens for generating any of the antibodies described herein are set forth herein. For example, to generate an antibody that binds to IL-27p28, a skilled artisan can immunize a suitable subject (e.g., a non-human mammal such as a rat, a mouse, a gerbil, a hamster, a dog, a cat, a pig, a goat, a horse, or a non-human primate) with IL-27. In some aspects, a full-length human IL-27p28 monomer polypeptide comprising the amino acid sequence set forth in SEQ ID NO: 2 is used as the immunogen.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some aspects, the methods include preparing a hybridoma cell line that secretes a monoclonal antibody that binds to the immunogen. For example, a suitable mammal such as a laboratory mouse is immunized with an IL-27 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol.

The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to human IL-27 and In some aspects, a skilled artisan can identify an anti-IL-27 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some aspects, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) JMB 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some aspects, the phage display antibody libraries can be generated using mRNA collected from B cells from the immunized mammals. For example, a splenic cell sample comprising B cells can be isolated from mice immunized with IL-27 polypeptide as described above. mRNA can be isolated from the cells and converted to cDNA using standard molecular biology techniques. See, e.g., Sambrook et al. (1989) "Molecular Cloning: A Laboratory Manual, 2$^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some aspects, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some aspects, require use of a helper phage. In some aspects, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human IL-27p28) using any immunological or biochemical based method known in the art. For example, specific binding of an antibody to IL-27p28, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immuno-specific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In aspects where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some aspects, the anti-IL-27 antibodies described herein comprise an altered heavy chain constant region that has reduced (or no) effector function relative to its corresponding unaltered constant region. Effector functions involving the constant region of the anti-IL-27 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular aspects, modulation includes situations in which an activity is abolished or completely absent.

In one aspect, the anti-IL-27 antibodies described herein comprise an IgG4 heavy chain constant region. In one aspect, the IgG4 heavy chain constant region is a wild type IgG4 heavy chain constant region. In another aspect, the IgG4 constant region comprises a mutation, e.g., one or both of S228P and L235E or L235A, e.g., according to EU numbering (Kabat, E. A., et al., supra). In one aspect, the anti-IL-27 antibodies described herein comprise an IgG1 constant region. In one aspect, the IgG1 heavy chain constant region is a wild type IgG1 heavy chain constant region. In another aspect, the IgG1 heavy chain constant region comprises a mutation.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some aspects, the anti-IL-27 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-IL-27 antibody described herein comprising an altered constant region displaying reduced ADCC and/or CDC may exhibit reduced or no ADCC and/or CDC activity.

In some aspects, an anti-IL-27 antibody described herein exhibits reduced or no effector function. In some aspects, an anti-IL-27 antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In some aspects, an anti-IL-27 antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively, or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

A. Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some aspects, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2): 155-159; and Pollock et al. (1999) *J Immunol Methods* 231(1-2): 147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3$^{rd}$ edition," Springer-Verlag, New York City, New York. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

B. Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some aspects, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (FLAG (DYKDDDDK (SEQ ID NO: 141)), polyhistidine (6-His; HHHHHH (SEQ ID NO: 142), hemagglutinin (HA; YPYDVPDYA (SEQ ID NO: 143)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}$P, $^{33}$P, $^{14}$C, $^{125}$I, $^{131}$I, $^{35}$S, and $^{3}$H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some aspects, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some aspects, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some aspects, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisič et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some aspects, the antibodies or antigen-binding fragments thereof described herein can be glycosylated. In some aspects, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Applications

The compositions described herein can be used in a number of diagnostic and therapeutic applications. For example, detectably labeled antigen-binding molecules can be used in assays to detect the presence or amount of the target antigens in a sample (e.g., a biological sample). The compositions can be used in in vitro assays for studying inhibition of target antigen function. In some aspects, e.g., in which the compositions bind to and inhibit a complement protein, the compositions can be used as positive controls in assays designed to identify additional novel compounds that inhibit complement activity or otherwise are useful for treating a complement-associated disorder. For example, a IL-27-inhibiting composition can be used as a positive control in an assay to identify additional compounds (e.g., small molecules, aptamers, or antibodies) that reduce or abrogate IL-27 production. The compositions can also be used in therapeutic methods as elaborated on below.

In some aspects, the disclosure provides a method of detecting IL-27 in a biological sample or in a subject, comprising (i) contacting the sample or the subject (and optionally, a reference sample or subject) with any antibody described herein under conditions that allow interaction of the antibody molecule and IL-27 to occur, and (ii) detecting formation of a complex between the antibody molecule and the sample or the subject (and optionally, the reference sample or subject).

Kits

A kit can include an anti-IL-27 antibody as disclosed herein, and instructions for use. The kits may comprise, in a suitable container, an anti-IL-27 antibody, one or more controls, and various buffers, reagents, enzymes and other standard ingredients well known in the art. In some aspects, the disclosure provides a kit comprising an anti-IL-27 antibody or antigen-binding portion as disclosed herein, and instructions for use in stimulating an immune response in a subject, or treating cancer in a subject, optionally with instructions for use in combination with one or more additional therapeutic agents or procedure as disclosed herein.

The container can include at least one vial, well, test tube, flask, bottle, syringe, or other container means, into which an anti-IL-27 antibody may be placed, and in some instances, suitably aliquoted. Where an additional component is provided, the kit can contain additional containers into which this component may be placed. The kits can also include a means for containing an anti-IL-27 antibody and any other reagent containers in close confinement for commercial sale. Such containers may include injection or blow-molded plastic containers into which the desired vials are retained. Containers and/or kits can include labeling with instructions for use and/or warnings.

EXAMPLES

While the present disclosure has been described with reference to the specific aspects thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: CDR Sequence Alignments

A number of sub-selections of anti-IL-27 antibodies of the instant disclosure share sequence homology across their CDR regions, providing a diversity of variant CDR sequences that have been validated as retaining functionality. It is expressly contemplated herein that the following consensus CDR sequences are fully supported by—and are therefore within the scope of—the instant disclosure.

For anti-IL-27 Ab1, anti-IL-27 Ab3, anti-IL-27 Ab4, anti-IL-27 Ab5, anti-IL-27 Ab6, and anti-IL-27 Ab7 antibodies, alignments of the CDR sequences of each of these anti-IL-27 antibodies revealed extensive homology, punctuated by variable residues. In particular, heavy chain CDR1 alignments revealed the following variable residues:

| HCDR1 (IMGT) CLUSTAL O(1.2.4) multiple sequence alignment | | | |
|---|---|---|---|
| 1 | GFTFRSYG | 8 | (SEQ ID NO: 119) |
| 5 | GFTFRSYG | 8 | (SEQ ID NO: 31) |
| 4 | GFTFASYG | 8 | (SEQ ID NO: 97) |

-continued

```
                   HCDR1 (IMGT)
        CLUSTAL O(1.2.4) multiple sequence alignment

2    GFTFSRTG        8    (SEQ ID NO: 53)

3    GFTFSRYG        8    (SEQ ID NO: 75)

6    GFTFSSYS        8    (SEQ ID NO: 9)
        ****
```

A consensus heavy chain CDR1 (IMGT) sequence for these homologous antibodies is therefore N-GFTF[S/A/R][S/R][T/Y][G/S]-C (SEQ ID NO: 144) and, accordingly, more generally contemplated herein as a consensus heavy chain CDR1 (IMGT) sequence is N-GFTFXXXX-C (SEQ ID NO: 145), where X is any amino acid residue.

Alignment of the anti-IL-27 Ab1, anti-IL-27 Ab3, anti-IL-27 Ab4, anti-IL-27 Abs, anti-IL-27 Ab6, and anti-IL-27 Ab7 antibody heavy chain CDR2 (IMGT) sequences revealed the following:

```
                   HCDR2 (IMGT)
        CLUSTAL O(1.2.4) multiple sequence alignment

10    ISSSGSYI        8    (SEQ ID NO: 120)

11    ISSSSSYI        8    (SEQ ID NO: 98)

7    ISSSSSYI        8    (SEQ ID NO: 32)

9    ISSSSSYI        8    (SEQ ID NO: 54)

8    ISSSSAYI        8    (SEQ ID NO: 76)

12    ISSSSSYI        8    (SEQ ID NO: 10)
        ****.:**
```

A consensus heavy chain CDR2 (IMGT) sequence for these homologous antibodies is therefore N-ISSS[S/G][S/A]YI-C (SEQ ID NO: 146) and, accordingly, more generally contemplated herein as a consensus heavy chain CDR2 (IMGT) sequence is N-ISSSXXYI-C(SEQ ID NO: 147), where X is any amino acid residue.

Alignments of the human CDR1 (NT) and human CDR2 (NT) sequences also revealed the following:

```
                   HCDR1 (NT)
        CLUSTAL O(1.2.4) multiple sequence alignment

13    FTFRSYGMN       9    (SEQ ID NO: 34)

16    FTFRSYGMN       9    (SEQ ID NO: 122)

17    FTFASYGMN       9    (SEQ ID NO: 100)

14    FTFSRTGMN       9    (SEQ ID NO: 56)

15    FTFSRYGMN       9    (SEQ ID NO: 78)

18    FTFSSYSMN       9    (SEQ ID NO: 12)
        ***    ***
```

```
                   HCDR2 (NT)
        CLUSTAL O(1.2.4) multiple sequence alignment

23    GISSSGSYIYYADSVKG    17    (SEQ ID NO: 123)

19    SISSSSSYIYYADSVKG    17    (SEQ ID NO: 35)

20    SISSSSSYIYYADSVKG    17    (SEQ ID NO: 57)
```

-continued

```
  22    SISSSSSYIYYADSVKG    17    (SEQ ID NO: 101)

21    SISSSSAYILYADSVKG    17    (SEQ ID NO: 79)

24    SISSSSSYIYYADSVKG    17    (SEQ ID NO: 13)
        .****.:** *******
```

Consensus heavy chain CDR1 (NT) and CDR2 (NT) sequences for these homologous antibodies are therefore N-FTF[S/A/R][S/R][T/Y][G/S]MN-C (SEQ ID NO: 148) and N-[G/S]ISSS[S/G][S/A]YI[L/Y]YADSVKG-C (SEQ ID NO: 149), respectively. In view of these consensus sequences, more generally contemplated herein are consensus heavy chain CDR1 (NT) and CDR2 (NT) sequences N-FTFXXXXMN-C (SEQ ID NO: 150) and N-XIS-SSXXYIXYADSVKG-C (SEQ ID NO: 151), respectively, where X is any amino acid residue.

Heavy chain CDR3 (IMGT or NT) and light chain CDRs CDR1 (IMGT or NT), CDR2 (IMGT or NT) and CDR3 (IMGT or NT) were fully conserved between anti-IL-27 Ab1, anti-IL-27 Ab3, anti-IL-27 Ab4, anti-IL-27 Abs, anti-IL-27 Ab6, and anti-IL-27 Ab7.

Example 2: In Vivo Administration of Anti-IL-27 Antibodies

A Phase 1, open-label, FIH, monotherapy dose-escalation, safety, and expansion study is ongoing to analyze the effects of in vivo administration of anti-IL-27 antibodies disclosed herein in the treatment of solid tumors. Part A consists of the anti-IL-27 monotherapy dose-escalation portion of the study and will enroll approximately 42 patients with advanced solid tumors. This dose escalation part will employ an Accelerated Phase (single patient) for Dose Levels 1-3, followed by a Standard Phase (3+3) for Dose Levels 4-8.

Part B will enroll patients with advanced or metastatic ccRCC (any clear cell component in the histologic definition) or HCC into indication-specific monotherapy expansion cohorts, to further examine the safety, efficacy, tolerability, PK, and pharmacodynamics of the anti-IL-27 antibody as a monotherapy using a 2-stage design. Stage 1 of each expansion cohort will enroll approximately 17 patients. If ≥1 of the 17 patients in Stage 1 has a confirmed radiographic response (complete response [CR] or partial response [PR]), then approximately 23 additional patients will be enrolled in Stage 2. Approximately 12 patients (out of approximately 40 patients) in each of the indication-specific cohorts will be required to have a soft tissue metastasis or primary tumor that is accessible for biopsy. The total number of patients enrolled in Part B will be approximately 80 (approximately 40 in each expansion cohort).

The study design is presented in FIG. 1.

The starting dose of the anti-IL-27 antibody monotherapy will be 0.003 mg/kg given IV q4 week. Subsequent anti-IL-27 antibody dose levels may be modified and additional dose levels and/or schedules may be investigated based on the recommendation of the Safety Review Committee (SRC).

TABLE 2

Proposed dose levels for monotherapy dose escalation.

| Dose level | Anti-IL-27 dose | Number of patients |
|---|---|---|
| 1 (starting dose) | 0.003 mg/kg | N = 1-6 |
| 2 | 0.03 mg/kg | N = 1-6 |
| 3 | 0.1 mg/kg | N = 1-6 |
| 4 | 0.3 mg/kg | N = 3-6 |
| 5 | 1.0 mg/kg | N = 3-6 |
| 6 | 3.0 mg/kg | N = 3-6 |
| 7 | 10.0 mg/kg | N = 3-6 |
| 8 | 20.0 mg/kg | N = 3-6 |

Note:
Escalation of dose levels may continue after completion of Dose Level 8 at the recommendation of the Safety Review Committee (SRC) at no more than 50% dose increases.

Monotherapy dose escalation will begin with an Accelerated Phase, whereby 1 patient each will be enrolled in Dose Levels 1-3 and DLTs and AEs will be monitored during the first cycle of study treatment (a cycle is defined as 4 weeks [28 days] from Day 1). Had a patient in the Accelerated Phase experienced a DLT or any ≥Grade 2 treatment-related adverse event during the first cycle, dose escalation would have converted to Standard Phase at that dose level. Had any dose level in the Accelerated Phase been converted to the Standard Phase, all subsequent dose levels would have been evaluated in Standard Phase for the remainder of dose escalation. As no DLTs were observed at Dose Levels 1-3, no conversion from Acclerated Phase to Standard Phase was required.

If ≥2 DLTs occur at Dose Level 1 (0.003 mg/kg), a Dose Level −1 may be considered. The dose for this level will be discussed with the SRC.

Assuming no conversion to Standard Phase during Accelerated Phase (Dose Levels 1, 2, and 3), dose escalation will transition to a traditional 3+3 design at Dose Level 4 (0.3 mg/kg), whereby 3 patients will be treated at a dose level and monitored for DLTs during the first cycle of study drug. If a DLT occurs in the first 3 patients, an additional 3 patients will be treated at that same dose level. If no DLTs occur in these additional 3 patients (ie, <2 DLTs per 6 patients), dose escalation may proceed to the next dose level.

In the Standard Phase of monotherapy dose escalation, once a dose level is cleared and enrollment in the next dose level has begun, up to 3 patients may be enrolled and treated in parallel in the previously cleared dose level at the Sponsor's discretion. For these patients, preference will be given to patients with ccRCC, HCC, and/or patients who agree to tumor biopsies.

Dose escalation will continue in monotherapy until 1 of the following occurs: (i) determination of a RP2D for each dosing schedule investigated; and (ii) recommendation by the SRC to halt dose escalation based on comprehensive review of all applicable data.

A RP2D will be determined by the SRC for the anti-IL-27 antibody monotherapy. A minimum of 6 patients must be treated at a particular dose level and schedule for it to be considered the RP2D. The RP2D will be based upon cumulative safety, PK, and pharmacodynamic data. If 2 or more patients at a dose level experience a DLT (out of 6 in total enrolled), this dose level is above the RP2D. The SRC may recommend investigating intermediate doses or alternative schedules to optimize RP2D determination.

The anti-IL-27 antibody will be administered as monotherapy in a q4 week schedule; 1 cycle of treatment will include 1 dose of the anti-IL-27 antibody. The SRC will monitor the safety, PK, and pharmacodynamics of the anti- IL-27 antibody during the study, and may recommend altering the dosing paradigm (e.g., dose level and/or schedule).

If not initiated on treatment at the RP2D, patients may have their dose escalated to a higher dose or change to a different dosing schedule if they have received their current dose level for at least 3 cycles, if no toxicities ≥Grade 1 on their current dose level are reported, and if they have not had a dose reduction. If any treatment-related ≥Grade 3 toxicity occurs at any level, no intrapatient dose escalation will be allowed at that level for any patient. Patients may only have their dose escalated or moved to an alternative dosing schedule at a dose level that has already been evaluated and is at or below the RP2D for the anti-IL-27 antibody monotherapy. There is no limit to how many dose levels a patient can be escalated (if below RP2D) as long as they meet the above criteria. Toxicities that occur during the first cycle of a higher dose for such a patient would not be considered DLTs.

Dose-limiting toxicities will be evaluated during the first treatment cycle (28 days) using NCI-CTCAE version 5.0 or higher and defined for Part A and Part C of the study. Patients must have received at least 50% of the prescribed dose of the anti-IL-27 antibody and have not discontinued study therapy in the first 28 days (Cycle 1) for reasons other than drug-related adverse events to be evaluable for DLTs. Patients unevaluable for DLTs will be replaced.

Toxicities (regardless of Grade) considered clearly related to disease progression, intercurrent illness, or concomitant medications are not considered DLTs. Grade 3 or Grade 4 non-hematologic laboratory abnormalities without clinical sequelae, resolving within 72 hours, and not requiring treatment, are not considered DLTs.

Toxicities that occur after the Cycle 1 DLT review period that have significant clinical impact will be considered by the SRC in the evaluation of dose selection. Patients who experience a DLT may have the opportunity to continue treatment at a lower dose.

The occurrence of any certain toxicities during Cycle 1 will be considered a DLT, if assessed by the Investigator to be possibly, probably, or definitely related to study treatment.

Part B: Anti-IL-27 Antibody Monotherapy Expansion

The Part B monotherapy expansion cohorts will evaluate the safety, efficacy, tolerability, PK, and pharmacodynamics of the anti-IL-27 antibody monotherapy at the RP2D in patients with ccRCC (any clear cell component in the histologic definition), HCC and non-small cell lung cancer (NSCLC) in indication-specific cohorts using a 2-stage design. Stage 1 of each expansion cohort will enroll approximately 17 patients. If ≥1 of the 17 patients in Stage 1 has a confirmed radiographic response (CR or PR), then approximately 23 additional patients will be enrolled in Stage 2. Approximately 12 patients (out of approximately 40 patients) in each of the indication-specific cohorts will be required to have a soft tissue metastasis or primary tumor that is accessible for biopsy. The total number of patients enrolled in Part B will be approximately 120 (approximately 40 in each expansion cohort).

Inclusion Criteria

All patients must meet the following criteria for inclusion:
1. Patients must be ≥18 years of age.
2. Locally advanced or metastatic (Stage IV) solid tumor that has progressed during or after standard therapy, and for whom no available therapies are appropriate (based on the judgment of the Investigator).

3. Patients in Part B with advanced or metastatic ccRCC, HCC or NSCLC must have at least 1 measurable lesion per Response Evaluation Criteria in Solid Tumors (RECIST) 1.1.

4. Patients with HCC in Part B must have at least 1 measurable target lesion according to modified RECIST (mRECIST) meeting the following criteria. Lesion(s) should be suitable for repeat measurement.

Hepatic target lesion(s) should be at least ≥1.0 cm (for typical, ie, arterial enhancing lesions, this should be of the viable tumor, whereas for atypical lesions, the longest diameter should be used).

Nonhepatic target lesion(s) can include the following:
Lymph node (LN) lesion measuring ≥1.5 cm in the short axis, unless it is a porta hepatis LN, which should be at least ≥2.0 cm in the short axis.
Non-nodal lesion measuring ≥1.0 cm in the longest diameter. Bone lesions are not eligible.

Lesions previously treated with radiation or other forms of locoregional therapy must show radiographic evidence of disease progression to be used as a target lesion.

5. Patients with HCC must have unresectable disease, Barcelona Clinic Liver Cancer Stage B (not eligible for transcatheter arterial chemoembolization) or Stage C.

6. For patients in Part B with ccRCC, demonstrated progressive disease (PD) during or after the most recent treatment regimen. Prior treatment history must include progression during or after treatment with regimen(s) that have included a vascular endothelial growth factor (VEGF)-targeted agent and a programmed death receptor-1 (PD-1)/programmed death-ligand 1 (PD-L1) immune checkpoint inhibitor. Patients who did not progress on but discontinued the VEGF-targeted agent for toxicity or intolerability are permitted.

7. For patients in Part B with HCC, demonstrated PD during or after the most recent treatment regimen. Prior treatment history must include progression during or after treatment with a VEGF-targeted agent. Patients who did not progress on but discontinued the VEGF-targeted agent for toxicity or intolerability are permitted.

8. For Part B patients in the tumor biopsy subsets only, must have tumor tissue that is accessible for pretreatment and on-treatment tumor biopsy in the opinion of the Investigator and be willing to undergo pretreatment and on-treatment biopsies per protocol.

9. Washout period from the last dose of previous anticancer therapy (chemotherapy, biologic, or other investigational agent) to the initiation of study drug must be >5 times the half-life of the agent or >21 days (whichever is shorter).
Note: The washout period for palliative radiotherapy to non-central nervous system disease is 7 days.

10. Resolution of non-immune related AEs secondary to prior anticancer therapy (excluding alopecia and peripheral neuropathy) to <Grade 1 per NCI-CTCAE version 5.0 or higher, and complete resolution of immune-related AEs secondary to prior checkpoint inhibitor therapy.
Note: Patients with other clinically stable or \ nonsignificant AEs related to prior therapy may be enrolled pending discussion with the Sponsor (e.g., controlled thyroid disorders, vitiligo, asymptomatic elevated amylase/lipase, type 1 diabetes on insulin, ≤Grade 2 controlled rash, ≤Grade 2 electrolyte abnormalities on a stable dose of supplementation).

11. Serum creatinine clearance ≥30 mL/min per Cockcroft-Gault formula or serum creatinine ≤2.0× the upper limit of normal (ULN).

12. Total bilirubin ≤1.5×ULN (<3×ULN if elevated because of Gilbert's syndrome, and ≤2×ULN for patients with HCC or patients with known liver metastases).

13. Aspartate aminotransferase/serum glutamic oxaloacetic transaminase (AST/SGOT) and alanine aminotransferase (ALT/SGPT)<2.5×ULN (<5×ULN if liver metastasis or for patients with HCC).

14. For patients with HCC, Child-Pugh class A or B7 with a serum albumin ≥2.8 g/dL (≥28 g/L).

15. Adequate hematologic function, defined as absolute neutrophil count (ANC)≥1.0×10$^9$/L, hemoglobin ≥9.0 g/dL, and platelet count ≥100×10$^9$/L. For patients with HCC, platelet count ≥75×10$^9$/L without transfusion.

16. Eastern Cooperative Oncology Group (ECOG) performance status 0-1.

17. Ejection fraction ≥50%, as measured by echocardiogram or multigated acquisition scan at Screening.

18. For women of childbearing potential (WCBP): negative serum f3 human chorionic gonadotropin pregnancy test within 1 week before first treatment (WCBP defined as a sexually mature woman who has not undergone surgical sterilization or who has not been naturally postmenopausal for at least 12 consecutive months for women >55 years of age).

19. Willingness of male and female patients who are not surgically sterile or postmenopausal to use medically acceptable methods of birth control for the duration of the study treatment period, including 75 days after the last dose of SRF388; male patients must refrain from donating sperm during this period. Sexually active men, and women using oral contraceptive pills, should also use barrier contraception. Azoospermic male patients and WCBP who are continuously not heterosexually active are exempt from contraceptive requirements. However, female patients must still undergo pregnancy testing as described in this section.

20. Ability to adhere to the study visit schedule and all protocol requirements.

21. Signed and dated institutional review board/independent ethics committee-approved informed consent form before any screening procedures are performed.

22. Patients with NSCLC must have histologically confirmed locally advanced and/or metastatic Stage IV NSCLC.

23. Patients with NSCLC must have demonstrated PD during or after the most recent treatment regimen. Prior treatment history must include progression during or after treatment with (1) anti-PD-(L)1 if disease has no driver alterations and (2) a targeted therapy if the patient has disease with driver alterations. Patients who did not progress on but discontinued the targeted agent for toxicity or intolerability are permitted.
Note: Patients with driver alterations are not required to have had prior anti-PD-(L)1 therapy.

Exclusion Criteria

Patients are to be excluded from the study if they meet any of the following criteria:

1. Previously received an anti-IL-27 antibody or anti-IL-27 targeted therapy.

2. For patients in Part B with renal cell carcinoma (RCC), non-clear cell RCC histology.

3. For patients in Part B, received >4 prior systemic regimens for Stage IV disease.

4. For patients with HCC, known fibrolamellar or mixed hepatocellular cholangiocarcinoma.

5. For patients with HCC, moderate or severe ascites.

6. Receiving chronic anti-coagulation therapy (eg, warfarin, enoxaparin) that cannot be safely discontinued temporarily for the required biopsies (only if in the applicable tumor biopsy subset).

7. History of Grade 4 allergic or anaphylactic reaction to any monoclonal antibody therapy, or any excipient in the study drugs.

8. Major surgery within 4 weeks prior to Screening.

9. Symptomatic or untreated brain metastases (including leptomeningeal metastases). Patients previously treated for brain metastases must be >28 days from completion of radiation treatment with follow-up imaging showing no progression.

10. Primary central nervous system malignancy.

11. Prior autologous stem cell transplant ≤3 months before the first dose of SRF388.

12. Prior allogeneic hematopoietic cell transplant within 6 months of the first dose of SRF388 or with a history of or current clinical Graft-Versus-Host Disease.

13. Known infection with HIV.

14. Known infection with hepatitis B virus (HBV) or hepatitis C virus (HCV). The following exceptions are permitted:

Patients with HCC: controlled active HBV or fully treated HCV infection is permitted. Antiviral therapy as per local standard of care should be continued.

For patients with HCC with active HBV, controlled disease is considered HBV DNA <500 IU/mL during the Screening Period with willingness to continue antiviral treatment during length of study. The patient must be on anti-HBV treatment (per local standard of care; eg, entecavir) for a minimum of 14 days prior to study entry.

For patients with HCC with HCV, only cured disease or HCV considered fully treated and no longer requiring antiviral therapy for control is permitted. No co-infection with HCV and HBV is allowed. Co-infection is defined as HCV RNA positive and hepatitis B surface antigen (HBsAg) positive. However, a patient who is HCV Ab+, hepatitis B core antibody (HBcAb)+but negative HBsAg is not considered co-infected and is permitted.

Patients with any solid tumor who have a history of cured HCV are permitted.

15. Active autoimmune disease requiring steroids or immunosuppressive (eg, cyclosporine) therapy or medical conditions requiring chronic steroid (ie, >10 mg/day prednisone or equivalent) or immunosuppressive therapy.

Note: Topical, intranasal, or inhaled corticosteroids are permitted. Physiologic replacement for patients with thyroid, adrenal, or pituitary insufficiency (eg, thyroxine, physiologic corticosteroids [≤10 mg/day of prednisone or its equivalent], or insulin) is allowed. Patients with a history of autoimmune disease may be eligible following discussion with the Medical Monitor.

16. Ongoing uncontrolled systemic bacterial, fungal, or viral infections at Screening.

Note: Oral antibiotics for a controlled infection are permitted. Patients on antimicrobial, antifungal, or antiviral prophylaxis are not specifically excluded if all other inclusion/exclusion criteria are met.

17. Administration of a live attenuated vaccine within 6 weeks before the first dose of study drug.

18. Baseline QT interval corrected (QTc) with Fridericia's method (QTcF)>480 ms.

Note: If 1 elevated QTc reading, the screening requirement can be met with the average of triplicate ECGs. Criterion does not apply to patients with a right or left bundle branch block.

19. Female patients who are pregnant or breastfeeding.

20. Another malignancy, other than those with negligible risk of death, including but not limited to non-melanoma skin cancer, low risk localized or cured prostate cancer, ductal carcinoma in situ, or carcinoma in situ of the cervix, within 2 years before Screening.

21. History of stroke, unstable angina, myocardial infarction, or ventricular arrhythmia requiring medication or mechanical control within 6 months before Screening.

22. Unstable or severe uncontrolled medical condition (eg, unstable cardiac function, unstable pulmonary condition including pneumonitis and/or interstitial lung disease, uncontrolled diabetes, symptomatic fistula) or any important medical illness or abnormal laboratory finding that would, in the Investigator's judgment, increase the risk to the patient associated with his or her participation in the study.

23. For patients with NSCLC, any component of small cell histology.

Biomarker Assessments

Samples will be collected for biomarker analysis to investigate the biological effects of anti-IL-27 at the molecular and cellular level, as well as to evaluate how changes in the markers and immune cell populations may relate to exposure and clinical outcomes. The goal of the biomarker assessments is to provide supportive data for the clinical trial. There may be circumstances when a decision is made to stop a collection, not perform, or discontinue an analysis due to either practical or strategic reasons (eg, inadequate sample number, sample quality issues precluding analysis, etc). Therefore, sample collection and/or analysis may be omitted at the discretion of the Sponsor.

Additional biomarker samples may be requested (when feasible) at the time of any unusual safety event (ie, an AE different in type and severity from that which is expected in the setting of anti-IL-27 use), or if a sample is found to be compromised.

The following biomarker samples may be analyzed: blood (whole blood and PBMCs) for immunophenotyping and immune monitoring (to monitor the effects of treatment on various peripheral blood immune cell populations; subsets may include, but are not limited to, monocytes, neutrophils, myeloid-derived suppressor cells, and T/NK/myeloid-cell populations); blood serum for cytokine/chemokine/soluble factors (for profiling of potential predictive and pharmacodynamic biomarkers of response and/or resistance to anti-IL-27; serum levels of soluble factors associated with cancer and immunological function will be assessed. Examples include but are not limited to: EBI3, IL-27, TNFα, MIP-la (CCL3), IFNγ, IL-10, and IL-6.

Example 3: In Vivo Administration of Anti-IL-27 Antibodies

Figure 1B:
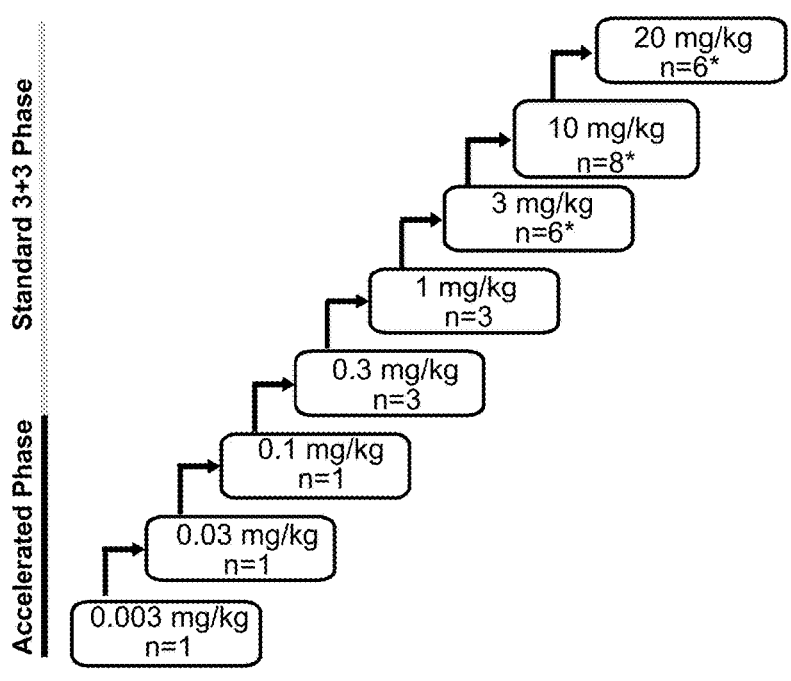
Figure 1C:
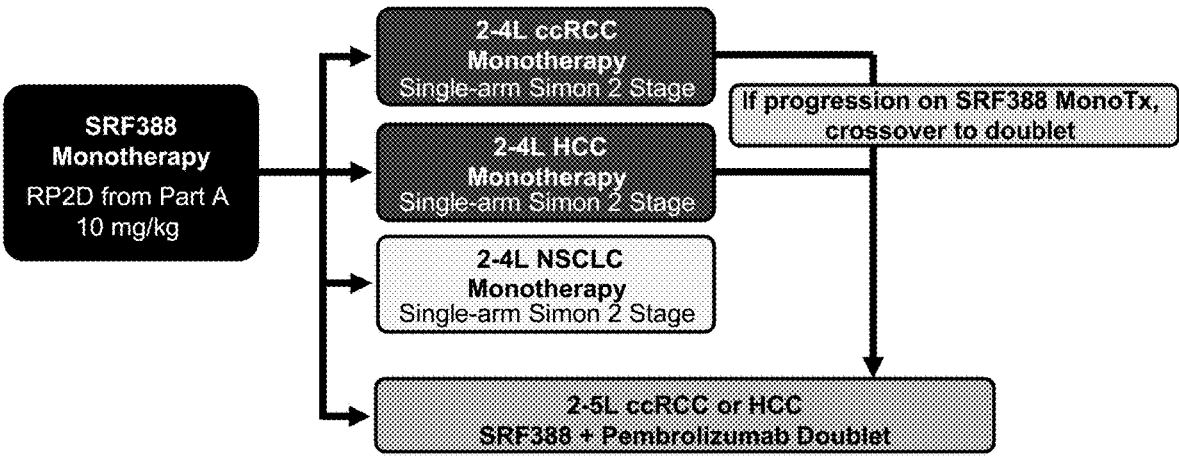

Patients with advanced solid tumors refractory to standard therapy were enrolled in an ongoing phase 1 dose-escalation study (accelerated single patient followed by standard 3+3) to establish the preliminary safety of anti-IL-27 Ab1 monotherapy and to identify a dose suitable for expansion (NCT04374877). The anti-IL-27 antibody was administered intravenously every 4 weeks on day one of each four-week cycle (FIG. 1). Anti-IL-27 Ab1 monotherapy expansions (Part B) are enrolling patients with advanced ccRCC, HCC and NSCLC in Simon 2-stage designs, and anti-IL-27 Ab1 will be explored in combination with pembrolizumab (Part C) in patients with advanced ccRCC and HCC (FIGS. 1A-1C).

In Part A, the dose escalation component, the primary end points were rate of dose limiting toxicities (DLTs), safety, and tolerability with overarching objective of RP2D determination. Key secondary end points included objective response rate (ORR) based on investigator review per RECIST v1.1 and iRECIST (if HCC, by mRECIST), pharmacokinetics, pharmacodynamic assessments (phosphorylated signal transducer and activator of transcription-1 (pSTAT1) levels in immune cell subsets), and serum concentrations of EBI3. Exploratory analyses planned to identity potential biomarkers of response and resistance. The safety analysis set included all patients who received any amount of study medication. The response evaluable analysis set included all patients with measurable disease at baseline who received at least one dose of anti-IL-27 Ab1 and had one post-baseline response assessment or who discontinued study treatment within 6 weeks (±2 weeks) of first dose. For the primary pharmacodynamic marker, fresh whole blood samples were analyzed by flow cytometry to monitor inhibition of pSTAT1.
Preliminary Study Results In Part A, dose escalation, of the study, twenty-one (21) patients have received the anti-IL-27 antibody at doses ranging from 0.003 to 10 mg/kg. Median age was 66 years, 67% were female, and ECOG PS was 0/1 (29%/71%) (Table 3). Median number of prior therapies was 2 (range 1-9), and 81% were anti-PD-L1 experienced (n=17). The only treatment-related adverse events observed across dose levels were low-grade fatigue (n=1, 8%), nausea (n=1, 8%) and excess salivation (n=1, 8%). No dose-limiting toxicities (DLTs) or ≥Grade 3 related toxicity have occurred, including through the first 4 patients at the 10 mg/kg dose level. There have been 6 reproted related TEAEs, which were all low grade, including fatigue (n=2), nausea (n=1), excess salivation (n=1), cough (n=1), and hyperthyroidism (n=1).

TABLE 3

| Part A, Dose Escalation Demographics and Baseline Characteristics (All patients, N = 21) | |
| --- | --- |
| Median age, years (range) | 66 (46, 83) |
| Sex, n (%) | |
| Male | 7 (33%) |
| Female | 14 (67%) |
| Ecog PS at baseline, n (%) | |
| 0 | 6 (29%) |
| 1 | 15 (71%) |
| Median time since initial diagnosis, months (range), n = 20 | 46 (6, 234) |
| Number of prior systemic therapies, n (%) | |
| 1 | 3 (14%) |
| 2 | 4 (19%) |
| 3 | 2 (10%) |
| 24 | 12 (57%) |
| Prior aPD-1/aPD-L1, n (%) | |
| Yes | 17 (81%) |
| No | 4 (19%) |

Figure 2:
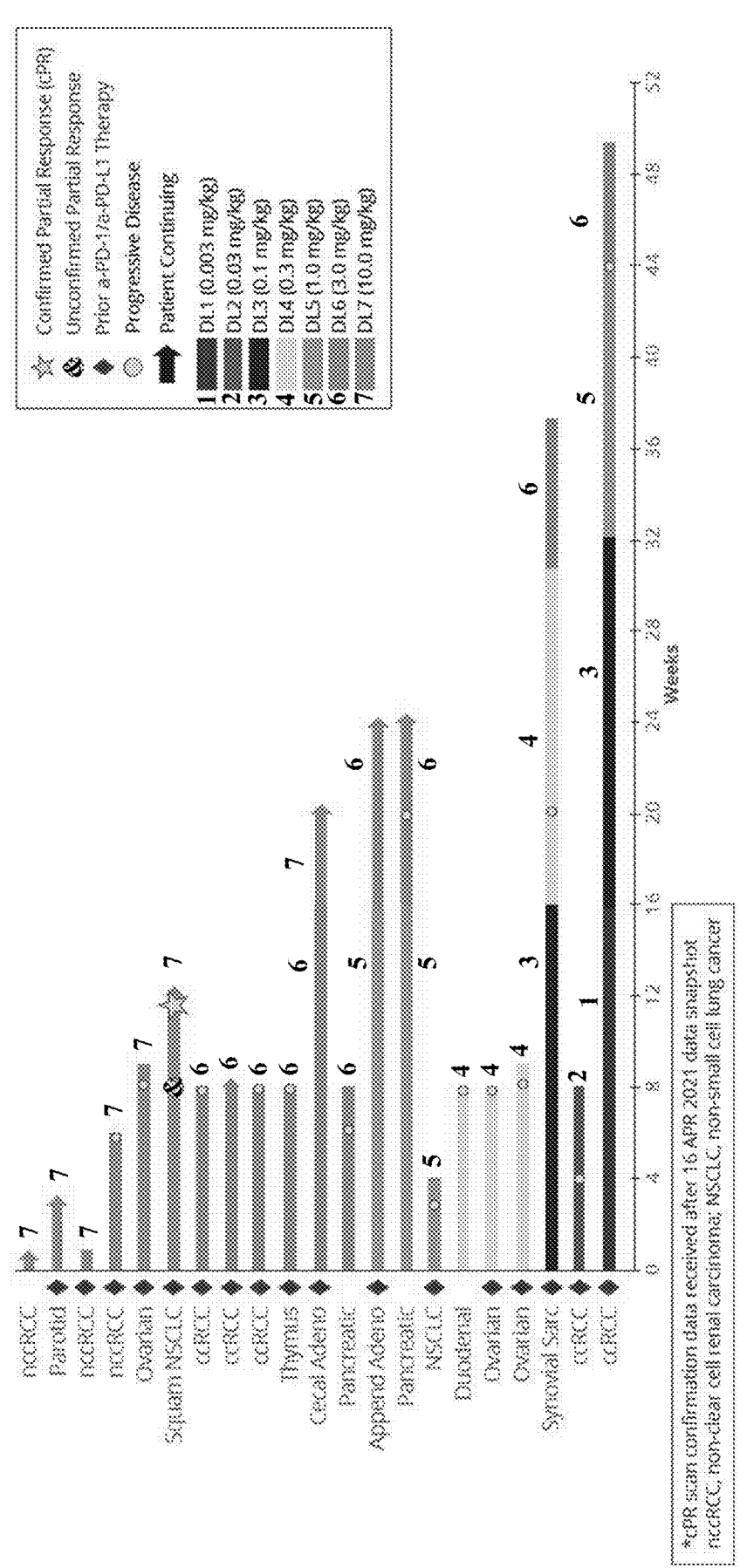
FIG. 2 is a Swimmer's plot showing the time on study and RECIST response grouped by starting dose.
Figure 3:
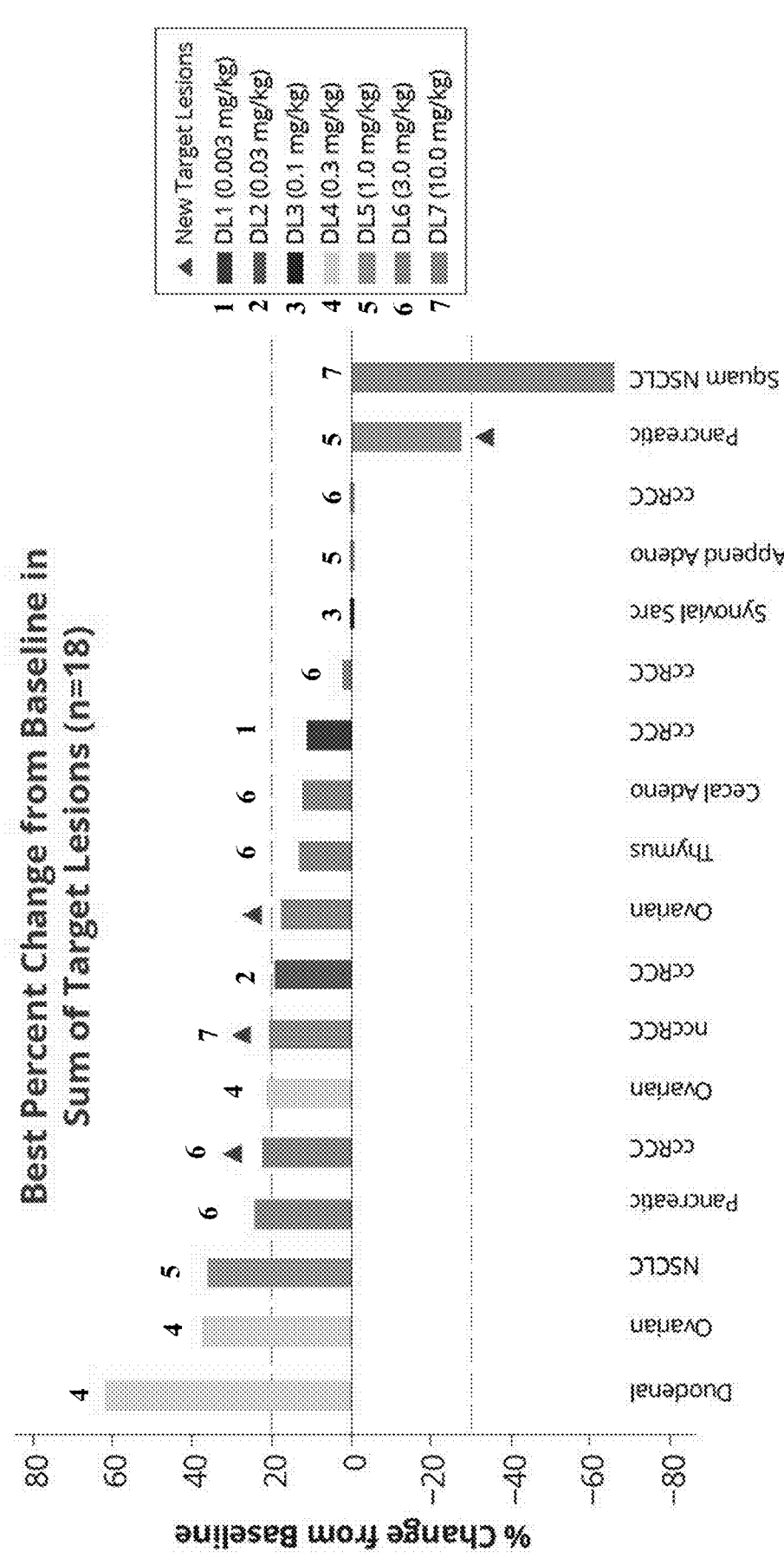
FIG. 3 is a waterfall plot illustrating the best percentage change in target lesions from baseline.

Mean time on study is 8 weeks (range 1-50), as measured by the days from the first dose to the last visit, including safety follow-up visits (FIG. 2). Five patients were escalated to higher doses on study, as depicted by changing of the lane color at the time of dose increase. Disease assessment was performed at week 8 and then every 12 weeks thereafter. Of the 18 evaluable patients, approximately 40% experienced clinical benefit in the form of disease stabilization or partial response, with 50% of disease stabilization persisting beyond 16 weeks. One patient (6%) exhibited a partial response, 7 patients (39%) exhibited stable disease, and 10 patients (55%) exhibited progressive disease, as measured by RECISTv1.1 (FIG. 3). One patient with RCC who received prior anti-PD-1 has prolonged stable disease for >9 months. In particular, one patient with NSCLC treated at 10 mg/kg experienced a rapid partial response evident at the first response assessment at 8 weeks, which was confirmed at 12 weeks.

Figure 4:
FIG. 4 is a graphical representation of the pharmacokinetics of anti-IL-27 Ab1 administered at doses of 0.03, 0.1, 0.3, 1, 3, and 10 mg/kg.
Figure 5C:
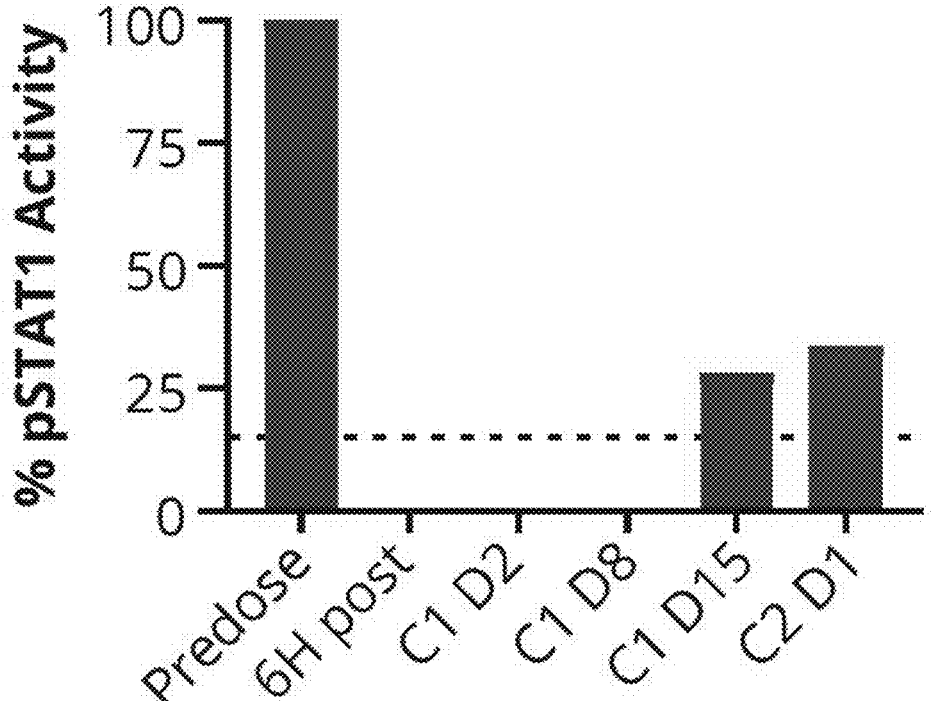
FIGS. 5C-5D are bar graphs illustrating pSTAT1 inhibition following administration of 0.1 mg/kg (FIG. 5C) or 1 mg/kg (FIG. 5D) anti-IL-27 Ab1 predose and up to cycle 2, day 1.
Figure 5D:
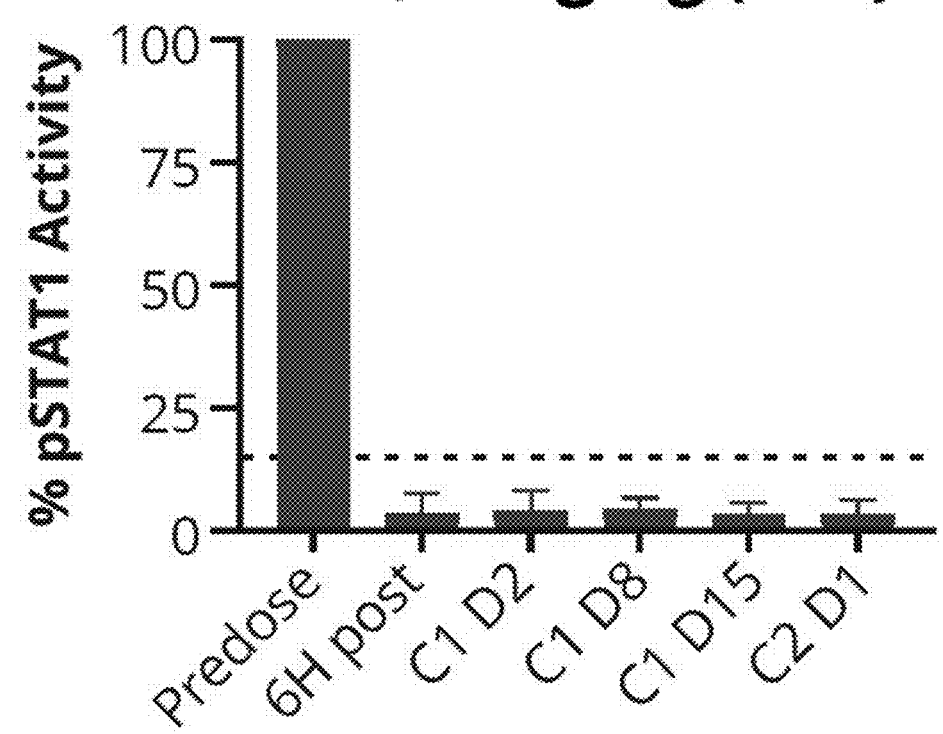
Figures 6A, 6B, 6C, 6D, 6E, 6F:
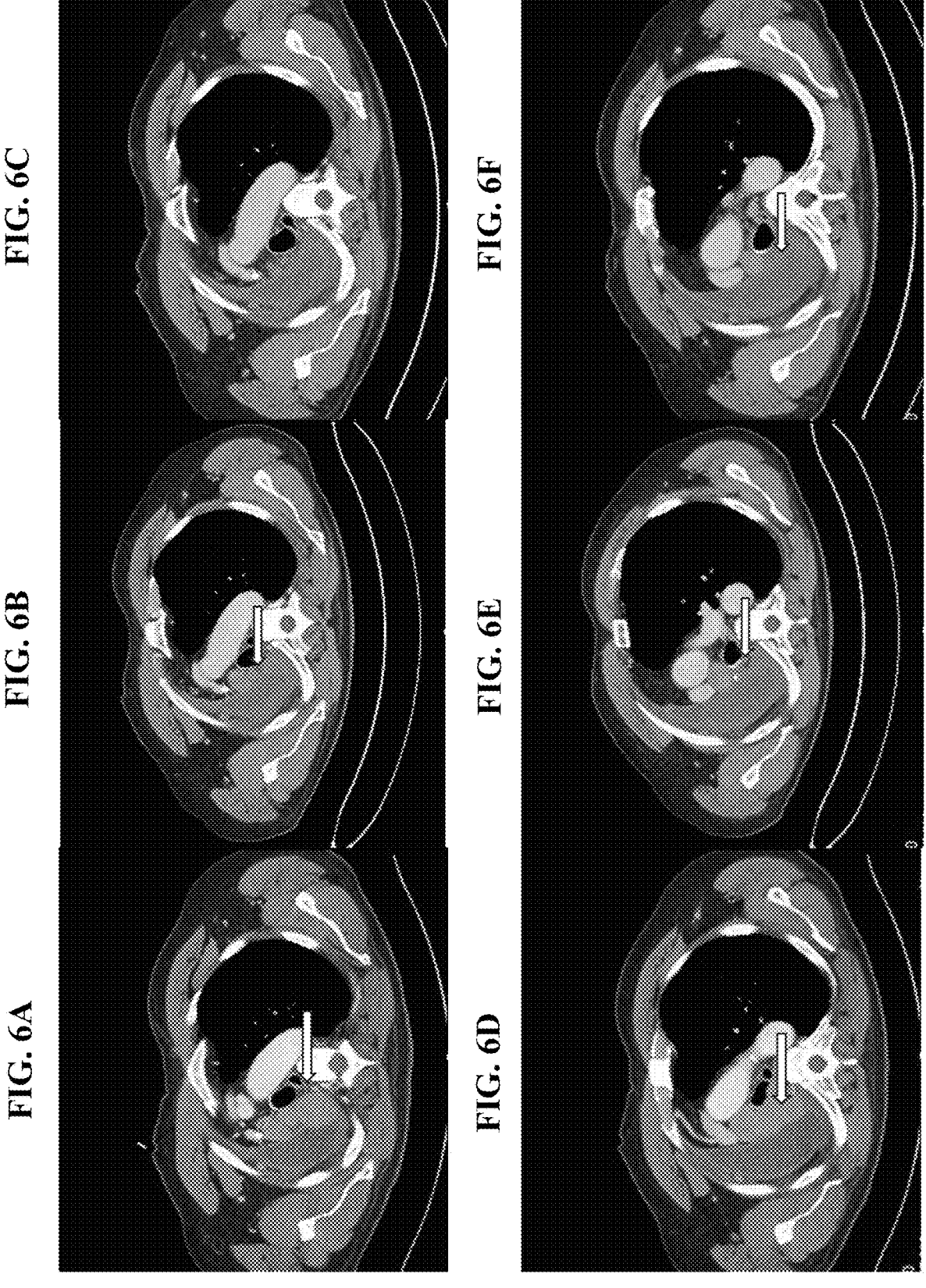
FIGS. 6A-6F are images of target lesions (target lesion 1, FIGS. 6A-6C; target lesion 2, FIGS. 6C-6F; arrows) in a 64-year-old patient with squamous cell non-small cell lung cancer with metastases to the mediastinal nodes, lung, and pleura who was enrolled at 10 mg/kg.

A prelimary PK analysis of patient samples who were administered 0.03 mg/kg, 0.1 mg/kg, 0.3 mg/kg, 1 mg/kg, 3 mg/kg and 10 mg/kg doses of anti-IL-27 antibody in Part A of the study was performed. Anti-IL-27 antibody PK are linear and dose proportional with estimated T½ being 11.7 (7.1-18.8) days (FIG. 4). There is evidence of accumulation and steady state reached by Cycle 3. There is no evidence of anti-drug antibody development to date.

Based on non-clinical efficacy models, goal serum trough drug concentrations are greater than 20× the IC90 for pSTAT1 signaling inhibition. Inhibition of downstream pSTAT signaling in whole blood served as a primary PD marker and we observed that complete pSTAT1 inhibition was maintained through trough at 0.3 mg/kg and above (FIGS. 5A-5D). Maximal inhibition of the IL-27 signaling pathway as measured by >90% pSTAT1 inhibition in whole blood was achieved starting at 0.3 mg/kg and above. Given combined evidence in the Hepa 1-6 mouse model of near-complete pathway inhibition and preclinical human equivalent dose modeling projecting biologically active doses, additional slots were opened for RCC and HCC starting at 1 mg/kg.

One particular patient is a 64-year-old man with squamous cell NSCLC with metastases to the mediastinal nodes, lung, pleura and adrenal gland, who is receiving anti-IL-27 antibody Ab1 at 10 mg/kg intravenously once every four weeks. The patient was previously treated with adjuvant gemcitabine/cisplatin, first line carboplatin/nab-paclitaxel/pembrolizumab (with a PD-L1 expression 10%), and second line docetaxel, with no response to any therapy and progressively symptomatic prior to anti-IL-27 antibody Ab1 initiation. This patient is experiencing a partial response with 42% tumor shrinkage after 2 cycles of anti-IL-27 antibody Ab1 administration in both mediastinal node target lesions as shown by the arrows with significant improvement in his dyspnea (FIGS. 6A-6F). This partial response was confirmed as a 66% decrease in target lesions after 3 cycles (FIGS. 6A-6F).

Anti-IL-27 Ab1 is well-tolerated at all tested doses to date in patients with advanced solid tumors. Preliminary results of IL-27 pathway blockade with a first-in-class therapeutic study of anti-IL-27 Ab1 shows evidence of single-agent activity even in heavily pre-treated patients, including a confirmed partial response in a patient with squamous cell NSCLC whose disease was resistant to three prior regimens including chemotherapy and PD-1 blockade, and multiple patients have experienced disease stabilization. PK are linear and dose-proportional with maximal target inhibition of downstream IL-27-mediated pSTAT1 maintained throughout the dosing interval. Preliminary results of IL-27 pathway blockade with a first-in-class immunotherapy support further evaluation of anti-IL-27 Ab1 as monotherapy and in combination with standard and investigational regimens in both immune checkpoint naïve and experienced patients with the initial focus planned in HCC, RCC, and NSCLC.

Updated Preliminary Study Results

In Part A, twenty-nine (29) patients have received the anti-IL-27 antibody at doses ranging from 0.003 to 20 mg/kg. Median age was 64 years, 62% were female, and ECOG PS was 0/1 (24%/76%) (Table 4). 62% of patients had received 3 or more lines off prior therapy, and 79% were anti-PD-(L)1 experienced (n=23). The only treatment-related adverse events observed across dose levels at >=10% was low-grade fatigue (n=3). No dose-limiting toxicities (DLTs), ≥Grade 3 related toxicity have occurred at any dose level. There have been 6 reported related TEAEs, which were all low grade, including fatigue (n=3), nausea (n=2), excess salivation (n=1), cough (n=1), and hyperthyroidism (n=1).

TABLE 4

Part A, Dose Escalation Demographics and
Baseline Characteristics (All patients, N = 29)

| | |
|---|---|
| Median age, years (range) | 64 (46, 83) |
| Sex, n (%) | |
| Male | 11 (38%) |
| Female | 18 (62%) |
| ECOG PS at baseline, n (%) | |
| 0 | 7 (24%) |
| 1 | 22 (76%) |
| Median time since initial diagnosis, months (range) | 43 (6, 234) |
| Number of prior systemic therapies, n (%) | |
| 1 | 7 (24%) |
| 2 | 4 (14%) |
| 3-4 | 7 (24%) |
| ≥5 | 11 (38%) |
| Prior aPD-1/aPD-L1, n (%) | |
| Yes | 23 (79%) |
| No | 6 (21%) |

Figure 7:
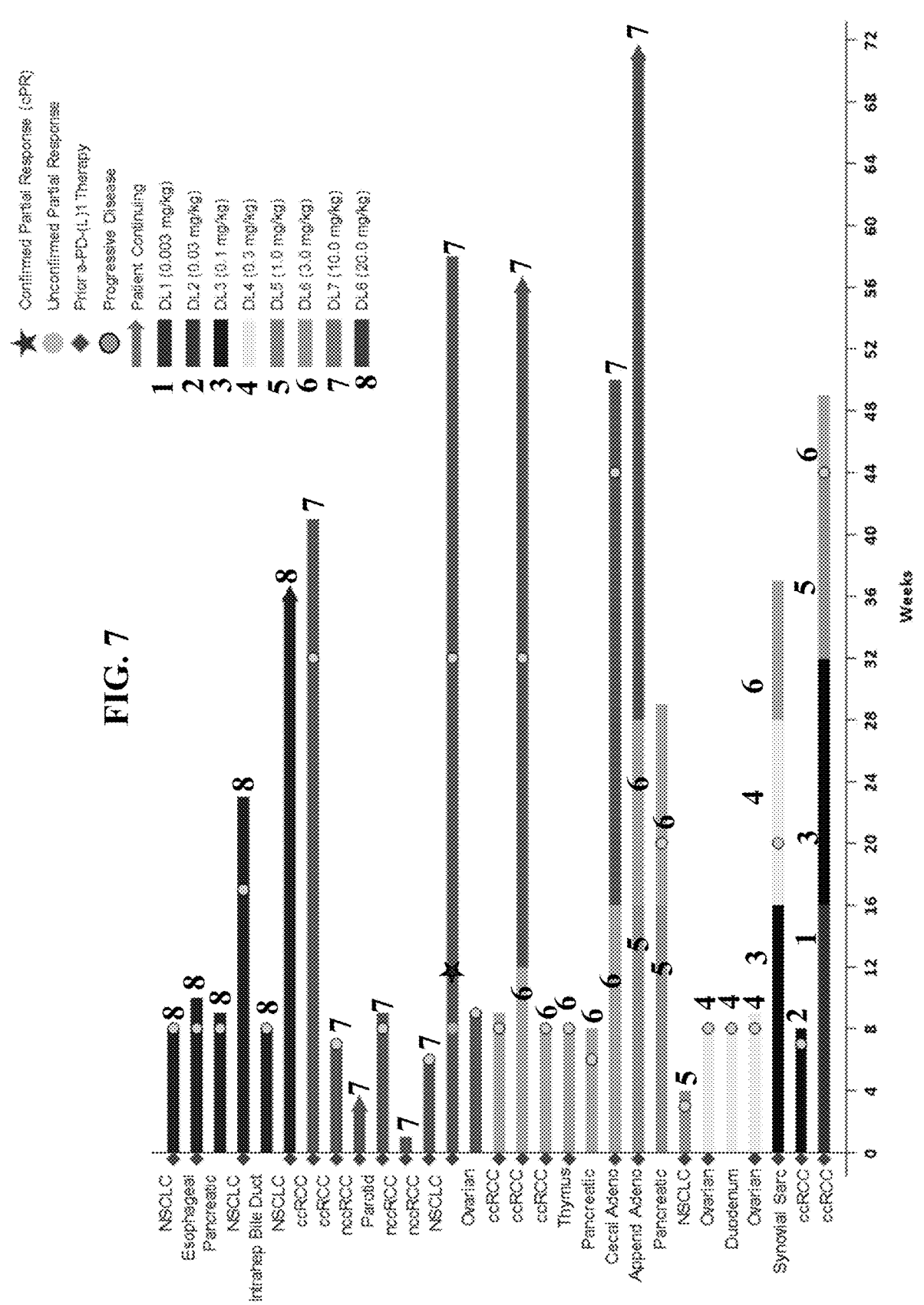
FIG. 7 is s a Swimmer's plot depicting time on study and RECIST response grouped by starting dose of the 29 patients enrolled in a dose escalation study. The median time on study was 9 weeks (with a range of 1 to 71 weeks).
Figure 8A:
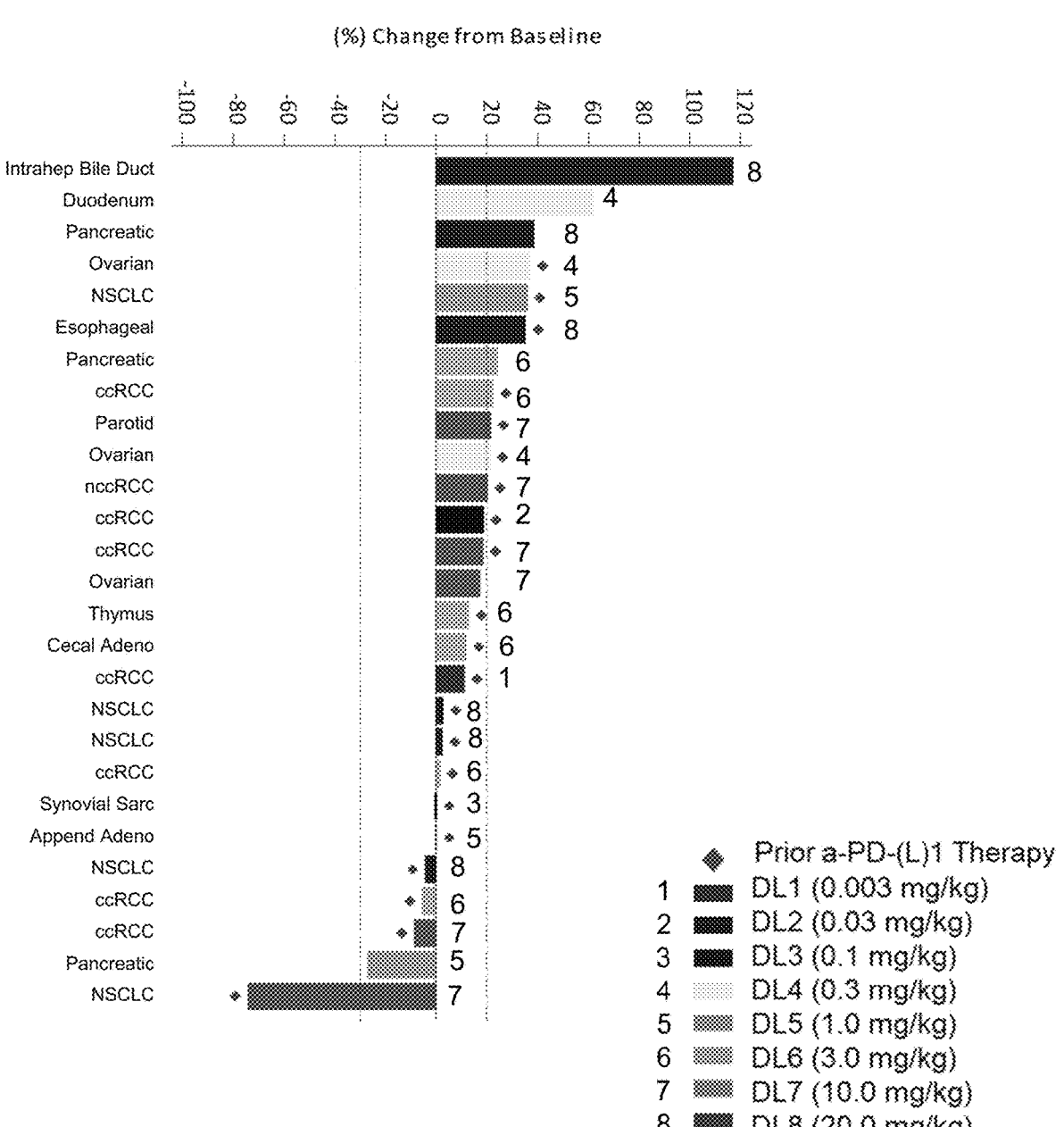
FIGS. 8A-8B show target lesion changes over time.
Figure 8B:
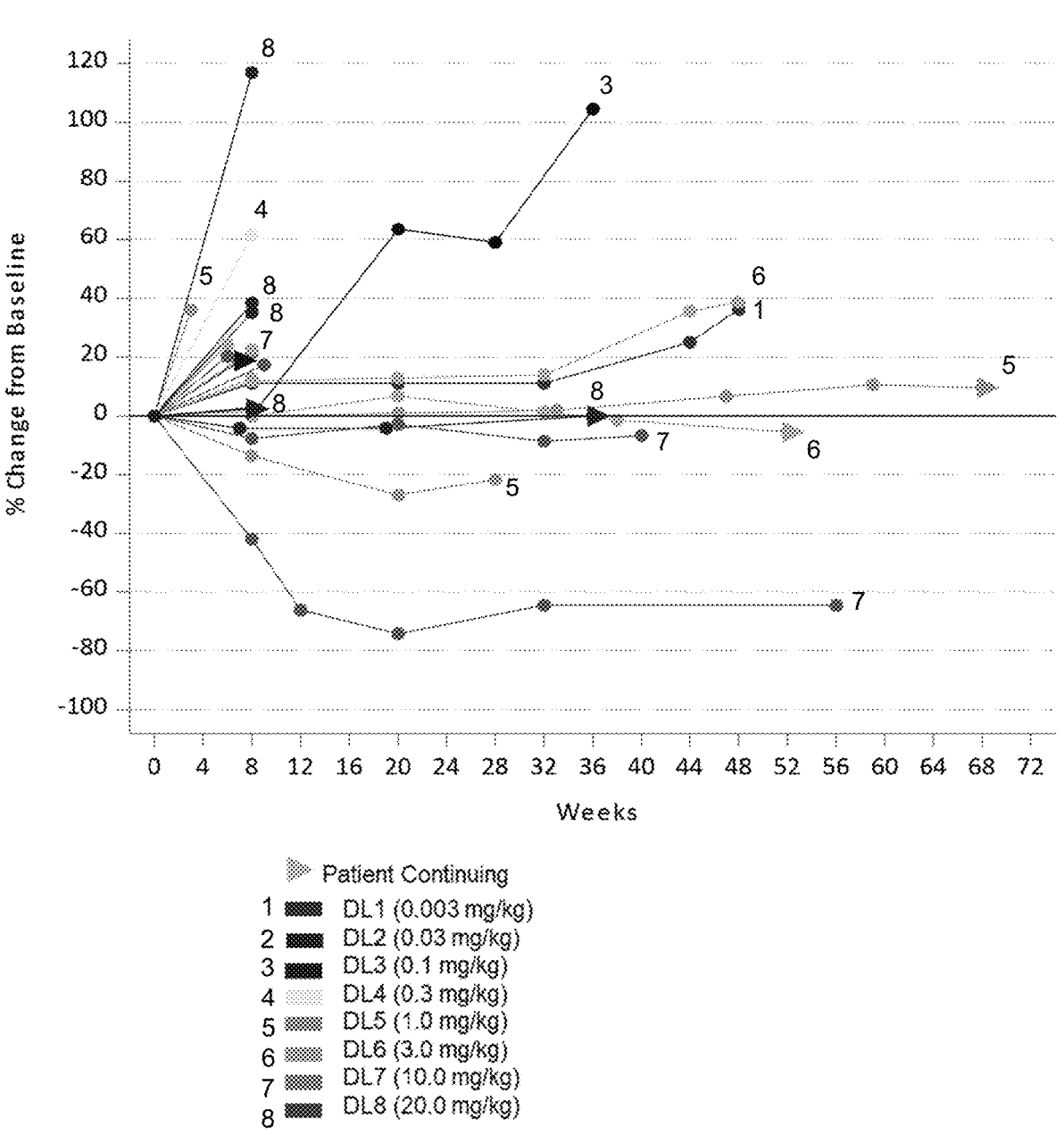

Mean time on study for Part A is 9 weeks (range 1-71), as measured by the days from the first dose to the last visit, including safety follow-up visits (FIG. 7). Six patients were escalated to higher doses on study, as depicted by changing of the lane color at the time of dose increase. Disease assessment was performed at week 8 and then every 12 weeks thereafter. Of the 27 evaluable patients, approximately 40% experienced clinical benefit in the form of disease stabilization or partial response, with 28% of disease stabilization persisting beyond 16 weeks. One patient (3.7%) exhibited a confirmed partial response, 10 patients (37%) exhibited stable disease, and 16 patients (59%) exhibited progressive disease, as measured by RECISTv1.1 (FIGS. 8A-8B). Three patients with RCC, cecal adenocarcinoma, and appendiceal adenocarinoma who received prior anti-PD-1 had prolonged stable disease at 9 months or beyond. One patient with NSCLC whose disease was primarily refractory to 3 prior therapies including platinum and taxane chemotherapies and PD-1 blockade was treated at 10 mg/kg and experienced a rapid partial response evident at the first response assessment at 8 weeks, which was confirmed at 12 weeks.

Figure 9A:
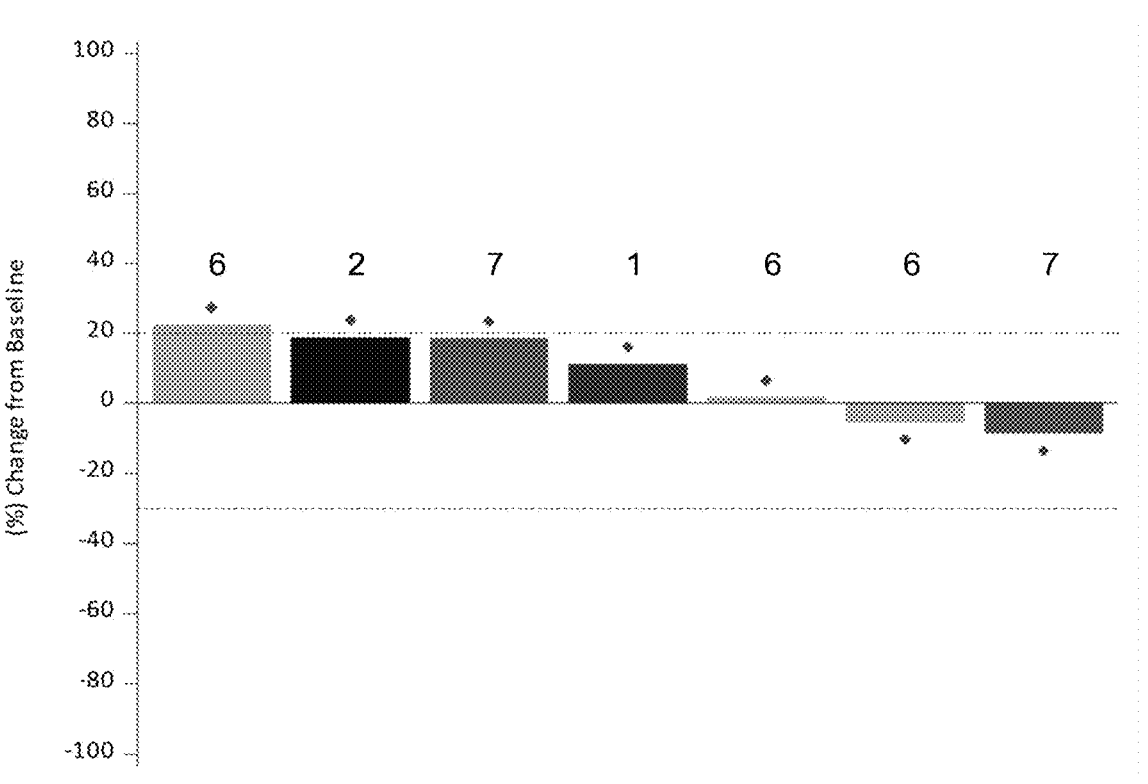
FIGS. 9A-9B are graphical representations of anti-IL-27 Ab1 monotherapy dose escalation response.
Figure 9A:
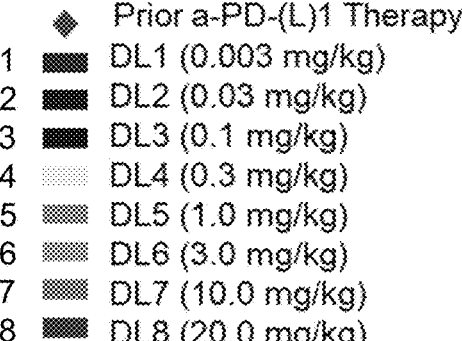
Figure 9B:
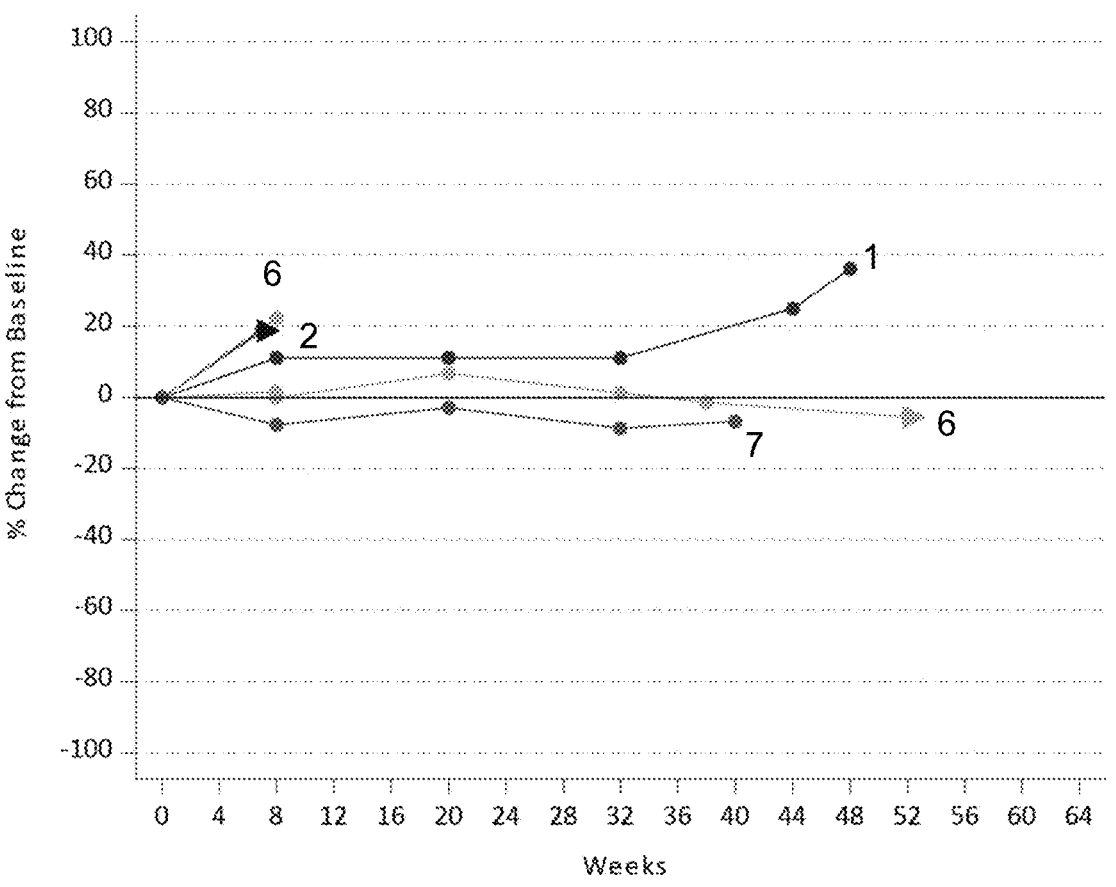

A review of the subset of ccRCC patients enrolled in Part A of the study was performed. Of the 29 patients in Part A, 7 were ccRCC patients. The majority were men (71%) and of intermediate risk (80%). This subset of patients was heavily pretreated with 29% having 3-4 prior lines of therapy and 43% having 5 or more prior lines. All had received prior PD-1 pathway blockade. Of these 7 patients, 43% (n=3) experienced disease stabilization for ≥20 weeks (range: 20-32) (FIGS. 9A-9B).

Figure 10A:
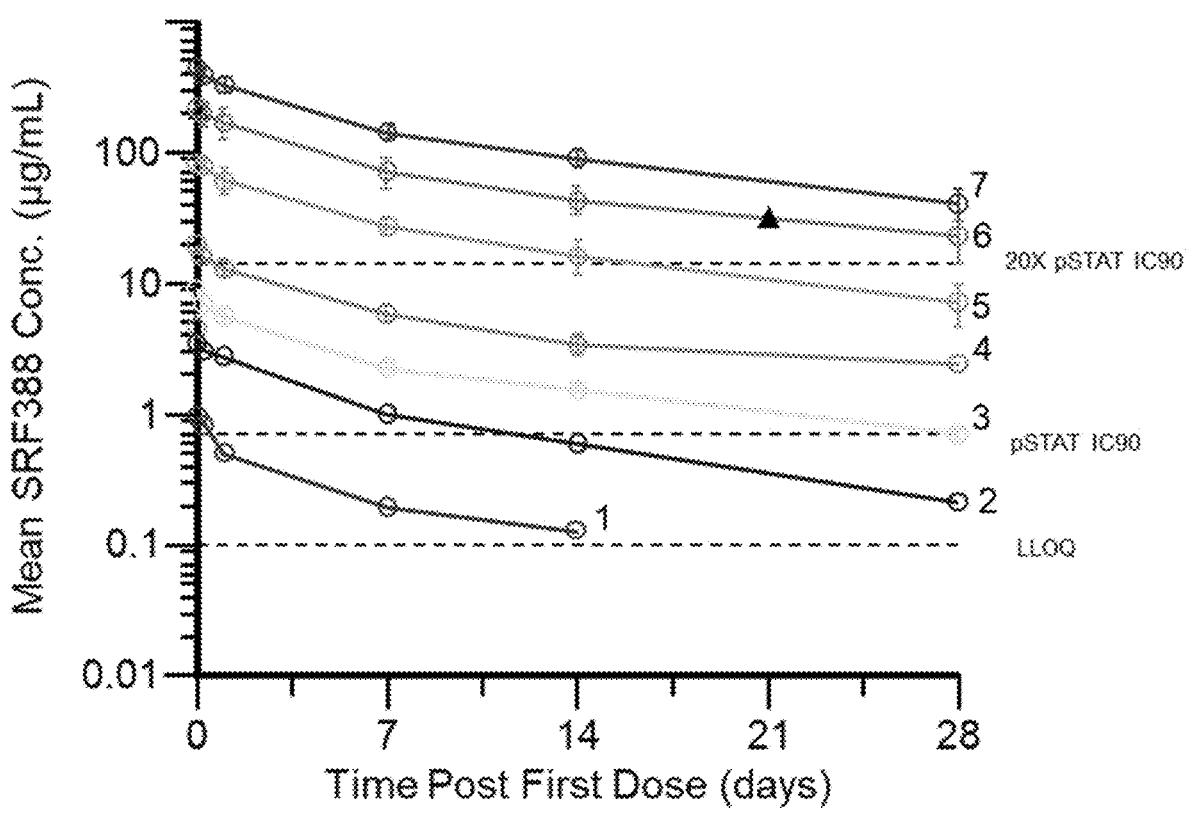
FIGS. 10A-10B are graphical representation of the anti-IL-27 Ab1 pharmokinetic profile.
Figure 10B:
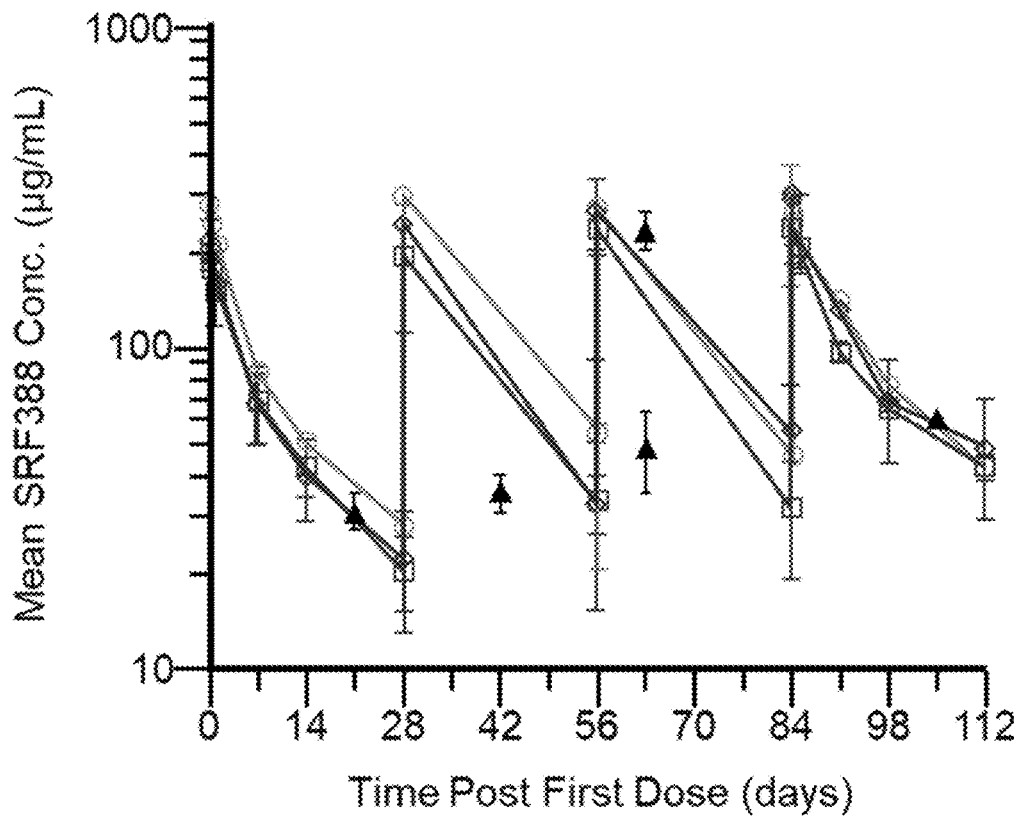

A subsequent PK analysis of patient samples who were administered 0.03 mg/kg, 0.1 mg/kg, 0.3 mg/kg, 1 mg/kg, 3 mg/kg, 10 mg/kg and 20 mg/kg doses of anti-IL-27 antibody in Part A of the study was performed, confirming that anti-IL-27 antibody PK are linear and dose proportional from 0.03 to 20 mg/kg. The terminal elimination half-life was estimated to be approximately 10 days, ranging from 6 to 13 days. Steady state was attained by Cycle 4, with an Accumulation Index of 1.2. Exposures (Cmax and AUC) in patients with ccRCC or HCC treated with 10 mg/kg anti-IL27 antibody as monotherapy were similar to those observed in the 10 mg/kg dose escalation cohort (FIGS. 10A-10B). Pre-exisiting low-titer anti-drug antibodies (ADA) were identified in the Cycle 1 pre-dose samples of 7 out of 63 patients; none were significantly boosed (increase in titer of >4-fold) post-treatment. Two out of 65 patients developed ADA after initiation of treatment.

The confirmed partial response in a 64-year NSCLC patient receiving anti-IL-27 antibody Ab1 at 10 mg/kg intravenously once every four weeks deepened to a 74% decrease in target lesions at cycle 6 response assessment.

The Part B Simon 2 Stage studies are ongoing with the primary endpoint of objective response. No concerning new safety signals have been identified thus far.

Figure 11A:
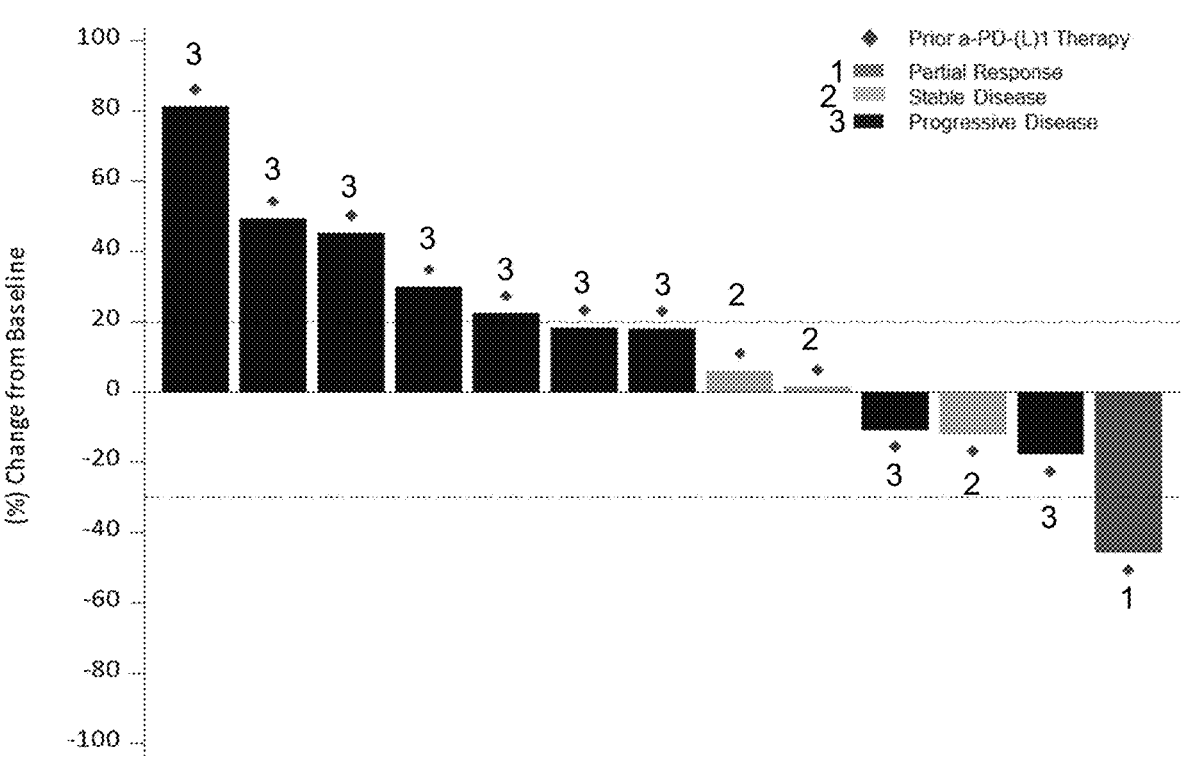
FIGS. 11A-11B are graphical representations of anti-IL-27 Ab1 ccRCC monotherapy dose escalation response.
Figure 11B:
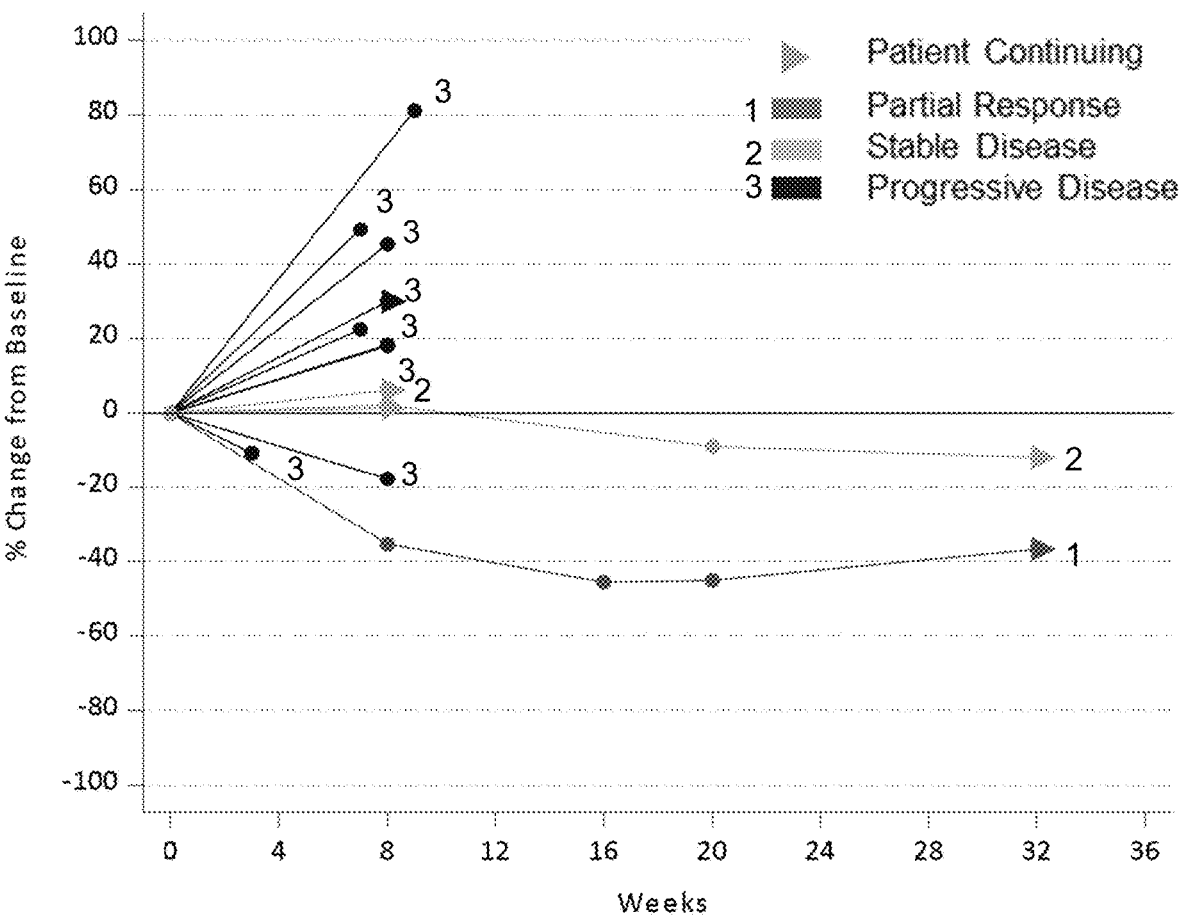

In the clear cell RCC cohort, 21 patients have been enrolled. Most of the population was male (91%), intermediate risk (57%) by International Metastatic RCC Database Consortium Risk Score ("IDMC") and had lung (71%) and nodal (100%) metastases. Close to 40% had liver (n=8) and bone disease (n=7) which generally correlate with worse prognosis. All patients were required to have had prior VEGF targeted therapy and PD-1 blockade alone or in combination (Table 5). Thirteen (13) patients were evaluable for investigator assessed RECISTv1.1 response (FIGS. 11A-11B). Disease control rate defined as CR/PR+SD was 31% including one patient with a confirmed partial response. Progressive disease was best response in 71%. The patient with a partial response experienced target lesion tumor shrinkage of 45%, which was confirmed at C6 and the patient remains on study at cycle 9.

TABLE 5

Part B, ccRCC Demographics and
Baseline Characteristics (All patients, N = 21)

| | |
|---|---|
| Median age, years (range) | 61 (42, 78) |
| Sex, n (%) | |
| Male | 19 (90.5%) |
| Female | 2 (9.5%) |
| ECOG PS at baseline, n (%) | |
| 0 | 10 (47.6%) |
| 1 | 11 (52.4%) |
| Median time since initial diagnosis, months (range) | 55 (26, 119) |

TABLE 5-continued

| Part B, ccRCC Demographics and Baseline Characteristics (All patients, N = 21) | |
| --- | --- |
| Number of prior systemic therapies, n (%) | |
| 1 | 0 (0%) |
| 2 | 5 (23.8%) |
| 3-4 | 16 (76.2%) |
| Prior aPD-1/aPD-L1, n (%) | |
| Yes | 21 (100%) |
| No | 0 (0%) |
| IDMC (one or more patients are missing data) | |
| Favorable | 4 (19%) |
| Intermediate | 12 (57.1%) |
| Poor | 2 (9.5%) |

Figure 12A:
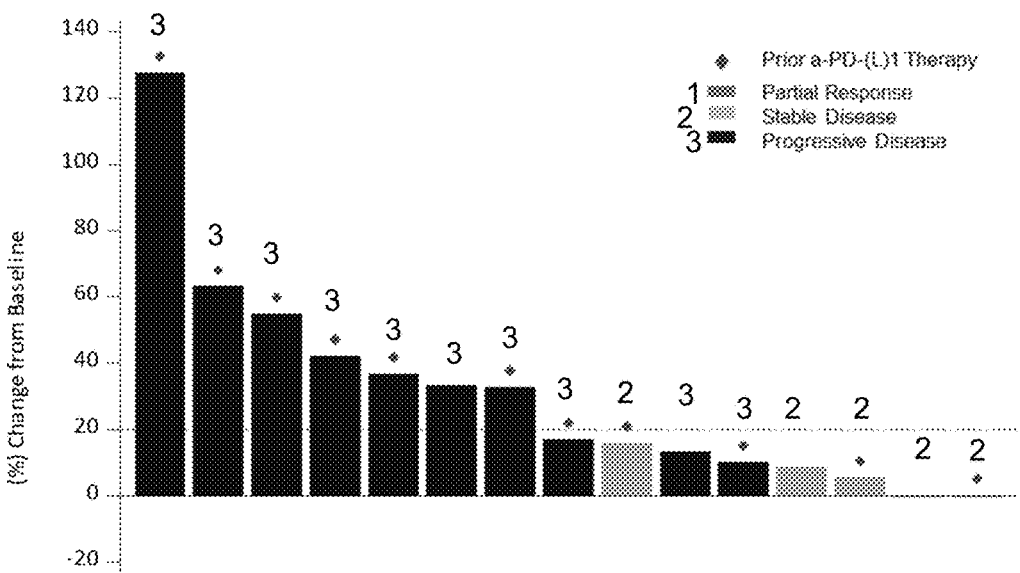
FIGS. 12A-12B are graphical representations of anti-IL-27 Ab1 HCC monotherapy response.
Figure 12B:
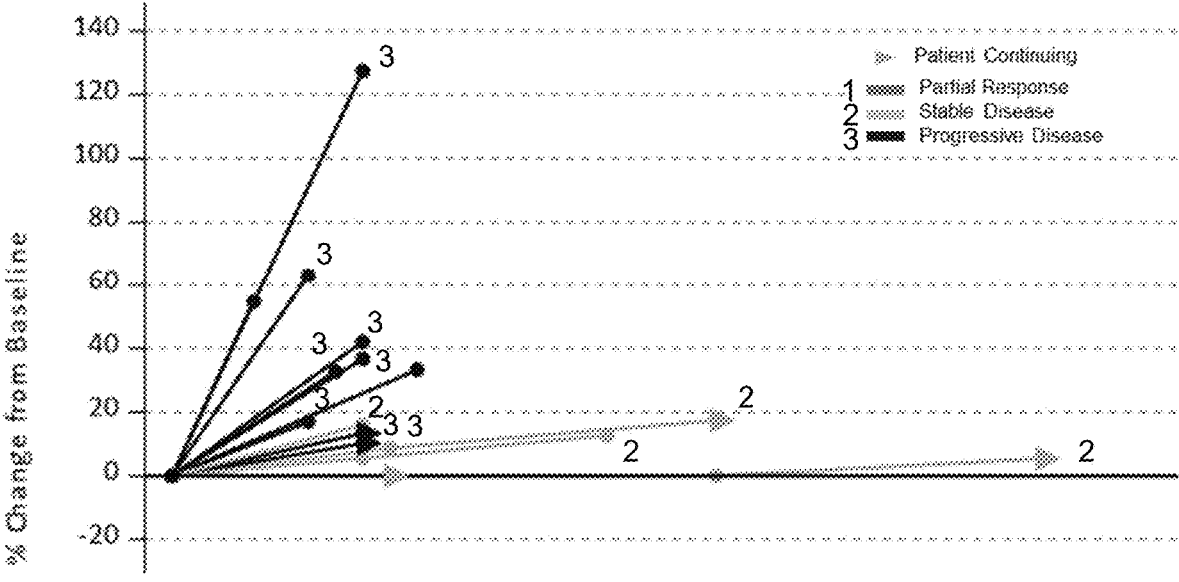

In the treatment-refractory HCC cohort, 17 patients were enrolled in a monotherapy expansion. It was an advanced treatment refractory population with a median progression free survival (PFS) of 7.2 weeks (6.3, NE). Of the 16 response evaluable patients, 31% (n=5) experienced stable disease and 69% (n=11) progressive disease as best response by RECISTv1.1 (FIGS. 12A-12B). Interrogation of baseline demographics highlights the advanced nature of the population enrolled: 53% 3-4 lines of prior therapy, 18% Child Pugh B7, 77% BCLC Stage C, 94% with ECOG 1, 59% AFP >=400. Only 18% ever had prior PR and 18% were primary treatment refractory to all prior lines of therapy (Table 6).

TABLE 6

| Part B, HCC Demographics and Baseline Characteristics (All patients, N = 17) | |
| --- | --- |
| Median age, years (range) | 64 (39, 77) |
| Sex, n (%) | |
| Male | 13 (76.5%) |
| Female | 4 (23.5%) |
| ECOG PS at baseline, n (%) | |
| 0 | 1 (5.9%) |
| 1 | 15 (94.1%) |
| Median time since initial diagnosis, months (range) | 27 (1, 137) |
| Number of prior systemic therapies, n (%) | |
| 1 | 1 (5.9%) |
| 2 | 7 (41.2%) |
| 3-4 | 9 (52.9%) |
| ≥5 | 0 (0%) |
| Prior aPD-1/aPD-L1, n (%) | |
| Yes | 12 (70.6%) |
| No | 5 (29.4%) |

Example 4: Determination of Anti-IL-27 Antibodies in Human Serum by Enzyme-Linked Immunosorbent Assay (ELISA)

An immunoassay method was used for the detection of anti-IL-27 Ab1 in human serum. In the sandwich ELISA, microtiter plates (96-well MaxiSorp plates, Cat #439454) were coated with recombinant human IL-27 (Peprotech, Lot #1215589) and stored at 4° C. overnight. The plates were washed and blocked for at least one hour at room temperature. Samples, including standards and quality controls (QCs), were diluted at a minimum required dilution (MRD) of 1:25 in assay buffer (1% bovine serum albumin, BSA, in phosphate-buffered saline/tween, PBST) then added onto the plate for one hour at room temperature. Anti-IL-27 Ab1 is detected by anti-human IgG1 antibody conjugated to horseradish peroxidase (HRP) (Southern Biotech, Lot #G4015-Q168B). KPL SureBlue™ peroxidase is used as a substrate for HRP. The reaction is stopped by 1N Hydrochloric acid. The color intensity is proportional to the quantity of anti-IL-27 Ab1.

Example 5: Determination of pSTAT Inhibition in Human Whole Blood

Whole blood samples from patients administered the anti-IL-27 antibody (anti-IL-27 Ab1) were evaluated in an assay to measure IL-27-mediated phosphorylation of STAT1. EDTA anticoagulated whole human blood, shipped overnight at room temperature, was used in this assay. 450 µL blood was distributed into each of three 15 mL conical tubes and warmed for 30 minutes at 37° C. in a 37° C. incubator. Anti-IL-27 antibody was diluted to 1 mg/mL in endotoxin-free PBS (Teknova #P0300) and 10 µL was added to one tube to serve as an antibody-spiked control. 10 µL PBS alone was added to the other two tubes for unstimulated and stimulated controls. Tubes were incubated for 30 minutes in a 37° C. incubator.

A 10 µg vial of recombinant human IL-27 (R&D Systems #2526-IL) was reconstituted to 100 µg/mL by adding 100 µL PBS+0.1% BSA (made from 10% BSA Sigma #A1595). A working stock of the recombinant hIL-27 (rhIL-27) was prepared by dilution to 2 µg/mL in endotoxin free PBS. After the 30-minute incubation, 50 µL of 2 µg/mL rhIL-27 was added to anti-IL-27 antibody-spiked and stimulated tubes. 50 µL PBS was added to unstimulated tube. The tubes were mixed and incubated for 30 minutes at 37° C.

After the 30-minute incubation, cells were fixed. Lyse/Fix reagent (BD #558049) was diluted 1:5 in sterile water (Hyclone #SH3052902) and warmed to 37° C. in a water bath. 5 mL diluted Lyse/Fix reagent was added to each tube and the tubes were mixed well by inversion. The tubes were incubated for 15 min at 37° C. After the 15-minute incubation, the tubes were centrifuged for 5 minutes at 1500 RPM at room temperature and supernatant was discarded by decanting. 5 mL of endotoxin-free PBS was added per tube and samples were mixed by pipetting up and down. The tubes were centrifuged for 5 minutes at 1500 RPM at room temperature and supernatant was discarded by careful aspiration.

The cell pellets were loosened by flicking the tube and then resuspended in 500 µL Perm III (stored at −20° C.) (BD #558050) with pipetting. The tubes were incubated overnight at −20° C. After the incubation, 1 mL Stain Buffer with BSA (BD #554657) was added and the tubes were centrifuged at 1500 RPM for 5 minutes at room temperature. The supernatant was discarded by careful aspiration and the cells were resuspended in 100 µL staining cocktail prepared in Stain Buffer with BSA as described in Table 7 below:

TABLE 7

| BD Catalog# | Antibody | Color | Dilution |
| --- | --- | --- | --- |
| 561811 | CD3 | FITC | 1:20 |
| 562069 | pSTAT1 Y701 | PE | 1:50 |

The tubes were incubated for 1 hour at room temperature in the dark. After the 1 hour incubation, 200 µL Stain Buffer with BSA was added to each tube and samples were centrifuged at 1500 RPM for 5 minutes at room temperature.

The supernatant was discarded from the plate by decanting and the cells were resuspended in 300 μL Stain Buffer with BSA for analysis by flow cytometry.

Figure 13A:
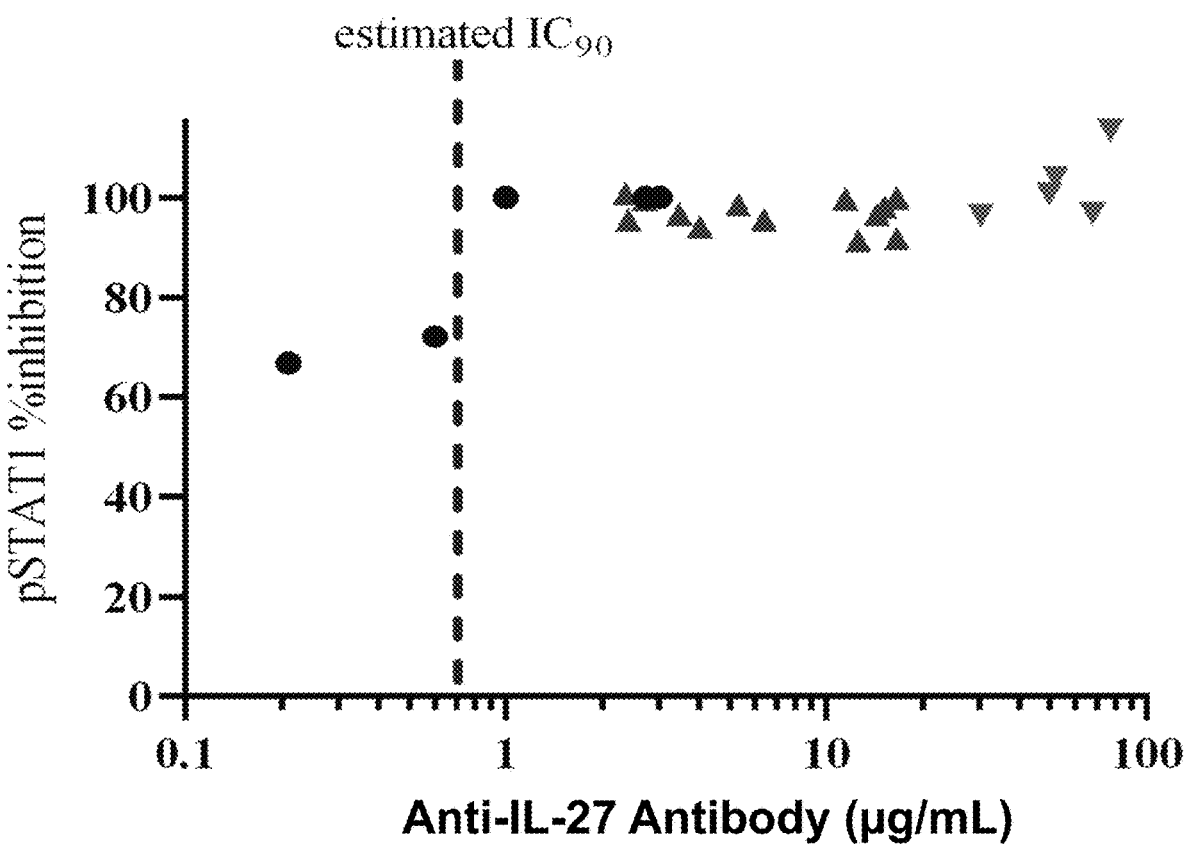
FIG. 13A is graphical representation of IL-27-dependent pSTAT1 inhibition in T cells from the blood of a patient following administration of 0.1 mg/kg, 1.0 mg/kg, and 3.0 mg/kg of an anti-IL-27 antibody (y-axis) and the corresponding serum levels of the anti-IL-27 antibody (x-axis) after anti-IL-27 antibody administration. The vertical dotted line represents the serum concentration of anti-IL27 antibody that results in 90% inhibition ($IC_{90}$) of IL-27-dependent pSTAT1 inhibition (0.7 µg/ml).
Figure 13B:
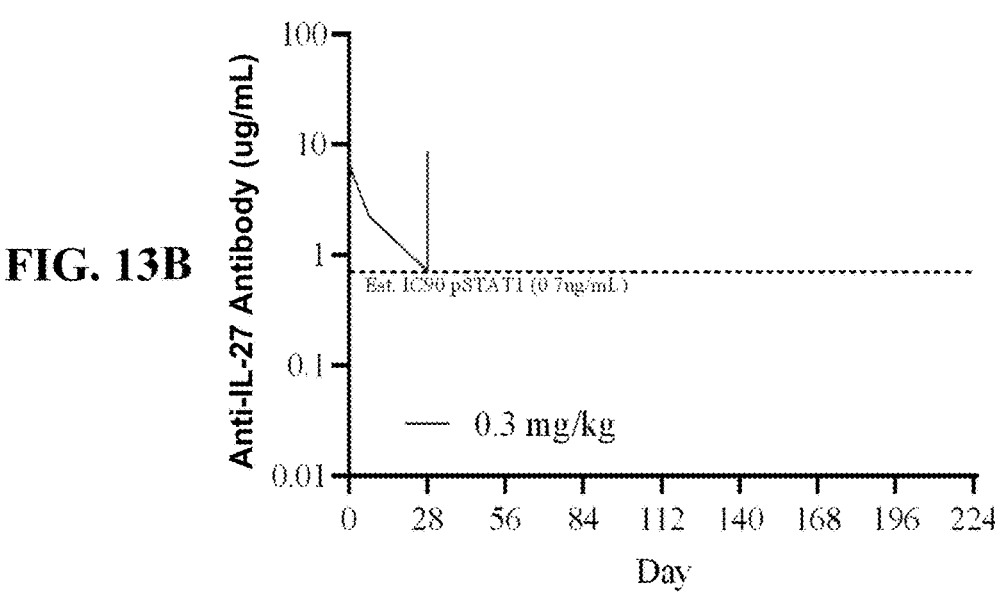
FIGS. 13B-13D show the pharmacokinetic analysis of anti-IL-27 antibody in the serum of subjects following repeated administration of 0.1 mg/kg (FIG. 13B), 1.0 mg/kg (FIG. 13C), and 3.0 mg/kg (FIG. 13D) of an anti-IL-27 antibody, once every 28 days. The serum level of anti-IL-27 antibody required to achieve the $IC_{90}$ for IL-27-dependent inhibition of pSTAT1 in T cells from the blood of a subject is indicated by the horizontal dotted line in FIGS. 13B-13D.
Figure 13C:
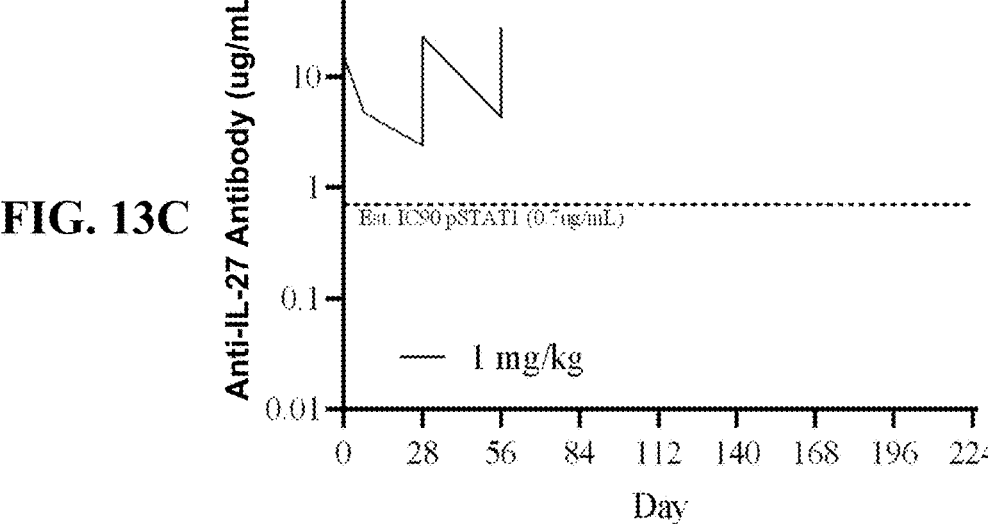
Figure 13D:
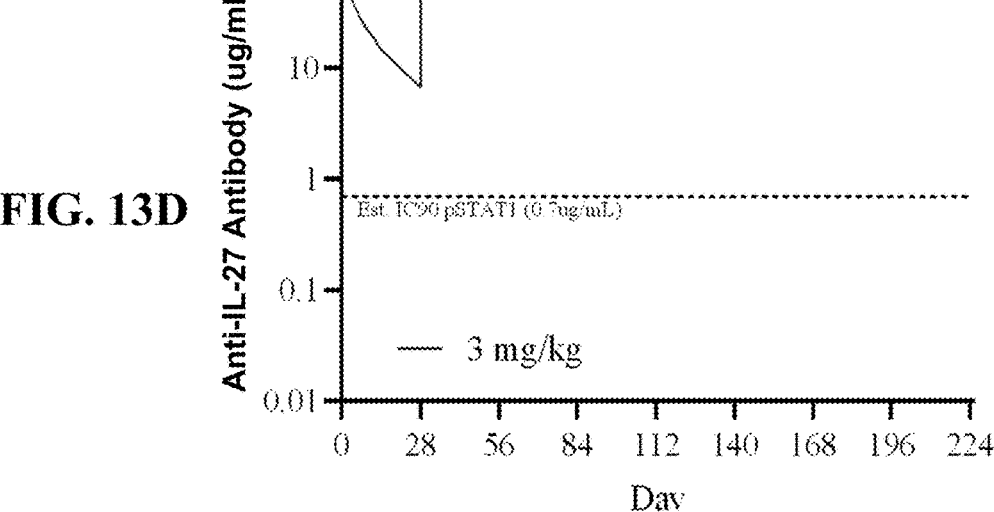

Administration of 0.3 mg/kg, 1 mg/kg, 3 mg/kg, or 10 mg/kg anti-IL-27 antibody resulted in at least 90% pSTAT1 signaling inhibition (FIGS. 13A-13D). This effect was most pronounced in subjects administered the 3 mg/kg dose of the anti-IL-27 antibody (FIG. 13D). Repeated administration of the anti-IL-27 antibody once every four weeks showed repeated decreases in pSTAT signaling (FIGS. 13B-13D).

Example 6: IL-27 Signaling Drives a Type 1 Interferon-Like Gene Expression Program of Immunoregulatory Pathways Associated with Cancer Progression Gene expression changes induced by IL-27 were examined in activated human CD4+ T cells, human PBMCs, and the IL-27RA-expressing lung cancer cell line NCI-H2228 by microarray or single cell RNA-sequencing. The resulting IL-27 signature genes were interrogated by gene enrichment analysis, including single cell RNA-seq analysis of the tumor microenvironment, from patients with NSCLC.

IL-27 induced a robust gene expression program in human immune cells that included several inhibitory receptors and canonical interferon regulated genes such as guanylate-binding proteins (GBPs) and interferon regulatory factors (IRFs). Gene set enrichment analysis (GSEA) and interferon signature analysis showed a striking overlap with those genes regulated by interferon-beta, a cytokine known to drive immune suppression associated with chronic viral infection that is used therapeutically for controlling inflammation associated with the autoimmune disease multiple sclerosis. Moreover, interferon regulated pathways have recently emerged as a mechanism of resistance to immune checkpoint blockade in cancer. Exploration of the IL-27 gene signature in published datasets showed enrichment in macrophage populations associated with progressive disease in patients with NSCLC. While many of the properties of IL-27-mediated immune regulation have focused on hematopoietic cells, IL-27RA is also expressed on tumor cells from NSCLC patients with progressive disease as well as lung cancer cell lines in which IL-27 can upregulate PD-L1, IDO1 and other canonical interferon regulated genes.

These studies elucidate the transcriptional networks that are engaged after IL-27 signaling in immune and cancer cells and highlight the parallels with interferon-associated immune regulation. Blockade of IL-27 provides a novel therapeutic strategy to alleviate a gene transcriptional program implicated in immune suppression and checkpoint resistance.

Example 7: Anti-IL-27 Ab1 Chemokine/Cytokine Multiplex Assays

Blood serum samples were collected from patients enrolled on the anti-IL-27 Ab1 clinical trial (see Example 2) at the following scheduled visits and timepoints: C1D1 pre-dose and 6 hours post-dose; C1D8; C2D1 pre-dose and 6 hours post-dose; and pre-dose for C3D1 and every subsequent treatment cycle. Serum protein expression was measured based on electrochemiluminescence (ECL) detection assays using commercially available multiplex chemokine and cytokine kits from Meso Scale Diagnostics (MSD; Rockville, MD, USA) across the following 4 panels: V-PLEX Plus Chemokine Panel 1 (human) Kit, V-PLEX Plus Proinflammatory Panel 1 (human Kit), V-PLEX Plus Cytokine Panel 1 (human) Kit, and V-PLEX PLUS TH17 Panel 1 (human) Kit.

Figure 14A:
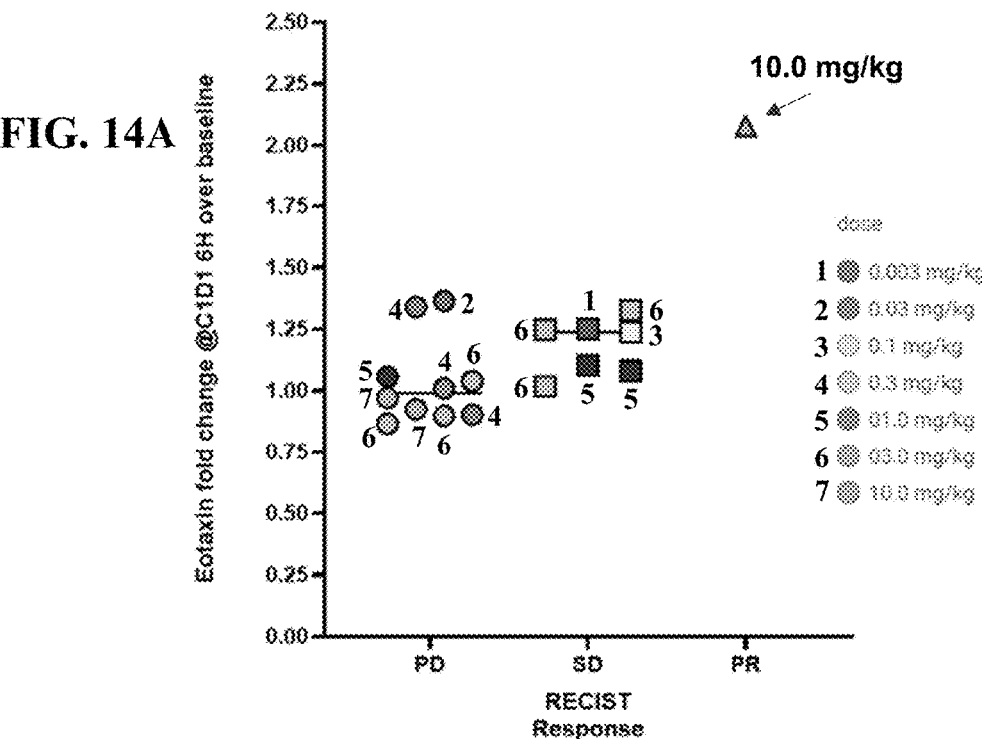
FIG. 14A is a graphical representation of Eotaxin-1 fold-change at C1D1 6-hour post dose time-point, relative to baseline, for patients exhibiting progressive disease (PD), stable disease (SD), or partial response (PR) following administration of varying doses of anti-IL-27 Ab1.
Figure 14B:
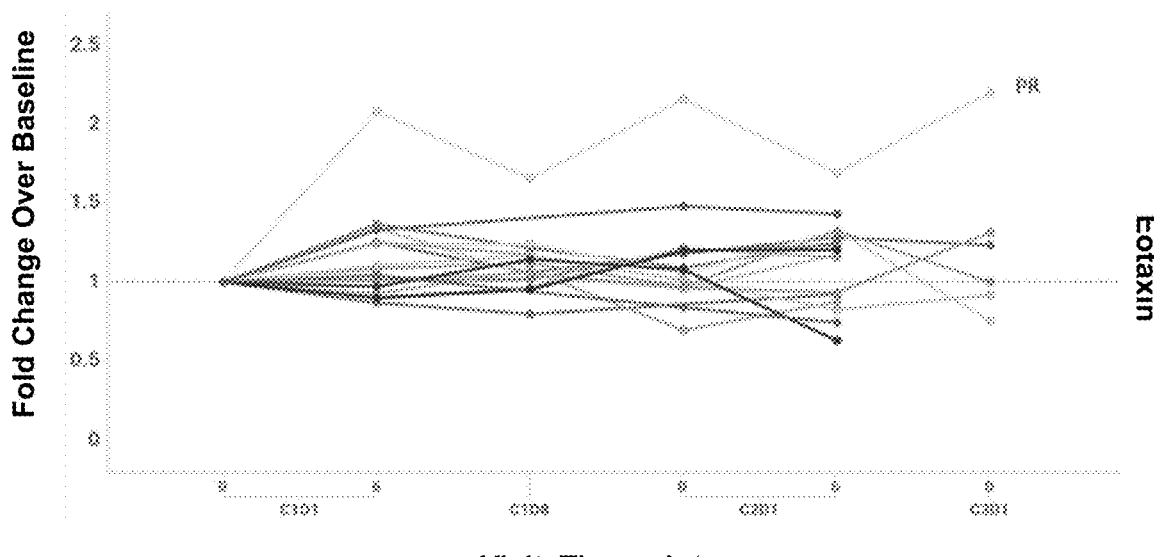
FIG. 14B is a graphical representation of a longitudinal analysis of Eotaxin-1 fold-change over baseline across C1D1 (predose and 6 hours post dose), C1D8, C2D1 (predose and 6 hours post dose), and C3D1 timepoints. The data for the patient exhibiting a partial response is labelled as "PR." Each data set represents a single patient.

Individual circulating chemokine and cytokine measurements relative to fold-change over baseline levels (i.e., C1D1 pre-dose sample) were examined for any correlative relationships with clinical response data to anti-IL-27 Ab1 monotherapy. From this analysis, an increased fold-change over baseline was observed in Eotaxin-1 (CCL11) levels at the C1D1 6-hour post-dose timepoint in a patient (902-002) that had experienced a confirmed partial response (PR) to anti-IL-27 Ab1 monotherapy when compared to the fold changes seen in other patients that had been clinically classified as having either progressive disease (PD) or stable disease (SD) (FIG. 14A). Further longitudinal analysis though cycle 3 demonstrated a sustained elevated fold change over baseline level of Eotaxin-1 (CCL11) in this patient with PR when compared with the other patients with PD and SD (FIG. 14B).

Figure 15:
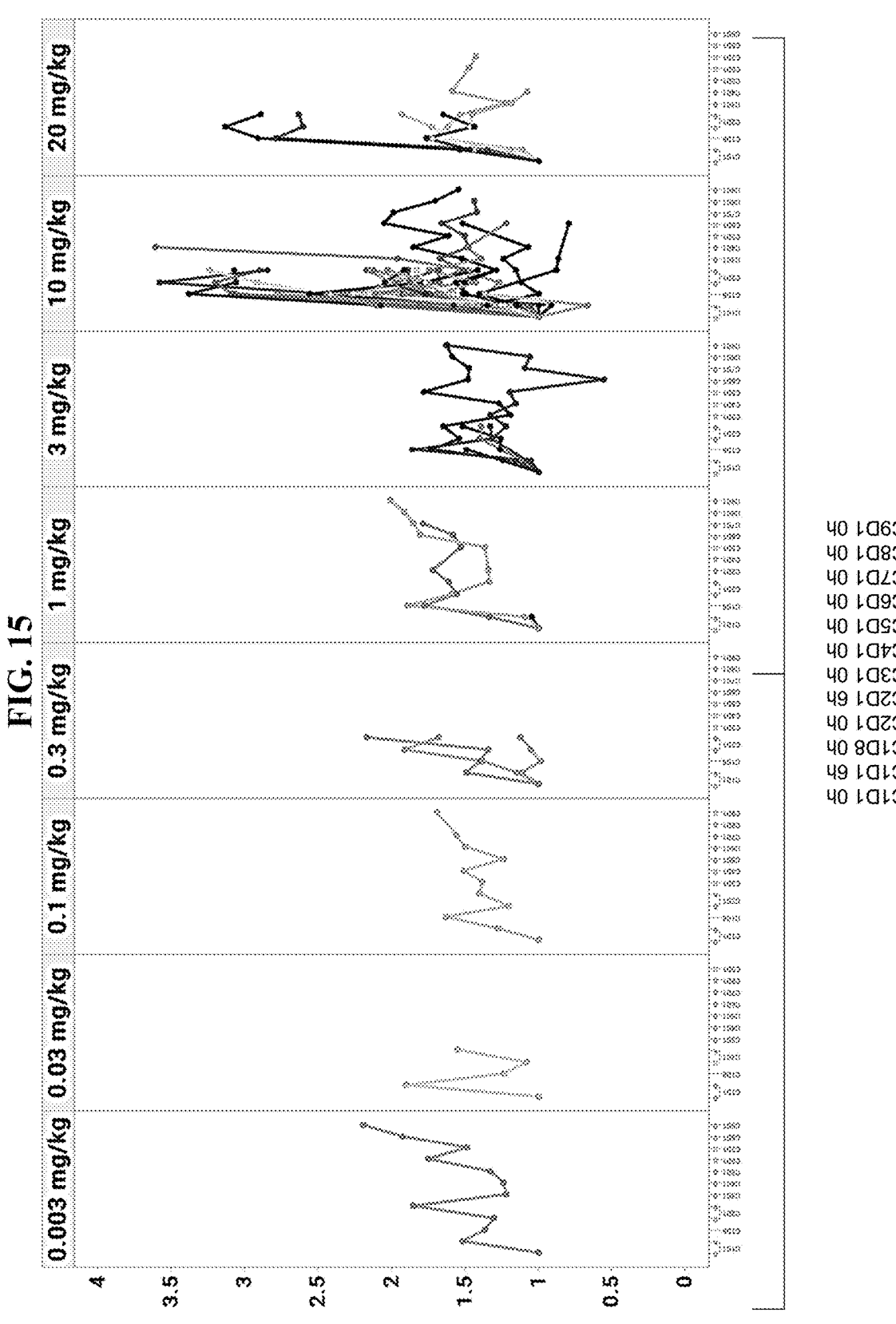
FIG. 15 shows IL-27 fold-change levels over baseline at various visits, times, and dosage cohorts for anti-IL-27 Ab1 monotherapy patients.

Circulating levels of IL-27 relative to fold-change over baseline levels (i.e., C1D1 pre-dose sample) were examined in patients from each SRF388 monotherapy dose cohort (0.003 mg/kg, 0.03 mg/kg, 0.1 mg/kg, 0.3 mg/kg, 1.0 mg/kg, 3 mg/kg, 10 mg/kg, and 20 mg/kg). IL-27 fold-change over baseline levels trend upward for most patients but does not appear to be a dose-dependent phenomon (FIG. 15). These observations have been described for other therapeutic antibodies against cytokines (Yang J. C. et al. 2003; NEJM; Bocci G. et al. 2004; Cancer Research) including bevacizumab and its effects on circulating levels of VEGF and attributed to decreased receptor-*mediated clearance.*

Figure 16:
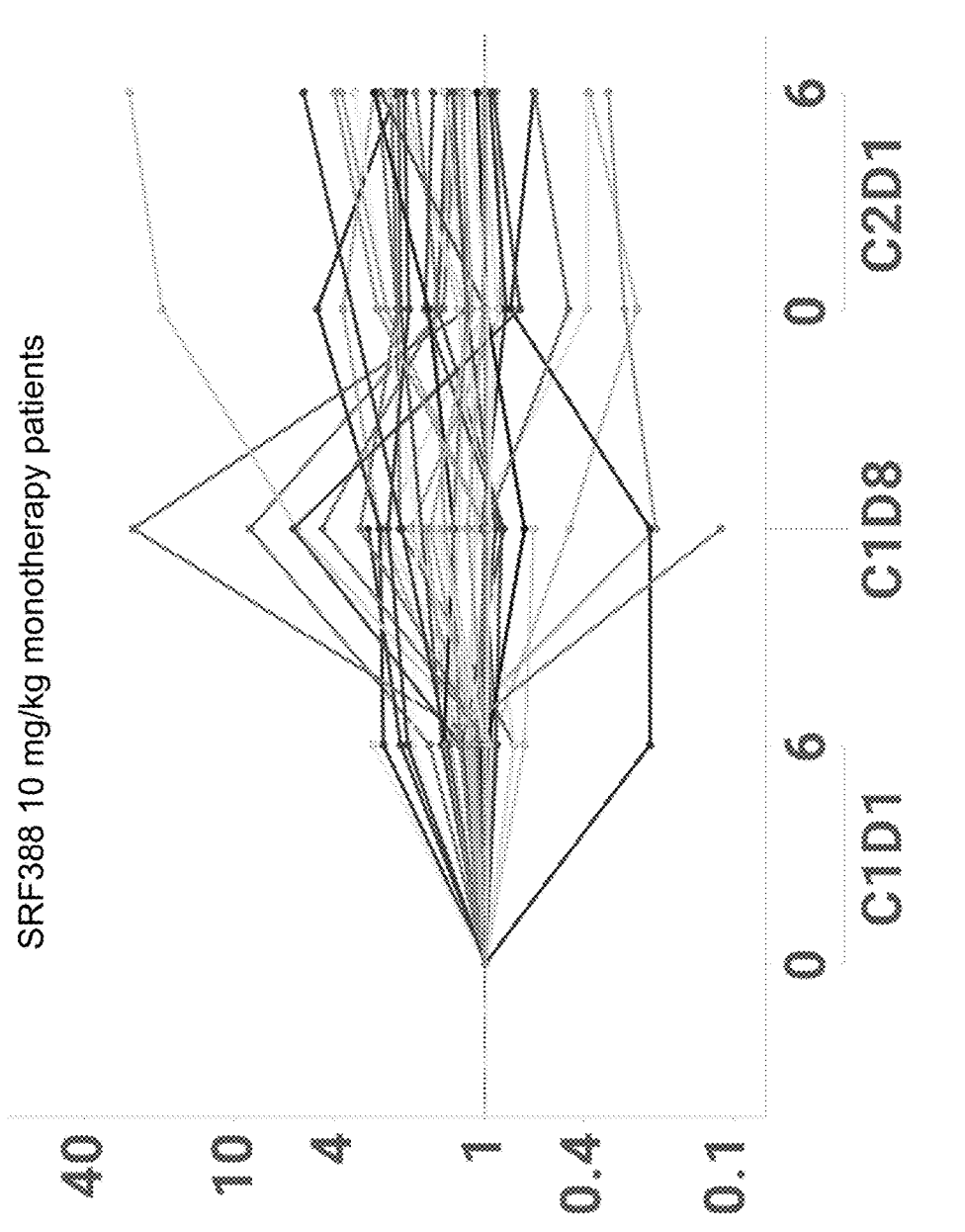
FIG. 16 shows circulating IFNγ fold-change levels over baseline at various visits and times for 10 mg/kg anti-IL-27 Ab1 monotherapy patients.

Circulating levels of IFNγ relative to fold-change over baseline levels (i.e., C1D1 pre-dose sample) were examined in patients from the anti-IL-27 Ab1 monotherapy patients. IFNγ fold-change levels over baseline appeared to increase in a large proportion of patients in the 10 mg/kg monotherapy cohort patients consistent with anti-IL-27 Ab1 mechanism of action (FIG. 16).

Figure 17G:
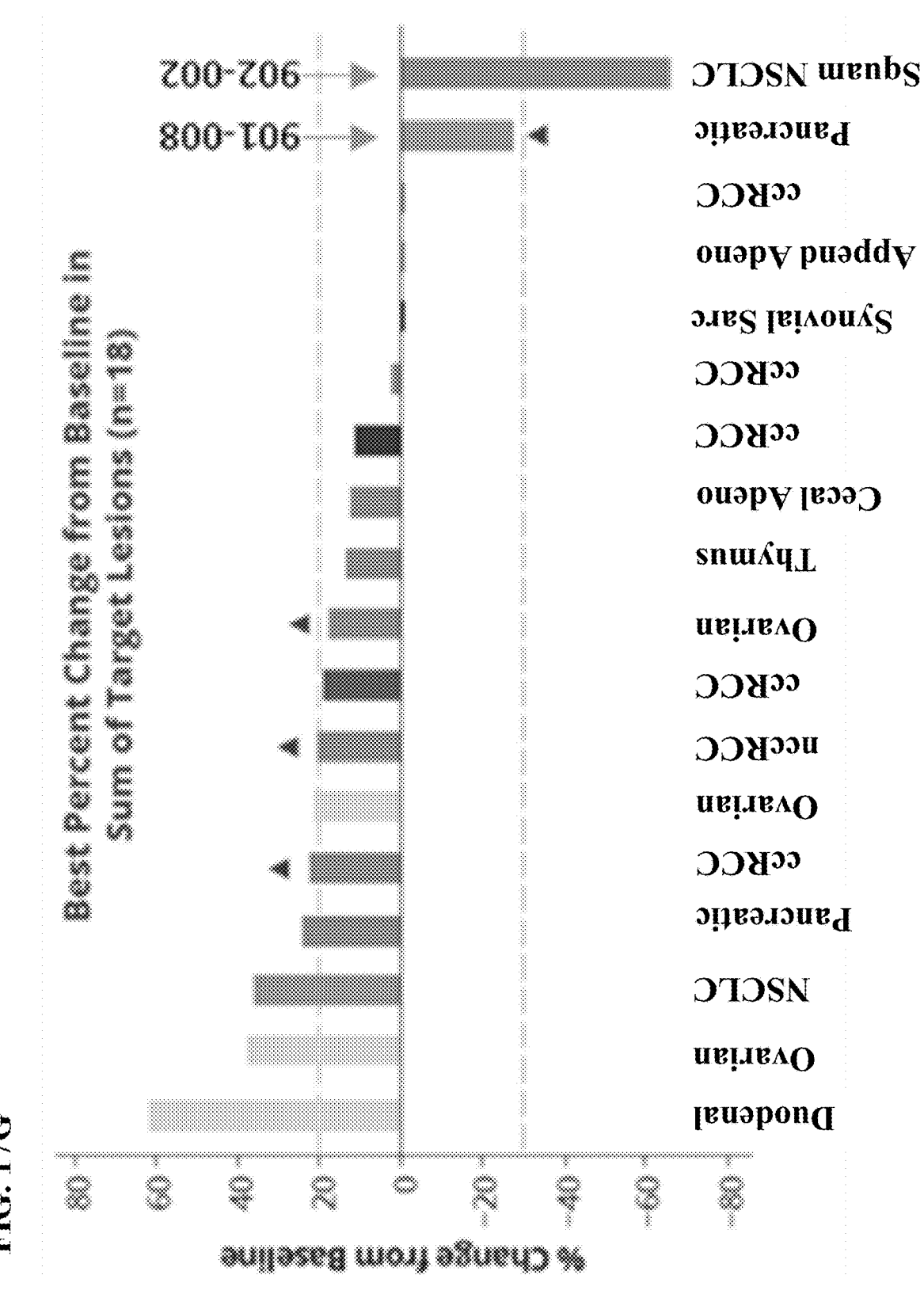
FIG. 17G is a waterfall plot showing the percent change from baseline in target lesions for patients characterized in FIGS. 17A-17F. Data corresponding to a confirmed partial response (PR; 902-002) patient and a stable disease (SD; 901-008) patient exhibiting tumor reduction are labelled (FIGS. 17A-17G).
Figure 18A:
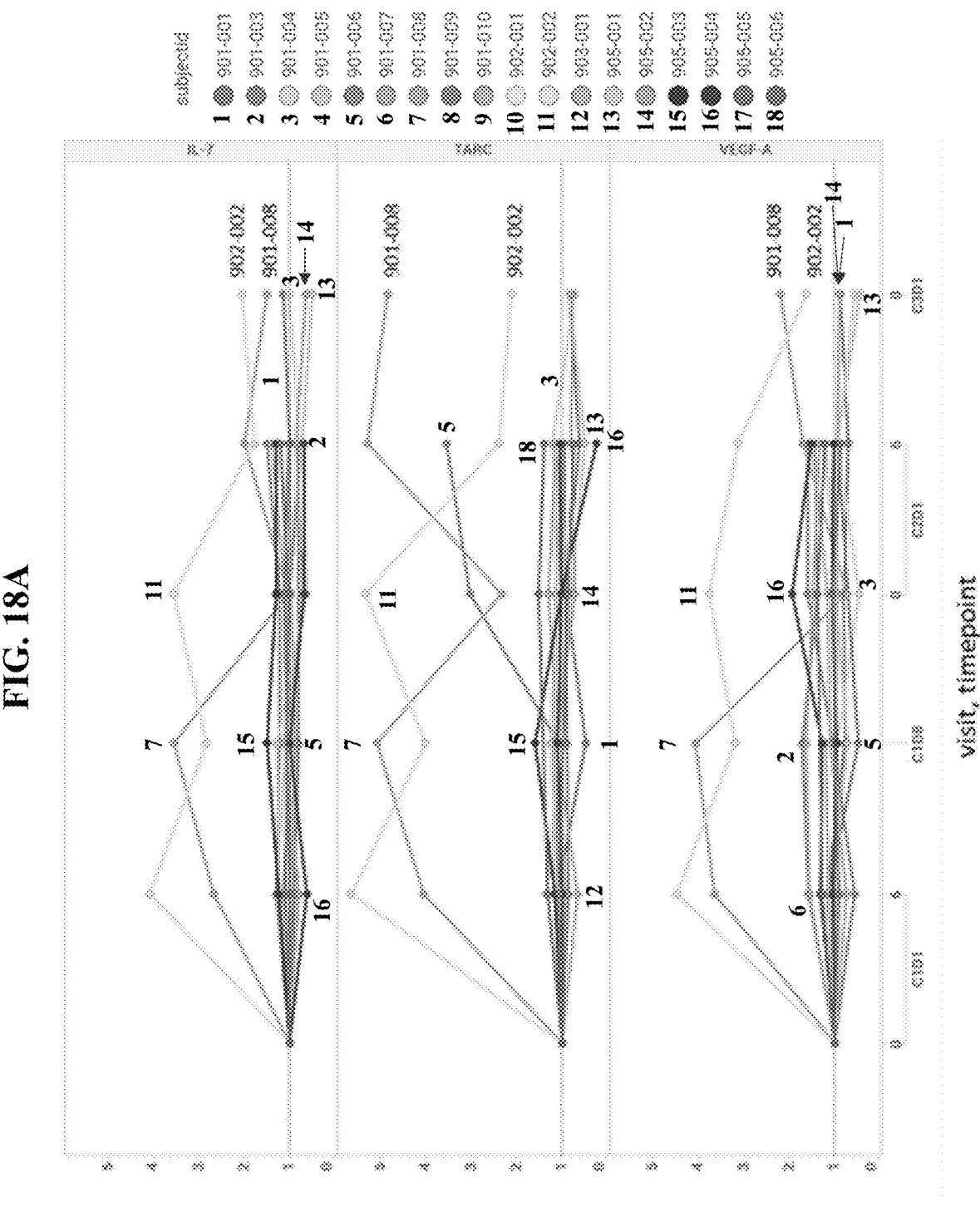
FIGS. 18A-18B are graphical representations of longitudinal analyses of IL-7, TARC (CCL17), and VEGF-A (FIG. 18A) and IL-8, MCP-1, and MCP-4 (FIG. 18B), as indicated, in samples obtained from patients administered anti-IL-27 Ab1. Data corresponding to a patient with a confirmed partial response (PR; 902-002) and a patient with stable disease (SD; 901-008) but exhibiting tumor reduction are labelled (FIGS. 18A-18B).
Figure 18B:
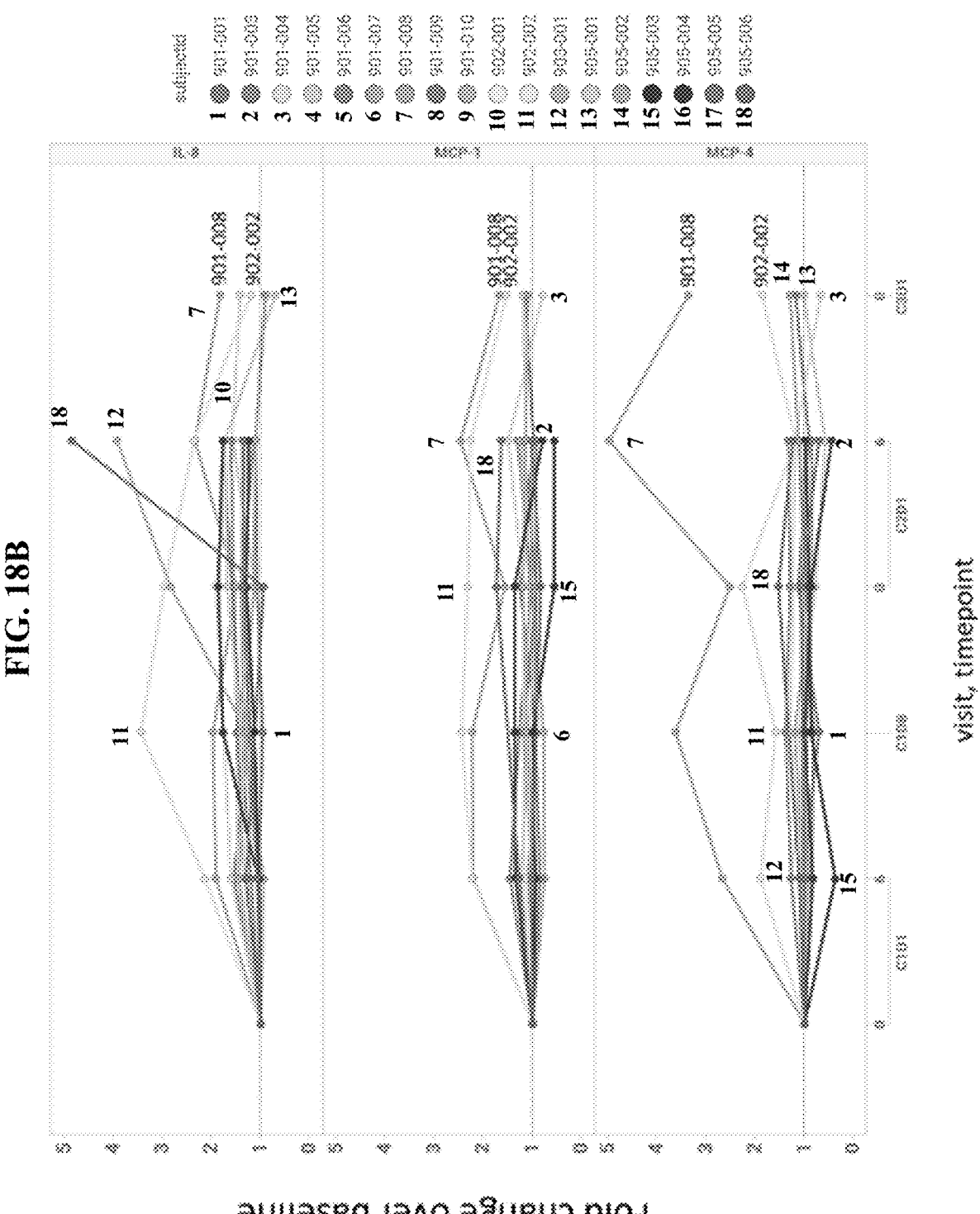

Additional clinical correlative analyses demonstrated further potential relationships with several other chemokines and cytokines and response to anti-IL-27 Ab1monotherapy, including TARC (CCL17; FIG. 17A), VEGF-A (FIG. 17B), IL-7 (FIG. 17C), IL-8 (FIG. 17D), MCP-1 (FIG. 17E), and MCP-4 (FIG. 17F). Similar to Eotaxin-1 (CCL11), we observed a fold change over baseline at the C1D1 6-hour post-dose in this set of proteins that was consistently elevated in the patient with PR when compared to the majority of patients in the PD and SD RECISTv1.1 response categories. Moreover, we noted that one of the patients with SD (901-008) also exhibited similar elevated fold change over baseline levels in this set of 6 proteins when compared to the remaining PD and SD patients. Although this patient did not meet RECIST response criteria to be classified as a PR, this patient did experience demonstrable tumor shrinkage in response to anti-IL-27 Ab1monotherapy (FIG. 17G). Longitudinal analyses of these chemokines and cytokines in these two patients though cycle 3 demonstrated that these fold-change elevations over baseline appeared to be relatively sustained, albeit to varying degrees over time (FIGS. 18A-18B).

Example 8: Analysis of Immunoregulatory Impact of IL-27 Signaling

IL-27 is a heterodimeric immunoregulatory cytokine that consists of 2 subunits: p28 and Epstein-Barr virus-induced gene 3 (EBI3). IL-27 signals through a heterodimeric receptor composed of glycoprotein 130 (gp130) and the IL-27 receptor subunit alpha, IL-27RA (WSX-1), which activates the JAK-STAT pathway to limit the duration and intensity of T cell-mediated immunity. IL-27 signaling through the JAK-STAT pathway results in altered immunoregulatory receptor expression and decreased proinflammatory cytokine secretion. The present example characterizes the immunoregulatory impact of IL-27 signaling by gene expression profiling.

Figure 19:
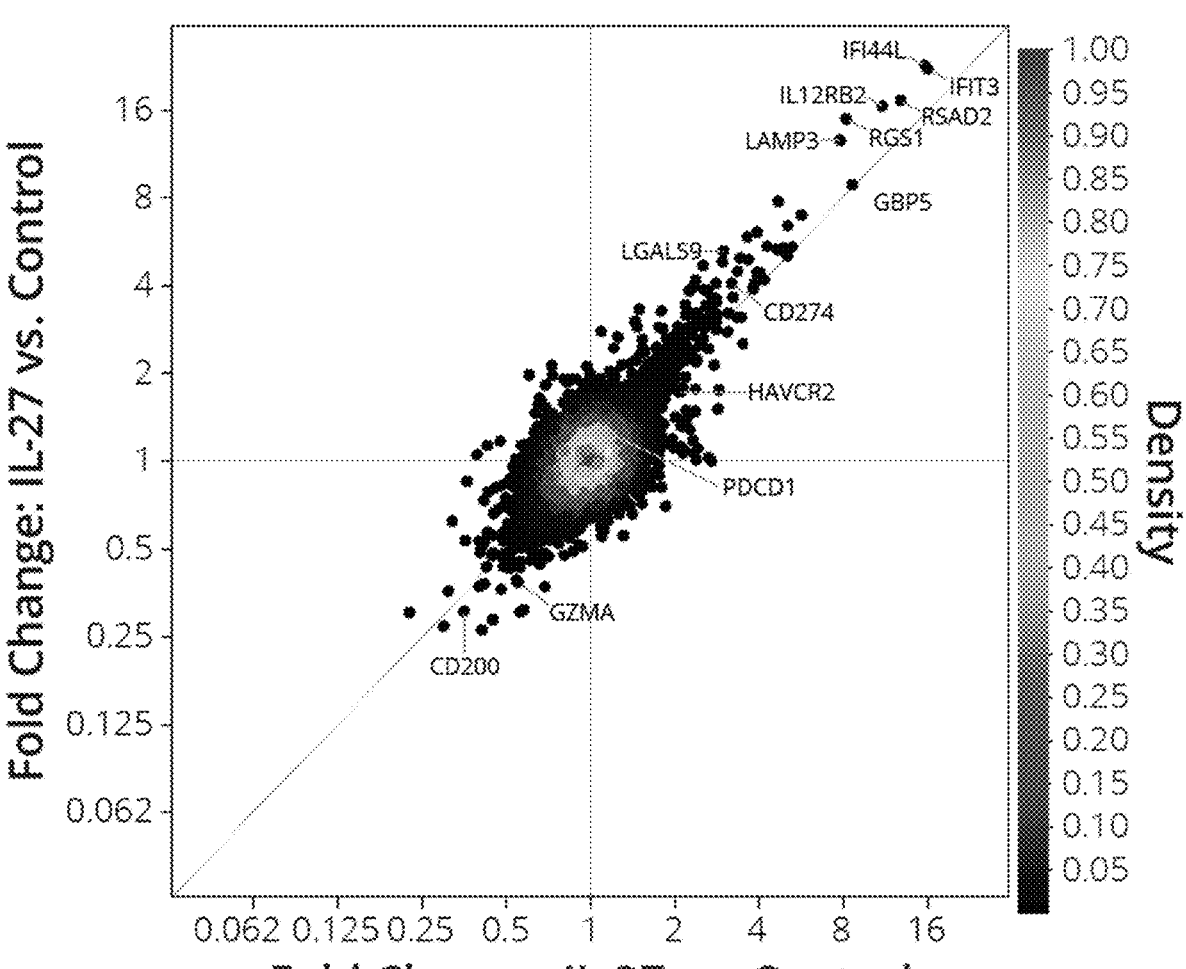
FIG. 19 is a scatter plot illustrating IL-27-induced changes in gene expression from two individuals.

To identify genes regulated by IL-27 signaling, PBMCs were isolated from healthy donors and stimulated in vitro for 3 days with anti-CD3 antibody (0.25 µg/mL, clone UCHT1) in the presence or absence of recombinant human IL-27 (100 ng/ml), recombinant human EBI3 (100 ng/ml), or recombinant human IL-25 (100 ng/ml) in 96-well plates. After this culture period, CD4$^+$ CD8$^-$ T cells were isolated by fluorescence activated cell sorting followed by RNA purification and processing for hybridization to HuGene 1.0ST arrays. Raw microarray data were normalized and differential gene expression was determined by comparing cytokine treatment to control conditions in two individual donors (FIG. 19). Genes that showed increased expression after IL-27 treatment were used for gene set enrichment analysis (GSEA). Several gene signatures from GSEA (e.g., hallmark IFNα signature) were then used to highlight the overlap in gene expression with the IL-27 signature.

Figures 20A, 20B, 20C:
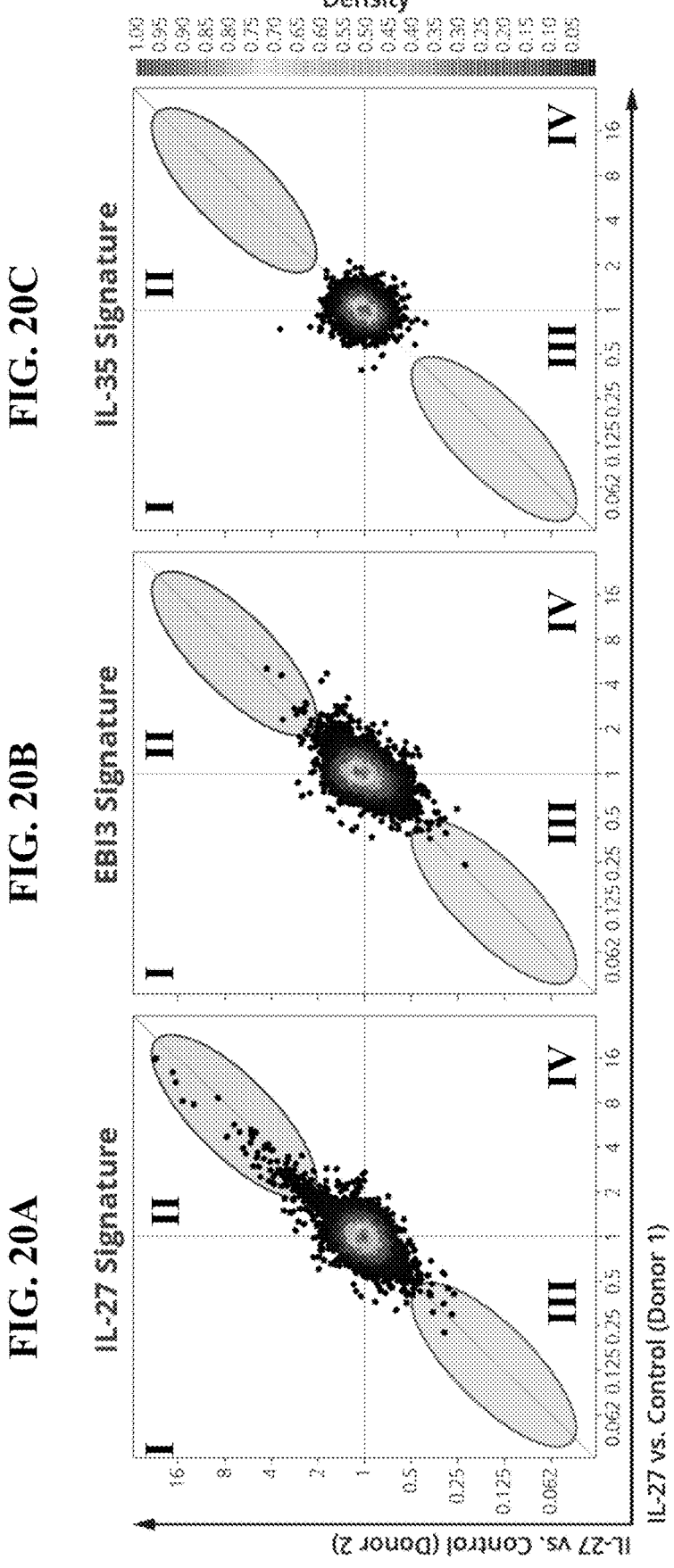
FIGS. 20A-20C are scatter plots illustrating changes in gene expression from two individuals following contact with IL-27 heterodimer (FIG. 20A), EBI3 alone (FIG. 20B), or IL-35 (FIG. 20C).

CD4+ T cells were isolated from activated PBMC cultures after treatment with rhIL-27, rhEBI3, or rhIL-35 cytokines at 100 ng/ml. The IL-27 heterodimer (FIG. 20A), but neither EBI3 alone (FIG. 20B) nor IL-35 (FIG. 20C), elicits robust gene expression changes in human CD4+ T cells from PBMCs.

Figure 21A:
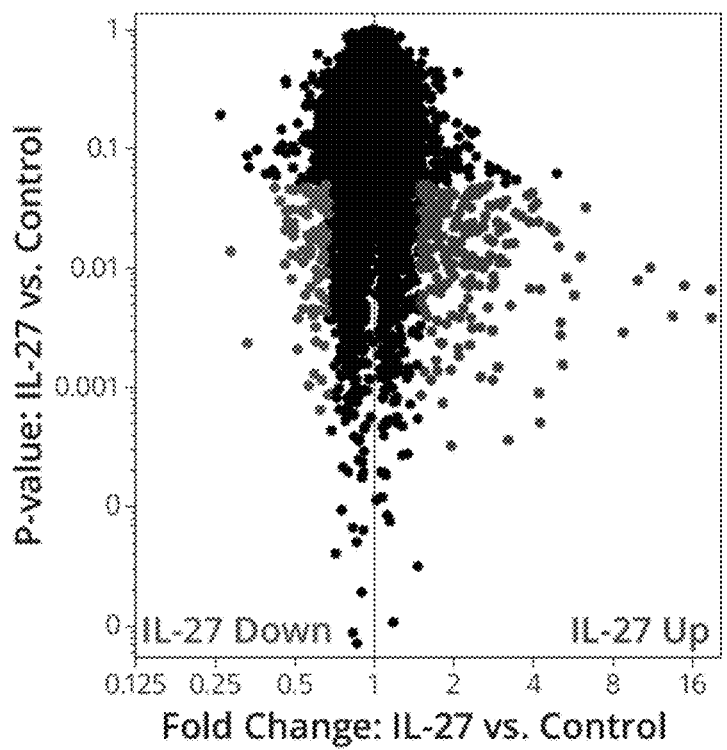
FIGS. 21A-21B are volcano plots representing a gene set enrichment analysis of the IL-27 gene signature from CD4+ T cells.
Figure 21B:
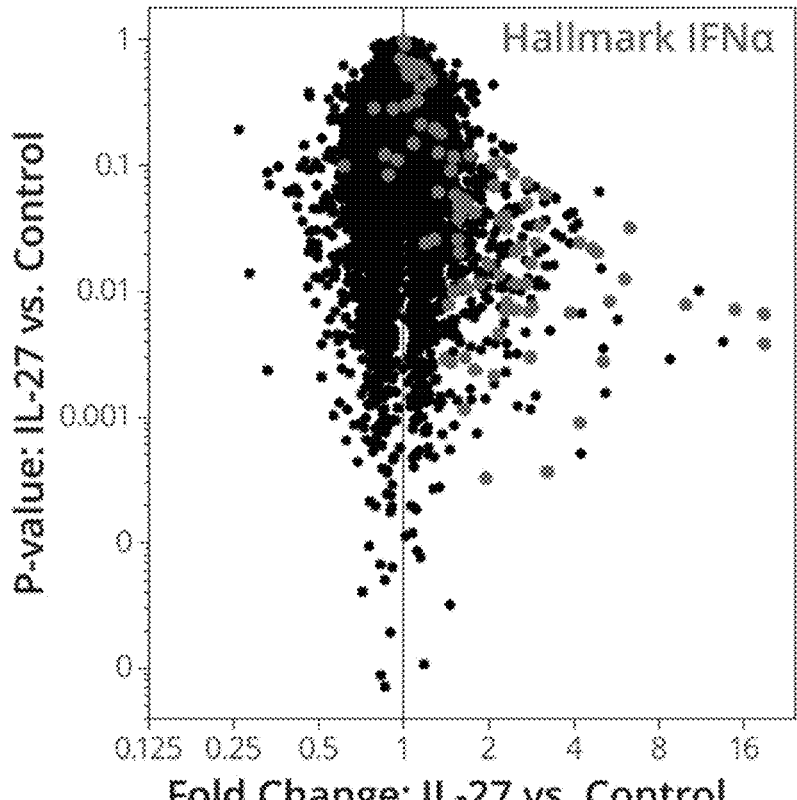

Gene set enrichment analysis of the IL-27 gene signature from CD4+ T cells shows an enrichment of mRNA signatures associated with interferon signaling (FIGS. 21A-21B). Hallmark IFNα signature genes (Table 8) are highlighted in FIG. 21B. Note that IL-27 does not increase the expression of interferon-γ (IFNγ) transcript or protein in these conditions.

TABLE 8

Enrichment of interferon-regulated genes.

| Gene Set Name | # Genes in Gene Set (K) | # Genes in Overlap (k) | k/K | p-value | FDR q-value |
|---|---|---|---|---|---|
| GSE13485_CTRL_ VS_DAY7_YF17D_ VACCINE_PBMC_DN | 200 | 46 | 0.23 | 1.00E−82 | 1.04E−78 |
| HALLMARK_ INTERFERON_ GAMMA_RESPONSE | 200 | 44 | 0.22 | 5.61E−78 | 1.948−74 |
| HALLMARK_ INTERFERON_ ALPHA_RESPONSE | 97 | 37 | 0.3814 | 1.82E−75 | 3.76E−72 |
| GSE13485_PRE_ VS_POST_YF17D_ VACCINATION_ PBMC_DN | 200 | 39 | 0.195 | 1.85E−66 | 2.738−63 |
| GSE10325_CD4_ TCELL_VS_LUPUS_ CD4_TCELL_DN | 200 | 37 | 0.185 | 5.38E−62 | 5.06E−59 |
| HECKER_IFNB1_ TARGETS | 95 | 26 | 0.2737 | 3.09E−48 | 1.78E−45 |
| BROWNIE_ INTERFERON_ RESPONSIVE_ GENES | 68 | 24 | 0.3529 | 1.16E−47 | 6.33E−45 |

TABLE 8-continued

Enrichment of interferon-regulated genes.

| Gene Set Name | # Genes in Gene Set (K) | # Genes in Overlap (k) | k/K | p-value | FDR q-value |
|---|---|---|---|---|---|
| MOSERLE IFNA RESPONSE | 31 | 20 | 0.6452 | 7.69E−47 | 3.98E−44 |

Figure 22A:
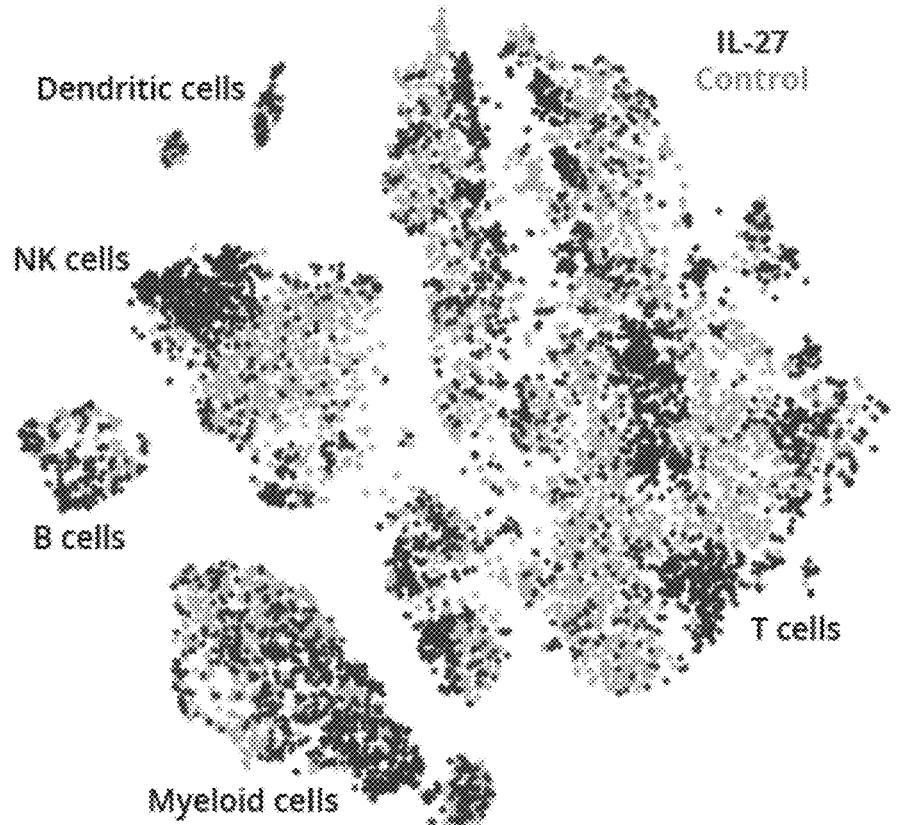
Figure 22B:
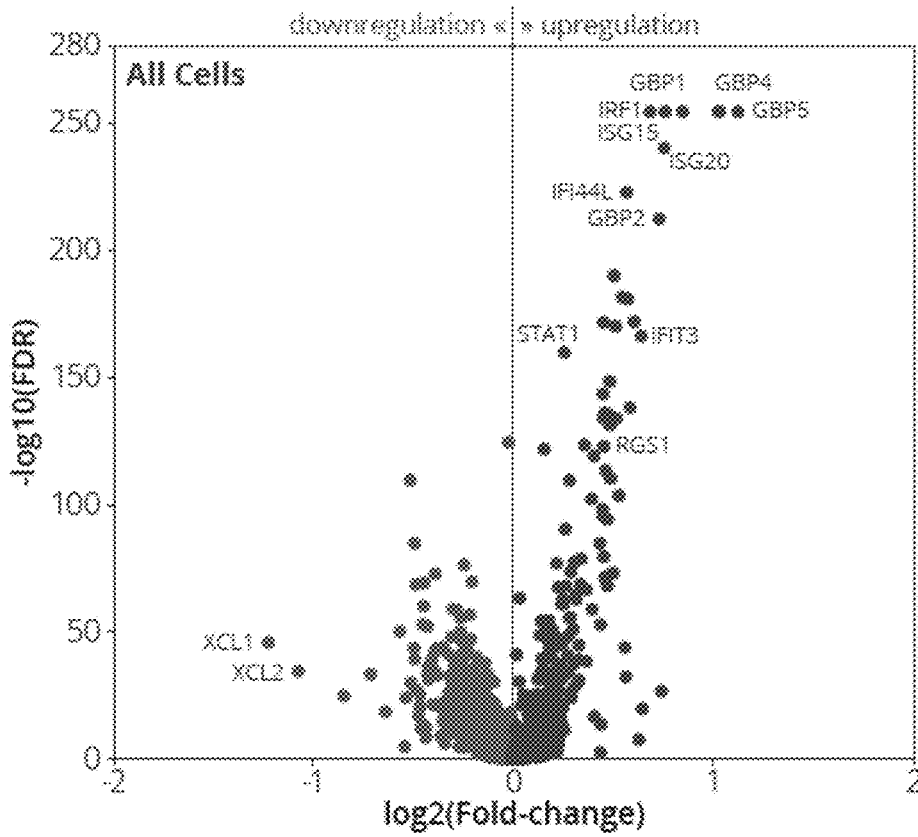

Single-cell RNA-sequencing analysis of human PBMCs identifies several immune cell populations exhibiting upregulation of interferon-stimulated genes (ISGs) after IL-27 stimulation (FIG. 22A). PBMCs were isolated from healthy donors then pooled and stimulated in vitro for 16 hours with anti-CD3 antibody (0.25 µg/mL, clone UCHT1) in the presence or absence of recombinant human IL-27 (100 ng/ml). Cells were then processed (10× Genomics), RNA was sequenced (Illumina, San Diego, CA), data was processed (Seurat), and subsequently visualized and analyzed (BBrowser, BioTuring, San Diego, CA). Differential gene expression was determined using the Venice algorithm within the differential expression module. Gene expression changes by IL-27 were determined in total PBMCs and also in defined cell subsets including NK cells, CD4+ T cells, B cells, monocytes, CD8+ T cells, and Treg cells. IL-27-mediated gene expression changes were identified in the total PBMC population and included many interferon-stimulated genes (FIG. 22B). Further, IL-27 upregulates ISGs in NK cells (FIG. 22C), monocytes (FIG. 22F), CD4+ T cells (FIG. 22D), CD8+ T cells (FIG. 22G), B cells (FIG. 22E), and Treg cells (FIG. 22H).

Interferon gene expression signatures from PBMCs stimulated with IFNa2, IFNb1, and IFNg (Wadell et al. 2018) were used to compare to the IL-27 gene signature identified from the scRNA-seq PBMC data set described in example 2. The IL-27 signature is enriched for IFNb stimulated genes. Values in Tables 9A-9F represent the differential gene expression from total PBMCs in IL-27 stimulated vs control conditions.

TABLE 9A

Common IFNα2, INFβ1, and IFNγ Genes

| Gene Symbol | Log2 (Fold-Change) | -log10 (FDR) |
|---|---|---|
| GBP1 | 0.761 | 254.34757 |
| GBP2 | 0.756 | 239.99398 |
| CD38 | 0.506 | 189.86262 |
| STAT1 | 0.513 | 170.09093 |
| PSMB9 | 0.452 | 143.37069 |
| RGS1 | 0.456 | 122.82467 |
| TNFSF10 | 0.53 | 103.62998 |
| UBE2L6 | 0.451 | 98.20054 |
| TAP1 | 0.451 | 95.66504 |
| SOCS1 | 0.474 | 94.35918 |
| AIM2 | 0.344 | 78.81771 |
| OAS1 | 0.228 | 67.60822 |
| SP100 | 0.317 | 64.70467 |
| FAS | 0.196 | 50.84631 |
| IFI44 | 0.18 | 48.28002 |
| STAT2 | 0.209 | 43.92146 |
| LAP3 | 0.275 | 40.79373 |
| CXCL10 | 0.564 | 32.29484 |
| CXCL9 | 0.743 | 26.66933 |
| APOL3 | 0.207 | 23.87797 |
| OAS3 | 0.115 | 22.34989 |

TABLE 9A-continued

| Common IFNα2, INFβ1, and IFNγ Genes | | |
|---|---|---|
| Gene Symbol | Log2 (Fold-Change) | -log10 (FDR) |
| IDO1 | 0.646 | 19.79276 |
| JAK2 | 0.112 | 16.70246 |
| SERPING1 | 0.155 | 13.51017 |
| GCH1 | 0.1 | 12.66507 |

TABLE 9B

| INFβ1 Unique Genes | | |
|---|---|---|
| Gene Symbol | log2 (Fold-Change) | -log10 (FDR) |
| PSMB8 | 0.33 | 39.0291 |
| TAPBP | 0.182 | 32.91509 |
| IRF9 | 0.177 | 32.74853 |
| NCF1 | 0.283 | 25.87378 |
| USP15 | 0.175 | 23.59477 |
| IRF4 | 0.193 | 21.39749 |
| NBN | 0.097 | 9.49568 |
| CFLAR | 0.102 | 9.45277 |
| PDE4B | 0.099 | 8.77495 |

TABLE 9C

| IFNγ Unique Genes | | |
|---|---|---|
| Gene Symbol | log2 (Fold-Change) | -log10 (FDR) |
| XRN1 | 0.462 | 135.99373 |
| IRF8 | 0.306 | 28.03915 |

TABLE 9D

| IFNα2 Unique Genes | | |
|---|---|---|
| Gene Symbol | log2 (Fold-Change) | -log10 (FDR) |
| IFI44L | 0.567 | 222.48149 |

TABLE 9E

| Common INFβ1 and IFNγ Genes | | |
|---|---|---|
| Gene Symbol | log2 (Fold-Change) | -log10 (FDR) |
| IRF1 | 0.686 | 254.34757 |
| TBX21 | 0.36 | 123.32113 |
| RALB | 0.09 | 17.76183 |
| FCGR1A | 0.162 | 14.95528 |

TABLE 9F

| Common IFNα2 and INFβ1 Genes | | |
|---|---|---|
| Gene Symbol | log2 (Fold-Change) | -log10 (FDR) |
| ISG20 | 1.029 | 254.34757 |
| ISG15 | 0.849 | 254.34757 |
| IFI35 | 0.546 | 181.42094 |

TABLE 9F-continued

| Common IFNα2 and INFβ1 Genes | | |
|---|---|---|
| Gene Symbol | log2 (Fold-Change) | -log10 (FDR) |
| MX1 | 0.606 | 171.79254 |
| IFI6 | 0.585 | 138.02846 |
| TRIM22 | 0.455 | 133.97689 |
| BST2 | 0.516 | 133.83498 |
| XAF1 | 0.487 | 131.1769 |
| IFI6 | 0.488 | 110.10541 |
| LY6E | 0.437 | 84.82341 |
| CD69 | 0.5 | 73.174 |
| OAS2 | 0.267 | 67.99451 |
| SAT1 | 0.319 | 62.81838 |
| IRF7 | 0.255 | 60.96008 |
| EIF2AK2 | 0.288 | 55.70977 |
| NUB1 | 0.283 | 55.62552 |
| MX2 | 0.179 | 45.90871 |
| SP110 | 0.181 | 42.14114 |
| PLSCR1 | 0.198 | 39.5995 |
| IFITM3 | 0.304 | 37.3479 |
| NMI | 0.237 | 37.25722 |
| LGALS3BP | 0.146 | 33.17046 |
| IFITM1 | 0.125 | 31.44208 |
| ADAR | 0.197 | 25.79626 |
| KLF6 | 0.183 | 25.47153 |
| DYNLT1 | 0.08 | 24.62869 |
| LAG3 | 0.294 | 24.13571 |
| MCL1 | 0.13 | 23.40519 |
| RBCK1 | 0.202 | 23.25179 |
| LAMP3 | 0.06 | 21.92573 |
| TRIM21 | 0.123 | 20.70122 |
| IRF2 | 0.155 | 19.3035 |
| IFITM2 | 0.244 | 14.66585 |
| GUK1 | 0.162 | 12.74087 |
| PML | 0.093 | 10.64515 |
| IFIT5 | 0.067 | 9.6502 |

Figure 23A:
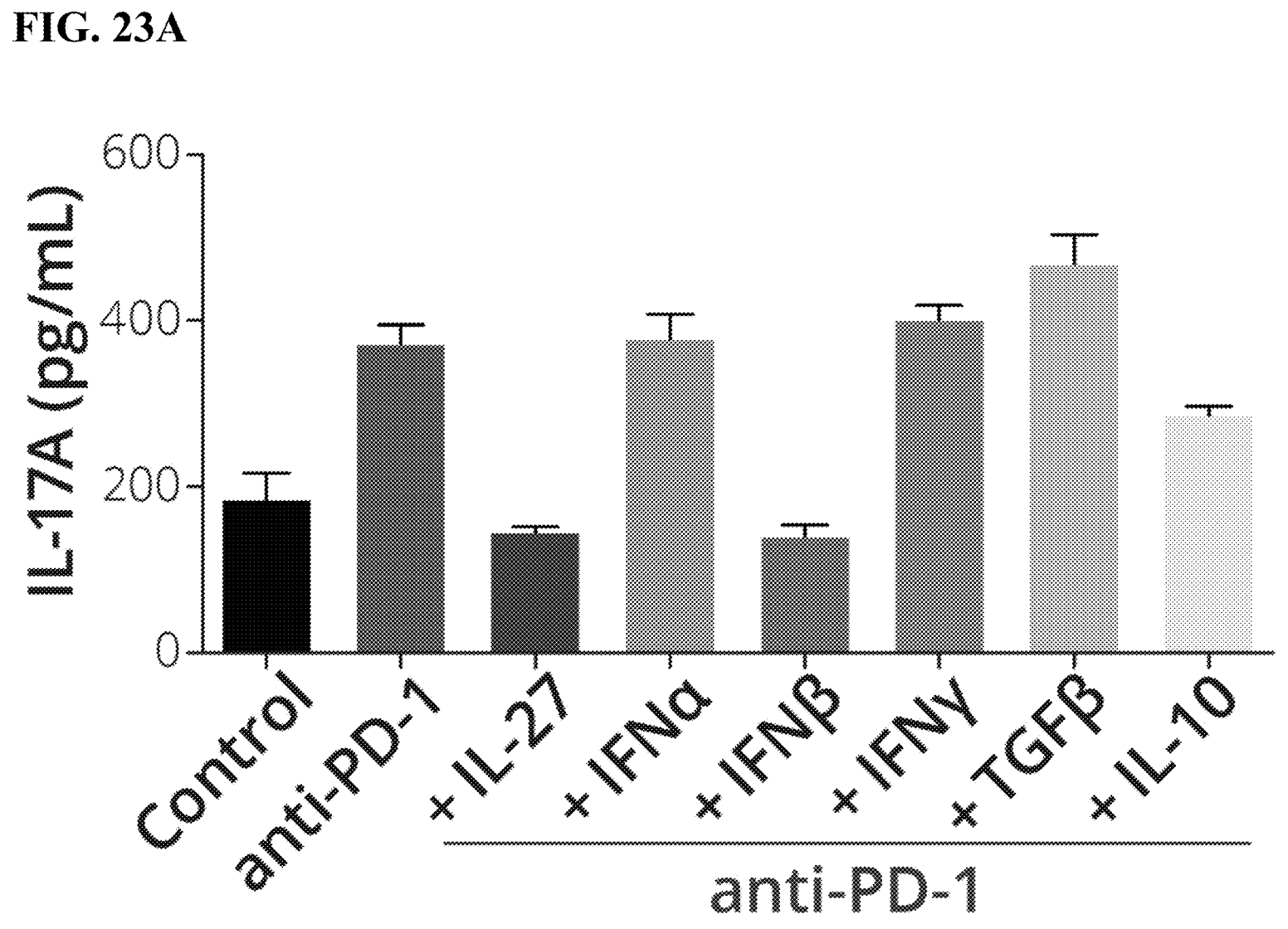
Figure 23B:
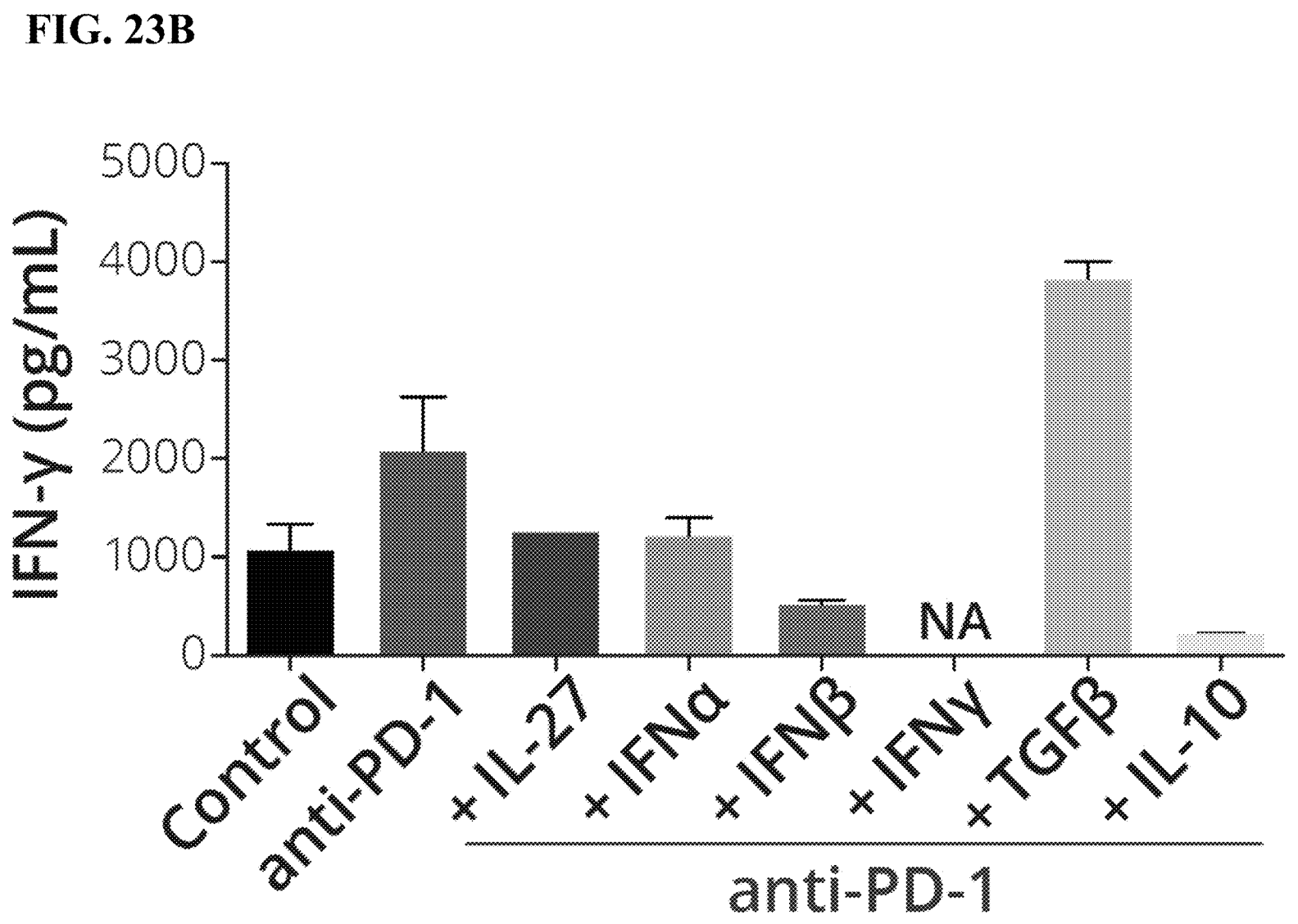

PBMCs from healthy donors were stimulated in vitro with anti-CD3 antibody (0.25 µg/mL) for 4 days in the absence (control) or presence of anti-PD-1 antibody (Pembrolizumab, 1 µg/mL) and various cytokines. Supernatants were then collected and tested for the presence of IL-17A (FIG. 23A) or IFN-γ (FIG. 23B) by MSD. Both IL-27 and IFNb inhibited cytokine production after anti-PD-1 blockade.

NSCLC patients with progressive disease show an enrichment of a macrophage population that expresses several ISGs and IL-27. Graphical abstract from Maynard et al. (NCBI BioProject #PRJNA591860, which is incorporated by reference herein in its entirety) highlights the macrophage population (MF2) with high expression of IDO1 and GBPS shows increased prevalence in patients with progressive disease (PD) compared to those with residual disease (RD) and treatment naïve (TN) patients. Single cell RNA-seq analysis of IL-27 transcript from Maynard et al. shows prominent expression in macrophage compared to other cell types in the NSCLC tumor microenvironment. Several genes from the MF2 signature (green highlights, Maynard et al. Table S4) are enriched in IL-27 positive macrophages compared to IL-27 negative macrophages. Macrophages from patients with progressive disease have more IL-27 transcript expression compared to those with RD or TN patients. IL-27 transcript is increased in macrophages from primary tumor and metastatic sites compared to macrophages from normal lung tissue. IL-27 transcript in macrophages is increased in patients with stage IV disease. The MF2 signature was also highlighted on an independent gene expression profile (Swaminathan et al 2013, GSE44955) comparing IL-27 cultured macrophages vs control condition. This data shows that most MF2 signature genes can be upregulated in macrophages by IL-27.

Figure 24A:
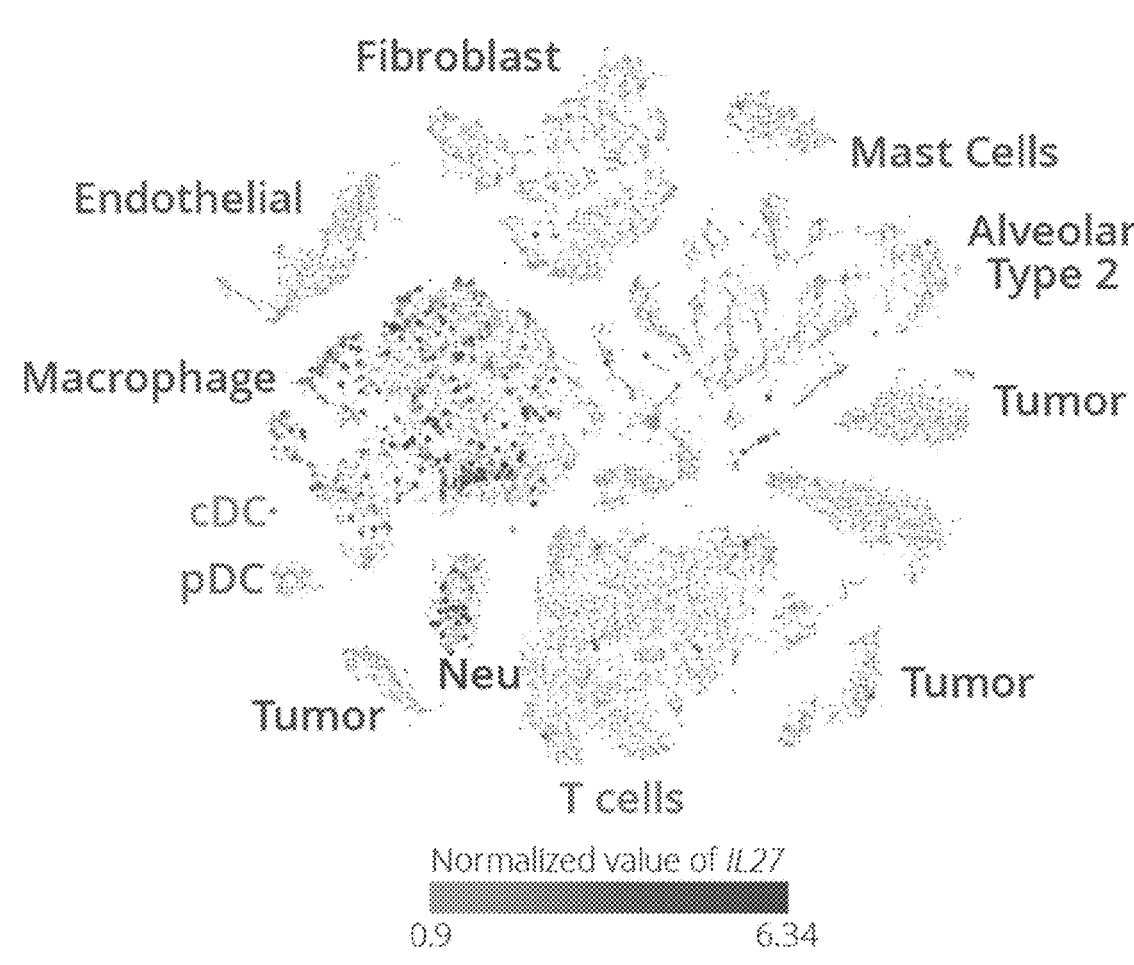
FIG. 24A shows the clustering of the various types of immune cells based on single-cell RNA-seq analysis of IL27 expression.
Figure 24B:
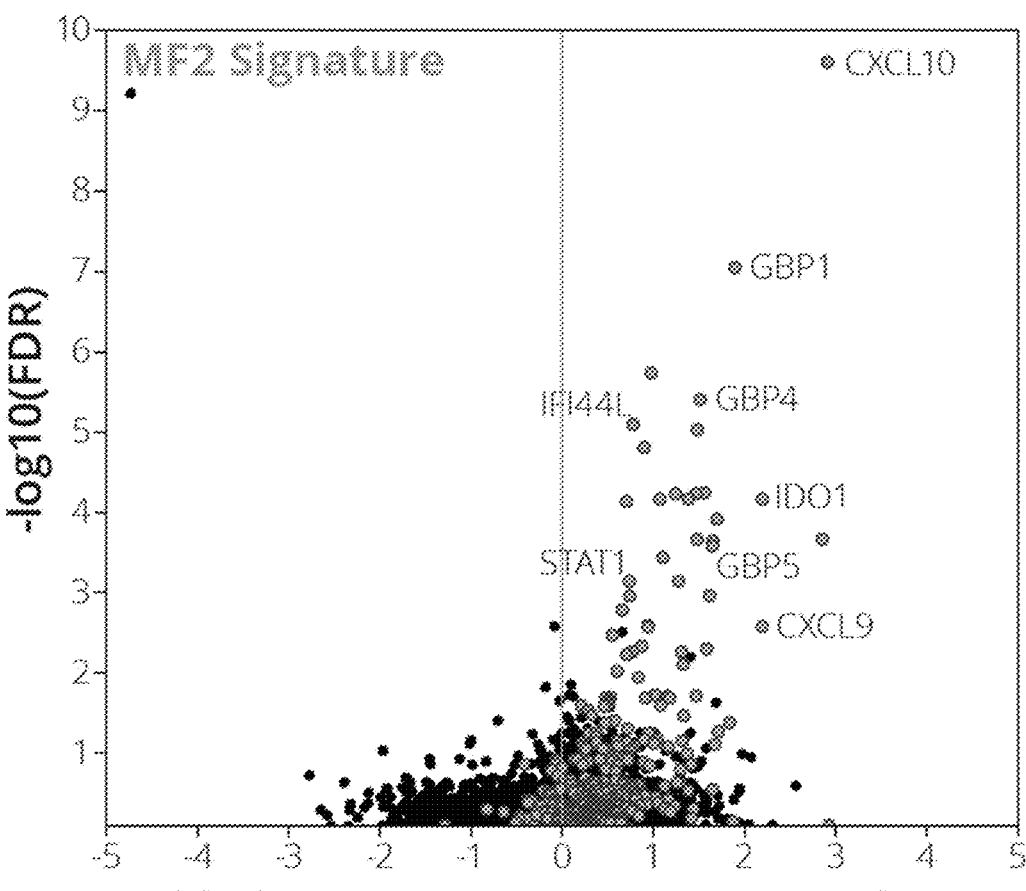
FIG. 24B is a scatter plot showing an MF2 macrophage gene signature associated with progressive disease contains several interferon-stimulated genes and is highly enriched in IL27-positive vs IL27-negative macrophages.
Figure 24F:
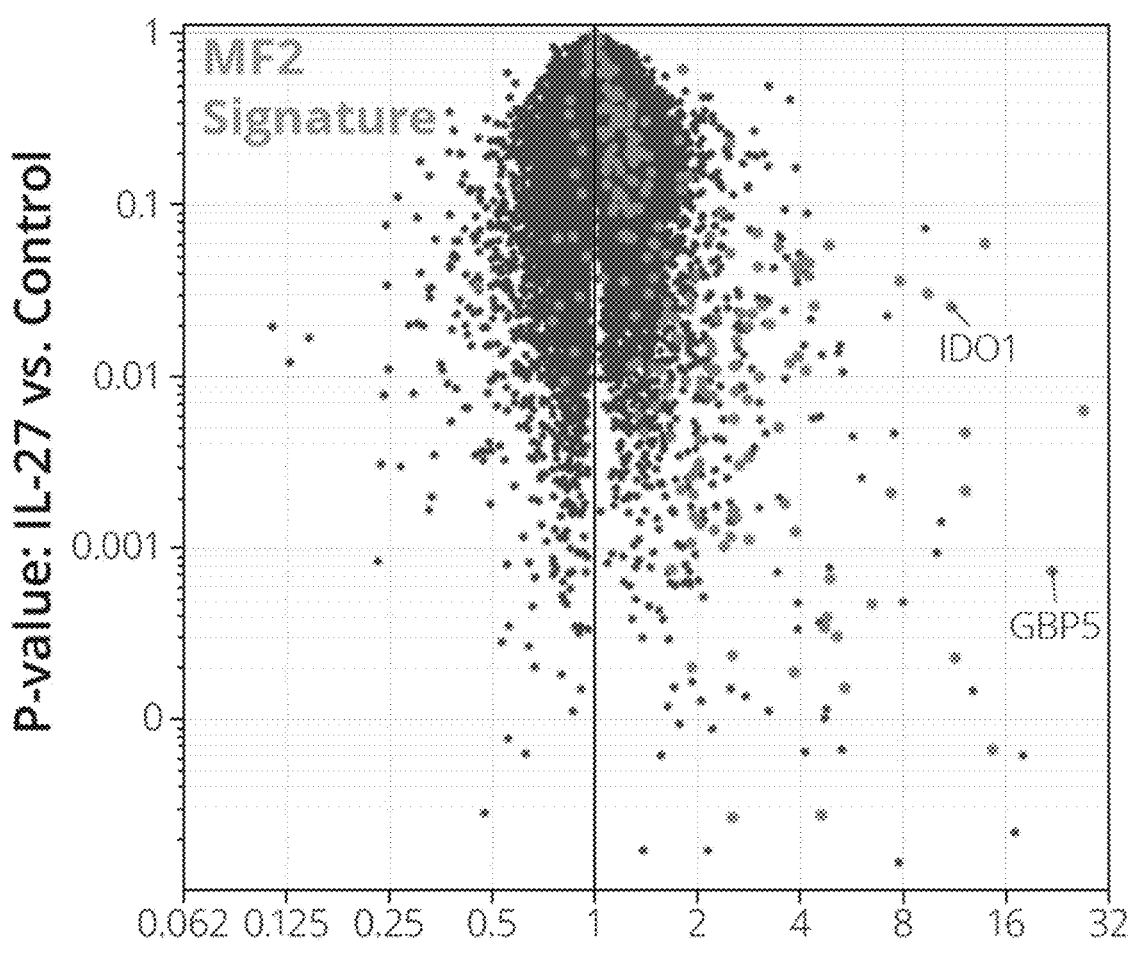
FIG. 24F is a volcano plot illustrating the MF2 signature genes (gray) of IL-27 stimulated monocyte-derived macrophages in vitro.

Single-cell RNA-seq analysis shows IL-27 is expressed in macrophages of the NSCLC tumor microenvironment (TME) and is increased in a macrophage subpopulation (MF2) associated with progressive disease (FIG. 24A). Further, the MF2 signature is highly enriched in IL27$^+$ macrophages as compared to IL27$^-$ macrophages (FIG. 24B). IL-27 is increased in macrophages from patients with progressive disease (FIG. 24C); in macrophages from metastatic and primary tumors compared to normal tissue (FIG. 24D); and in macrophages from patients with Stage IV disease (FIG. 24D). In addition, the MF2 signature is upregulated in macrophages by IL27 (FIG. 24F, gray data points).

Figures 24G, 24H:
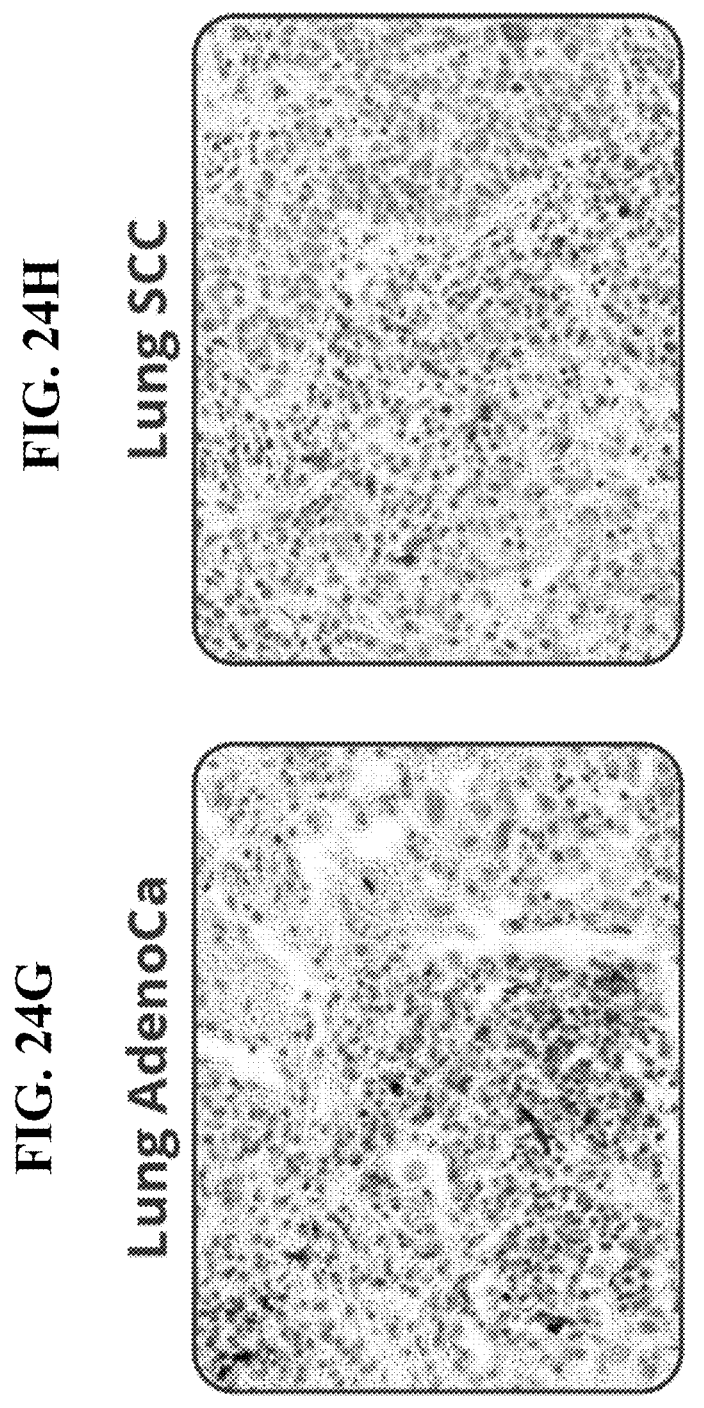
Figure 25A:
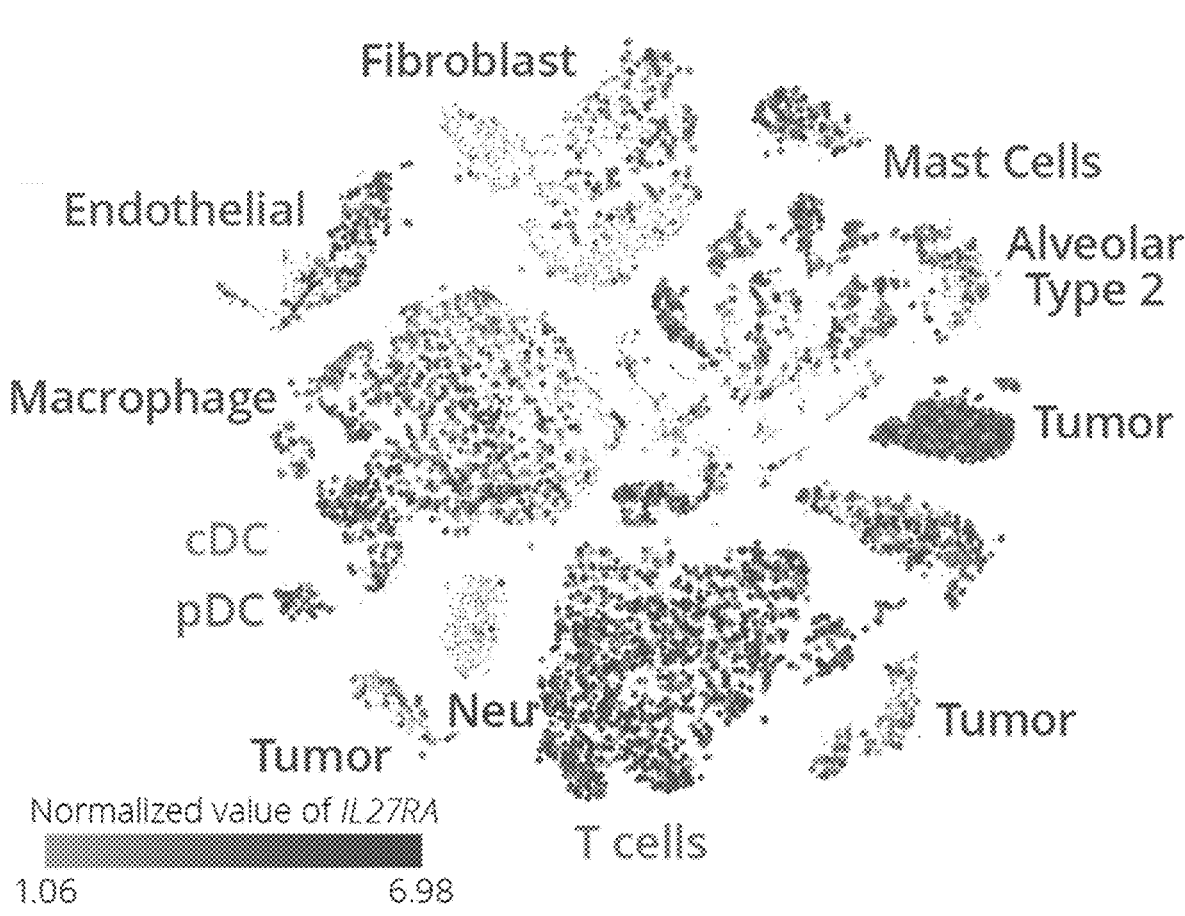
FIG. 25A shows the clustering of the various types of cells in the tumor microenvironment based on single-cell RNA-seq analysis of IL27 expression.
Figures 25B, 25C:
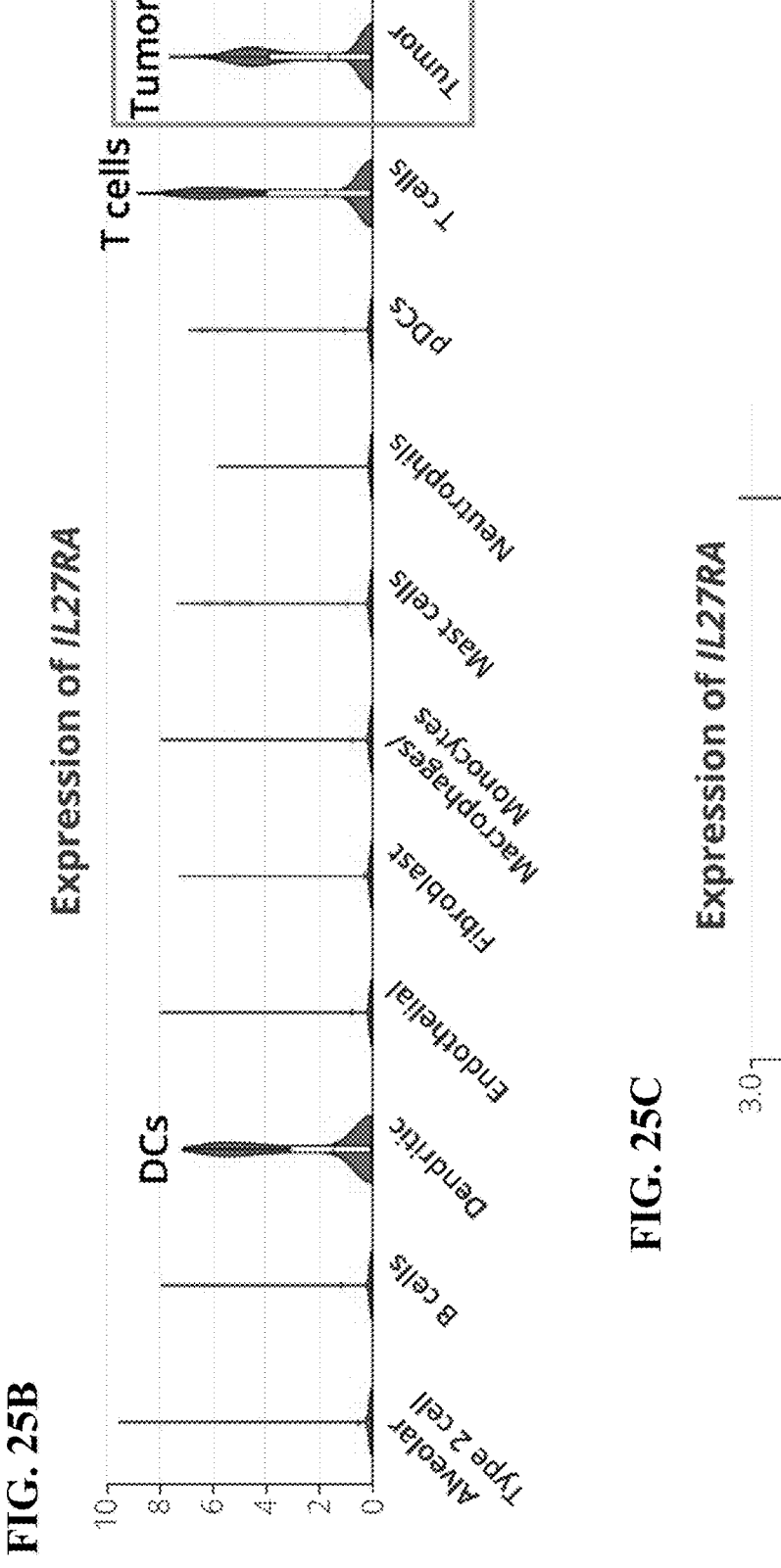
FIG. 25B is a violin plot of IL27RA expression in different cell populations compared to tumor cells.
FIG. 25C is a violin plot of IL27RA expression in tumor cells from patients with progressive disease compared to tumor cells from patients with residual disease or who are treatment naïve.

IL-27-positive macrophages were detected in the tumor microenvironment (TME) of lung adenocarcinoma (FIG. 24G; AdenoCa) and lung squamous cell carcinoma (FIG. 24H; SCC) by immunohistochemistry (IHC). IHC on formalin-fixed, paraffin-embedded (FFPE) tissue samples of NSCLC was performed by staining tissue microarrays (TMAs) from US Biomax (Derwood, MD) with an affinity purified goat polyclonal antibody against recombinant human IL-27 (p28 and EBI3) from R&D Systems at 10 microg/mL. Slides were deparaffinized, dewaxed, and rehydrated and stained in a Leica Bond RX automated stainer (Leica Biosystems, Wetzlar, Germany). Antigen retrieval was performed with Bond Epitope Retrieval Solution 2 (EDTA, pH 9) at 100° C. for 10 min. Slides were manually dehydrated and coverslipped and digitally scanned with an Aperio Versa 2000 scanner Single cell RNA-seq analysis of IL27RA transcript from Maynard et al. (NCBI BioProject #PRJNA591860) shows expression in several cell types in the NSCLC tumor microenvironment including some tumor cells (FIG. 25A). IL27RA expression was observed across various cell types within the NSCLC tumor microenvironment, including higher expression in dendritic cells, T cells, and tumor cells (FIG. 25B). For tumor tissue, the expression of IL27RA was higher in patients with progressive disease compared to those with residual disease or patients that are treatment naïve (FIG. 25C).

Figure 26A:
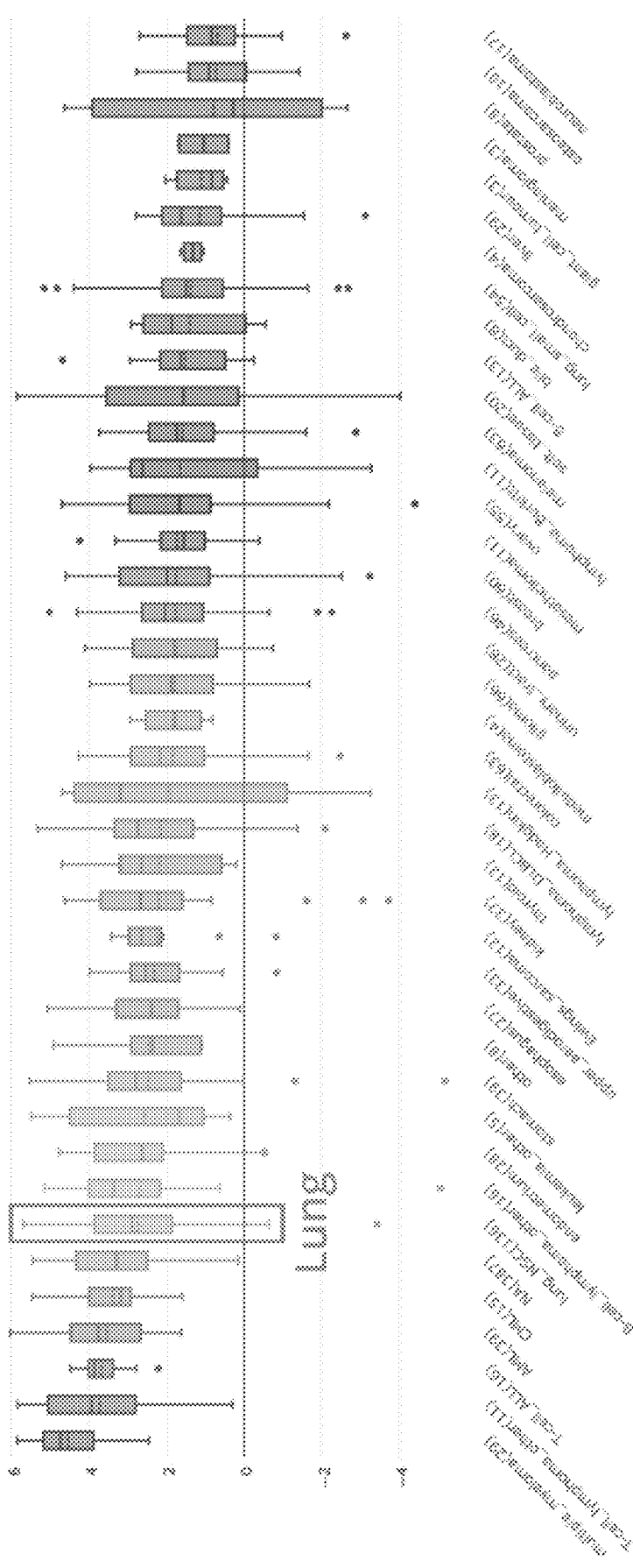
FIG. 26A is a bar graph illustrating IL27RA mRNA transcript expression across the Cancer Cell Line Encyclopedia (CCLE) for various lung cancer cell lines including NCI-H2228.
Figures 26B, 26C:
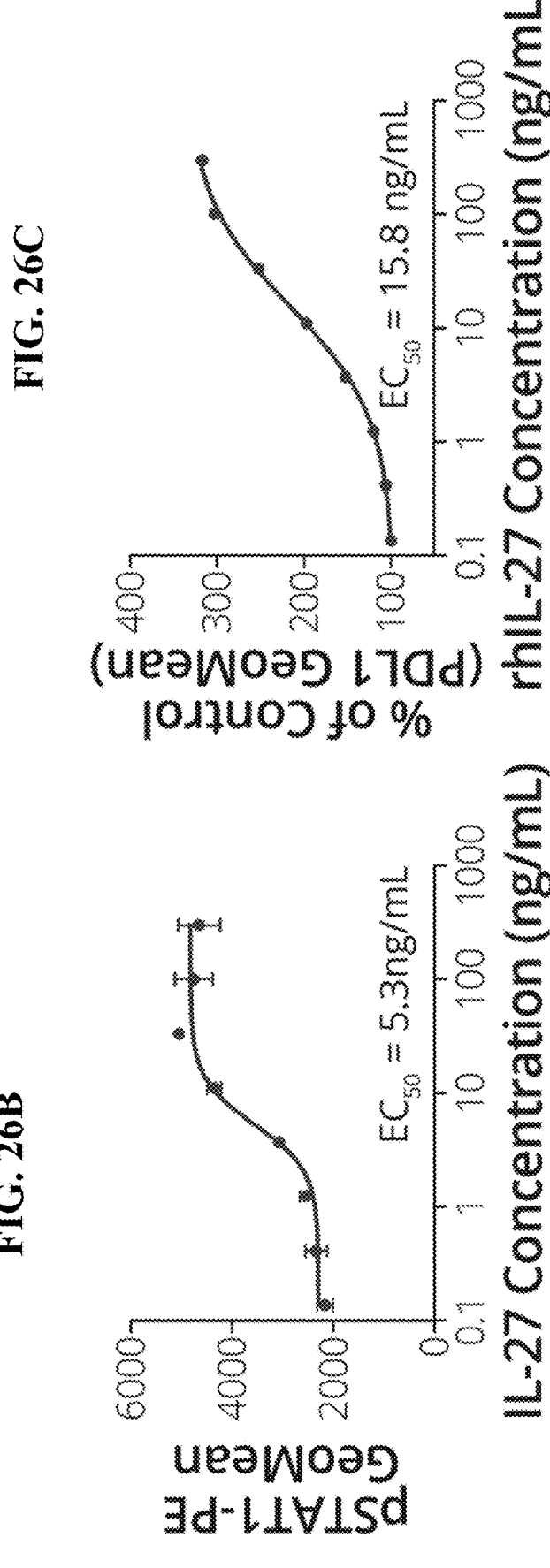
FIGS. 26B-26C are graphical representations illustrating pSTAT1 levels (FIG. 26B) and PDL1 expression (FIG. 26C) in NCI-H2228 lung cancer cells after IL-27 stimulation.
Figure 26D:
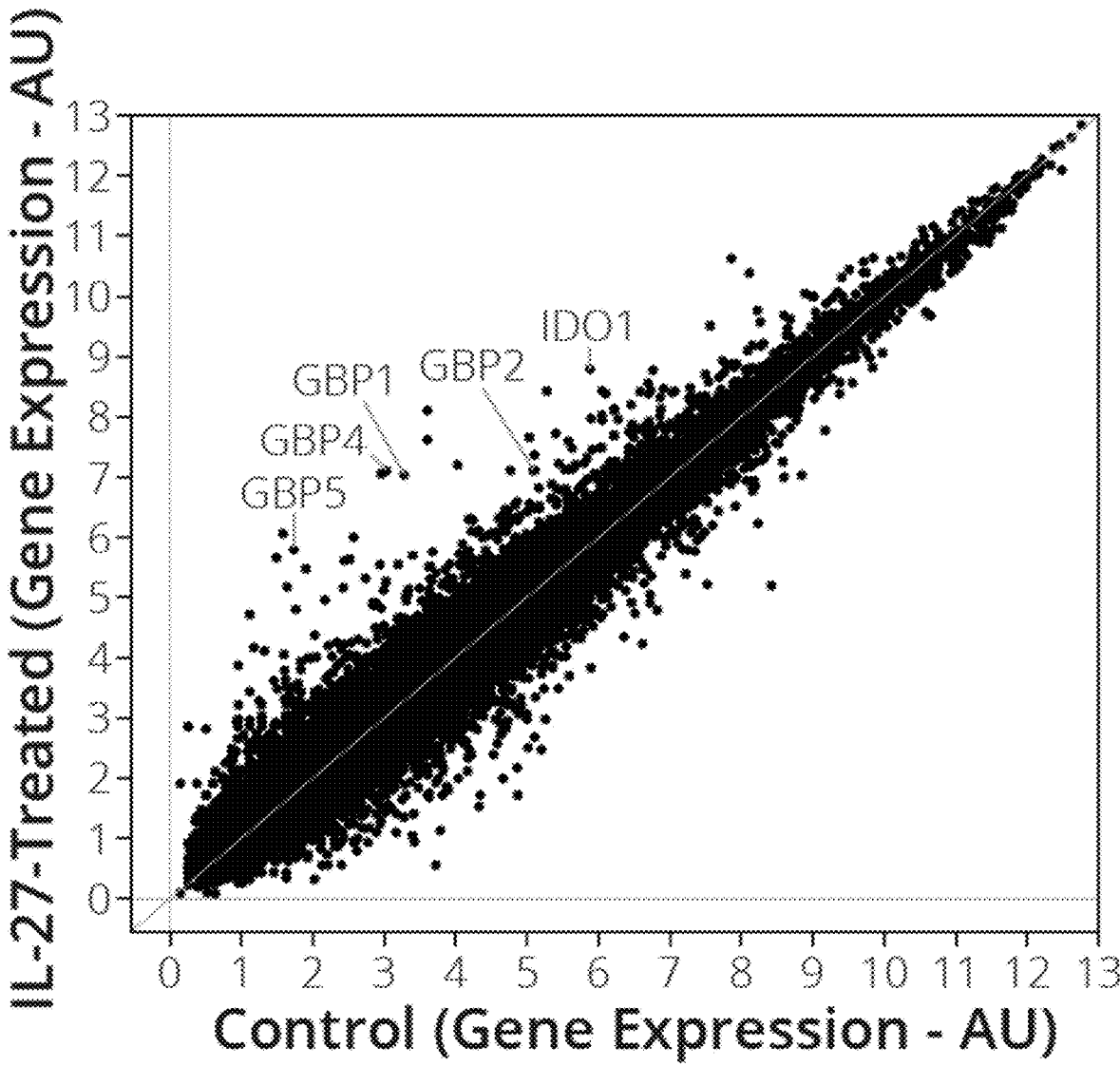
FIG. 26D is a graphical representation of microarray profiling of NCI-H228 cells cultured in the presence or absence of IL-27 for 48 hrs. Several interferon-responsive genes are flagged (FIG. 26D).

Data from the Cancer Cell Line Encyclopedia (CCLE) shows IL27RA transcript expression in lung cancer cell lines, including NCI-H2228 (FIG. 26A). Culturing NCI-H2228 cells in vitro with various concentrations of recombinant human IL-27 leads to the dose dependent increase in STAT1 phosphorylation (downstream of IL-27RA signaling) and PD-L1 expression by flow cytometry (FIGS. 26B-26C). NCI-H2228 cells were also cultured in vitro in the presence or absence of recombinant human IL-27 (100 ng/ml) for 48 hrs followed by RNA purification and processing for hybridization to HuGene 1.0ST arrays. Raw microarray data were normalized and differential gene expression was determined by comparing IL-27 treatment (y-axis) to control conditions (x-axis) (FIG. 26D). IL-27 upregulated several ISGs including IDO1 and GBPS.

These data show that IL-27 induced robust gene expression in human immune cells that included several inhibitory receptors and canonical interferon-regulated genes such as guanylate-binding proteins and interferon regulatory factors. Gene Set Enrichment Analysis and interferon signature analysis demonstrated a striking overlap with those genes regulated by interferon-beta, a cytokine known to drive immune suppression associated with chronic viral infection. Interferon-beta is used therapeutically for controlling inflammation associated with the autoimmune disease multiple sclerosis.

Both IL-27 and IFNβ can counteract some of the immune stimulatory properties of PD-1 blockade. Interferon-regulated pathways have recently emerged as a mechanism of resistance to immune checkpoint blockade in cancer. Exploration of the IL-27 gene signature in published datasets showed enrichment in macrophage populations associated with progressive disease in patients with NSCLC. While many of the properties of IL-27—mediated immune regulation have focused on hematopoietic cells, there is demonstrated IL-27RA expression on tumor cells from NSCLC patients with progressive disease. IL-27RA is also expressed on lung cancer cell lines in which IL-27 can upregulate PD-L1, IDO1, and other canonical interferon-regulated genes.

These studies elucidate the transcriptional networks that are engaged after IL-27 signaling in immune and cancer cells and highlight the parallels with interferon-associated immune regulation.

What is claimed is:

1. A method of stimulating an immune response or treating an IL-27-associated cancer in a human subject in need thereof comprising administering to the human subject an antibody that antagonizes human IL-27, or an antigen binding portion thereof, wherein the antibody or antigen binding portion thereof:

specifically binds to an epitope comprising one or more amino acids of (i) amino acids 37 to 56 corresponding to SEQ ID NO: 2 (IL-27p28), (ii) amino acids 142 to 164 corresponding to SEQ ID NO: 2 (IL-27p28), or (iii) both (i) and (ii);

comprises a heavy chain CDR1 comprising the amino acid sequence set forth in SEQ ID NO: 119, a heavy chain CDR2 comprising the amino acid sequence set forth in SEQ ID NO: 120, a heavy chain CDR3 comprising the amino acid sequence set forth in SEQ ID NO: 121, a light chain CDR1 comprising the amino acid sequence set forth in SEQ ID NO: 127, a light chain CDR2 comprising the amino acid sequence set forth in SEQ ID NO: 128, and a light chain CDR3 comprising the amino acid sequence set forth in SEQ ID NO: 129; and is administered at a dose of about 10 mg/kg to about 20 mg/kg.

2. The method of claim 1, wherein the antibody or antigen binding portion thereof is administered once about every week, once about every two weeks, once about every three weeks, once about every four weeks, once about every 6 weeks, once about every 8 weeks, or once about every 12 weeks.

3. The method of claim 1, wherein the antibody or antigen binding portion thereof is administered at a dose of:

(i) about 10 mg/kg once about every four weeks;

(ii) about 13 mg/kg once about every four weeks;

(iii) about 16 mg/kg once about every four weeks; or (iv) about 20 mg/kg once about every four weeks.

4. The method of claim 1, wherein the antibody or antigen binding portion thereof is administered at a dose of:

(i) about 10 mg/kg once about every three weeks;

(ii) about 13 mg/kg once about every three weeks;

(iii) about 16 mg/kg once about every three weeks; or (iv) about 20 mg/kg once about every three weeks.

5. The method of claim 1, wherein the antibody or antigen binding portion thereof:

(i) inhibits or reduces IL-27-dependent STAT1 and/or STAT3 phosphorylation in a cell in the subject;

(ii) inhibits or reduces inhibition of CD161 expression in a cell in the subject;

(iii) inhibits or reduces PD-L1 expression in a cell in the subject;

(iv) induces or enhances PD-1 mediated secretion of one or more cytokines from a cell in the subject;

(v) alters the expression of TIM-3 in a cell in the subject; or (vi) any combination of (i) to (v).

6. The method of claim 5, wherein the cell is a tumor cell or an immune cell.

7. The method of claim 1, wherein the epitope comprises one or more amino acids of Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164 of SEQ ID NO: 2 (IL-27p28).

8. The method of claim 1, wherein the epitope consists or consists essentially of (i) Gln37, Leu38, Glu42, Glu46, Val49, Ser50, Leu53, Lys56, Leu142, Asp143, Asp146, Leu147, Arg149, His150, Arg152, Phe153, Leu156, Ala157, Gly159, Phe160, Asn161, Leu162, and Glu164 of SEQ ID NO: 2 (IL-27p28); or (ii) Gln37, Leu38, Glu42, Glu46, Val49, Ser50, Leu53, Lys56, Leu142, Asp143, Arg145, Asp146, Leu147, Arg149, His150, Arg152, Phe153, Leu156, Ala157, Gly159, Phe160, Asn161, Leu162, Pro163, and Glu164, of SEQ ID NO: 2 (IL-27p28).

9. The method of claim 1, wherein the antibody or the antigen binding portion thereof comprises:

(a) a heavy chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 125;

(b) a light chain variable region comprising an amino acid sequence that has at least about 85%, at least about 90%, at least about 95%, at least about 96%, at least about 97%, at least about 98%, or at least about 99% sequence identity to the amino acid sequence set forth in SEQ ID NO: 133; or (c) both (a) and (b).

10. The method of claim 1, wherein the antibody or the antigen binding portion thereof comprises:

(a) a heavy chain variable region comprising the amino acid sequence set forth in SEQ ID NO: 125;

(b) a light chain variable region comprising the amino acid sequence set forth in SEQ ID NO: 133; or (c) both (a) and (b).

11. The method of claim 1, wherein (i) the antibody or the antigen binding portion thereof comprises a heavy chain comprising the amino acid sequence set forth in SEQ ID NO: 135 and a light chain comprising the amino acid sequence set forth in SEQ ID NO: 137; or the antibody or the antigen binding portion thereof comprises a heavy chain comprising the amino acid sequence set forth in SEQ ID NO: 139 and a light chain comprising the amino acid sequence set forth in SEQ ID NO: 137.

12. The method of claim 2, wherein the IL-27-associated cancer is selected from lung cancer, sarcoma, testicular cancer, ovarian cancer, pancreas cancer, breast cancer, melanoma, head and neck cancer, colorectal cancer, bladder cancer, endometrial cancer, prostate cancer, thyroid cancer, hepatocellular carcinoma (HCC), gastric cancer, brain cancer, lymphoma, leukemia, renal cancer, and any combination thereof.

13. The method of claim 1, further comprising administering an additional therapeutic agent to the subject.

14. The method of claim 13, wherein the additional therapeutic agent comprises a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, a cellular immunotherapy, a biologic agent, or a combination thereof.

15. The method of claim 13, wherein the additional therapeutic agent comprises a PD-1 antagonist, a PD-L1 inhibitor, a TIM-3 inhibitor, a LAG-3 inhibitor, a TIGIT inhibitor, a CD112R inhibitor, a TAM inhibitor, a STING agonist, a 4-1BB agonist, a multityrosine kinase inhibitor, an anti-VEGF blocking antibody, a CTLA-4 antagonist, a HIF2 antagonist, a TGFb antagonist, an mTOR inhibitor, an adenosine pathway inhibitor, an anti-CCR8 antibody, a cytokine-based regimen, a PARP inhibitor, or a combination thereof.

16. The method of claim 15, wherein (i) the PD-1 antagonist is selected from the group consisting of: PDR001, nivolumab, pembrolizumab, pidilizumab, MEDI0680, REGN2810, TSR-042, PF-06801591, and AMP-224; and (ii) the PD-L1 inhibitor is selected from the group consisting of: FAZ053, Atezolizumab, Avelumab, Durvalumab, and BMS-936559.

17. The method of claim 1, wherein following administration of the antibody or antigen binding portion thereof, the subject exhibits:

(i) increased expression of one or more biomarkers selected from the group consisting of EBI3, IL-27, TNFα, MIP-1α (CCL3), IFNγ, IL-10, IL-6, and any combination thereof; wherein the increased expression of the one or more biomarkers is relative to the expression of the one or more biomarker prior to the administration;

(ii) increased expression of EBI3; wherein the increased expression EBI3 is relative to the expression EBI3 prior to the administration;

(iii) increased expression of one or more biomarkers selected from the group consisting of Eotaxin-1 (CCL11), TARC (CCL17), VEGF-A, IL-7, IL-8, MCP-1, MCP-4, and any combination thereof; wherein the increased expression of the one or more biomarkers is relative to the expression of the one or more biomarker prior to the administration; and/or (iv) an increased circulating level of IFNγ, relative to the circulating level of IFNγ prior to the administration.

18. The method of claim 1, wherein the IL-27-associated cancer is non-small cell lung cancer.

19. The method of claim 1, wherein the IL-27-associated cancer is hepatocellular carcinoma.

20. The method of claim 1, wherein the IL-27-associated cancer is gastric cancer.

21. The method of claim 1, wherein the IL-27-associated cancer is renal cell carcinoma.

22. The method of claim 1, wherein the IL-27-associated cancer is gastroesophageal cancer.

\* \* \* \* \*

SEQUENCE LISTING

```
<160> NUMBER OF SEQ ID NOS: 156

<210> SEQ ID NO 1
<211> LENGTH: 229
<212> TYPE: PRT
<213> ORGANISM: Artificial Sequence
<220> FEATURE:
<223> OTHER INFORMATION: human EBI3 protein

<400> SEQUENCE: 1

Met Thr Pro Gln Leu Leu Leu Ala Leu Val Leu Trp Ala Ser Cys Pro
1               5                   10                  15

Pro Cys Ser Gly Arg Lys Gly Pro Pro Ala Ala Leu Thr Leu Pro Arg
            20                  25                  30

Val Gln Cys Arg Ala Ser Arg Tyr Pro Ile Ala Val Asp Cys Ser Trp
        35                  40                  45

Thr Leu Pro Pro Ala Pro Asn Ser Thr Ser Pro Val Ser Phe Ile Ala
    50                  55                  60

Thr Tyr Arg Leu Gly Met Ala Ala Arg Gly His Ser Trp Pro Cys Leu
65                  70                  75                  80
```

-continued

```
Gln Gln Thr Pro Thr Ser Thr Ser Cys Thr Ile Thr Asp Val Gln Leu
            85              90              95

Phe Ser Met Ala Pro Tyr Val Leu Asn Val Thr Ala Val His Pro Trp
            100             105             110

Gly Ser Ser Ser Ser Phe Val Pro Phe Ile Thr Glu His Ile Ile Lys
            115             120             125

Pro Asp Pro Pro Glu Gly Val Arg Leu Ser Pro Leu Ala Glu Arg Gln
    130             135             140

Leu Gln Val Gln Trp Glu Pro Pro Gly Ser Trp Pro Phe Pro Glu Ile
145             150             155             160

Phe Ser Leu Lys Tyr Trp Ile Arg Tyr Lys Arg Gln Gly Ala Ala Arg
                165             170             175

Phe His Arg Val Gly Pro Ile Glu Ala Thr Ser Phe Ile Leu Arg Ala
                180             185             190

Val Arg Pro Arg Ala Arg Tyr Tyr Val Gln Val Ala Ala Gln Asp Leu
            195             200             205

Thr Asp Tyr Gly Glu Leu Ser Asp Trp Ser Leu Pro Ala Thr Ala Thr
    210             215             220

Met Ser Leu Gly Lys
225

<210> SEQ ID NO 2
<211> LENGTH: 243
<212> TYPE: PRT
<213> ORGANISM: Artificial Sequence
<220> FEATURE:
<223> OTHER INFORMATION: human p28 protein

<400> SEQUENCE: 2

Met Gly Gln Thr Ala Gly Asp Leu Gly Trp Arg Leu Ser Leu Leu Leu
1               5               10              15

Leu Pro Leu Leu Leu Val Gln Ala Gly Val Trp Gly Phe Pro Arg Pro
            20              25              30

Pro Gly Arg Pro Gln Leu Ser Leu Gln Glu Leu Arg Arg Glu Phe Thr
            35              40              45

Val Ser Leu His Leu Ala Arg Lys Leu Leu Ser Glu Val Arg Gly Gln
    50              55              60

Ala His Arg Phe Ala Glu Ser His Leu Pro Gly Val Asn Leu Tyr Leu
65              70              75              80

Leu Pro Leu Gly Glu Gln Leu Pro Asp Val Ser Leu Thr Phe Gln Ala
            85              90              95

Trp Arg Arg Leu Ser Asp Pro Glu Arg Leu Cys Phe Ile Ser Thr Thr
            100             105             110

Leu Gln Pro Phe His Ala Leu Leu Gly Gly Leu Gly Thr Gln Gly Arg
            115             120             125

Trp Thr Asn Met Glu Arg Met Gln Leu Trp Ala Met Arg Leu Asp Leu
    130             135             140

Arg Asp Leu Gln Arg His Leu Arg Phe Gln Val Leu Ala Ala Gly Phe
145             150             155             160

Asn Leu Pro Glu Glu Glu Glu Glu Glu Glu Glu Glu Glu Glu Glu Glu
                165             170             175

Arg Lys Gly Leu Leu Pro Gly Ala Leu Gly Ser Ala Leu Gln Gly Pro
            180             185             190

Ala Gln Val Ser Trp Pro Gln Leu Leu Ser Thr Tyr Arg Leu Leu His
            195             200             205
```

-continued

```
Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 3
<211> LENGTH: 636
<212> TYPE: PRT
<213> ORGANISM: Artificial Sequence
<220> FEATURE:
<223> OTHER INFORMATION: human WSX1

<400> SEQUENCE: 3

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
                20                  25                  30

Gln Gly Ser Ala Gly Pro Leu Gln Cys Tyr Gly Val Gly Pro Leu Gly
            35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Pro Thr Trp Pro Ser His Lys
145                 150                 155                 160

Val Leu Ile Cys Gln Phe His Tyr Arg Arg Cys Gln Glu Ala Ala Trp
                165                 170                 175

Thr Leu Leu Glu Pro Glu Leu Lys Thr Ile Pro Leu Thr Pro Val Glu
            180                 185                 190

Ile Gln Asp Leu Glu Leu Ala Thr Gly Tyr Lys Val Tyr Gly Arg Cys
        195                 200                 205

Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                245                 250                 255

Ala Pro Gly Pro Cys Val Gln Val Ser Tyr Lys Val Trp Phe Trp Val
            260                 265                 270

Gly Gly Arg Glu Leu Ser Pro Glu Gly Ile Thr Cys Cys Cys Ser Leu
        275                 280                 285

Ile Pro Ser Gly Ala Glu Trp Ala Arg Val Ser Ala Val Asn Ala Thr
    290                 295                 300

Ser Trp Glu Pro Leu Thr Asn Leu Ser Leu Val Cys Leu Asp Ser Ala
305                 310                 315                 320
```

-continued

```
Ser Ala Pro Arg Ser Val Ala Val Ser Ser Ile Ala Gly Ser Thr Glu
            325                 330                 335

Leu Leu Val Thr Trp Gln Pro Gly Pro Gly Glu Pro Leu Glu His Val
            340                 345                 350

Val Asp Trp Ala Arg Asp Gly Asp Pro Leu Glu Lys Leu Asn Trp Val
            355                 360                 365

Arg Leu Pro Pro Gly Asn Leu Ser Ala Leu Leu Pro Gly Asn Phe Thr
    370                 375                 380

Val Gly Val Pro Tyr Arg Ile Thr Val Thr Ala Val Ser Ala Ser Gly
385                 390                 395                 400

Leu Ala Ser Ala Ser Ser Val Trp Gly Phe Arg Glu Glu Leu Ala Pro
            405                 410                 415

Leu Val Gly Pro Thr Leu Trp Arg Leu Gln Asp Ala Pro Pro Gly Thr
            420                 425                 430

Pro Ala Ile Ala Trp Gly Glu Val Pro Arg His Gln Leu Arg Gly His
            435                 440                 445

Leu Thr His Tyr Thr Leu Cys Ala Gln Ser Gly Thr Ser Pro Ser Val
    450                 455                 460

Cys Met Asn Val Ser Gly Asn Thr Gln Ser Val Thr Leu Pro Asp Leu
465                 470                 475                 480

Pro Trp Gly Pro Cys Glu Leu Trp Val Thr Ala Ser Thr Ile Ala Gly
            485                 490                 495

Gln Gly Pro Pro Gly Pro Ile Leu Arg Leu His Leu Pro Asp Asn Thr
            500                 505                 510

Leu Arg Trp Lys Val Leu Pro Gly Ile Leu Phe Leu Trp Gly Leu Phe
            515                 520                 525

Leu Leu Gly Cys Gly Leu Ser Leu Ala Thr Ser Gly Arg Cys Tyr His
    530                 535                 540

Leu Arg His Lys Val Leu Pro Arg Trp Val Trp Glu Lys Val Pro Asp
545                 550                 555                 560

Pro Ala Asn Ser Ser Ser Gly Gln Pro His Met Glu Gln Val Pro Glu
            565                 570                 575

Ala Gln Pro Leu Gly Asp Leu Pro Ile Leu Glu Val Glu Glu Met Glu
            580                 585                 590

Pro Pro Pro Val Met Glu Ser Ser Gln Pro Ala Gln Ala Thr Ala Pro
            595                 600                 605

Leu Asp Ser Gly Tyr Glu Lys His Phe Leu Pro Thr Pro Glu Glu Leu
    610                 615                 620

Gly Leu Leu Gly Pro Pro Arg Pro Gln Val Leu Ala
625                 630                 635

<210> SEQ ID NO 4
<211> LENGTH: 918
<212> TYPE: PRT
<213> ORGANISM: Artificial Sequence
<220> FEATURE:
<223> OTHER INFORMATION: human gp130 protein

<400> SEQUENCE: 4

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45
```

```
Val Leu Lys Glu Lys Cys Met Asp Tyr Phe His Val Asn Ala Asn Tyr
    50              55              60

Ile Val Trp Lys Thr Asn His Phe Thr Ile Pro Lys Glu Gln Tyr Thr
65              70              75              80

Ile Ile Asn Arg Thr Ala Ser Ser Val Thr Phe Thr Asp Ile Ala Ser
                85              90              95

Leu Asn Ile Gln Leu Thr Cys Asn Ile Leu Thr Phe Gly Gln Leu Glu
                100             105             110

Gln Asn Val Tyr Gly Ile Thr Ile Ile Ser Gly Leu Pro Pro Glu Lys
        115             120             125

Pro Lys Asn Leu Ser Cys Ile Val Asn Glu Gly Lys Lys Met Arg Cys
    130             135             140

Glu Trp Asp Gly Gly Arg Glu Thr His Leu Glu Thr Asn Phe Thr Leu
145             150             155             160

Lys Ser Glu Trp Ala Thr His Lys Phe Ala Asp Cys Lys Ala Lys Arg
                165             170             175

Asp Thr Pro Thr Ser Cys Thr Val Asp Tyr Ser Thr Val Tyr Phe Val
                180             185             190

Asn Ile Glu Val Trp Val Glu Ala Glu Asn Ala Leu Gly Lys Val Thr
                195             200             205

Ser Asp His Ile Asn Phe Asp Pro Val Tyr Lys Val Lys Pro Asn Pro
    210             215             220

Pro His Asn Leu Ser Val Ile Asn Ser Glu Glu Leu Ser Ser Ile Leu
225             230             235             240

Lys Leu Thr Trp Thr Asn Pro Ser Ile Lys Ser Val Ile Ile Leu Lys
                245             250             255

Tyr Asn Ile Gln Tyr Arg Thr Lys Asp Ala Ser Thr Trp Ser Gln Ile
                260             265             270

Pro Pro Glu Asp Thr Ala Ser Thr Arg Ser Ser Phe Thr Val Gln Asp
        275             280             285

Leu Lys Pro Phe Thr Glu Tyr Val Phe Arg Ile Arg Cys Met Lys Glu
    290             295             300

Asp Gly Lys Gly Tyr Trp Ser Asp Trp Ser Glu Glu Ala Ser Gly Ile
305             310             315             320

Thr Tyr Glu Asp Arg Pro Ser Lys Ala Pro Ser Phe Trp Tyr Lys Ile
                325             330             335

Asp Pro Ser His Thr Gln Gly Tyr Arg Thr Val Gln Leu Val Trp Lys
        340             345             350

Thr Leu Pro Pro Phe Glu Ala Asn Gly Lys Ile Leu Asp Tyr Glu Val
        355             360             365

Thr Leu Thr Arg Trp Lys Ser His Leu Gln Asn Tyr Thr Val Asn Ala
    370             375             380

Thr Lys Leu Thr Val Asn Leu Thr Asn Asp Arg Tyr Leu Ala Thr Leu
385             390             395             400

Thr Val Arg Asn Leu Val Gly Lys Ser Asp Ala Ala Val Leu Thr Ile
                405             410             415

Pro Ala Cys Asp Phe Gln Ala Thr His Pro Val Met Asp Leu Lys Ala
                420             425             430

Phe Pro Lys Asp Asn Met Leu Trp Val Glu Trp Thr Thr Pro Arg Glu
        435             440             445

Ser Val Lys Lys Tyr Ile Leu Glu Trp Cys Val Leu Ser Asp Lys Ala
    450             455             460

Pro Cys Ile Thr Asp Trp Gln Gln Glu Asp Gly Thr Val His Arg Thr
```

-continued

```
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
                660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895
```

```
Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 5
<211> LENGTH: 232
<212> TYPE: PRT
<213> ORGANISM: Artificial Sequence
<220> FEATURE:
<223> OTHER INFORMATION: Human IgG1

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 6
<211> LENGTH: 229
<212> TYPE: PRT
<213> ORGANISM: Artificial Sequence
<220> FEATURE:
<223> OTHER INFORMATION: Human IgG4

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
```

-continued

```
            35                  40                  45
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 229
<212> TYPE: PRT
<213> ORGANISM: Artificial Sequence
<220> FEATURE:
<223> OTHER INFORMATION: Human IgG4 (S228P)

<400> SEQUENCE: 7

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

```
                    165                 170                 175
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Lys
225
```

<210> SEQ ID NO 8
<211> LENGTH: 229
<212> TYPE: PRT
<213> ORGANISM: Artificial Sequence
<220> FEATURE:
<223> OTHER INFORMATION: Human IgG4 (S228P / L235E)

<400> SEQUENCE: 8

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Lys
225
```

<210> SEQ ID NO 9
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 9

-continued

```
Gly Phe Thr Phe Ser Ser Tyr Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 10

Ile Ser Ser Ser Ser Ser Tyr Ile
1               5

<210> SEQ ID NO 11
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 11

Ala Arg Asp Gly Gly Arg Thr Ser Tyr Thr Ala Thr Ala His Asn Trp
1               5                   10                  15

Phe Asp Pro

<210> SEQ ID NO 12
<211> LENGTH: 9
<212> TYPE: PRT
<213> ORGANISM: Artificial Sequence
<220> FEATURE:
<223> OTHER INFORMATION: Heavy chain CDR1

<400> SEQUENCE: 12

Phe Thr Phe Ser Ser Tyr Ser Met Asn
1               5

<210> SEQ ID NO 13
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 13

Ser Ile Ser Ser Ser Ser Ser Tyr Ile Tyr Tyr Ala Asp Ser Val Lys
1               5                   10                  15

Gly

<210> SEQ ID NO 14
<211> LENGTH: 19
<212> TYPE: PRT
<213> ORGANISM: Artificial Sequence
<220> FEATURE:
<223> OTHER INFORMATION: Heavy Chain CDR3

<400> SEQUENCE: 14

Ala Arg Asp Gly Gly Arg Thr Ser Tyr Thr Ala Thr Ala His Asn Trp
1               5                   10                  15

Phe Asp Pro

<210> SEQ ID NO 15
<211> LENGTH: 126
<212> TYPE: PRT
<213> ORGANISM: Artificial Sequence
```

<220> FEATURE:
<223> OTHER INFORMATION: Heavy Chain

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
        115                 120                 125

<210> SEQ ID NO 16
<211> LENGTH: 378
<212> TYPE: DNA
<213> ORGANISM: Artificial Sequence
<220> FEATURE:
<223> OTHER INFORMATION: DNA Heavy Chain

<400> SEQUENCE: 16
gaggtgcagc tggtggagtc tggggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca acgccaagaa ctcactgtat     240
ctgcaaatga acagcctgag agccgaggac acggcggtgt actactgcgc cagagatggt     300
ggaagaacgt cctacaccgc cacagcccac aattggttcg accctgggg acagggtaca      360 ttggtcaccg tctcctca                                                   378

<210> SEQ ID NO 17
<211> LENGTH: 12
<212> TYPE: PRT
<213> ORGANISM: Artificial Sequence
<220> FEATURE:
<223> OTHER INFORMATION: Light Chain CDR1

<400> SEQUENCE: 17

Gln Ser Val Leu Phe Ser Ser Asn Asn Lys Asn Tyr
1               5                   10

<210> SEQ ID NO 18
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 18

Trp Ala Ser
1

```
<210> SEQ ID NO 19
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 19

Gln Gln His Ala Ser Ala Pro Pro Thr
1               5

<210> SEQ ID NO 20
<211> LENGTH: 17
<212> TYPE: PRT
<213> ORGANISM: Artificial Sequence
<220> FEATURE:
<223> OTHER INFORMATION: Light Chain CDR1

<400> SEQUENCE: 20

Lys Ser Ser Gln Ser Val Leu Phe Ser Ser Asn Asn Lys Asn Tyr Leu
1               5                   10                  15

Ala

<210> SEQ ID NO 21
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 21

Trp Ala Ser Thr Arg Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 22

Gln Gln His Ala Ser Ala Pro Pro Thr
1               5

<210> SEQ ID NO 23
<211> LENGTH: 113
<212> TYPE: PRT
<213> ORGANISM: Artificial Sequence
<220> FEATURE:
<223> OTHER INFORMATION: Light Chain

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 24
<211> LENGTH: 339
<212> TYPE: DNA
<213> ORGANISM: Artificial Sequence
<220> FEATURE:
<223> OTHER INFORMATION: DNA Light Chain

<400> SEQUENCE: 24
gacatcgtga tgacccagtc tccagactcc ctggctgtgt ctctgggcga gagggccacc       60
atcaactgca agtccagcca gagtgtttta ttcagctcca acaataagaa ctacttagct      120
tggtaccagc agaaaccagg acagcctcct aagctgctca tttactgggc atctacccgg      180
gaatccgggg tccctgaccg attcagtggc agcgggtctg ggacagattt cactctcacc      240
atcagcagcc tgcaggctga agatgtggca gtttattact gtcagcagca cgccagtgcc      300
cctcctactt ttggcggagg gaccaaggtt gagatcaaa                             339

<210> SEQ ID NO 25
<211> LENGTH: 456
<212> TYPE: PRT
<213> ORGANISM: Artificial Sequence
<220> FEATURE:
<223> OTHER INFORMATION: Heavy Chain

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

```
Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455
```

<210> SEQ ID NO 26
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 26

```
gaggtgcagc tggtggagtc tggggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctcagc gagcaccaaa ggcccgagcg tgtttccgct ggcgccgagc     420
agcaaaagca ccagcggcgg caccgcggcg ctgggctgcc tggtgaaaga ttattttccg     480
gaaccggtga ccgtgagctg gaacagcggc gcgctgacca gcggcgtgca tacctttccg     540
gcggtgctgc agagcagcgg cctgtatagc ctgagcagcg tggtgaccgt gccgagcagc     600
agcctgggca cccagaccta tatttgcaac gtgaaccata aaccgagcaa caccaaagtg     660
```

-continued

```
gataaaaaag tggaaccgaa aagctgcgat aaaacccata cctgcccgcc gtgcccggcg      720
ccggaactgc tgggcggccc gagcgtgttt ctgtttccgc cgaaaccgaa agataccctg      780
atgattagcc gcaccccgga agtgacctgc gtggtggtgg atgtgagcca tgaagatccg      840
gaagtgaaat ttaactggta tgtggatggc gtggaagtgc ataacgcgaa aaccaaaccg      900
cgcgaagaac agtataacag cacctatcgc gtggtgagcg tgctgaccgt gctgcatcag      960
gattggctga acggcaaaga atataaatgc aaagtgagca caaagcgct gccggcgccg     1020 attgaaaaaa ccattagcaa agcgaaaggc cagccgcgcg aaccgcaggt gtatccctg     1080 ccgccgagcc gcgatgaact gaccaaaaac caggtgagcc tgacctgcct ggtgaaaggc     1140
ttttatccga gcgatattgc ggtggaatgg gaaagcaacg gccagccgga aaacaactat     1200
aaaaccaccc cgccggtgct ggatagcgat ggcagctttt ttctgtatag caaactgacc     1260
gtggataaaa gccgctggca gcagggcaac gtgtttagct gcagcgtgat gcatgaagcg     1320
ctgcataacc attatacocca gaaaagcctg agcctgagcc cgggcaaa              1368
```

```
<210> SEQ ID NO 27
<211> LENGTH: 220
<212> TYPE: PRT
<213> ORGANISM: Artificial Sequence
<220> FEATURE:
<223> OTHER INFORMATION: Light Chain

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 28
```

<211> LENGTH: 660
<212> TYPE: DNA
<213> ORGANISM: Artificial Sequence
<220> FEATURE:
<223> OTHER INFORMATION: DNA Light Chain

<400> SEQUENCE: 28

```
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaac gtacggtggc cgctcccttc     360
gtgttcatct tcccacccctc cgacgagcag ctgaagtccg gcaccgcctc cgtcgtgtgc     420
ctgctgaaca acttctaccc tcgcgaggcc aaagtgcagt ggaaagtgga caacgcctg      480 cagtccggca actcccagga atccgtcacc gagcaggact ccaaggacag cacctactcc     540
ctgtcctcca ccctgaccct gtccaaggcc gactacgaga gcacaaaagt gtacgcctgc     600
gaagtgaccc accaggggcct gtccagcccc gtgaccaagt ccttcaaccg gggcgagtgc     660
```

<210> SEQ ID NO 29
<211> LENGTH: 452
<212> TYPE: PRT
<213> ORGANISM: Artificial Sequence
<220> FEATURE:
<223> OTHER INFORMATION: Heavy Chain

<400> SEQUENCE: 29

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205
```

```
Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
    435                 440                 445

Leu Ser Leu Gly
    450
```

```
<210> SEQ ID NO 30
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 30
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggccgtgt actactgcgc cagagatggt     300
ggaagaacgt cctacaccgc cacagcccac aattggttcg accctggggg acagggtaca     360
ttggtcaccg tctcctcagc ttccaccaag ggcccctccg tgttccctct ggccccttgc     420
tcccggtcca cctccgagtc taccgccgct ctgggctgcc tcgtgaagga ctacttcccc     480
gagcccgtga ccgtgtcctg gaactctggc gccctgacct ccggcgtgca caccttccct     540
gccgtgctgc agtcctccgg cctgtactcc ctgtccagcg tcgtgaccgt gccctcctcc     600
agcctgggca ccaagaccta cacctgtaac gtggaccaca gccctccaa caccaaagtg     660
```

-continued

```
gacaagcggg tggaatctaa gtacggccct ccctgccctt cctgccctgc ccctgagttc   720
ctgggcggac cttccgtgtt cctgttccct ccaaagccca aggacaccct gatgatctcc   780
cggacccctg aagtgacctg cgtggtggtg gacgtgtccc aggaagatcc cgaagtccag   840
ttcaattggt acgtggacgg cgtggaagtg cacaacgcca agaccaagcc cagagaggaa   900
cagttcaact ccacctaccg ggtggtgtcc gtgctgaccg tgctgcacca ggactggctg   960
aacggcaaag agtacaagtg caaagtgtcc aacaagggcc tgccctccag catcgaaaag  1020
accatctcca aggccaaggg ccagccccgc gagccccaag tgtacaccct gcctcccagc  1080
caggaagaga tgaccaagaa tcaagtgtcc ctgacttgtc tggtcaaggg cttctacccc  1140
tccgatatcg ccgtggagtg ggagtccaac ggccagcccg agaacaacta caagaccacc  1200
cctcccgtgc tggactccga cggctccttc ttcctgtact ctcggctgac cgtggacaag  1260
tcccggtggc aggaaggcaa cgtcttctcc tgctccgtga tgcacgaggc cctgcacaac  1320
cactacaccc agaagtccct gtccctgtct ctgggc                           1356
```

```
<210> SEQ ID NO 31
<211> LENGTH: 8
<212> TYPE: PRT
<213> ORGANISM: Artificial Sequence
<220> FEATURE:
<223> OTHER INFORMATION: Heavy Chain CDR1

<400> SEQUENCE: 31

Gly Phe Thr Phe Arg Ser Tyr Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 32

Ile Ser Ser Ser Ser Ser Tyr Ile
1               5

<210> SEQ ID NO 33
<211> LENGTH: 19
<212> TYPE: PRT
<213> ORGANISM: Artificial Sequence
<220> FEATURE:
<223> OTHER INFORMATION: Heavy Chain CDR3

<400> SEQUENCE: 33

Ala Arg Asp Gly Gly Arg Thr Ser Tyr Thr Ala Thr Ala His Asn Trp
1               5                   10                  15

Phe Asp Pro

<210> SEQ ID NO 34
<211> LENGTH: 9
<212> TYPE: PRT
<213> ORGANISM: Artificial Sequence
<220> FEATURE:
<223> OTHER INFORMATION: Heavy Chain CDR1

<400> SEQUENCE: 34

Phe Thr Phe Arg Ser Tyr Gly Met Asn
1               5
```

```
<210> SEQ ID NO 35
<211> LENGTH: 17
<212> TYPE: PRT
<213> ORGANISM: Artificial Sequence
<220> FEATURE:
<223> OTHER INFORMATION: Heavy Chain CDR2

<400> SEQUENCE: 35

Ser Ile Ser Ser Ser Ser Ser Tyr Ile Tyr Tyr Ala Asp Ser Val Lys
1               5                   10                  15

Gly

<210> SEQ ID NO 36
<211> LENGTH: 19
<212> TYPE: PRT
<213> ORGANISM: Artificial Sequence
<220> FEATURE:
<223> OTHER INFORMATION: Heavy Chain CDR3

<400> SEQUENCE: 36

Ala Arg Asp Gly Gly Arg Thr Ser Tyr Thr Ala Thr Ala His Asn Trp
1               5                   10                  15

Phe Asp Pro

<210> SEQ ID NO 37
<211> LENGTH: 126
<212> TYPE: PRT
<213> ORGANISM: Artificial Sequence
<220> FEATURE:
<223> OTHER INFORMATION: Heavy Chain

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
            115                 120                 125

<210> SEQ ID NO 38
<211> LENGTH: 378
<212> TYPE: DNA
<213> ORGANISM: Artificial Sequence
<220> FEATURE:
<223> OTHER INFORMATION: DNA Heavy Chain

<400> SEQUENCE: 38
gaggtgcagc tggtggagtc tggggggaggc ctggtcaagc ctggggggtc cctgagactc      60
tcctgtgcag cctctggatt caccttccgg agctatggga tgaactgggt ccgccaggct     120
ccagggaagg ggctggagtg ggtctcatcc attagtagta gtagtagtta catatactac     180
```
gcagactcag tgaagggccg attcaccatc tccagagaca acgccaagaa ctcactgtat      240
ctgcaaatga acagcctgag agccgaggac acggcggtgt actactgcgc cagagatggt      300
ggaagaacgt cctacaccgc cacagcccac aattggttcg acccctgggg acagggtaca      360
ttggtcaccg tctcctca                                                  378

<210> SEQ ID NO 39
<211> LENGTH: 12
<212> TYPE: PRT
<213> ORGANISM: Artificial Sequence
<220> FEATURE:
<223> OTHER INFORMATION: Light Chain CDR1

<400> SEQUENCE: 39

Gln Ser Val Leu Phe Ser Ser Asn Asn Lys Asn Tyr
1               5                   10

<210> SEQ ID NO 40
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 40

Trp Ala Ser
1

<210> SEQ ID NO 41
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 41

Gln Gln His Ala Ser Ala Pro Pro Thr
1               5

<210> SEQ ID NO 42
<211> LENGTH: 17
<212> TYPE: PRT
<213> ORGANISM: Artificial Sequence
<220> FEATURE:
<223> OTHER INFORMATION: Light Chain CDR1

<400> SEQUENCE: 42

Lys Ser Ser Gln Ser Val Leu Phe Ser Ser Asn Asn Lys Asn Tyr Leu
1               5                   10                  15

Ala

<210> SEQ ID NO 43
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 43

Trp Ala Ser Thr Arg Glu Ser
1               5

<210> SEQ ID NO 44
<211> LENGTH: 9

<212> TYPE: PRT
<213> ORGANISM: Artificial Sequence
<220> FEATURE:
<223> OTHER INFORMATION: Light Chain CDR3

<400> SEQUENCE: 44

Gln Gln His Ala Ser Ala Pro Pro Thr
1               5

<210> SEQ ID NO 45
<211> LENGTH: 113
<212> TYPE: PRT
<213> ORGANISM: Artificial Sequence
<220> FEATURE:
<223> OTHER INFORMATION: Light Chain

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 46
<211> LENGTH: 339
<212> TYPE: DNA
<213> ORGANISM: Artificial Sequence
<220> FEATURE:
<223> OTHER INFORMATION: DNA Light Chain

<400> SEQUENCE: 46
gacatcgtga tgacccagtc tccagactcc ctggctgtgt ctctgggcga gagggccacc        60
atcaactgca agtccagcca gagtgtttta ttcagctcca acaataagaa ctacttagct       120
tggtaccagc agaaaccagg acagcctcct aagctgctca tttactgggc atctacccgg       180
gaatccgggg tccctgaccg attcagtggc agcgggtctg ggacagattt cactctcacc       240
atcagcagcc tgcaggctga agatgtggca gtttattact gtcagcagca cgccagtgcc       300
cctcctactt ttggcggagg gaccaaggtt gagatcaaa                              339

<210> SEQ ID NO 47
<211> LENGTH: 456
<212> TYPE: PRT
<213> ORGANISM: Artificial Sequence
<220> FEATURE:
<223> OTHER INFORMATION: Heavy Chain

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr

-continued

```
              20                25                30
Gly Met Asn Trp Val Arg Gln Ala Pro Gly Lys Gly Leu Glu Trp Val
          35                40                45
Ser Ser Ile Ser Ser Ser Ser Ser Tyr Ile Tyr Tyr Ala Asp Ser Val
      50                55                60
Lys Gly Arg Phe Thr Ile Ser Arg Asp Asn Ala Lys Asn Ser Leu Tyr
65                    70                75                    80
Leu Gln Met Asn Ser Leu Arg Ala Glu Asp Thr Ala Val Tyr Tyr Cys
              85                90                95
Ala Arg Asp Gly Gly Arg Thr Ser Tyr Thr Ala Thr Ala His Asn Trp
          100               105               110
Phe Asp Pro Trp Gly Gln Gly Thr Leu Val Thr Val Ser Ser Ala Ser
          115               120               125
Thr Lys Gly Pro Ser Val Phe Pro Leu Ala Pro Ser Ser Lys Ser Thr
          130               135               140
Ser Gly Gly Thr Ala Ala Leu Gly Cys Leu Val Lys Asp Tyr Phe Pro
145               150               155               160
Glu Pro Val Thr Val Ser Trp Asn Ser Gly Ala Leu Thr Ser Gly Val
              165               170               175
His Thr Phe Pro Ala Val Leu Gln Ser Ser Gly Leu Tyr Ser Leu Ser
          180               185               190
Ser Val Val Thr Val Pro Ser Ser Ser Leu Gly Thr Gln Thr Tyr Ile
          195               200               205
Cys Asn Val Asn His Lys Pro Ser Asn Thr Lys Val Asp Lys Lys Val
      210               215               220
Glu Pro Lys Ser Cys Asp Lys Thr His Thr Cys Pro Pro Cys Pro Ala
225               230               235               240
Pro Glu Leu Leu Gly Gly Pro Ser Val Phe Leu Phe Pro Pro Lys Pro
              245               250               255
Lys Asp Thr Leu Met Ile Ser Arg Thr Pro Glu Val Thr Cys Val Val
          260               265               270
Val Asp Val Ser His Glu Asp Pro Glu Val Lys Phe Asn Trp Tyr Val
          275               280               285
Asp Gly Val Glu Val His Asn Ala Lys Thr Lys Pro Arg Glu Glu Gln
      290               295               300
Tyr Asn Ser Thr Tyr Arg Val Val Ser Val Leu Thr Val Leu His Gln
305               310               315               320
Asp Trp Leu Asn Gly Lys Glu Tyr Lys Cys Lys Val Ser Asn Lys Ala
              325               330               335
Leu Pro Ala Pro Ile Glu Lys Thr Ile Ser Lys Ala Lys Gly Gln Pro
          340               345               350
Arg Glu Pro Gln Val Tyr Thr Leu Pro Pro Ser Arg Asp Glu Leu Thr
          355               360               365
Lys Asn Gln Val Ser Leu Thr Cys Leu Val Lys Gly Phe Tyr Pro Ser
      370               375               380
Asp Ile Ala Val Glu Trp Glu Ser Asn Gly Gln Pro Glu Asn Asn Tyr
385               390               395               400
Lys Thr Thr Pro Pro Val Leu Asp Ser Asp Gly Ser Phe Phe Leu Tyr
              405               410               415
Ser Lys Leu Thr Val Asp Lys Ser Arg Trp Gln Gln Gly Asn Val Phe
          420               425               430
Ser Cys Ser Val Met His Glu Ala Leu His Asn His Tyr Thr Gln Lys
          435               440               445
```

Ser Leu Ser Leu Ser Pro Gly Lys
    450                 455

<210> SEQ ID NO 48
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 48
gaggtgcagc tggtggagtc tggggggaggc ctggtcaagc ctggggggtc cctgagactc      60
tcctgtgcag cctctggatt caccttccgg agctatggga tgaactgggt ccgccaggct     120
ccagggaagg ggctggagtg ggtctcatcc attagtagta gtagtagtta catatactac     180
gcagactcag tgaagggccg attcaccatc tccagagaca acgccaagaa ctcactgtat     240
ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctcagc gagcaccaaa ggcccgagcg tgtttccgct ggcgccgagc     420
agcaaaagca ccagcggcgg caccgcgcgc ctgggctgcc tggtgaaaga ttattttccg     480
gaaccggtga ccgtgagctg gaacagcggc gcgctgacca cggcgtgca tacctttccg     540 gcggtgctgc agagcagcgg cctgtatagc ctgagcagcg tggtgaccgt gccgagcagc     600
agcctgggca cccagaccta tatttgcaac gtgaaccata aaccgagcaa caccaaagtg     660
gataaaaaag tggaaccgaa aagctgcgat aaaacccata cctgcccgcc gtgcccggcg     720
ccggaactgc tgggcggccc gagcgtgttt ctgtttccgc cgaaaccgaa agatacctg     780 atgattagcc gcacccccgga agtgacctgc gtggtggtgg atgtgagcca tgaagatccg     840
gaagtgaaat ttaactggta tgtggatggc gtggaagtgc ataacgcgaa aaccaaaccg     900
cgcgaagaac agtataacag cacctatcgc gtggtgagcg tgctgaccgt gctgcatcag     960
gattggctga acggcaaaga atataaatgc aaagtgagca caaagcgct gccggcgccg    1020 attgaaaaaa ccattagcaa agcgaaaggc cagccgcgcg aaccgcaggt gtatacctg    1080 ccgccgagcc gcgatgaact gaccaaaaac caggtgagcc tgacctgcct ggtgaaaggc    1140 tttatccga gcgatattgc ggtggaatgg gaaagcaacg gccagccgga aaacaactat    1200
aaaaccaccc gcgccggtgct ggatagcgat ggcagctttt ttctgtatag caaactgacc    1260
gtggataaaa gccgctggca gcagggcaac gtgtttagct gcagcgtgat gcatgaagcg    1320
ctgcataacc attatcccca gaaaagcctg agcctgagcc cgggcaaa          1368

<210> SEQ ID NO 49
<211> LENGTH: 220
<212> TYPE: PRT
<213> ORGANISM: Artificial Sequence
<220> FEATURE:
<223> OTHER INFORMATION: Light Chain

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Gln
            85              90              95

His Ala Ser Ala Pro Pro Thr Phe Gly Gly Gly Thr Lys Val Glu Ile
            100             105             110

Lys Arg Thr Val Ala Ala Pro Ser Val Phe Ile Phe Pro Pro Ser Asp
            115             120             125

Glu Gln Leu Lys Ser Gly Thr Ala Ser Val Val Cys Leu Leu Asn Asn
    130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
            195             200             205

Ser Pro Val Thr Lys Ser Phe Asn Arg Gly Glu Cys
    210             215             220
```

```
<210> SEQ ID NO 50
<211> LENGTH: 660
<212> TYPE: DNA
<213> ORGANISM: Artificial Sequence
<220> FEATURE:
<223> OTHER INFORMATION: DNA Light Chain

<400> SEQUENCE: 50
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaac gtacggtggc cgctccctcc     360
gtgttcatct tcccaccctc cgacgagcag ctgaagtccg gcaccgcctc cgtcgtgtgc     420
ctgctgaaca acttctaccc tcgcgaggcc aaagtgcagt ggaaagtgga caacgccctg     480
cagtccggca actcccagga atccgtcacc gagcaggact ccaaggacag cacctactcc     540
ctgtcctcca ccctgaccct gtccaaggcc gactacgaga gcacaaagt gtacgcctgc     600 gaagtgaccc accagggcct gtccagcccc gtgaccaagt ccttcaaccg gggcgagtgc     660
```

```
<210> SEQ ID NO 51
<211> LENGTH: 452
<212> TYPE: PRT
<213> ORGANISM: Artificial Sequence
<220> FEATURE:
<223> OTHER INFORMATION: Heavy Chain

<400> SEQUENCE: 51

Glu Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Arg Ser Tyr
```

```
              20                25                30
Gly Met Asn Trp Val Arg Gln Ala Pro Gly Lys Gly Leu Glu Trp Val
              35                40                45

Ser Ser Ile Ser Ser Ser Ser Ser Tyr Ile Tyr Tyr Ala Asp Ser Val
      50                55                60

Lys Gly Arg Phe Thr Ile Ser Arg Asp Asn Ala Lys Asn Ser Leu Tyr
65                70                75                80

Leu Gln Met Asn Ser Leu Arg Ala Glu Asp Thr Ala Val Tyr Tyr Cys
              85                90                95

Ala Arg Asp Gly Gly Arg Thr Ser Tyr Thr Ala Thr Ala His Asn Trp
              100               105               110

Phe Asp Pro Trp Gly Gln Gly Thr Leu Val Thr Val Ser Ser Ala Ser
      115               120               125

Thr Lys Gly Pro Ser Val Phe Pro Leu Ala Pro Cys Ser Arg Ser Thr
      130               135               140

Ser Glu Ser Thr Ala Ala Leu Gly Cys Leu Val Lys Asp Tyr Phe Pro
145               150               155               160

Glu Pro Val Thr Val Ser Trp Asn Ser Gly Ala Leu Thr Ser Gly Val
              165               170               175

His Thr Phe Pro Ala Val Leu Gln Ser Ser Gly Leu Tyr Ser Leu Ser
              180               185               190

Ser Val Val Thr Val Pro Ser Ser Ser Leu Gly Thr Lys Thr Tyr Thr
              195               200               205

Cys Asn Val Asp His Lys Pro Ser Asn Thr Lys Val Asp Lys Arg Val
      210               215               220

Glu Ser Lys Tyr Gly Pro Pro Cys Pro Ser Cys Pro Ala Pro Glu Phe
225               230               235               240

Leu Gly Gly Pro Ser Val Phe Leu Phe Pro Pro Lys Pro Lys Asp Thr
              245               250               255

Leu Met Ile Ser Arg Thr Pro Glu Val Thr Cys Val Val Val Asp Val
              260               265               270

Ser Gln Glu Asp Pro Glu Val Gln Phe Asn Trp Tyr Val Asp Gly Val
              275               280               285

Glu Val His Asn Ala Lys Thr Lys Pro Arg Glu Glu Gln Phe Asn Ser
      290               295               300

Thr Tyr Arg Val Val Ser Val Leu Thr Val Leu His Gln Asp Trp Leu
305               310               315               320

Asn Gly Lys Glu Tyr Lys Cys Lys Val Ser Asn Lys Gly Leu Pro Ser
              325               330               335

Ser Ile Glu Lys Thr Ile Ser Lys Ala Lys Gly Gln Pro Arg Glu Pro
              340               345               350

Gln Val Tyr Thr Leu Pro Pro Ser Gln Glu Glu Met Thr Lys Asn Gln
              355               360               365

Val Ser Leu Thr Cys Leu Val Lys Gly Phe Tyr Pro Ser Asp Ile Ala
      370               375               380

Val Glu Trp Glu Ser Asn Gly Gln Pro Glu Asn Asn Tyr Lys Thr Thr
385               390               395               400

Pro Pro Val Leu Asp Ser Asp Gly Ser Phe Phe Leu Tyr Ser Arg Leu
              405               410               415

Thr Val Asp Lys Ser Arg Trp Gln Glu Gly Asn Val Phe Ser Cys Ser
              420               425               430

Val Met His Glu Ala Leu His Asn His Tyr Thr Gln Lys Ser Leu Ser
              435               440               445
```

-continued

Leu Ser Leu Gly
    450

<210> SEQ ID NO 52
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 52
gaggtgcagc tggtggagtc tggggggaggc ctggtcaagc ctgggggggtc cctgagactc      60 tcctgtgcag cctctggatt caccttccgg agctatggga tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat     240 ctgcaaatga acagcctgag agccgaggac acggcggtgt actactgcgc cagagatggt     300
ggaagaacgt cctacaccgc cacagcccac aattggttcg accccgtggg acagggtaca     360
ttggtcaccg tctcctcagc ttccaccaag ggcccctccg tgttccctct ggcccttgc     420 tccccggtcca cctccgagtc taccgccgct ctgggctgcc tcgtgaagga ctacttcccc     480
gagcccgtga ccgtgtcctg gaactctggc gccctgacct ccggcgtgca caccttccct     540
gccgtgctgc agtcctccgg cctgtactcc ctgtccagcg tcgtgaccgt gccctcctcc     600
agcctgggca ccaagaccta cacctgtaac gtggaccaca gccctccaa caccaaagtg     660 gacaagcggg tggaatctaa gtacggccct ccctgccctt cctgccctgc ccctgagttc     720
ctgggcggac cttccgtgtt cctgttccct ccaaagccca aggacaccct gatgatctcc     780
cggacccctg aagtgacctg cgtggtggtg gacgtgtccc aggaagatcc cgaagtccag     840
ttcaattggt acgtggacgg cgtggaagtg cacaacgcca gaccaagcc cagagaggaa     900 cagttcaact ccacctaccg ggtggtgtcc gtgctgaccg tgctgcacca ggactggctg     960
aacggcaaag agtacaagtg caaagtgtcc aacaagggcc tgccctccag catcgaaaag    1020
accatctcca aggccaaggg ccagccccgc gagccccaag tgtacaccct gcctcccagc    1080
caggaagaga tgaccaagaa tcaagtgtcc ctgacttgtc tggtcaaggg cttctacccc    1140
tccgatatcg ccgtggagtg ggagtccaac ggccagcccg agaacaacta caagaccacc    1200
cctcccgtgc tggactccga cggctccttc ttcctgtact ctcggctgac cgtggacaag    1260
tcccggtggc aggaaggcaa cgtcttctcc tgctccgtga tgcacgaggc cctgcacaac    1320
cactacaccc agaagtccct gtccctgtct ctgggc                              1356

<210> SEQ ID NO 53
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 53

Gly Phe Thr Phe Ser Arg Thr Gly
1               5

<210> SEQ ID NO 54
<211> LENGTH: 8
<212> TYPE: PRT
<213> ORGANISM: Artificial Sequence
<220> FEATURE:

-continued

<223> OTHER INFORMATION: Heavy chain CDR2

<400> SEQUENCE: 54

Ile Ser Ser Ser Ser Ser Tyr Ile
1               5

<210> SEQ ID NO 55
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 55

Ala Arg Asp Gly Gly Arg Thr Ser Tyr Thr Ala Thr Ala His Asn Trp
1               5                   10                  15

Phe Asp Pro

<210> SEQ ID NO 56
<211> LENGTH: 9
<212> TYPE: PRT
<213> ORGANISM: Artificial Sequence
<220> FEATURE:
<223> OTHER INFORMATION: Heavy chain CDR1

<400> SEQUENCE: 56

Phe Thr Phe Ser Arg Thr Gly Met Asn
1               5

<210> SEQ ID NO 57
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 57

Ser Ile Ser Ser Ser Ser Ser Tyr Ile Tyr Tyr Ala Asp Ser Val Lys
1               5                   10                  15

Gly

<210> SEQ ID NO 58
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 58

Ala Arg Asp Gly Gly Arg Thr Ser Tyr Thr Ala Thr Ala His Asn Trp
1               5                   10                  15

Phe Asp Pro

<210> SEQ ID NO 59
<211> LENGTH: 126
<212> TYPE: PRT
<213> ORGANISM: Artificial Sequence
<220> FEATURE:
<223> OTHER INFORMATION: Heavy chain

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Thr

-continued

```
               20                25                30

Gly Met Asn Trp Val Arg Gln Ala Pro Gly Lys Gly Leu Glu Trp Val
          35                40                45

Ser Ser Ile Ser Ser Ser Ser Ser Tyr Ile Tyr Tyr Ala Asp Ser Val
     50                55                60

Lys Gly Arg Phe Thr Ile Ser Arg Asp Asn Ala Lys Asn Ser Leu Tyr
65                70                75                80

Leu Gln Met Asn Ser Leu Arg Ala Glu Asp Thr Ala Val Tyr Tyr Cys
               85                90                95

Ala Arg Asp Gly Gly Arg Thr Ser Tyr Thr Ala Thr Ala His Asn Trp
          100               105               110

Phe Asp Pro Trp Gly Gln Gly Thr Leu Val Thr Val Ser Ser
          115               120               125
```

<210> SEQ ID NO 60
<211> LENGTH: 378
<212> TYPE: DNA
<213> ORGANISM: Artificial Sequence
<220> FEATURE:
<223> OTHER INFORMATION: DNA Heavy chain

<400> SEQUENCE: 60

```
gaggtgcagc tggtggagtc tggggggaggc ctggtcaagc ctggggggtc cctgagactc      60
tcctgtgcag cctctggatt caccttcagt aggactggga tgaactgggt ccgccaggct     120
ccagggaagg ggctggaatg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctca                                                     378
```

<210> SEQ ID NO 61
<211> LENGTH: 12
<212> TYPE: PRT
<213> ORGANISM: Artificial Sequence
<220> FEATURE:
<223> OTHER INFORMATION: Light chain CDR1

<400> SEQUENCE: 61

```
Gln Ser Val Leu Phe Ser Ser Asn Asn Lys Asn Tyr
1               5                10
```

<210> SEQ ID NO 62
<211> LENGTH: 3
<212> TYPE: PRT
<213> ORGANISM: Artificial Sequence
<220> FEATURE:
<223> OTHER INFORMATION: Light chain CDR2

<400> SEQUENCE: 62

```
Trp Ala Ser
1
```

<210> SEQ ID NO 63
<211> LENGTH: 9
<212> TYPE: PRT
<213> ORGANISM: Artificial Sequence
<220> FEATURE:
<223> OTHER INFORMATION: Light chain CDR3

<400> SEQUENCE: 63

-continued

```
Gln Gln His Ala Ser Ala Pro Pro Thr
1               5

<210> SEQ ID NO 64
<211> LENGTH: 17
<212> TYPE: PRT
<213> ORGANISM: Artificial Sequence
<220> FEATURE:
<223> OTHER INFORMATION: Light chain CDR1

<400> SEQUENCE: 64

Lys Ser Ser Gln Ser Val Leu Phe Ser Ser Asn Asn Lys Asn Tyr Leu
1               5                   10                  15

Ala

<210> SEQ ID NO 65
<211> LENGTH: 7
<212> TYPE: PRT
<213> ORGANISM: Artificial Sequence
<220> FEATURE:
<223> OTHER INFORMATION: Light chain CDR2

<400> SEQUENCE: 65

Trp Ala Ser Thr Arg Glu Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Light chain CDR3

<400> SEQUENCE: 66

Gln Gln His Ala Ser Ala Pro Pro Thr
1               5

<210> SEQ ID NO 67
<211> LENGTH: 113
<212> TYPE: PRT
<213> ORGANISM: Artificial Sequence
<220> FEATURE:
<223> OTHER INFORMATION: Light chain

<400> SEQUENCE: 67

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys
```

```
<210> SEQ ID NO 68
<211> LENGTH: 339
<212> TYPE: DNA
<213> ORGANISM: Artificial Sequence
<220> FEATURE:
<223> OTHER INFORMATION: DNA Light chain

<400> SEQUENCE: 68
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaa                            339

<210> SEQ ID NO 69
<211> LENGTH: 456
<212> TYPE: PRT
<213> ORGANISM: Artificial Sequence
<220> FEATURE:
<223> OTHER INFORMATION: Heavy Chain

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Thr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255
```

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 70
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 70
gaggtgcagc tggtggagtc tgggggaggc ctggtcaagc ctggggggtc cctgagactc        60
tcctgtgcag cctctggatt caccttcagt aggactggga tgaactgggt ccgccaggct       120
ccagggaagg ggctggaatg ggtctcatcc attagtagta gtagtagtta catatactac       180
gcagactcag tgaagggccg attcaccatc tccagagaca acgccaagaa ctcactgtat       240
ctgcaaatga acagcctgag agccgaggac acggcggtgt actactgcgc cagagatggt       300
ggaagaacgt cctacaccgc cacagcccac aattggttcg accctggggg acagggtaca       360
ttggtcaccg tctcctcagc gagcaccaaa ggcccgagcg tgtttccgct ggcgccgagc       420
agcaaaagca ccagcggcgg caccgcggcg ctgggctgcc tggtgaaaga ttattttccg       480
gaaccggtga ccgtgagctg gaacagcggc gcgctgacca cggcgtgca taccttttccg       540 gcggtgctgc agagcagcgg cctgtatagc ctgagcagcg tggtgaccgt gccgagcagc       600
agcctgggca cccagaccta tatttgcaac gtgaaccata aaccgagcaa caccaaagtg       660
gataaaaaag tggaaccgaa aagctgcgat aaaacccata cctgcccgcc gtgcccggcg       720
ccggaactgc tgggcggccc gagcgtgttt ctgtttccgc cgaaaccgaa agatacgctg       780
atgattagcc gcaccccgga agtgacctgc gtggtggtgg atgtgagcca tgaagatccg       840
gaagtgaaat ttaactggta tgtggatggc gtggaagtgc ataacgcgaa aaccaaaccg       900

-continued

```
cgcgaagaac agtataacag cacctatcgc gtggtgagcg tgctgaccgt gctgcatcag      960
gattggctga acggcaaaga atataaatgc aaagtgagca caaagcgct gccggcgccg      1020 attgaaaaaa ccattagcaa agcgaaaggc cagccgcgcg aaccgcaggt gtataccctg     1080
ccgccgagcc gcgatgaact gaccaaaaac caggtgagcc tgacctgcct ggtgaaaggc     1140
ttttatccga gcgatattgc ggtggaatgg gaaagcaacg gccagccgga aaacaactat     1200
aaaaccaccc cgccggtgct ggatagcgat ggcagctttt ttctgtatag caaactgacc     1260
gtggataaaa gccgctggca gcagggcaac gtgtttagct gcagcgtgat gcatgaagcg     1320
ctgcataacc attataccca gaaaagcctg agcctgagcc cgggcaaa              1368
```

```
<210> SEQ ID NO 71
<211> LENGTH: 220
<212> TYPE: PRT
<213> ORGANISM: Artificial Sequence
<220> FEATURE:
<223> OTHER INFORMATION: Light Chain

<400> SEQUENCE: 71

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 72
<211> LENGTH: 660
<212> TYPE: DNA
<213> ORGANISM: Artificial Sequence
<220> FEATURE:
<223> OTHER INFORMATION: DNA Light Chain

<400> SEQUENCE: 72
gacatcgtga tgacccagtc tccagactcc ctggctgtgt ctctgggcga gagggccacc      60
```

-continued

```
atcaactgca agtccagcca gagtgtttta ttcagctcca acaataagaa ctacttagct      120
tggtaccagc agaaaccagg acagcctcct aagctgctca tttactgggc atctacccgg      180
gaatccgggg tccctgaccg attcagtggc agcgggtctg ggacagattt cactctcacc      240
atcagcagcc tgcaggctga agatgtggca gtttattact gtcagcagca cgccagtgcc      300
cctcctactt ttggcggagg gaccaaggtt gagatcaaac gtacggtggc cgctccctcc      360
gtgttcatct tcccaccctc cgacgagcag ctgaagtccg gcaccgcctc cgtcgtgtgc      420
ctgctgaaca acttctaccc tcgcgaggcc aaagtgcagt ggaaagtgga caacgccctg      480
cagtccggca actcccagga atccgtcacc gagcaggact ccaaggacag cacctactcc      540
ctgtcctcca ccctgaccct gtccaaggcc gactacgaga gcacaaagt gtacgcctgc      600 gaagtgaccc accagggcct gtccagcccc gtgaccaagt ccttcaaccg gggcgagtgc      660
```

```
<210> SEQ ID NO 73
<211> LENGTH: 452
<212> TYPE: PRT
<213> ORGANISM: Artificial Sequence
<220> FEATURE:
<223> OTHER INFORMATION: Heavy Chain

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Thr
                20                  25                  30

Gly Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
        210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
            435                 440                 445

Leu Ser Leu Gly
    450
```

<210> SEQ ID NO 74
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 74

```
gaggtgcagc tggtggagtc tggggggaggc ctggtcaagc ctggggggtc cctgagactc       60
tcctgtgcag cctctggatt caccttcagt aggactggga tgaactgggt ccgccaggct      120
ccagggaagg ggctggaatg ggtctcatcc attagtagta gtagtagtta catatactac      180
gcagactcag tgaagggccg attcaccatc tccagagaca acgccaagaa ctcactgtat      240
ctgcaaatga acagcctgag agccgaggac acggcggtgt actactgcgc cagagatggt      300
ggaagaacgt cctacaccgc cacagcccac aattggttcg acccctgggg acagggtaca      360
ttggtcaccg tctcctcagc ttccaccaag ggcccctccg tgttccctct ggcccccttgc      420 tcccggtcca cctccgagtc taccgccgct ctgggctgcc tcgtgaagga ctacttcccc      480
gagcccgtga ccgtgtcctg gaactctggc gccctgacct ccggcgtgca caccttccct      540
gccgtgctgc agtcctccgg cctgtactcc ctgtccagcg tcgtgaccgt gccctcctcc      600
agcctgggca ccaagaccta cacctgtaac gtggaccaca gcccctccaa caccaaagtg      660
gacaagcggg tggaatctaa gtacggcccct ccctgcccct cctgccctgc ccctgagttc      720
ctgggcggac cttccgtgtt cctgttccct ccaaagccca aggacaccct gatgatctcc      780
cggacccctg aagtgacctg cgtggtggtg gacgtgtccc aggaagatcc cgaagtccag      840
ttcaattggt acgtggacgg cgtggaagtg cacaacgcca agaccaagcc cagagaggaa      900
```

```
cagttcaact ccacctaccg ggtggtgtcc gtgctgaccg tgctgcacca ggactggctg      960
aacggcaaag agtacaagtg caaagtgtcc aacaagggcc tgccctccag catcgaaaag     1020
accatctcca aggccaaggg ccagccccgc gagccccaag tgtacaccct gcctcccagc     1080
caggaagaga tgaccaagaa tcaagtgtcc ctgacttgtc tggtcaaggg cttctacccc     1140
tccgatatcg ccgtggagtg ggagtccaac ggccagcccg agaacaacta caagaccacc     1200
cctcccgtgc tggactccga cggctccttc ttcctgtact ctcggctgac cgtggacaag     1260
tcccggtggc aggaaggcaa cgtcttctcc tgctccgtga tgcacgaggc cctgcacaac     1320
cactacaccc agaagtccct gtccctgtct ctgggc                               1356
```

```
<210> SEQ ID NO 75
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 75

Gly Phe Thr Phe Ser Arg Tyr Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 76

Ile Ser Ser Ser Ser Ala Tyr Ile
1               5

<210> SEQ ID NO 77
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 77

Ala Arg Asp Gly Gly Arg Thr Ser Tyr Thr Ala Thr Ala His Asn Trp
1               5                   10                  15

Phe Asp Pro

<210> SEQ ID NO 78
<211> LENGTH: 9
<212> TYPE: PRT
<213> ORGANISM: Artificial Sequence
<220> FEATURE:
<223> OTHER INFORMATION: Heavy chain CDR1

<400> SEQUENCE: 78

Phe Thr Phe Ser Arg Tyr Gly Met Asn
1               5

<210> SEQ ID NO 79
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 79
```

-continued

```
Ser Ile Ser Ser Ser Ser Ala Tyr Ile Leu Tyr Ala Asp Ser Val Lys
1               5                   10                  15

Gly

<210> SEQ ID NO 80
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 80

Ala Arg Asp Gly Gly Arg Thr Ser Tyr Thr Ala Thr Ala His Asn Trp
1               5                   10                  15

Phe Asp Pro

<210> SEQ ID NO 81
<211> LENGTH: 126
<212> TYPE: PRT
<213> ORGANISM: Artificial Sequence
<220> FEATURE:
<223> OTHER INFORMATION: Heavy chain

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
            35                  40                  45

Ser Ser Ile Ser Ser Ser Ser Ala Tyr Ile Leu Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
            115                 120                 125

<210> SEQ ID NO 82
<211> LENGTH: 378
<212> TYPE: DNA
<213> ORGANISM: Artificial Sequence
<220> FEATURE:
<223> OTHER INFORMATION: DNA Heavy chain

<400> SEQUENCE: 82
gaggtgcagc tggtggagtc tgggggaggc ctggtcaagc ctggggggtc cctgagactc      60
tcctgtgcag cctctggatt caccttcagt aggtatggga tgaactgggt ccgccaggct     120
ccagggaagg ggctggagtg ggtctcatcc attagtagta gtagtgctta catactgtac     180
gcagactcag tgaagggccg attcaccatc tccagagaca acgccaagaa ctcactgtat     240
ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctca                                                   378
```

<210> SEQ ID NO 83
<211> LENGTH: 12
<212> TYPE: PRT
<213> ORGANISM: Artificial Sequence
<220> FEATURE:
<223> OTHER INFORMATION: Light chain CDR1

<400> SEQUENCE: 83

Gln Ser Val Leu Phe Ser Ser Asn Asn Lys Asn Tyr
1               5                   10

<210> SEQ ID NO 84
<211> LENGTH: 3
<212> TYPE: PRT
<213> ORGANISM: Artificial Sequence
<220> FEATURE:
<223> OTHER INFORMATION: Light chain CDR2

<400> SEQUENCE: 84

Trp Ala Ser
1

<210> SEQ ID NO 85
<211> LENGTH: 9
<212> TYPE: PRT
<213> ORGANISM: Artificial Sequence
<220> FEATURE:
<223> OTHER INFORMATION: Light chain CDR3

<400> SEQUENCE: 85

Gln Gln His Ala Ser Ala Pro Pro Thr
1               5

<210> SEQ ID NO 86
<211> LENGTH: 17
<212> TYPE: PRT
<213> ORGANISM: Artificial Sequence
<220> FEATURE:
<223> OTHER INFORMATION: Light chain CDR1

<400> SEQUENCE: 86

Lys Ser Ser Gln Ser Val Leu Phe Ser Ser Asn Asn Lys Asn Tyr Leu
1               5                   10                  15

Ala

<210> SEQ ID NO 87
<211> LENGTH: 7
<212> TYPE: PRT
<213> ORGANISM: Artificial Sequence
<220> FEATURE:
<223> OTHER INFORMATION: Light chain CDR2

<400> SEQUENCE: 87

Trp Ala Ser Thr Arg Glu Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Light chain CDR3

<400> SEQUENCE: 88

Gln Gln His Ala Ser Ala Pro Pro Thr
1               5

-continued

```
<210> SEQ ID NO 89
<211> LENGTH: 113
<212> TYPE: PRT
<213> ORGANISM: Artificial Sequence
<220> FEATURE:
<223> OTHER INFORMATION: Light Chain

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 90
<211> LENGTH: 339
<212> TYPE: DNA
<213> ORGANISM: Artificial Sequence
<220> FEATURE:
<223> OTHER INFORMATION: DNA Light Chain

<400> SEQUENCE: 90
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaa                            339

<210> SEQ ID NO 91
<211> LENGTH: 456
<212> TYPE: PRT
<213> ORGANISM: Artificial Sequence
<220> FEATURE:
<223> OTHER INFORMATION: Heavy Chain

<400> SEQUENCE: 91

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ala Tyr Ile Leu Tyr Ala Asp Ser Val
    50                  55                  60

Lys Gly Arg Phe Thr Ile Ser Arg Asp Asn Ala Lys Asn Ser Leu Tyr
```

```
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455
```

<210> SEQ ID NO 92
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 92

```
gaggtgcagc tggtggagtc tggggggaggc ctggtcaagc ctggggggtc cctgagactc       60
tcctgtgcag cctctggatt caccttcagt aggtatggga tgaactgggt ccgccaggct      120
ccagggaagg ggctggagtg ggtctcatcc attagtagta gtagtgctta catactgtac      180
gcagactcag tgaagggccg attcaccatc tccagagaca cgccaagaa ctcactgtat       240 ctgcaaatga acagcctgag agccgaggac acggcggtgt actactgcgc cagagatggt      300
ggaagaacgt cctacaccgc cacagcccac aattggttcg acccctgggg acagggtaca      360
ttggtcaccg tctcctcagc gagcaccaaa ggcccgagcg tgtttccgct ggcgccgagc      420
agcaaaagca ccagcggcgg caccgcggcg ctgggctgcc tggtgaaaga ttattttccg      480
gaaccggtga ccgtgagctg gaacagcggc gcgctgacca gcggcgtgca tacctttccg      540
gcggtgctgc agagcagcgg cctgtatagc ctgagcagcg tggtgaccgt gccgagcagc      600
agcctgggca cccagaccta tatttgcaac gtgaaccata aaccgagcaa caccaaagtg      660
gataaaaaag tggaaccgaa aagctgcgat aaaacccata cctgcccgcc gtgcccggcg      720
ccggaactgc tgggcggccc gagcgtgttt ctgtttccgc cgaaaccgaa agatacccctg      780 atgattagcc gcacccccgga agtgacctgc gtggtggtgg atgtgagcca tgaagatccg      840
gaagtgaaat ttaactggta tgtggatggc gtggaagtgc ataacgcgaa aaccaaaccg      900
cgcgaagaac agtataacag cacctatcgc gtggtgagcg tgctgaccgt gctgcatcag      960
gattggctga acggcaaaga atataaatgc aaagtgagca caaagcgct gccggcgccg      1020 attgaaaaaa ccattagcaa agcgaaaggc cagccgcgcg aaccgcaggt gtatacccctg     1080 ccgccgagcc gcgatgaact gaccaaaaac caggtgagcc tgacctgcct ggtgaaaggc      1140
ttttatccga gcgatattgc ggtggaatgg gaaagcaacg gccagccgga aaacaactat      1200
aaaaccaccc cgccggtgct ggatagcgat ggcagctttt ttctgtatag caaactgacc      1260
gtggataaaa gccgctggca gcagggcaac gtgtttagct gcagcgtgat gcatgaagcg      1320
ctgcataacc attatcccca gaaaagcctg agcctgagcc cgggcaaa                   1368
```

<210> SEQ ID NO 93
<211> LENGTH: 220
<212> TYPE: PRT
<213> ORGANISM: Artificial Sequence
<220> FEATURE:
<223> OTHER INFORMATION: Light Chain

<400> SEQUENCE: 93

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

-continued

```
His Ala Ser Ala Pro Pro Thr Phe Gly Gly Thr Lys Val Glu Ile
            100             105             110

Lys Arg Thr Val Ala Ala Pro Ser Val Phe Ile Phe Pro Pro Ser Asp
        115                 120             125

Glu Gln Leu Lys Ser Gly Thr Ala Ser Val Val Cys Leu Leu Asn Asn
    130                 135             140

Phe Tyr Pro Arg Glu Ala Lys Val Gln Trp Lys Val Asp Asn Ala Leu
145                 150             155             160

Gln Ser Gly Asn Ser Gln Glu Ser Val Thr Glu Gln Asp Ser Lys Asp
                165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
            195             200             205

Ser Pro Val Thr Lys Ser Phe Asn Arg Gly Glu Cys
            210             215             220

<210> SEQ ID NO 94
<211> LENGTH: 660
<212> TYPE: DNA
<213> ORGANISM: Artificial Sequence
<220> FEATURE:
<223> OTHER INFORMATION: DNA Light Chain

<400> SEQUENCE: 94
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaac gtacggtggc cgctccctcc     360
gtgttcatct cccacccotc cgacgagcag ctgaagtccg gcaccgcctc cgtcgtgtgc     420
ctgctgaaca acttctaccc tcgcgaggcc aaagtgcagt ggaaagtgga caacgccctg     480
cagtccggca actcccagga atccgtcacc gagcaggact ccaaggacag cacctactcc     540
ctgtcctcca ccctgaccct gtccaaggcc gactacgaga gcacaaagt gtacgcctgc      600 gaagtgaccc accagggcct gtccagcccc gtgaccaagt ccttcaaccg gggcgagtgc     660

<210> SEQ ID NO 95
<211> LENGTH: 452
<212> TYPE: PRT
<213> ORGANISM: Artificial Sequence
<220> FEATURE:
<223> OTHER INFORMATION: Heavy CHain

<400> SEQUENCE: 95

Glu Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Arg Tyr
            20              25              30

Gly Met Asn Trp Val Arg Gln Ala Pro Gly Lys Gly Leu Glu Trp Val
        35                  40              45

Ser Ser Ile Ser Ser Ser Ser Ala Tyr Ile Leu Tyr Ala Asp Ser Val
    50                  55              60

Lys Gly Arg Phe Thr Ile Ser Arg Asp Asn Ala Lys Asn Ser Leu Tyr
```

```
        65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
               100                 105                 110

Phe Asp Pro Trp Gly Gln Gly Thr Leu Val Thr Val Ser Ser Ala Ser
               115                 120                 125

Thr Lys Gly Pro Ser Val Phe Pro Leu Ala Pro Cys Ser Arg Ser Thr
       130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
               165                 170                 175

His Thr Phe Pro Ala Val Leu Gln Ser Ser Gly Leu Tyr Ser Leu Ser
               180                 185                 190

Ser Val Val Thr Val Pro Ser Ser Ser Leu Gly Thr Lys Thr Tyr Thr
               195                 200                 205

Cys Asn Val Asp His Lys Pro Ser Asn Thr Lys Val Asp Lys Arg Val
       210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
               245                 250                 255

Leu Met Ile Ser Arg Thr Pro Glu Val Thr Cys Val Val Val Asp Val
               260                 265                 270

Ser Gln Glu Asp Pro Glu Val Gln Phe Asn Trp Tyr Val Asp Gly Val
               275                 280                 285

Glu Val His Asn Ala Lys Thr Lys Pro Arg Glu Glu Gln Phe Asn Ser
       290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
               325                 330                 335

Ser Ile Glu Lys Thr Ile Ser Lys Ala Lys Gly Gln Pro Arg Glu Pro
               340                 345                 350

Gln Val Tyr Thr Leu Pro Pro Ser Gln Glu Glu Met Thr Lys Asn Gln
               355                 360                 365

Val Ser Leu Thr Cys Leu Val Lys Gly Phe Tyr Pro Ser Asp Ile Ala
       370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
               405                 410                 415

Thr Val Asp Lys Ser Arg Trp Gln Glu Gly Asn Val Phe Ser Cys Ser
               420                 425                 430

Val Met His Glu Ala Leu His Asn His Tyr Thr Gln Lys Ser Leu Ser
       435                 440                 445

Leu Ser Leu Gly
       450
```

<210> SEQ ID NO 96
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 96

```
gaggtgcagc tggtggagtc tggggggaggc ctggtcaagc ctggggggtc cctgagactc      60
tcctgtgcag cctctggatt caccttcagt aggtatggga tgaactgggt ccgccaggct     120
ccagggaagg ggctggagtg ggtctcatcc attagtagta gtagtgctta catactgtac     180
gcagactcag tgaagggccg attcaccatc tccagagaca cgccaagaa ctcactgtat     240 ctgcaaatga acagcctgag agccgaggac acggcggtgt actactgcgc cagagatggt     300
ggaagaacgt cctacaccgc cacagcccac aattggttcg accccctgggg acagggtaca     360 ttggtcaccg tctcctcagc ttccaccaag ggcccctccg tgttccctct ggcccccttgc     420 tcccggtcca cctccgagtc taccgccgct ctgggctgcc tcgtgaagga ctacttcccc     480
gagcccgtga ccgtgtcctg gaactctggc gccctgacct ccggcgtgca caccttccct     540
gccgtgctgc agtcctccgg cctgtactcc ctgtccagcg tcgtgaccgt gccctcctcc     600
agcctgggca ccaagaccta cacctgtaac gtggaccaca gccctccaa caccaaagtg     660 gacaagcggg tggaatctaa gtacggccct ccctgcccctt cctgccctgc ccctgagttc     720
ctgggcggac cttccgtgtt cctgttccct ccaaagccca aggacaccct gatgatctcc     780
cggacccctg aagtgacctg cgtggtggtg gacgtgtccc aggaagatcc cgaagtccag     840
ttcaattggt acgtggacgg cgtggaagtg cacaacgcca gaccaagcc cagagaggaa     900 cagttcaact ccacctaccg ggtggtgtcc gtgctgaccg tgctgcacca ggactggctg     960
aacggcaaag agtacaagtg caaagtgtcc aacaagggcc tgccctccag catcgaaaag    1020
accatctcca aggccaaggg ccagccccgc gagcccaag tgtacaccct gcctcccagc    1080
caggaagaga tgaccaagaa tcaagtgtcc ctgacttgtc tggtcaaggg cttctacccc    1140
tccgatatcg ccgtggagtg gggagtccaac ggccagcccg agaacaacta caagaccacc    1200
cctcccgtgc tggactccga cggctccttc ttcctgtact ctcggctgac cgtggacaag    1260
tcccggtggc aggaaggcaa cgtcttctcc tgctccgtga tgcacgaggc cctgcacaac    1320
cactacaccc agaagtccct gtccctgtct ctgggc                              1356
```

<210> SEQ ID NO 97
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 97

```
Gly Phe Thr Phe Ala Ser Tyr Gly
1               5
```

<210> SEQ ID NO 98
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 98

```
Ile Ser Ser Ser Ser Ser Tyr Ile
1               5
```

<210> SEQ ID NO 99

```
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 99

Ala Arg Asp Gly Gly Arg Thr Ser Tyr Thr Ala Thr Ala His Asn Trp
1               5                   10                  15

Phe Asp Pro

<210> SEQ ID NO 100
<211> LENGTH: 9
<212> TYPE: PRT
<213> ORGANISM: Artificial Sequence
<220> FEATURE:
<223> OTHER INFORMATION: Heavy chain CDR1

<400> SEQUENCE: 100

Phe Thr Phe Ala Ser Tyr Gly Met Asn
1               5

<210> SEQ ID NO 101
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 101

Ser Ile Ser Ser Ser Ser Ser Tyr Ile Tyr Tyr Ala Asp Ser Val Lys
1               5                   10                  15

Gly

<210> SEQ ID NO 102
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 102

Ala Arg Asp Gly Gly Arg Thr Ser Tyr Thr Ala Thr Ala His Asn Trp
1               5                   10                  15

Phe Asp Pro

<210> SEQ ID NO 103
<211> LENGTH: 126
<212> TYPE: PRT
<213> ORGANISM: Artificial Sequence
<220> FEATURE:
<223> OTHER INFORMATION: Heavy chain

<400> SEQUENCE: 103

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Ser Tyr
            20                  25                  30

Gly Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
```

-continued

```
65              70              75              80

Leu Gln Met Asn Ser Leu Arg Ala Glu Asp Thr Ala Val Tyr Tyr Cys
                85              90              95

Ala Arg Asp Gly Gly Arg Thr Ser Tyr Thr Ala Thr Ala His Asn Trp
            100             105             110

Phe Asp Pro Trp Gly Gln Gly Thr Leu Val Thr Val Ser Ser
        115             120             125
```

```
<210> SEQ ID NO 104
<211> LENGTH: 378
<212> TYPE: DNA
<213> ORGANISM: Artificial Sequence
<220> FEATURE:
<223> OTHER INFORMATION: DNA Heavy Chain

<400> SEQUENCE: 104
gaggtgcagc tggtggagtc tggggggaggc ctggtcaagc ctggggggtc cctgagactc      60
tcctgtgcag cctctggatt caccttcgct agctatggga tgaactgggt ccgccaggct     120
ccagggaagg ggctggagtg ggtctcatcc attagtagtt ctagtagtta catatactac     180
gcagactcag tgaagggccg attcaccatc tccagagaca acgccaagaa ctcactgtat     240
ctgcaaatga acagcctgag agccgaggac acggcggtgt actactgcgc cagagatggt     300
ggaagaacgt cctacaccgc cacagcccac aattggttcg accccctgggg acagggtaca     360 ttggtcaccg tctcctca                                                   378
```

```
<210> SEQ ID NO 105
<211> LENGTH: 12
<212> TYPE: PRT
<213> ORGANISM: Artificial Sequence
<220> FEATURE:
<223> OTHER INFORMATION: Light Chain CDR1

<400> SEQUENCE: 105

Gln Ser Val Leu Phe Ser Ser Asn Asn Lys Asn Tyr
1               5                   10
```

```
<210> SEQ ID NO 106
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 106

Trp Ala Ser
1
```

```
<210> SEQ ID NO 107
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 107

Gln Gln His Ala Ser Ala Pro Pro Thr
1               5
```

```
<210> SEQ ID NO 108
<211> LENGTH: 17
<212> TYPE: PRT
<213> ORGANISM: Artificial Sequence
```

<220> FEATURE:
<223> OTHER INFORMATION: Light Chain CDR1

<400> SEQUENCE: 108

Lys Ser Ser Gln Ser Val Leu Phe Ser Ser Asn Asn Lys Asn Tyr Leu
1               5                   10                  15

Ala

<210> SEQ ID NO 109
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 109

Trp Ala Ser Thr Arg Glu Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 110

Gln Gln His Ala Ser Ala Pro Pro Thr
1               5

<210> SEQ ID NO 111
<211> LENGTH: 113
<212> TYPE: PRT
<213> ORGANISM: Artificial Sequence
<220> FEATURE:
<223> OTHER INFORMATION: Light Chain

<400> SEQUENCE: 111

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 112
<211> LENGTH: 339
<212> TYPE: DNA
<213> ORGANISM: Artificial Sequence
<220> FEATURE:
<223> OTHER INFORMATION: DNA Light Chain

<400> SEQUENCE: 112

```
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaa                            339
```

<210> SEQ ID NO 113
<211> LENGTH: 456
<212> TYPE: PRT
<213> ORGANISM: Artificial Sequence
<220> FEATURE:
<223> OTHER INFORMATION: Heavy Chain

<400> SEQUENCE: 113

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300
```

```
Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
    450                 455
```

<210> SEQ ID NO 114
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 114

```
gaggtgcagc tggtggagtc tgggggaggc ctggtcaagc ctggggggtc cctgagactc     60
tcctgtgcag cctctggatt caccttcgct agctatggga tgaactgggt ccgccaggct    120
ccagggaagg ggctggagtg ggtctcatcc attagtagtt ctagtagtta catatactac    180
gcagactcag tgaagggccg attcaccatc tccagagaca cgccaagaa ctcactgtat     240 ctgcaaatga acagcctgag agccgaggac acggcggtgt actactgcgc cagagatggt    300
ggaagaacgt cctacaccgc cacagcccac aattggttcg accctggggg acagggtaca    360
ttggtcaccg tctcctcagc gagcaccaaa ggcccgagcg tgtttccgct ggcgccgagc    420
agcaaaagca ccagcggcgg caccgcggcg ctgggctgcc tggtgaaaga ttattttccg    480
gaaccggtga ccgtgagctg gaacagcggc gcgctgacca cggcgtgca tacctttccg    540 gcggtgctgc agagcagcgg cctgtatagc ctgagcagcg tggtgaccgt gccgagcagc    600
agcctgggca cccagaccta tatttgcaac gtgaaccata aaccgagcaa caccaaagtg    660
gataaaaaag tggaaccgaa aagctgcgat aaaacccata cctgcccgcc gtgcccggcg    720
ccggaactgc tgggcggccc gagcgtgttt ctgtttccgc cgaaaccgaa agataccctg    780
atgattagcc gcacccccgga agtgacctgc gtggtggtgg atgtgagcca tgaagatccg    840
gaagtgaaat ttaactggta tgtggatggc gtggaagtgc ataacgcgaa aaccaaaccg    900
cgcgaagaac agtataacag cacctatcgc gtggtgagcg tgctgaccgt gctgcatcag    960
gattggctga acggcaaaga atataaatgc aaagtgagca caaagcgct gccggcgccg   1020 attgaaaaaa ccattagcaa agcgaaaggc cagccgcgcg aaccgcaggt gtatacctg    1080 ccgccgagcc gcgatgaact gaccaaaaac caggtgagcc tgacctgcct ggtgaaaggc   1140
ttttatccga gcgatattgc ggtggaatgg gaaagcaacg gccagccgga aaacaactat   1200
```
aaaaccaccc cgccggtgct ggatagcgat ggcagctttt ttctgtatag caaactgacc      1260
gtggataaaa gccgctggca gcagggcaac gtgtttagct gcagcgtgat gcatgaagcg      1320
ctgcataacc attataccca gaaaagcctg agcctgagcc cgggcaaa                   1368

<210> SEQ ID NO 115
<211> LENGTH: 220
<212> TYPE: PRT
<213> ORGANISM: Artificial Sequence
<220> FEATURE:
<223> OTHER INFORMATION: Light Chain

<400> SEQUENCE: 115

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 116
<211> LENGTH: 660
<212> TYPE: DNA
<213> ORGANISM: Artificial Sequence
<220> FEATURE:
<223> OTHER INFORMATION: DNA Light Chain

<400> SEQUENCE: 116
gacatcgtga tgacccagtc tccagactcc ctggctgtgt ctctgggcga gagggccacc        60
atcaactgca agtccagcca gagtgtttta ttcagctcca acaataagaa ctacttagct       120
tggtaccagc agaaaccagg acagcctcct aagctgctca tttactgggc atctacccgg       180
gaatccgggg tccctgaccg attcagtggc agcgggtctg ggacagattt cactctcacc       240
atcagcagcc tgcaggctga agatgtggca gtttattact gtcagcagca cgccagtgcc       300

```
cctcctactt ttggcggagg gaccaaggtt gagatcaaac gtacggtggc cgctccctcc      360
gtgttcatct tcccaccctc cgacgagcag ctgaagtccg gcaccgcctc cgtcgtgtgc      420
ctgctgaaca acttctaccc tcgcgaggcc aaagtgcagt ggaaagtgga caacgccctg      480
cagtccggca actcccagga atccgtcacc gagcaggact ccaaggacag cacctactcc      540
ctgtcctcca ccctgaccct gtccaaggcc gactacgaga agcacaaagt gtacgcctgc      600
gaagtgaccc accagggcct gtccagcccc gtgaccaagt ccttcaaccg gggcgagtgc      660
```

```
<210> SEQ ID NO 117
<211> LENGTH: 452
<212> TYPE: PRT
<213> ORGANISM: Artificial Sequence
<220> FEATURE:
<223> OTHER INFORMATION: Heavy Chain

<400> SEQUENCE: 117

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
    290                 295                 300
```

```
Thr Tyr Arg Val Val Ser Val Leu Thr Val Leu His Gln Asp Trp Leu
305             310             315             320

Asn Gly Lys Glu Tyr Lys Cys Lys Val Ser Asn Lys Gly Leu Pro Ser
                325             330             335

Ser Ile Glu Lys Thr Ile Ser Lys Ala Lys Gly Gln Pro Arg Glu Pro
            340             345             350

Gln Val Tyr Thr Leu Pro Pro Ser Gln Glu Glu Met Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Arg Leu
            405             410             415

Thr Val Asp Lys Ser Arg Trp Gln Glu Gly Asn Val Phe Ser Cys Ser
            420             425             430

Val Met His Glu Ala Leu His Asn His Tyr Thr Gln Lys Ser Leu Ser
        435             440             445

Leu Ser Leu Gly
    450
```

```
<210> SEQ ID NO 118
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 118
gaggtgcagc tggtggagtc tggggggaggc ctggtcaagc ctggggggtc cctgagactc      60
tcctgtgcag cctctggatt caccttcgct agctatggga tgaactgggt ccgccaggct     120
ccagggaagg ggctggagtg ggtctcatcc attagtagtt ctagtagtta catatactac     180
gcagactcag tgaagggccg attcaccatc tccagagaca acgccaagaa ctcactgtat     240
ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctcagc ttccaccaag ggcccctccg tgttccctct ggccccttgc     420
tcccggtcca cctccgagtc taccgccgct ctgggctgcc tcgtgaagga ctacttcccc     480
gagcccgtga ccgtgtcctg gaactctggc gccctgacct ccggcgtgca caccttccct     540
gccgtgctgc agtcctccgg cctgtactcc ctgtccagcg tcgtgaccgt gccctcctcc     600
agctgggcca ccaagaccta cacctgtaac gtggaccaca gcccctccaa caccaaagtg     660
gacaagcggg tggaatctaa gtacggccct ccctgccctt cctgccctgc ccctgagttc     720
ctgggcggac cttccgtgtt cctgttccct ccaaagccca aggacaccct gatgatctcc     780
cggacccctg aagtgacctg cgtggtggtg gacgtgtccc aggaagatcc cgaagtccag     840
ttcaattggt acgtggacgg cgtggaagtg cacaacgcca agaccaagcc cagagaggaa     900
cagttcaact ccacctaccg ggtggtgtcc gtgctgaccg tgctgcacca ggactggctg     960
aacggcaaag agtacaagtg caaagtgtcc aacaagggcc tgccctccag catcgaaaag    1020
accatctcca aggccaaggg ccagccccgc gagcccaag tgtacaccct gcctcccagc    1080
caggaagaga tgaccaagaa tcaagtgtcc ctgacttgtc tggtcaaggg cttctacccc    1140
tccgatatcg ccgtggagtg ggagtccaac ggccagcccg agaacaacta caagaccacc    1200
```
cctcccgtgc tggactccga cggctccttc ttcctgtact ctcggctgac cgtggacaag          1260
tcccggtggc aggaaggcaa cgtcttctcc tgctccgtga tgcacgaggc cctgcacaac          1320
cactacaccc agaagtccct gtccctgtct ctgggc                                    1356

<210> SEQ ID NO 119
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 119

Gly Phe Thr Phe Arg Ser Tyr Gly
1               5

<210> SEQ ID NO 120
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 120

Ile Ser Ser Ser Gly Ser Tyr Ile
1               5

<210> SEQ ID NO 121
<211> LENGTH: 19
<212> TYPE: PRT
<213> ORGANISM: Artificial Sequence
<220> FEATURE:
<223> OTHER INFORMATION: Heavy chain CDR3

<400> SEQUENCE: 121

Ala Arg Asp Gly Gly Arg Thr Ser Tyr Thr Ala Thr Ala His Asn Trp
1               5                   10                  15

Phe Asp Pro

<210> SEQ ID NO 122
<211> LENGTH: 9
<212> TYPE: PRT
<213> ORGANISM: Artificial Sequence
<220> FEATURE:
<223> OTHER INFORMATION: Heavy chain CDR1

<400> SEQUENCE: 122

Phe Thr Phe Arg Ser Tyr Gly Met Asn
1               5

<210> SEQ ID NO 123
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 123

Gly Ile Ser Ser Ser Gly Ser Tyr Ile Tyr Tyr Ala Asp Ser Val Lys
1               5                   10                  15

Gly

<210> SEQ ID NO 124
<211> LENGTH: 19

```
<212> TYPE: PRT
<213> ORGANISM: Artificial Sequence
<220> FEATURE:
<223> OTHER INFORMATION: Heavy chain CDR3

<400> SEQUENCE: 124

Ala Arg Asp Gly Gly Arg Thr Ser Tyr Thr Ala Thr Ala His Asn Trp
1               5                   10                  15

Phe Asp Pro

<210> SEQ ID NO 125
<211> LENGTH: 126
<212> TYPE: PRT
<213> ORGANISM: Artificial Sequence
<220> FEATURE:
<223> OTHER INFORMATION: Heavy Chain

<400> SEQUENCE: 125

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Gly Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
        115                 120                 125

<210> SEQ ID NO 126
<211> LENGTH: 378
<212> TYPE: DNA
<213> ORGANISM: Artificial Sequence
<220> FEATURE:
<223> OTHER INFORMATION: DNA Heavy Chain

<400> SEQUENCE: 126
gaggtgcagc tggtggagtc tgggggaggc ctggtcaagc ctggggggtc cctgagactc      60
tcctgtgcag cctctggatt caccttccgt agctatggga tgaactgggt ccgccaggct     120
ccagggaagg ggctggagtg ggtctcaggt attagtagta gtggtagtta catatactac     180
gcagactcag tgaagggccg attcaccatc tccagagaca cgccaagaa ctcactgtat      240 ctgcaaatga acagcctgag agccgaggac acggcggtgt actactgcgc cagagatggt     300
ggaagaacgt cctacaccgc cacagcccac aattggttcg acccctgggg acagggtaca     360
ttggtcaccg tctcctca                                                   378

<210> SEQ ID NO 127
<211> LENGTH: 12
<212> TYPE: PRT
<213> ORGANISM: Artificial Sequence
<220> FEATURE:
<223> OTHER INFORMATION: Light Chain CDR1

<400> SEQUENCE: 127
```

Gln Ser Val Leu Phe Ser Ser Asn Asn Lys Asn Tyr
1               5                   10

<210> SEQ ID NO 128
<211> LENGTH: 3
<212> TYPE: PRT
<213> ORGANISM: Artificial Sequence
<220> FEATURE:
<223> OTHER INFORMATION: Light Chain CDR2

<400> SEQUENCE: 128

Trp Ala Ser
1

<210> SEQ ID NO 129
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 129

Gln Gln His Ala Ser Ala Pro Pro Thr
1               5

<210> SEQ ID NO 130
<211> LENGTH: 17
<212> TYPE: PRT
<213> ORGANISM: Artificial Sequence
<220> FEATURE:
<223> OTHER INFORMATION: Light Chain CDR1

<400> SEQUENCE: 130

Lys Ser Ser Gln Ser Val Leu Phe Ser Ser Asn Asn Lys Asn Tyr Leu
1               5                   10                  15

Ala

<210> SEQ ID NO 131
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 131

Trp Ala Ser Thr Arg Glu Ser
1               5

<210> SEQ ID NO 132
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 132

Gln Gln His Ala Ser Ala Pro Pro Thr
1               5

<210> SEQ ID NO 133
<211> LENGTH: 113
<212> TYPE: PRT
<213> ORGANISM: Artificial Sequence
<220> FEATURE:
<223> OTHER INFORMATION: Light Chain

<400> SEQUENCE: 133

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

His Ala Ser Ala Pro Pro Thr Phe Gly Gly Gly Thr Lys Val Glu Ile
            100                 105                 110

Lys

<210> SEQ ID NO 134
<211> LENGTH: 339
<212> TYPE: DNA
<213> ORGANISM: Artificial Sequence
<220> FEATURE:
<223> OTHER INFORMATION: DNA Light Chain

<400> SEQUENCE: 134
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaa                             339

<210> SEQ ID NO 135
<211> LENGTH: 456
<212> TYPE: PRT
<213> ORGANISM: Artificial Sequence
<220> FEATURE:
<223> OTHER INFORMATION: Heavy Chain

<400> SEQUENCE: 135

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Gly Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser

-continued

```
                115                 120                 125
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
                275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 136
<211> LENGTH: 1368
<212> TYPE: DNA
<213> ORGANISM: Artificial Sequence
<220> FEATURE:
<223> OTHER INFORMATION: DNA Heavy Chain

<400> SEQUENCE: 136
gaggtgcagc tggtggagtc tggggggaggc ctggtcaagc ctggggggtc cctgagactc      60
tcctgtgcag cctctggatt caccttccgt agctatggga tgaactgggt ccgccaggct     120
```

-continued

```
ccagggaagg ggctggagtg ggtctcaggt attagtagta gtggtagtta catatactac    180
gcagactcag tgaagggccg attcaccatc tccagagaca cgccaagaa ctcactgtat    240 ctgcaaatga acagcctgag agccgaggac acggcggtgt actactgcgc cagagatggt    300
ggaagaacgt cctacaccgc cacagcccac aattggttcg acccctgggg acagggtaca    360
ttggtcaccg tctcctcagc gagcaccaaa ggcccgagcg tgtttccgct ggcgccgagc    420
agcaaaagca ccagcggcgg caccgcggcg ctgggctgcc tggtgaaaga ttattttccg    480
gaaccggtga ccgtgagctg gaacagcggc gcgctgacca gcggcgtgca taccttccg    540 gcggtgctgc agagcagcgg cctgtatagc ctgagcagcg tggtgaccgt gccgagcagc    600
agcctgggca cccagaccta tatttgcaac gtgaaccata aaccgagcaa caccaaagtg    660
gataaaaaag tggaaccgaa aagctgcgat aaaacccata cctgcccgcc gtgcccggcg    720
ccggaactgc tgggcggccc gagcgtgttt ctgtttccgc cgaaaccgaa agataccctg    780
atgattagcc gcacccccgga agtgacctgc gtggtggtgg atgtgagcca tgaagatccg    840
gaagtgaaat ttaactggta tgtggatggc gtggaagtgc ataacgcgaa aaccaaaccg    900
cgcgaagaac agtataacag cacctatcgc gtggtgagcg tgctgaccgt gctgcatcag    960
gattggctga cggcaaaga atataaatgc aaagtgagca caaagcgct gccggcgccg    1020 attgaaaaaa ccattagcaa agcgaaaggc cagccgcgcg aaccgcaggt gtataccctg    1080
ccgccgagcc gcgatgaact gaccaaaaac caggtgagcc tgacctgcct ggtgaaaggc    1140
ttttatccga gcgatattgc ggtggaatgg gaaagcaacg gccagccgga aaacaactat    1200
aaaaccaccc cgccggtgct ggatagcgat ggcagctttt ttctgtatag caaactgacc    1260
gtggataaaa gccgctggca gcagggcaac gtgtttagct gcagcgtgat gcatgaagcg    1320
ctgcataacc attatacccca gaaaagcctg agcctgagcc cgggcaaa    1368
```

<210> SEQ ID NO 137
<211> LENGTH: 220
<212> TYPE: PRT
<213> ORGANISM: Artificial Sequence
<220> FEATURE:
<223> OTHER INFORMATION: Light Chain

<400> SEQUENCE: 137

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 138
<211> LENGTH: 660
<212> TYPE: DNA
<213> ORGANISM: Artificial Sequence
<220> FEATURE:
<223> OTHER INFORMATION: DNA Light CHain

<400> SEQUENCE: 138

```
gacatcgtga tgacccagtc tccagactcc ctggctgtgt ctctgggcga gagggccacc      60
atcaactgca agtccagcca gagtgtttta ttcagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagca cgccagtgcc     300
cctcctactt ttggcggagg gaccaaggtt gagatcaaac gtacggtggc cgctccctcc     360
gtgttcatct tcccaccctc cgacgagcag ctgaagtccg gcaccgcctc cgtcgtgtgc     420
ctgctgaaca acttctaccc tcgcgaggcc aaagtgcagt ggaaagtgga caacgccctg     480
cagtccggca actcccagga atccgtcacc gagcaggact ccaaggacag cacctactcc     540
ctgtcctcca ccctgaccct gtccaaggcc gactacgaga gcacaaagt gtacgcctgc      600 gaagtgaccc accagggcct gtccagcccc gtgaccaagt ccttcaaccg gggcgagtgc     660
```

<210> SEQ ID NO 139
<211> LENGTH: 452
<212> TYPE: PRT
<213> ORGANISM: Artificial Sequence
<220> FEATURE:
<223> OTHER INFORMATION: Heavy Chain

<400> SEQUENCE: 139

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Gly Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
```

```
            115                 120                 125
Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Lys Thr Tyr Thr
                195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
    275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Gln Glu Glu Met Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
    435                 440                 445

Leu Ser Leu Gly
    450
```

```
<210> SEQ ID NO 140
<211> LENGTH: 1356
<212> TYPE: DNA
<213> ORGANISM: Artificial Sequence
<220> FEATURE:
<223> OTHER INFORMATION: DNA Heavy Chain

<400> SEQUENCE: 140
gaggtgcagc tggtggagtc tgggggaggc ctggtcaagc ctggggggtc cctgagactc      60
tcctgtgcag cctctggatt caccttccgt agctatggga tgaactgggt ccgccaggct     120
```

-continued

```
ccagggaagg ggctggagtg ggtctcaggt attagtagta gtggtagtta catatactac      180
gcagactcag tgaagggccg attcaccatc tccagagaca acgccaagaa ctcactgtat      240
ctgcaaatga acagcctgag agccgaggac acggcggtgt actactgcgc cagagatggt      300
ggaagaacgt cctacaccgc cacagcccac aattggttcg acccctgggg acagggtaca      360
ttggtcaccg tctcctcagc ttccaccaag ggcccctccg tgttccctct ggcccccttgc     420 tcccggtcca cctccgagtc taccgccgct ctgggctgcc tcgtgaagga ctacttcccc      480
gagcccgtga ccgtgtcctg gaactctggc gccctgacct ccggcgtgca caccttccct      540
gccgtgctgc agtcctccgg cctgtactcc ctgtccagcg tcgtgaccgt gccctcctcc      600
agcctgggca ccaagaccta cacctgtaac gtggaccaca gccctccaa caccaaagtg       660 gacaagcggg tggaatctaa gtacggccct ccctgccctt cctgccctgc ccctgagttc      720
ctgggcggac cttccgtgtt cctgttccct ccaaagccca aggacaccct gatgatctcc      780
cggacccctg aagtgacctg cgtggtggtg gacgtgtccc aggaagatcc cgaagtccag      840
ttcaattggt acgtggacgg cgtggaagtg cacaacgcca agaccaagcc cagagaggaa      900
cagttcaact ccacctaccg ggtggtgtcc gtgctgaccg tgctgcacca ggactggctg      960
aacggcaaag agtacaagtg caaagtgtcc aacaagggcc tgccctccag catcgaaaag     1020
accatctcca aggccaaggg ccagccccgc gagccccaag tgtacaccct gcctcccagc     1080
caggaagaga tgaccaagaa tcaagtgtcc ctgacttgtc tggtcaaggg cttctacccc     1140
tccgatatcg ccgtggagtg gggagtccaac ggccagcccg agaacaacta caagaccacc     1200
cctcccgtgc tggactccga cggctccttc ttcctgtact ctcggctgac cgtggacaag     1260
tcccggtggc aggaaggcaa cgtcttctcc tgctccgtga tgcacgaggc cctgcacaac     1320
cactacaccc agaagtccct gtccctgtct ctgggc                                1356
```

```
<210> SEQ ID NO 141
<211> LENGTH: 8
<212> TYPE: PRT
<213> ORGANISM: Artificial Sequence
<220> FEATURE:
<223> OTHER INFORMATION: FLAG

<400> SEQUENCE: 141

Asp Tyr Lys Asp Asp Asp Asp Lys
1               5

<210> SEQ ID NO 142
<211> LENGTH: 6
<212> TYPE: PRT
<213> ORGANISM: Artificial Sequence
<220> FEATURE:
<223> OTHER INFORMATION: 6-HIS

<400> SEQUENCE: 142

His His His His His His
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic HA

<400> SEQUENCE: 143

Tyr Pro Tyr Asp Val Pro Asp Tyr Ala
```

1               5

<210> SEQ ID NO 144
<211> LENGTH: 8
<212> TYPE: PRT
<213> ORGANISM: Artificial Sequence
<220> FEATURE:
<223> OTHER INFORMATION: consensus heavy chain CDR1
<220> FEATURE:
<221> NAME/KEY: misc_feature
<222> LOCATION: (5)..(5)
<223> OTHER INFORMATION: Wherein Xaa can be Ser, Ala, or Arg
<220> FEATURE:
<221> NAME/KEY: misc_feature
<222> LOCATION: (6)..(6)
<223> OTHER INFORMATION: Wherein Xaa can be Ser or Arg
<220> FEATURE:
<221> NAME/KEY: misc_feature
<222> LOCATION: (7)..(7)
<223> OTHER INFORMATION: Wherein Xaa can be Thr or Tyr
<220> FEATURE:
<221> NAME/KEY: misc_feature
<222> LOCATION: (8)..(8)
<223> OTHER INFORMATION: Wherein Xaa can be Gly or Ser

<400> SEQUENCE: 144

Gly Phe Thr Phe Xaa Xaa Xaa Xaa
1               5

<210> SEQ ID NO 145
<211> LENGTH: 8
<212> TYPE: PRT
<213> ORGANISM: Artificial Sequence
<220> FEATURE:
<223> OTHER INFORMATION: consensus heavy chain CDR1
<220> FEATURE:
<221> NAME/KEY: misc_feature
<222> LOCATION: (5)..(8)
<223> OTHER INFORMATION: Xaa can be any naturally occurring amino acid

<400> SEQUENCE: 145

Gly Phe Thr Phe Xaa Xaa Xaa Xaa
1               5

<210> SEQ ID NO 146
<211> LENGTH: 8
<212> TYPE: PRT
<213> ORGANISM: Artificial Sequence
<220> FEATURE:
<223> OTHER INFORMATION: consensus heavy chain CDR2
<220> FEATURE:
<221> NAME/KEY: misc_feature
<222> LOCATION: (5)..(5)
<223> OTHER INFORMATION: Wherein Xaa can be Ser or Gly
<220> FEATURE:
<221> NAME/KEY: misc_feature
<222> LOCATION: (6)..(6)
<223> OTHER INFORMATION: Wherein Xaa can be Ser or Ala

<400> SEQUENCE: 146

Ile Ser Ser Ser Xaa Xaa Tyr Ile
1               5

<210> SEQ ID NO 147
<211> LENGTH: 8
<212> TYPE: PRT
<213> ORGANISM: Artificial Sequence
<220> FEATURE:
<223> OTHER INFORMATION: consensus heavy chain CDR2
<220> FEATURE:
<221> NAME/KEY: misc_feature
<222> LOCATION: (5)..(6)

```
<223> OTHER INFORMATION: Xaa can be any naturally occurring amino acid

<400> SEQUENCE: 147

Ile Ser Ser Ser Xaa Xaa Tyr Ile
1               5

<210> SEQ ID NO 148
<211> LENGTH: 9
<212> TYPE: PRT
<213> ORGANISM: Artificial Sequence
<220> FEATURE:
<223> OTHER INFORMATION: consensus heavy chain CDR1
<220> FEATURE:
<221> NAME/KEY: misc_feature
<222> LOCATION: (4)..(4)
<223> OTHER INFORMATION: Wherein Xaa can be Ser, Ala, or Arg
<220> FEATURE:
<221> NAME/KEY: misc_feature
<222> LOCATION: (5)..(5)
<223> OTHER INFORMATION: Wherein Xaa can be Ser or Arg
<220> FEATURE:
<221> NAME/KEY: misc_feature
<222> LOCATION: (6)..(6)
<223> OTHER INFORMATION: Wherein Xaa can be Thr or Tyr
<220> FEATURE:
<221> NAME/KEY: misc_feature
<222> LOCATION: (7)..(7)
<223> OTHER INFORMATION: Wherein Xaa can be Gly or Ser

<400> SEQUENCE: 148

Phe Thr Phe Xaa Xaa Xaa Xaa Met Asn
1               5

<210> SEQ ID NO 149
<211> LENGTH: 17
<212> TYPE: PRT
<213> ORGANISM: Artificial Sequence
<220> FEATURE:
<223> OTHER INFORMATION: consensus heavy chain CDR2
<220> FEATURE:
<221> NAME/KEY: misc_feature
<222> LOCATION: (1)..(1)
<223> OTHER INFORMATION: Wherein Xaa can be Gly or Ser
<220> FEATURE:
<221> NAME/KEY: misc_feature
<222> LOCATION: (6)..(6)
<223> OTHER INFORMATION: Wherein Xaa can be Gly or Ser
<220> FEATURE:
<221> NAME/KEY: misc_feature
<222> LOCATION: (7)..(7)
<223> OTHER INFORMATION: Wherein Xaa can be Ser or Ala
<220> FEATURE:
<221> NAME/KEY: misc_feature
<222> LOCATION: (10)..(10)
<223> OTHER INFORMATION: Wherein Xaa can be Leu or Tyr

<400> SEQUENCE: 149

Xaa Ile Ser Ser Ser Xaa Xaa Tyr Ile Xaa Tyr Ala Asp Ser Val Lys
1               5                   10                  15

Gly

<210> SEQ ID NO 150
<211> LENGTH: 9
<212> TYPE: PRT
<213> ORGANISM: Artificial Sequence
<220> FEATURE:
<223> OTHER INFORMATION: consensus heavy chain CDR1
<220> FEATURE:
<221> NAME/KEY: misc_feature
<222> LOCATION: (4)..(7)
<223> OTHER INFORMATION: Xaa can be any naturally occurring amino acid
```

```
<400> SEQUENCE: 150

Phe Thr Phe Xaa Xaa Xaa Xaa Met Asn
1               5

<210> SEQ ID NO 151
<211> LENGTH: 17
<212> TYPE: PRT
<213> ORGANISM: Artificial Sequence
<220> FEATURE:
<223> OTHER INFORMATION: consensus heavy chain CDR2
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 151

Xaa Ile Ser Ser Ser Xaa Xaa Tyr Ile Xaa Tyr Ala Asp Ser Val Lys
1               5                   10                  15

Gly

<210> SEQ ID NO 152
<211> LENGTH: 8
<212> TYPE: PRT
<213> ORGANISM: Artificial Sequence
<220> FEATURE:
<223> OTHER INFORMATION: heavy chain CDR2
<220> FEATURE:
<221> NAME/KEY: misc_feature
<222> LOCATION: (2)..(8)
<223> OTHER INFORMATION: Xaa can be any naturally occurring amino acid

<400> SEQUENCE: 152

Ile Xaa Xaa Xaa Xaa Xaa Xaa Xaa
1               5

<210> SEQ ID NO 153
<211> LENGTH: 5
<212> TYPE: PRT
<213> ORGANISM: Artificial Sequence
<220> FEATURE:
<223> OTHER INFORMATION: Heavy chain CDR3
<220> FEATURE:
<221> NAME/KEY: misc_Feature
<222> LOCATION: (3)..(3)
<223> OTHER INFORMATION: Wherein Xaa can be any amino acid and can
      repeat between 6 and 15 times
<220> FEATURE:
<221> NAME/KEY: misc_feature
<222> LOCATION: (5)..(5)
<223> OTHER INFORMATION: Xaa can be any naturally occurring amino acid

<400> SEQUENCE: 153

Ala Arg Xaa Asp Xaa
1               5

<210> SEQ ID NO 154
<211> LENGTH: 7
```

```
<212> TYPE: PRT
<213> ORGANISM: Artificial Sequence
<220> FEATURE:
<223> OTHER INFORMATION: Light chain CDR1
<220> FEATURE:
<221> NAME/KEY: Misc_feature
<222> LOCATION: (3)..(3)
<223> OTHER INFORMATION: Wherein Xaa can be any amino acid and repeat
      itself between 1 and 3 times
<220> FEATURE:
<221> NAME/KEY: Misc_feature
<222> LOCATION: (6)..(6)
<223> OTHER INFORMATION: Wherein Xaa can be any amino acid and repeat
      itself between 0 and 4 times

<400> SEQUENCE: 154

Gln Ser Xaa Ser Ser Xaa Tyr
1               5

<210> SEQ ID NO 155
<211> LENGTH: 3
<212> TYPE: PRT
<213> ORGANISM: Artificial Sequence
<220> FEATURE:
<223> OTHER INFORMATION: light chain CDR2
<220> FEATURE:
<221> NAME/KEY: misc_feature
<222> LOCATION: (1)..(2)
<223> OTHER INFORMATION: Xaa can be any naturally occurring amino acid

<400> SEQUENCE: 155

Xaa Xaa Ser
1

<210> SEQ ID NO 156
<211> LENGTH: 9
<212> TYPE: PRT
<213> ORGANISM: Artificial Sequence
<220> FEATURE:
<223> OTHER INFORMATION: Light chain CDR3
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Wherein Xaa can be any amino acid and repeat
      itself 0 to 1 times

<400> SEQUENCE: 156

Gln Gln Xaa Xaa Xaa Xaa Pro Xaa Thr
1               5
```